(12) United States Patent
Datta et al.

(10) Patent No.: US 7,932,231 B2
(45) Date of Patent: Apr. 26, 2011

(54) COMPOSITIONS AND METHODS FOR STIMULATING GASTROINTESTINAL MOTILITY

(75) Inventors: Rakesh Datta, Brookline, MA (US); Zheng Xin Dong, Holliston, MA (US)

(73) Assignee: IPSEN Pharma, S.A.S., Paris (FR)

( * ) Notice: Subject to any disclaimer, the term of this patent is extended or adjusted under 35 U.S.C. 154(b) by 449 days.

(21) Appl. No.: 11/992,780

(22) PCT Filed: Sep. 28, 2006

(86) PCT No.: PCT/US2006/038027
§ 371 (c)(1),
(2), (4) Date: Mar. 29, 2008

(87) PCT Pub. No.: WO2007/041278
PCT Pub. Date: Apr. 12, 2007

(65) Prior Publication Data
US 2009/0304724 A1    Dec. 10, 2009

Related U.S. Application Data

(60) Provisional application No. 60/721,916, filed on Sep. 29, 2005.

(51) Int. Cl.
*A61K 38/08* (2006.01)
*A61K 35/37* (2006.01)
(52) U.S. Cl. .................. 514/21.8; 530/330; 424/551
(58) Field of Classification Search .................. None
See application file for complete search history.

(56) References Cited

U.S. PATENT DOCUMENTS 7,456,253 B2 *  11/2008  Dong ........................... 530/330
2002/0042419 A1   4/2002  Hakkinen
2005/0148515 A1   7/2005  Dong et al.
2007/0191283 A1 *  8/2007  Polvino ........................... 514/19
2008/0261873 A1  10/2008  Geesaman

FOREIGN PATENT DOCUMENTS

WO    WO 03/051389    6/2003
WO    WO 2004/009616   1/2004
WO    WO 2004/014415   2/2004

OTHER PUBLICATIONS

Murray, 2005, Neurogastroenterology, 54, 1693-1698.*
McDowell, 1995, PNAS, 92, 11165-11169.*
Trudel, 2003, Peptides, 24, 531-534.*
Kojima, M. and Kangawa, K., "Ghrelin: Structure and Function", 2005, Physiol. Rev., 85:495-522.
Murray, C. D. R., et al, "Ghrelin enhances gastric emptying in diabetic gastroparesis: a double blind, placebo controlled, crossover study", Gut, 2005, 54:1693-1698.
Masuda, Y. et al., "Ghrelin stimulates gastric acid secretion and motility in rats", Biochem. Biophys Res. Comm., 2000, 276:905-908.
Peeters, T. L., "Central and peripheral mechanisms by which ghrelin regulates gut motility", J. Physiol and Pharmacol., 2003, 54(Supp4):95-103.
Poitras, P. et al., "Gastrokinetic effect of ghrelin analog RC-1139 in the rat Effect on post-operative and on morphine induced ileus", Peptides, 2005, 26:1598-1601.
Trudel, L. et al., "Two new peptides to improve post-operative gastric ileus in dog", Peptides, 2003, 24:531-534.

* cited by examiner

*Primary Examiner* — Cecilia Tsang
*Assistant Examiner* — Satyanarayana R Gudibande
(74) *Attorney, Agent, or Firm* — Yankwich & Associates; Alan F. Feeney; Tony K. Uhm

(57) ABSTRACT

The present invention relates to a method of treating a transient impairment of the motility of the gastrointestinal system resulting from postoperative ileus in a patient wherein said method includes the step of administering a therapeutically effective amount of a peptidyl analog of ghrelin to said patient.

25 Claims, 5 Drawing Sheets

SEQUENCE LISTING

<160> NUMBER OF SEQ ID NOS: 342

<210> SEQ ID NO 1
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl or 1-octanesulfonyl, Glu modified with O-hexyl
      or NH-hexyl, or Cys modified with S-decyl or S(CH2)9CH3
<220> FEATURE:
<221> NAME/KEY: MOD_RES
<222> LOCATION: (28)..(28)
<223> OTHER INFORMATION: AMIDATION

<400> SEQUENCE: 1

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MOD_RES
<222> LOCATION: (28)..(28)
<223> OTHER INFORMATION: AMIDATION

<400> SEQUENCE: 2

Gly Xaa Ser Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 28

```
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu),
      beta-cyclohexylAla (Cha), or Lys
<220> FEATURE:
<221> NAME/KEY: MOD_RES
<222> LOCATION: (28)..(28)
<223> OTHER INFORMATION: AMIDATION

<400> SEQUENCE: 3

Gly Ser Ser Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 4

Gly Xaa Ser Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 5
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 5

Gly Xaa Ser Phe Leu Ser Pro Glu His Gln Arg Xaa Gln Gln Arg Lys
1               5                   10                  15
```

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 6

Gly Xaa Ser Phe Leu Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 7
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 7

Gly Xaa Ser Phe Leu Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 8
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)

```
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 8

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 9
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), 4-ketoPro
      (Ktp), or 1,2,3,4-tetrahydroisoquinoline-3-carboxylic acid (Tic)
<220> FEATURE:
<221> NAME/KEY: MOD_RES
<222> LOCATION: (28)..(28)
<223> OTHER INFORMATION: AMIDATION

<400> SEQUENCE: 9

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c), 4-amino-4-carboxytetrahydropyran (Act), or
      alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 10

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 11
```

```
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 11

Gly Xaa Ser Phe Leu Ser Pro Xaa His Gln Arg Val Gln Gln Arg Lys
1               5                  10                  15

Glu Ser Lys Lys Pro Pro Ala Lys Leu Gln Pro Arg
            20                  25

<210> SEQ ID NO 12
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 12

Gly Xaa Ser Phe Leu Ser Pro Glu His Xaa Arg Val Gln Gln Arg Lys
1               5                  10                  15

Glu Ser Lys Lys Pro Pro Ala Lys Leu Gln Pro Arg
            20                  25

<210> SEQ ID NO 13
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (6)..(6)
<223> OTHER INFORMATION: Xaa = alpha-aminoisobutyric acid (Aib),
     4-amino-4-carboxytetrahydropyran (Act), Thr, or
     alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 13

Gly Ser Ser Phe Leu Xaa Pro Glu His Gln Arg Val Gln Gln Arg Lys
1               5                  10                  15

Glu Ser Lys Lys Pro Pro Ala Lys Leu Gln Pro Arg
            20                  25
```

```
<210> SEQ ID NO 14
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric
      acid (Aib)
<220> FEATURE:
<221> NAME/KEY: MOD_RES
<222> LOCATION: (28)..(28)
<223> OTHER INFORMATION: AMIDATION

<400> SEQUENCE: 14

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 15
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 15

Gly Ser Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 16
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 16

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 17
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 17

Gly Ser Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 18
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MOD_RES
<222> LOCATION: (28)..(28)
<223> OTHER INFORMATION: AMIDATION

<400> SEQUENCE: 18

Gly Xaa Xaa Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 19
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MOD_RES
```

```
<222> LOCATION: (28)..(28)
<223> OTHER INFORMATION: AMIDATION

<400> SEQUENCE: 19

Gly Ser Xaa Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 20
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 20

Gly Xaa Xaa Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 21
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 21

Gly Xaa Xaa Phe Leu Ser Pro Glu His Gln Arg Xaa Gln Gln Arg Lys
1               5                   10                  15

Glu Ser Lys Lys Pro Pro Ala Lys Leu Gln Pro Arg
            20                  25
```

```
<210> SEQ ID NO 22
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 22

Gly Xaa Xaa Phe Leu Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 23
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 23

Gly Xaa Xaa Phe Leu Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 24
<211> LENGTH: 28
<212> TYPE: PRT
```

```
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 24

Gly Xaa Xaa Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 25
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro(Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 25

Gly Xaa Xaa Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 26
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
```

```
          (A5c), or 4-amino-4-carboxytetrahydropyran (Act)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 26

Gly Xaa Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 27
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or Glu modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 27

Gly Xaa Xaa Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 28
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or Glu modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 28

Gly Xaa Xaa Phe Leu Ser Pro Glu His Xaa Arg Val Gln Gln Arg Lys
```

```
                1               5                  10              15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 29

Gly Ser Xaa Phe Leu Xaa Pro Glu His Gln Arg Val Gln Gln Arg Lys
1               5                  10                  15

Glu Ser Lys Lys Pro Pro Ala Lys Leu Gln Pro Arg
            20                  25

<210> SEQ ID NO 30
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 30

Gly Ser Xaa Phe Leu Ser Pro Glu His Gln Arg Xaa Gln Gln Arg Lys
1               5                  10                  15

Glu Ser Lys Lys Pro Pro Ala Lys Leu Gln Pro Arg
            20                  25

<210> SEQ ID NO 31
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or 2,4-diaminobutyric acid (Dab) modified
      with octanesulfonyl
<220> FEATURE:
```

```
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 31

Gly Ser Xaa Phe Leu Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 32
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or 2,4-diaminobutyric acid (Dab) modified
      with octanesulfonyl
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 32

Gly Ser Xaa Phe Leu Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 33
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION
```

```
<400> SEQUENCE: 33

Gly Ser Xaa Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 34
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 34

Gly Ser Xaa Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 35
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl, or Glu modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 35

Gly Ser Xaa Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 36
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
```

```
<223> OTHER INFORMATION: Xaa = 2,3-diaminopropionic acid (Dap) modified
      with octanesulfonyl, or Glu modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 36

Gly Ser Xaa Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 37
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 37

Gly Xaa Ser Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 38
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
```

```
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 38

Gly Ser Ser Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 39
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 39

Gly Xaa Ser Phe Leu Xaa Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 40
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala  (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
```

```
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 40

Gly Xaa Ser Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 41
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 41

Gly Xaa Ser Phe Leu Ser Xaa Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 42
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
```

```
<221> NAME/KEY: MOD_RES
<222> LOCATION: (28)..(28)
<223> OTHER INFORMATION: AMIDATION

<400> SEQUENCE: 42

Gly Xaa Ser Phe Leu Ser Pro Xaa His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 43
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 43

Gly Xaa Ser Phe Leu Ser Pro Glu His Xaa Arg Xaa Gln Gln Xaa Lys
1               5                   10                  15

Glu Ser Lys Lys Pro Pro Ala Lys Leu Gln Pro Arg
            20                  25

<210> SEQ ID NO 44
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION
```

```
<400> SEQUENCE: 44

Gly Xaa Ser Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 45
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 45

Gly Ser Ser Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 46
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 46

Gly Xaa Ser Phe Leu Xaa Pro Glu His Gln Arg Xaa Gln Gln Arg Xaa
1               5                   10                  15
```

Glu Ser Lys Lys Pro Pro Ala Lys Leu Gln Pro Arg
            20                  25

<210> SEQ ID NO 47
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 47

Gly Xaa Ser Phe Leu Ser Pro Glu Xaa Gln Arg Xaa Gln Gln Arg Xaa
1               5                   10                  15

Glu Ser Lys Lys Pro Pro Ala Lys Leu Gln Pro Arg
            20                  25

<210> SEQ ID NO 48
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 48

Gly Xaa Ser Phe Leu Ser Xaa Glu His Gln Arg Xaa Gln Gln Arg Xaa

```
                1               5                  10                  15
Glu Ser Lys Lys Pro Pro Ala Lys Leu Gln Pro Arg
            20                  25

<210> SEQ ID NO 49
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 49

Gly Xaa Ser Phe Leu Ser Pro Xaa His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 50
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 50

Gly Xaa Ser Phe Leu Ser Pro Glu His Xaa Arg Xaa Gln Gln Arg Xaa
1               5                   10                  15

Glu Ser Lys Lys Pro Pro Ala Lys Leu Gln Pro Arg
            20                  25
```

```
<210> SEQ ID NO 51
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 51

Gly Ser Ser Phe Leu Xaa Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 52
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 52

Gly Ser Ser Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 53
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
```

```
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 53

Gly Ser Ser Phe Leu Ser Xaa Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 54
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 54

Gly Ser Ser Phe Leu Ser Pro Xaa His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 55
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
```

```
<220> FEATURE:
<221> NAME/KEY: MOD_RES
<222> LOCATION: (28)..(28)
<223> OTHER INFORMATION: AMIDATION

<400> SEQUENCE: 55

Gly Ser Ser Phe Leu Ser Pro Glu His Xaa Arg Xaa Gln Gln Xaa Lys
1               5                   10                  15

Glu Ser Lys Lys Pro Pro Ala Lys Leu Gln Pro Arg
            20                  25

<210> SEQ ID NO 56
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 56

Gly Ser Ser Phe Leu Xaa Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 57
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 57

Gly Ser Ser Phe Leu Ser Pro Glu Xaa Gln Arg Xaa Gln Gln Arg Xaa
```

-continued

```
1               5                   10                  15
Glu Ser Lys Lys Pro Pro Ala Lys Leu Gln Pro Arg
            20                  25
```

<210> SEQ ID NO 58
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 58

```
Gly Ser Ser Phe Leu Ser Xaa Glu His Gln Arg Xaa Gln Gln Arg Xaa
1               5                   10                  15
Glu Ser Lys Lys Pro Pro Ala Lys Leu Gln Pro Arg
            20                  25
```

<210> SEQ ID NO 59
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 59

```
Gly Ser Ser Phe Leu Ser Pro Xaa His Gln Arg Xaa Gln Gln Arg Xaa
1               5                   10                  15
Glu Ser Lys Lys Pro Pro Ala Lys Leu Gln Pro Arg
            20                  25
```

<210> SEQ ID NO 60
<211> LENGTH: 28
<212> TYPE: PRT
<213> ORGANISM: Artificial
<220> FEATURE:

```
<223> OTHER INFORMATION: Peptidyl ghrelin analog
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 60

Gly Ser Ser Phe Leu Ser Pro Glu His Xaa Arg Xaa Gln Gln Arg Xaa
1               5                   10                  15

Glu Ser Lys Lys Pro Pro Ala Lys Leu Gln Pro Arg
            20                  25

<210> SEQ ID NO 61
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-Hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), or homoLeu (hLeu)
<220> FEATURE:
<221> NAME/KEY: MOD_RES
<222> LOCATION: (28)..(28)
<223> OTHER INFORMATION: AMIDATION

<400> SEQUENCE: 61

Gly Xaa Glu Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 62
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c)
      alpha-aminoisobutyric acid (Aib), homoLeu (hLeu), or
      beta-cyclohexylAla (Cha)
<220> FEATURE:
```

```
<221> NAME/KEY: MOD_RES
<222> LOCATION: (28)..(28)
<223> OTHER INFORMATION: AMIDATION

<400> SEQUENCE: 62

Gly Ser Glu Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 63
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 63

Gly Xaa Glu Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 64
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala  (Taz),
      beta-(2-thienyl)Ala (2-Thi), beta-(2-furyl)Ala (2-Fua), Apc or
      alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 64

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25
```

20          25

<210> SEQ ID NO 65
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 65

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 66
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 66

Gly Ser Glu Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 67
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: modified with NH-hexyl
<220> FEATURE:
<221> NAME/KEY: MISC_FEATURE

```
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MOD_RES
<222> LOCATION: (28)..(28)
<223> OTHER INFORMATION: AMIDATION

<400> SEQUENCE: 67

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 68
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MOD_RES
<222> LOCATION: (28)..(28)
<223> OTHER INFORMATION: AMIDATION

<400> SEQUENCE: 68

Gly Ser Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 69
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib) or beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
```

```
<220> FEATURE:
<221> NAME/KEY: MOD_RES
<222> LOCATION: (28)..(28)
<223> OTHER INFORMATION: AMIDATION

<400> SEQUENCE: 69

Gly Xaa Glu Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 70
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 70

Gly Ser Glu Phe Xaa Ser Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 71
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
```

US 7,932,231 B2
213                                                                                                214
-continued

```
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 71

Gly Xaa Glu Phe Leu Xaa Pro Glu His Gln Arg Xaa Gln Gln Xaa Lys
1               5                   10                  15

Glu Ser Lys Lys Pro Pro Ala Lys Leu Gln Pro Arg
            20                  25

<210> SEQ ID NO 72
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 72

Gly Xaa Glu Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 73
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
```

```
        (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 73

Gly Xaa Glu Phe Leu Ser Xaa Glu His Gln Arg Xaa Gln Gln Xaa Lys
1               5                  10                  15

Glu Ser Lys Lys Pro Pro Ala Lys Leu Gln Pro Arg
            20                  25

<210> SEQ ID NO 74
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 74

Gly Xaa Glu Phe Leu Ser Pro Xaa His Gln Arg Xaa Gln Gln Xaa Lys
1               5                  10                  15

Glu Ser Lys Lys Pro Pro Ala Lys Leu Gln Pro Arg
            20                  25

<210> SEQ ID NO 75
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
```

```
<221> NAME/KEY: MISC_FEATURE
<222> LOCATION: (9)..(9)
<223> OTHER INFORMATION: Xaa = beta-(4-pyridiyl)Ala (4-Pal)
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 75

Gly Xaa Glu Phe Leu Ser Pro Glu Xaa Gln Arg Xaa Gln Gln Xaa Lys
1               5                  10                  15

Glu Ser Lys Lys Pro Pro Ala Lys Leu Gln Pro Arg
            20                  25

<210> SEQ ID NO 76
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 76

Gly Xaa Glu Phe Leu Ser Pro Glu His Xaa Arg Xaa Gln Gln Xaa Lys
1               5                  10                  15

Glu Ser Lys Lys Pro Pro Ala Lys Leu Gln Pro Arg
            20                  25

<210> SEQ ID NO 77
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c), 1-amino-1-cyclopentanecarboxylic acid (A5c),
      alpha-aminoisobutyric acid (Aib), homoLeu (hLeu), or
      beta-cyclohexylAla (Cha)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 77

Gly Xaa Glu Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 78
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 78

Gly Ser Glu Phe Xaa Ser Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 79
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
```

```
<222> LOCATION: (3)..(3)
<223> OTHER INFORMATION: modified with NH-hexyl
<220> FEATURE:
<221> NAME/KEY: MISC_FEATURE
<222> LOCATION: (6)..(6)
<223> OTHER INFORMATION: Xaa = alpha-aminoisobutyric acid (Aib),
      4-amino-4-carboxytetrahydropyran (Act), Thr, or
      alpha-aminobutyric acid (Abu)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 79

Gly Xaa Glu Phe Leu Xaa Pro Glu His Gln Arg Xaa Gln Gln Arg Xaa
1               5                   10                  15

Glu Ser Lys Lys Pro Pro Ala Lys Leu Gln Pro Arg
            20                  25

<210> SEQ ID NO 80
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(2-pyridiyl)Ala (2-Pal), beta-(4-pyridiyl)Ala (4-Pal),
      beta-(4-thiazolyl)Ala (Taz), beta-(2-thienyl)Ala (2-Thi),
      beta-(2-furyl)Ala (2-Fua), Apc, or alpha-aminoisobutyric acid
      (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 80

Gly Xaa Glu Phe Leu Ser Pro Glu Xaa Gln Arg Xaa Gln Gln Arg Xaa
1               5                   10                  15

Glu Ser Lys Lys Pro Pro Ala Lys Leu Gln Pro Arg
            20                  25

<210> SEQ ID NO 81
<211> LENGTH: 28
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 5,5-dimethylthiazolidine-4-carboxylic
      acid (Dmt), thiazolidine-4-carboxylic acid (Thz), 4-hydroxyPro
      (4-Hyp), pipecolic acid (Pip), 3,4-dehydroPro (Dhp), or 4-ketoPro
      (Ktp)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 81

Gly Xaa Glu Phe Leu Ser Xaa Glu His Gln Arg Xaa Gln Gln Arg Xaa
1               5                  10                  15

Glu Ser Lys Lys Pro Pro Ala Lys Leu Gln Pro Arg
            20                  25

<210> SEQ ID NO 82
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 82

Gly Xaa Glu Phe Leu Ser Pro Xaa His Gln Arg Xaa Gln Gln Arg Xaa
1               5                  10                  15

Glu Ser Lys Lys Pro Pro Ala Lys Leu Gln Pro Arg
            20                  25
```

-continued

```
<210> SEQ ID NO 83
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (16)..(16)
<223> OTHER INFORMATION: Xaa = Apc
<220> FEATURE:
<221> NAME/KEY: MOD_RES
<222> LOCATION: (28)..(28)
<223> OTHER INFORMATION: AMIDATION

<400> SEQUENCE: 83

Gly Xaa Glu Phe Leu Ser Pro Glu His Xaa Arg Xaa Gln Gln Arg Xaa
1               5                   10                  15

Glu Ser Lys Lys Pro Pro Ala Lys Leu Gln Pro Arg
            20                  25

<210> SEQ ID NO 84
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Glu modified with O-hexyl or NH-hexyl, or
      2,3-diaminopropionic acid (Dap) modified with 1-octanesulfonyl
<220> FEATURE:
<221> NAME/KEY: MOD_RES
<222> LOCATION: (28)..(28)
<223> OTHER INFORMATION: AMIDATION

<400> SEQUENCE: 84

Gly Xaa Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 85
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
```

```
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Glu modified with NH-hexyl, or
      2,3-diaminopropionic acid (Dap) modified with 1-octanesulfonyl
<220> FEATURE:
<221> NAME/KEY: MOD_RES
<222> LOCATION: (28)..(28)
<223> OTHER INFORMATION: AMIDATION

<400> SEQUENCE: 85

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 86
<211> LENGTH: 27
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = 5-amino-n-valeric acid (Ava)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with 1-octanesulfonyl
<220> FEATURE:
<221> NAME/KEY: MOD_RES
<222> LOCATION: (27)..(27)
<223> OTHER INFORMATION: AMIDATION

<400> SEQUENCE: 86

Ser Xaa Xaa Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 87
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (5)..(5)
<223> OTHER INFORMATION: AMIDATION

<400> SEQUENCE: 87

Gly Ser Ser Phe Leu
1               5

<210> SEQ ID NO 88
<211> LENGTH: 6
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
```

```
<220> FEATURE:
<221> NAME/KEY: MOD_RES
<222> LOCATION: (6)..(6)
<223> OTHER INFORMATION: AMIDATION

<400> SEQUENCE: 88

Gly Ser Ser Phe Leu Ser
1               5

<210> SEQ ID NO 89
<211> LENGTH: 7
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (7)..(7)
<223> OTHER INFORMATION: AMIDATION

<400> SEQUENCE: 89

Gly Ser Ser Phe Leu Ser Pro
1               5

<210> SEQ ID NO 90
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 90

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 91
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
```

-continued

```
<222> LOCATION: (5)..(5)
<223> OTHER INFORMATION: AMIDATION

<400> SEQUENCE: 91

Gly Xaa Glu Phe Leu
1               5

<210> SEQ ID NO 92
<211> LENGTH: 6
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (6)..(6)
<223> OTHER INFORMATION: AMIDATION

<400> SEQUENCE: 92

Gly Xaa Glu Phe Leu Ser
1               5

<210> SEQ ID NO 93
<211> LENGTH: 7
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (7)..(7)
<223> OTHER INFORMATION: AMIDATION

<400> SEQUENCE: 93

Gly Xaa Glu Phe Leu Ser Pro
1               5

<210> SEQ ID NO 94
<211> LENGTH: 8
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
```

```
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = Arg or Lys
<220> FEATURE:
<221> NAME/KEY: MOD_RES
<222> LOCATION: (8)..(8)
<223> OTHER INFORMATION: AMIDATION

<400> SEQUENCE: 94

Gly Xaa Glu Phe Leu Ser Pro Xaa
1               5

<210> SEQ ID NO 95
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with n-butyryl, isobutyryl,
      n-octanoyl, or acyl (Ac)
<220> FEATURE:
<221> NAME/KEY: MOD_RES
<222> LOCATION: (28)..(28)
<223> OTHER INFORMATION: AMIDATION

<400> SEQUENCE: 95

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 96
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 96

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 97
<211> LENGTH: 28
<212> TYPE: PRT
```

```
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with n-butyryl, or acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 97

Gly Xaa Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 98
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Ser or Thr
<220> FEATURE:
<221> NAME/KEY: MOD_RES
<222> LOCATION: (28)..(28)
<223> OTHER INFORMATION: AMIDATION

<400> SEQUENCE: 98

Gly Xaa Xaa Phe Leu Ser Pro Arg His Gln Arg Val Gln Gln Arg Lys
 1               5                  10                  15

Glu Ser Lys Lys Pro Pro Ala Lys Leu Gln Pro Arg
            20                  25

<210> SEQ ID NO 99
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = Ser, alpha-aminoisobutyric acid (Aib), or
      alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 99

Gly Xaa Thr Phe Leu Xaa Pro Glu His Gln Arg Val Gln Gln Arg Lys
```

```
                1               5                  10                 15
Glu Ser Lys Lys Pro Pro Ala Lys Leu Gln Pro Arg
            20                  25

<210> SEQ ID NO 100
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (5)..(5)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 100

Gly Ser Thr Phe Xaa Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 101
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(4-thiazolyl)Ala (Taz), or beta-(2-thienyl)Ala (2-Thi)
<220> FEATURE:
<221> NAME/KEY: MOD_RES
<222> LOCATION: (28)..(28)
<223> OTHER INFORMATION: AMIDATION

<400> SEQUENCE: 101

Gly Xaa Thr Phe Leu Ser Pro Glu Xaa Gln Arg Val Gln Gln Arg Lys
1               5                   10                  15
Glu Ser Lys Lys Pro Pro Ala Lys Leu Gln Pro Arg
            20                  25

<210> SEQ ID NO 102
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid (Thz),
      4-hydroxyPro (4-Hyp), 3,4-dehydroPro (Dhp), pipecolic acid (Pip),
      or 1,2,3,4-tetrahydroisoquinoline-3-carboxylic acid (Tic)
<220> FEATURE:
<221> NAME/KEY: MOD_RES
<222> LOCATION: (28)..(28)
<223> OTHER INFORMATION: AMIDATION
```

```
<400> SEQUENCE: 102

Gly Xaa Thr Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 103
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = beta-cyclohexylAla (Cha)
<220> FEATURE:
<221> NAME/KEY: MOD_RES
<222> LOCATION: (28)..(28)
<223> OTHER INFORMATION: AMIDATION

<400> SEQUENCE: 103

Gly Xaa Thr Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 104
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 104

Gly Xaa Thr Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 105
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with n-butyryl or acyl (Ac)
```

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 105

Gly Xaa Thr Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 106
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 106

Gly Xaa Thr Phe Leu Ser Pro Arg His Xaa Arg Val Gln Gln Arg Lys
 1               5                  10                  15

Glu Ser Lys Lys Pro Pro Ala Lys Leu Gln Pro Arg
            20                  25

<210> SEQ ID NO 107
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 107

Gly Ser Thr Phe Leu Ser Pro Xaa His Gln Arg Val Gln Gln Arg Lys
 1               5                  10                  15

Glu Ser Lys Lys Pro Pro Ala Lys Leu Gln Pro Arg
            20                  25

<210> SEQ ID NO 108
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (9)..(9)
<223> OTHER INFORMATION: Xaa = beta-(4-thiazolyl)Ala (Taz),
```

```
        beta-(3-pyridiyl)Ala (3-Pal), beta-(4-pyridiyl)Ala (4-Pal), or
        beta-(2-thienyl)Ala (2-Thi)
<220> FEATURE:
<221> NAME/KEY: MOD_RES
<222> LOCATION: (28)..(28)
<223> OTHER INFORMATION: AMIDATION

<400> SEQUENCE: 108

Gly Ser Thr Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 109
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (7)..(7)
<223> OTHER INFORMATION: Xaa = 4-hydroxyPro (4-Hyp)
<220> FEATURE:
<221> NAME/KEY: MOD_RES
<222> LOCATION: (28)..(28)
<223> OTHER INFORMATION: AMIDATION

<400> SEQUENCE: 109

Gly Ser Thr Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 110
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 110

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 111
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
```

```
<222> LOCATION: (2)..(2)
<223> OTHER INFORMATION: Xaa = D-beta-(2-naphthyl)-L-Ala (D-2-Nal),
      D-4,4'-biphenylAla (D-Bip), D-beta,beta-diphenylAla  (D-Dip),
      D-4-benzoylphenylAla (D-Bpa), or D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 111

Xaa Xaa Xaa Phe Lys
1               5

<210> SEQ ID NO 112
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal),
      beta-(2-thienyl)Ala (2-Thi), beta-(4-thiazolyl)Ala  (Taz),
      beta-(2-furyl)Ala (2-Fua), beta-(3-thienyl)Ala (3-Thi), or
      pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 112

Xaa Xaa Xaa Xaa Lys
1               5

<210> SEQ ID NO 113
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-pyridiyl)Ala (4-Pal), ornithine
      (Orn), Thr(Bzl), pentafluorophenylAla (Pff), beta-(2-thienyl)Ala
      (2-Thi), beta-(4-thiazolyl)Ala (Taz), or beta-(3-pyridiyl)Ala
      (3-Pal), or beta-(3-thienyl)Ala (3-Thi)
```

```
<220> FEATURE:
<221> NAME/KEY: MOD_RES
<222> LOCATION: (5)..(5)
<223> OTHER INFORMATION: AMIDATION

<400> SEQUENCE: 113

Xaa Xaa Xaa Xaa Lys
1               5

<210> SEQ ID NO 114
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-4-benzoylphenylAla (D-Bpa)
<220> FEATURE:
<221> NAME/KEY: MOD_RES
<222> LOCATION: (5)..(5)
<223> OTHER INFORMATION: AMIDATION

<400> SEQUENCE: 114

Xaa Xaa Xaa Phe Lys
1               5

<210> SEQ ID NO 115
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal),
      beta-(4-pyridiyl)Ala (4-Pal), Thr(Bzl), pentafluorophenylAla
      (Pff), beta-(2-thienyl)Ala (2-Thi), beta-(4-thiazolyl)Ala (Taz),
      beta-(2-furyl)Ala (2-Fua), or beta-(3-thienyl)Ala (3-Thi)
<220> FEATURE:
<221> NAME/KEY: MOD_RES
<222> LOCATION: (4)..(4)
<223> OTHER INFORMATION: AMIDATION

<400> SEQUENCE: 115

Xaa Xaa Xaa Xaa
1

<210> SEQ ID NO 116
<211> LENGTH: 4
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal),
      beta-(2-thienyl)Ala (2-Thi), beta-(2-furyl)Ala (2-Fua),
      pentafluorophenylAla (Pff), or beta-(4-thiazolyl)Ala  (Taz)
<220> FEATURE:
<221> NAME/KEY: MOD_RES
<222> LOCATION: (4)..(4)
<223> OTHER INFORMATION: AMIDATION

<400> SEQUENCE: 116

Xaa Xaa Xaa Xaa
1

<210> SEQ ID NO 117
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-4,4'-biphenylAla (D-Bip) or beta,
      beta-diphenylAla (D-Dip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 117

Xaa Xaa Xaa Phe
1

<210> SEQ ID NO 118
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-beta,beta-diphenylAla (D-Dip) or
      D-3-benzothienylAla (D-Bal)
```

```
<220> FEATURE:
<221> NAME/KEY: MOD_RES
<222> LOCATION: (4)..(4)
<223> OTHER INFORMATION: AMIDATION

<400> SEQUENCE: 118

Xaa Xaa Xaa Phe
1

<210> SEQ ID NO 119
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 119

Xaa Xaa Xaa Phe
1

<210> SEQ ID NO 120
<211> LENGTH: 3
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (3)..(3)
<223> OTHER INFORMATION: Xaa = D-beta-(2-naphthyl)-L-Ala (D-2-Nal)
      attached via a pseudo-peptide bond (psi) to
      2'-(4-phenyl)imidazolyl (Pim)

<400> SEQUENCE: 120

Xaa Xaa Xaa
1

<210> SEQ ID NO 121
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
```

```
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi),
      beta-(4-thiazolyl)Ala (Taz), beta-(2-furyl)Ala (2-Fua),
      beta-(3-thienyl)Ala (3-Thi), or pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 121

Xaa Xaa Xaa Xaa Lys
1               5

<210> SEQ ID NO 122
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal),
      D-beta-(1-naphthyl)-L-Ala (D-1-Nal), or D-3-benzothienylAla
      (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 122

Xaa Xaa Xaa Phe Xaa
1               5

<210> SEQ ID NO 123
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal),
      or D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION
```

```
<400> SEQUENCE: 123

Xaa Xaa Xaa Phe Lys
1               5

<210> SEQ ID NO 124
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi),
      beta-(4-thiazolyl)Ala (Taz), beta-(2-furyl)Ala (2-Fua),
      beta-(3-thienyl)Ala (3-Thi), or pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 124

Xaa Xaa Xaa Xaa Lys
1               5

<210> SEQ ID NO 125
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal), or
      D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 125

Xaa Xaa Xaa Phe
1

<210> SEQ ID NO 126
<211> LENGTH: 3
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
```

```
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal),
      D-beta-(1-naphthyl)-L-Ala (D-1-Nal), or D-3-benzothienylAla
      (D-Bal)
<220> FEATURE:
<221> NAME/KEY: MISC_FEATURE
<222> LOCATION: (3)..(3)
<223> OTHER INFORMATION: Xaa = D-Trp attached via a pseudo-peptide bond
      (psi) to 2'-(4-phenyl)imidazolyl (Pim)

<400> SEQUENCE: 126

Xaa Xaa Xaa
1

<210> SEQ ID NO 127
<211> LENGTH: 3
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MISC_FEATURE
<222> LOCATION: (2)..(2)
<223> OTHER INFORMATION: Xaa = D-Ser(Bzl)
<220> FEATURE:
<221> NAME/KEY: MISC_FEATURE
<222> LOCATION: (3)..(3)
<223> OTHER INFORMATION: Xaa = D-Trp attached via a pseudo-peptide bond
      (psi) to 2'-(4-phenyl)imidazolyl (Pim)

<400> SEQUENCE: 127

Xaa Xaa Xaa
1

<210> SEQ ID NO 128
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz),
      beta-(2-thienyl)Ala (2-Thi), beta-(2-furyl)Ala (2-Fua),
      beta-(3-thienyl)Ala (3-Thi), or pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 128

Xaa Xaa Xaa Xaa Lys
1               5
```

```
<210> SEQ ID NO 129
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp, D-beta-(1-naphthyl)-L-Ala
      (D-1-Nal), or D-beta-(2-naphthyl)-L-Ala (D-2-Nal)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 129

Xaa Xaa Xaa Phe Xaa
1               5

<210> SEQ ID NO 130
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = (D-Bal)
<220> FEATURE:
<221> NAME/KEY: MISC_FEATURE
<222> LOCATION: (3)..(3)
<223> OTHER INFORMATION: Xaa = D-Trp, D-beta-(1-naphthyl)-L-Ala
      (D-1-Nal), D-beta-(2-naphthyl)-L-Ala (D-2-Nal), or
      D-3-benzothienylAla (D-Bal)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 130

Xaa Xaa Xaa Phe Xaa
1               5

<210> SEQ ID NO 131
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
```

```
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal),
      or D-Trp
<220> FEATURE:
<221> NAME/KEY: MOD_RES
<222> LOCATION: (5)..(5)
<223> OTHER INFORMATION: AMIDATION

<400> SEQUENCE: 131

Xaa Xaa Xaa Phe Lys
1               5

<210> SEQ ID NO 132
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal),
      D-beta-(2-naphthyl)-L-Ala (D-2-Nal), or D-3-benzothienylAla
      (D-Bal)
<220> FEATURE:
<221> NAME/KEY: MOD_RES
<222> LOCATION: (5)..(5)
<223> OTHER INFORMATION: AMIDATION

<400> SEQUENCE: 132

Xaa Xaa Xaa Phe Lys
1               5

<210> SEQ ID NO 133
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi),
      beta-(4-thiazolyl)Ala (Taz), beta-(2-furyl)Ala (2-Fua),
      beta-(2-pyridiyl)Ala (2-Pal), beta-(3-pyridiyl)Ala (3-Pal),
      beta-(3-thienyl)Ala (3-Thi), beta-(4-pyridiyl)Ala (4-Pal),
      or pentafluorophenylAla (Pff)
<220> FEATURE:
<221> NAME/KEY: MOD_RES
<222> LOCATION: (4)..(4)
```

```
<223> OTHER INFORMATION: AMIDATION

<400> SEQUENCE: 133

Xaa Xaa Xaa Xaa
1

<210> SEQ ID NO 134
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi),
      beta-(4-thiazolyl)Ala (Taz), beta-(2-furyl)Ala (2-Fua),
      beta-(2-pyridiyl)Ala (2-Pal), beta-(3-pyridiyl)Ala (3-Pal),
      beta-(3-thienyl)Ala (3-Thi), beta-(4-pyridiyl)Ala (4-Pal),
      or pentafluorophenylAla (Pff)
<220> FEATURE:
<221> NAME/KEY: MOD_RES
<222> LOCATION: (4)..(4)
<223> OTHER INFORMATION: AMIDATION

<400> SEQUENCE: 134

Xaa Xaa Xaa Xaa
1

<210> SEQ ID NO 135
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal),
      D-3-benzothienylAla (D-Bal), or D-beta-(2-naphthyl)-L-Ala
      (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 135
```

```
Xaa Xaa Xaa Xaa Xaa
1               5

<210> SEQ ID NO 136
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal),
      D-3-benzothienylAla (D-Bal), or D-beta-(2-naphthyl)-L-Ala
      (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 136

Xaa Xaa Xaa Xaa Xaa
1               5

<210> SEQ ID NO 137
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(3-thienyl)Ala (3-Thi), pentafluorophenylAla (Pff), or
      beta-(2-thienyl)Ala (2-Thi)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 137

Xaa Xaa Xaa Xaa Xaa
1               5
```

```
<210> SEQ ID NO 138
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
    beta-(2-thienyl)Ala (2-Thi), beta-(3-thienyl)Ala (3-Thi),
    or pentafluorophenylAla (Pff)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 138

Xaa Xaa Xaa Xaa Xaa
1               5

<210> SEQ ID NO 139
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
    beta-(2-thienyl)Ala (2-Thi), beta-(3-thienyl)Ala (3-Thi),
    pentafluorophenylAla (Pff), or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 139

Xaa Xaa Xaa Xaa Lys
1               5

<210> SEQ ID NO 140
<211> LENGTH: 5
<212> TYPE: PRT
<213> ORGANISM: Artificial
```

-continued

```
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-3-benzothienylAla  (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi),
      pentafluorophenylAla (Pff), or beta-(4-thiazolyl)Ala (Taz)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 140

Xaa Xaa Xaa Xaa Xaa
1               5

<210> SEQ ID NO 141
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi),
      pentafluorophenylAla (Pff), or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 141

Xaa Xaa Xaa Xaa Lys
1               5

<210> SEQ ID NO 142
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
```

```
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-pyridiyl)Ala (2-Pal), beta-(2-thienyl)Ala (2-Thi),
      beta-(3-pyridiyl)Ala (3-Pal), beta-(3-thienyl)Ala (3-Thi),
      beta-(4-pyridiyl)Ala (4-Pal), pentafluorophenylAla (Pff),
      Phe, or beta-(4-thiazolyl)Ala (Taz)
<220> FEATURE:
<221> NAME/KEY: MOD_RES
<222> LOCATION: (4)..(4)
<223> OTHER INFORMATION: AMIDATION

<400> SEQUENCE: 142

Xaa Xaa Xaa Xaa
1

<210> SEQ ID NO 143
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(3-thienyl)Ala (3-Thi), pentafluorophenylAla (Pff),
      or beta-(2-thienyl)Ala (2-Thi)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 143

Xaa Xaa Xaa Xaa Xaa
1               5

<210> SEQ ID NO 144
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla  (D-Bal)
```

```
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-pyridiyl)Ala (2-Pal), beta-(3-pyridiyl)Ala (3-Pal),
      beta-(3-thienyl)Ala (3-Thi), beta-(4-pyridiyl)Ala (4-Pal),
      or pentafluorophenylAla (Pff)
<220> FEATURE:
<221> NAME/KEY: MOD_RES
<222> LOCATION: (4)..(4)
<223> OTHER INFORMATION: AMIDATION

<400> SEQUENCE: 144

Xaa Xaa Xaa Xaa
1

<210> SEQ ID NO 145
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-3-benzothienylAla  (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi),
      pentafluorophenylAla (Pff), Phe, or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 145

Xaa Xaa Xaa Xaa Lys
1               5

<210> SEQ ID NO 146
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-3-benzothienylAla  (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      pentafluorophenylAla (Pff), or beta-(4-thiazolyl)Ala  (Taz)
```

```
<220> FEATURE:
<221> NAME/KEY: MOD_RES
<222> LOCATION: (4)..(4)
<223> OTHER INFORMATION: AMIDATION

<400> SEQUENCE: 146

Xaa Xaa Xaa Xaa
1

<210> SEQ ID NO 147
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(3-thienyl)Ala (3-Thi), pentafluorophenylAla (Pff), or
      beta-(2-thienyl)Ala (2-Thi)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 147

Xaa Xaa Xaa Xaa Xaa
1               5

<210> SEQ ID NO 148
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi), or
      pentafluorophenylAla (Pff)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
```

```
<222> LOCATION: (5)..(5)
<223> OTHER INFORMATION: AMIDATION

<400> SEQUENCE: 148

Xaa Xaa Xaa Xaa Xaa
1               5

<210> SEQ ID NO 149
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi),
      pentafluorophenylAla (Pff), Phe, or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 149

Xaa Xaa Xaa Xaa Lys
1               5

<210> SEQ ID NO 150
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      pentafluorophenylAla (Pff), or beta-(4-thiazolyl)Ala (Taz)
<220> FEATURE:
<221> NAME/KEY: MOD_RES
<222> LOCATION: (4)..(4)
<223> OTHER INFORMATION: AMIDATION

<400> SEQUENCE: 150

Xaa Xaa Xaa Xaa
1

<210> SEQ ID NO 151
<211> LENGTH: 5
```

```
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(3-thienyl)Ala (3-Thi), pentafluorophenylAla (Pff), or
      beta-(2-thienyl)Ala (2-Thi)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 151

Xaa Xaa Xaa Xaa Xaa
1               5

<210> SEQ ID NO 152
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      pentafluorophenylAla (Pff), or beta-(4-thiazolyl)Ala (Taz)
<220> FEATURE:
<221> NAME/KEY: MOD_RES
<222> LOCATION: (4)..(4)
<223> OTHER INFORMATION: AMIDATION

<400> SEQUENCE: 152

Xaa Xaa Xaa Xaa
1

<210> SEQ ID NO 153
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
```

```
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-4,4'-biphenylAla  (D-Bip)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi),
      pentafluorophenylAla (Pff), or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 153

Xaa Xaa Xaa Xaa Lys
1               5

<210> SEQ ID NO 154
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-4,4'-biphenylAla  (D-Bip)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      pentafluorophenylAla (Pff), or beta-(4-thiazolyl)Ala (Taz)
<220> FEATURE:
<221> NAME/KEY: MOD_RES
<222> LOCATION: (4)..(4)
<223> OTHER INFORMATION: AMIDATION

<400> SEQUENCE: 154

Xaa Xaa Xaa Xaa
1

<210> SEQ ID NO 155
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-4,4'-biphenylAla  (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
```

```
<222> LOCATION: (4)..(4)
<223> OTHER INFORMATION: Xaa = beta-(2-furyl)Ala (2-Fua),
      beta-(2-thienyl)Ala (2-Thi), beta-(3-thienyl)Ala (3-Thi),
      pentafluorophenylAla (Pff), or beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 155

Xaa Xaa Xaa Xaa Lys
1               5

<210> SEQ ID NO 156
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-4,4'-biphenylAla  (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-furyl)Ala (2-Fua),
      pentafluorophenylAla (Pff), or beta-(4-thiazolyl)Ala (Taz)
<220> FEATURE:
<221> NAME/KEY: MOD_RES
<222> LOCATION: (4)..(4)
<223> OTHER INFORMATION: AMIDATION

<400> SEQUENCE: 156

Xaa Xaa Xaa Xaa
1

<210> SEQ ID NO 157
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = Phe, beta-(2-thienyl)Ala (2-Thi),
      beta-(4-thiazolyl)Ala (Taz), beta-(3-thienyl)Ala (3-Thi),
      beta-(2-furyl)Ala (2-Fua), pentafluorophenylAla (Pff),
      beta-(4-pyridiyl)Ala (4-Pal), beta-(3-pyridiyl)Ala (3-Pal), or
      beta-(2-pyridiyl)Ala (2-Pal)
<220> FEATURE:
<221> NAME/KEY: MOD_RES
<222> LOCATION: (4)..(4)
<223> OTHER INFORMATION: AMIDATION
```

<400> SEQUENCE: 157

Xaa Xaa Xaa Xaa
1

<210> SEQ ID NO 158
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = Phe, beta-(2-thienyl)Ala (2-Thi),
      beta-(3-thienyl)Ala (3-Thi), beta-(4-thiazolyl)Ala (Taz),
      beta-(2-furyl)Ala (2-Fua), or pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 158

Xaa Xaa Xaa Xaa Lys
1               5

<210> SEQ ID NO 159
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi),
      beta-(3-thienyl)Ala (3-Thi), beta-(2-furyl)Ala (2-Fua), or
      pentafluorophenylAla (Pff)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 159

Xaa Xaa Xaa Xaa Xaa
1               5

```
<210> SEQ ID NO 160
<211> LENGTH: 5
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-thienyl)Ala (3-Thi),
      beta-(2-furyl)Ala (2-Fua), or pentafluorophenylAla (Pff)
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 160

Xaa Xaa Xaa Xaa Xaa
1               5

<210> SEQ ID NO 161
<211> LENGTH: 4
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MISC_FEATURE
<222> LOCATION: (4)..(4)
<223> OTHER INFORMATION: Xaa = beta-(4-thiazolyl)Ala (Taz),
      beta-(2-furyl)Ala (2-Fua), or pentafluorophenylAla (Pff)
<220> FEATURE:
<221> NAME/KEY: MOD_RES
<222> LOCATION: (4)..(4)
<223> OTHER INFORMATION: AMIDATION

<400> SEQUENCE: 161

Xaa Xaa Xaa Xaa
1

<210> SEQ ID NO 162
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
```

```
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 162

Gly Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 163
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 163

Gly Ser Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 164
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 164

Gly Ser Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 165
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
```

```
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 165

Gly Ser Glu Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 166
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 166

Gly Xaa Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 167
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 167

Gly Xaa Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 168
<211> LENGTH: 28
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 168

Gly Xaa Ser Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 169
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 169

Gly Xaa Glu Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 170
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
```

```
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 170

Gly Xaa Ser Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 171
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 171

Gly Xaa Glu Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 172
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 172

Gly Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 173
<211> LENGTH: 28
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 173

Gly Ser Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 174
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 174

Gly Ser Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 175
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 175

Gly Ser Glu Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 176
<211> LENGTH: 28
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 176

Gly Xaa Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 177
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 177

Gly Xaa Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 178
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 178
```

Gly Xaa Ser Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 179
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 179

Gly Xaa Glu Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 180
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 180

Gly Xaa Ser Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 181
<211> LENGTH: 28
<212> TYPE: PRT
<213> ORGANISM: Artificial

```
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 181

Gly Xaa Glu Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 182
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 182

Gly Ser Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 183
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 183

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 184
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl or 1-heptanol
<220> FEATURE:
<221> NAME/KEY: MOD_RES
<222> LOCATION: (17)..(17)
<223> OTHER INFORMATION: modified with NH-hexyl or 1-heptanol
<220> FEATURE:
<221> NAME/KEY: MOD_RES
<222> LOCATION: (28)..(28)
<223> OTHER INFORMATION: AMIDATION

<400> SEQUENCE: 184

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 185
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 185

Gly Ser Glu Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 186
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 186

Gly Ser Ser Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25
```

<210> SEQ ID NO 187
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 187

Gly Ser Xaa Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 188
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 188

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 189
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

```
<400> SEQUENCE: 189

Gly Ser Xaa Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 190
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 190

Gly Ser Glu Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 191
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (17)..(17)
<223> OTHER INFORMATION: modified with (S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 191

Gly Ser Ser Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 192
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with (S-(CH2)9CH3
<220> FEATURE:
<221> NAME/KEY: MOD_RES
<222> LOCATION: (17)..(17)
<223> OTHER INFORMATION: modified with (S-(CH2)9CH3
<220> FEATURE:
<221> NAME/KEY: MOD_RES
<222> LOCATION: (28)..(28)
<223> OTHER INFORMATION: AMIDATION
```

-continued

```
<400> SEQUENCE: 192

Gly Ser Cys Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 193
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 193

Gly Ser Glu Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 194
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 194

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 195
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with n-octanoyl
```

```
<220> FEATURE:
<221> NAME/KEY: MOD_RES
<222> LOCATION: (28)..(28)
<223> OTHER INFORMATION: AMIDATION

<400> SEQUENCE: 195

Gly Ser Cys Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 196
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib), or
      1-amino-1-cyclopentanecarboxylic acid (A5c)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 196

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 197
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib), or
      1-amino-1-cyclopentanecarboxylic acid (A5c)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 197

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 198
<211> LENGTH: 28
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid (Thz),
      4-hydroxyPro (4-Hyp), 3,4-dehydroPro (Dhp), pipecolic acid (Pip),
      or 1,2,3,4-tetrahydroisoquinoline-3-carboxylic acid (Tic)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 198

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 199
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = thiazolidine-4-carboxylic acid (Thz)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 199

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 200
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MISC_FEATURE
<222> LOCATION: (7)..(7)
<223> OTHER INFORMATION: Xaa = 4-hydroxyPro (4-Hyp), 3,4-dehydroPro
      (Dhp), pipecolic acid (Pip), or 1,2,3,4-tetrahydroisoquinoline-3-
      carboxylic acid (Tic)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 200

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 201
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 201

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 202
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 202

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 203
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(4-pyridiyl)Ala (4-Pal), beta-(4-thiazolyl)Ala (Taz), or
      beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 203

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 204
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(4-pyridiyl)Ala (4-Pal), beta-(4-thiazolyl)Ala (Taz), or
      beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 204

Gly Xaa Glu Phe Leu Ser Pro Glu Xaa Gln Arg Val Gln Gln Arg Lys
1               5                   10                  15
```

Glu Ser Lys Lys Pro Pro Ala Lys Leu Gln Pro Arg
            20                  25

<210> SEQ ID NO 205
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 205

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 206
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 206

Gly Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 207
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE

```
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 207

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 208
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (9)..(9)
<223> OTHER INFORMATION: Xaa = beta-(4-thiazolyl)Ala (Taz),
      beta-(3-pyridiyl)Ala (3-Pal), beta-(4-pyridiyl)Ala (4-Pal), or
      beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 208

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 209
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 209

Gly Ser Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 210
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)Ala  (Taz),
      beta-(3-pyridiyl)Ala (3-Pal), beta-(4-pyridiyl)Ala (4-Pal), or
      beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 210

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 211
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 211

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 212
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(2)
<223> OTHER INFORMATION: Xaa = alpha-aminoisobutyric acid (Aib)
<220> FEATURE:
<221> NAME/KEY: MOD_RES
```

```
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 212

Xaa Xaa Glu Phe Leu Ser Pro Glu His Xaa Arg Val Gln Gln Arg Lys
1               5                   10                  15
Glu Ser Lys Lys Pro Pro Ala Lys Leu Gln Pro Arg
            20                  25

<210> SEQ ID NO 213
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with 1-heptanol or NH-hexyl
<220> FEATURE:
<221> NAME/KEY: MOD_RES
<222> LOCATION: (17)..(17)
<223> OTHER INFORMATION: modified with 1-heptanol or NH-hexyl
<220> FEATURE:
<221> NAME/KEY: MOD_RES
<222> LOCATION: (28)..(28)
<223> OTHER INFORMATION: AMIDATION

<400> SEQUENCE: 213

Gly Ser Asp Phe Leu Ser Pro Glu His Gln Arg Val Gln Gln Arg Lys
1               5                   10                  15
Asp Ser Lys Lys Pro Pro Ala Lys Leu Gln Pro Arg
            20                  25

<210> SEQ ID NO 214
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (17)..(17)
<223> OTHER INFORMATION: modified with biotinyl
<220> FEATURE:
<221> NAME/KEY: MOD_RES
<222> LOCATION: (28)..(28)
<223> OTHER INFORMATION: AMIDATION

<400> SEQUENCE: 214

Gly Ser Ser Phe Leu Ser Pro Glu His Gln Arg Val Gln Gln Arg Lys
1               5                   10                  15
Lys Ser Lys Lys Pro Pro Ala Lys Leu Gln Pro Arg
            20                  25

<210> SEQ ID NO 215
<211> LENGTH: 28
<212> TYPE: PRT
<213> ORGANISM: Artificial
```

```
<220> FEATURE:
<223> OTHER INFORMATION: Peptidyl ghrelin analog
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 215

Gly Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 216
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 216

Gly Ser Ser Phe Leu Ser Pro Glu His Gln Arg Val Gln Gln Arg Lys
1               5                   10                  15
Glu Glu Lys Lys Pro Pro Ala Lys Leu Gln Pro Arg
            20                  25

<210> SEQ ID NO 217
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 217

Gly Ser Glu Phe Leu Ser Pro Glu His Gln Arg Val Gln Gln Arg Lys
1               5                   10                  15
Glu Glu Lys Lys Pro Pro Ala Lys Leu Gln Pro Arg
            20                  25

<210> SEQ ID NO 218
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
```

```
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 218

Gly Ser Glu Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 219
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 219

Gly Xaa Ser Phe Leu Ser Pro Glu His Gln Arg Val Gln Gln Arg Lys
 1               5                  10                  15

Glu Glu Lys Lys Pro Pro Ala Lys Leu Gln Pro Arg
            20                  25

<210> SEQ ID NO 220
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 220

Gly Xaa Glu Phe Leu Ser Pro Glu His Gln Arg Val Gln Gln Arg Lys
 1               5                  10                  15

Glu Glu Lys Lys Pro Pro Ala Lys Leu Gln Pro Arg
            20                  25
```

```
<210> SEQ ID NO 221
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 221

Gly Xaa Ser Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 222
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 222

Gly Xaa Glu Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 223
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
```

```
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 223

Gly Xaa Ser Phe Leu Ser Pro Glu His Xaa Arg Val Gln Gln Arg Lys
 1               5                  10                  15

Glu Glu Lys Lys Pro Pro Ala Lys Leu Gln Pro Arg
            20                  25

<210> SEQ ID NO 224
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 224

Gly Xaa Glu Phe Leu Ser Pro Glu His Xaa Arg Val Gln Gln Arg Lys
 1               5                  10                  15

Glu Glu Lys Lys Pro Pro Ala Lys Leu Gln Pro Arg
            20                  25

<210> SEQ ID NO 225
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 225

Gly Ser Ser Phe Leu Ser Pro Glu His Gln Arg Val Gln Gln Arg Lys
 1               5                  10                  15

Glu Ser Ser Lys Pro Pro Ala Lys Leu Gln Pro Arg
            20                  25
```

```
<210> SEQ ID NO 226
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 226

Gly Ser Ser Phe Leu Ser Pro Glu His Gln Arg Val Gln Gln Arg Lys
1               5                   10                  15
Glu Ser Glu Lys Pro Pro Ala Lys Leu Gln Pro Arg
            20                  25

<210> SEQ ID NO 227
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 227

Gly Ser Glu Phe Leu Ser Pro Glu His Gln Arg Val Gln Gln Arg Lys
1               5                   10                  15
Glu Ser Glu Lys Pro Pro Ala Lys Leu Gln Pro Arg
            20                  25

<210> SEQ ID NO 228
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 228

Gly Ser Glu Phe Leu Ser Pro Glu His Gln Arg Val Gln Gln Arg Lys
1               5                   10                  15
Glu Ser Ser Lys Pro Pro Ala Lys Leu Gln Pro Arg
            20                  25
```

```
<210> SEQ ID NO 229
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 229

Gly Xaa Ser Phe Leu Ser Pro Glu His Gln Arg Val Gln Gln Arg Lys
1               5                   10                  15
Glu Ser Glu Lys Pro Pro Ala Lys Leu Gln Pro Arg
            20                  25

<210> SEQ ID NO 230
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 230

Gly Xaa Glu Phe Leu Ser Pro Glu His Gln Arg Val Gln Gln Arg Lys
1               5                   10                  15
Glu Ser Glu Lys Pro Pro Ala Lys Leu Gln Pro Arg
            20                  25

<210> SEQ ID NO 231
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 231

Gly Xaa Ser Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 232
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 232

Gly Xaa Glu Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 233
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 233

Gly Xaa Ser Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25
```

```
<210> SEQ ID NO 234
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 234

Gly Xaa Glu Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25

<210> SEQ ID NO 235
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 235

Gly Ser Ser Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 236
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 236

Gly Ser Ser Phe Leu Ser Pro Glu His Gln Arg Val Gln Gln Arg Lys
1               5                   10                  15
```

Glu Ser Lys Glu Pro Pro Ala Lys Leu Gln Pro Arg
            20                  25

<210> SEQ ID NO 237
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 237

Gly Ser Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 238
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 238

Gly Ser Glu Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 239
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 239

Gly Xaa Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 240
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 240

Gly Xaa Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 241
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 241

Gly Xaa Ser Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25

<210> SEQ ID NO 242
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE

```
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 242

Gly Xaa Glu Phe Leu Ser Pro Xaa His Gln Arg Val Gln Gln Arg Lys
 1               5                  10                  15

Glu Ser Lys Glu Pro Pro Ala Lys Leu Gln Pro Arg
             20                  25

<210> SEQ ID NO 243
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 243

Gly Xaa Ser Phe Leu Ser Pro Glu His Xaa Arg Val Gln Gln Arg Lys
 1               5                  10                  15

Glu Ser Lys Glu Pro Pro Ala Lys Leu Gln Pro Arg
             20                  25

<210> SEQ ID NO 244
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
```

```
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 244

Gly Xaa Glu Phe Leu Ser Pro Glu His Xaa Arg Val Gln Gln Arg Lys
1               5                   10                  15

Glu Ser Lys Glu Pro Pro Ala Lys Leu Gln Pro Arg
            20                  25

<210> SEQ ID NO 245
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 245

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 246
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 246

Gly Ser Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 247
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
```

```
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 247

Gly Ser Glu Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 248
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 248

Gly Ser Glu Phe Leu Ser Pro Glu His Gln Arg Val Gln Gln Arg Lys
1               5                   10                  15
Ser Ser Lys Lys Pro Pro Ala Lys Leu Gln Pro Arg
            20                  25

<210> SEQ ID NO 249
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 249

Gly Ser Ser Phe Leu Ser Pro Glu His Gln Arg Val Gln Gln Arg Lys
1               5                   10                  15
```

Xaa Ser Lys Lys Pro Pro Ala Lys Leu Gln Pro Arg
            20                  25

<210> SEQ ID NO 250
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 250

Gly Ser Xaa Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 251
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 251

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 252
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES

```
<222> LOCATION: (1)..(1)
<223> OTHER INFORMATION: modified with acyl (Ac)
<220> FEATURE:
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 252

Gly Ser Xaa Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 253
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (17)..(17)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 253

Gly Ser Glu Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 254
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 254

Gly Ser Ser Phe Leu Ser Pro Glu His Gln Arg Val Gln Gln Arg Lys
```

```
Cys Ser Lys Lys Pro Pro Ala Lys Leu Gln Pro Arg
            20                  25

<210> SEQ ID NO 255
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 255

Gly Ser Cys Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 256
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 256

Gly Ser Glu Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 257
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
```

```
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 257

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 258
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 258

Gly Ser Cys Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 259
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib), or
      1-amino-1-cyclopentanecarboxylic acid (A5c)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 259
```

```
Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

<210> SEQ ID NO 260
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid (Thz),
      4-hydroxyPro (4-Hyp), 3,4-dehydroPro (Dhp), pipecolic acid (Pip),
      or 1,2,3,4-tetrahydroisoquinoline-3-carboxylic acid (Tic)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 260

```
Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25
```

<210> SEQ ID NO 261
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = thiazolidine-4-carboxylic acid (Thz),
      4-hydroxyPro (4-Hyp), 3,4-dehydroPro (Dhp), pipecolic acid (Pip),
      or 1,2,3,4-tetrahydroisoquinoline-3-carboxylic acid (Tic)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 261

```
Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 262
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 262

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 263
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
     beta-(4-pyridiyl)Ala (4-Pal), beta-(4-thiazolyl)Ala (Taz), or
     beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 263

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25
```

-continued

```
<210> SEQ ID NO 264
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridiyl)Ala (3-Pal),
      beta-(4-pyridiyl)Ala (4-Pal), beta-(4-thiazolyl)Ala (Taz), or
      beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 264

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 265
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 265

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 266
```

```
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 266

Gly Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 267
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 267

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 268
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
```

```
<223> OTHER INFORMATION: modified with acyl (Ac)
<220> FEATURE:
<221> NAME/KEY: MISC_FEATURE
<222> LOCATION: (9)..(9)
<223> OTHER INFORMATION: Xaa = beta-(4-thiazolyl)Ala  (Taz),
      beta-(3-pyridiyl)Ala (3-Pal), beta-(4-pyridiyl)Ala (4-Pal), or
      beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 268

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 269
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 269

Gly Ser Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 270
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)Ala  (Taz),
      beta-(3-pyridiyl)Ala (3-Pal), beta-(4-pyridiyl)Ala (4-Pal), or
```

```
                beta-(2-thienyl)Ala (2-Thi)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 270

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 271
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = alpha-aminoisobutyric acid (Aib) modified
      with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 271

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 272
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = alpha-aminoisobutyric acid (Aib) modified
      with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
```

```
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 272

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 273
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 273

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 274
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with 1-heptanol or NH-hexyl
<220> FEATURE:
<221> NAME/KEY: MOD_RES
<222> LOCATION: (17)..(17)
<223> OTHER INFORMATION: modified with 1-heptanol or NH-hexyl
<220> FEATURE:
<221> NAME/KEY: MOD_RES
<222> LOCATION: (28)..(28)
<223> OTHER INFORMATION: AMIDATION

<400> SEQUENCE: 274

Gly Ser Asp Phe Leu Ser Pro Glu His Gln Arg Val Gln Gln Arg Lys
```

-continued

```
1               5                   10                  15
Asp Ser Lys Lys Pro Pro Ala Lys Leu Gln Pro Arg
            20                  25

<210> SEQ ID NO 275
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with biotinyl
<220> FEATURE:
<221> NAME/KEY: MOD_RES
<222> LOCATION: (28)..(28)
<223> OTHER INFORMATION: AMIDATION

<400> SEQUENCE: 275

Gly Xaa Glu Phe Leu Ser Pro Glu His Xaa Arg Val Gln Gln Arg Lys
1               5                   10                  15

Lys Ser Lys Lys Pro Pro Ala Lys Leu Gln Pro Arg
            20                  25

<210> SEQ ID NO 276
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 276

Gly Ser Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 277
<211> LENGTH: 28
<212> TYPE: PRT
<213> ORGANISM: Artificial
<220> FEATURE:
<223> OTHER INFORMATION: Peptidyl ghrelin analog
```

```
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 277

Gly Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 278
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 278

Gly Ser Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 279
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 279

Gly Ser Glu Phe Leu Ser Pro Glu His Gln Arg Val Gln Gln Ser Lys
```

```
1               5                  10                  15
Glu Ser Lys Lys Pro Pro Ala Lys Leu Gln Pro Arg
            20                  25
```

<210> SEQ ID NO 280
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 280

```
Gly Xaa Ser Phe Leu Ser Pro Glu His Gln Arg Val Gln Gln Glu Lys
1               5                  10                  15
Glu Ser Lys Lys Pro Pro Ala Lys Leu Gln Pro Arg
            20                  25
```

<210> SEQ ID NO 281
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 281

```
Gly Xaa Glu Phe Leu Ser Pro Glu His Gln Arg Val Gln Gln Glu Lys
1               5                  10                  15
Glu Ser Lys Lys Pro Pro Ala Lys Leu Gln Pro Arg
            20                  25
```

<210> SEQ ID NO 282
<211> LENGTH: 28
<212> TYPE: PRT
<213> ORGANISM: Artificial
<220> FEATURE:
<223> OTHER INFORMATION: Peptidyl ghrelin analog

```
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 282

Gly Xaa Ser Phe Leu Ser Pro Xaa His Gln Arg Val Gln Gln Glu Lys
 1               5                  10                  15

Glu Ser Lys Lys Pro Pro Ala Lys Leu Gln Pro Arg
            20                  25

<210> SEQ ID NO 283
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 283

Gly Xaa Glu Phe Leu Ser Pro Xaa His Gln Arg Val Gln Gln Glu Lys
 1               5                  10                  15

Glu Ser Lys Lys Pro Pro Ala Lys Leu Gln Pro Arg
            20                  25

<210> SEQ ID NO 284
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
```

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 284

Gly Xaa Ser Phe Leu Ser Pro Glu His Xaa Arg Val Gln Gln Glu Lys
1               5                  10                  15

Glu Ser Lys Lys Pro Pro Ala Lys Leu Gln Pro Arg
            20                  25

<210> SEQ ID NO 285
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 285

Gly Xaa Glu Phe Leu Ser Pro Glu His Xaa Arg Val Gln Gln Glu Lys
1               5                  10                  15

Glu Ser Lys Lys Pro Pro Ala Lys Leu Gln Pro Arg
            20                  25

<210> SEQ ID NO 286
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (16)..(16)
<223> OTHER INFORMATION: modified with NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 286

Gly Ser Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 287
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 287

Gly Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 288
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 288

Gly Ser Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 289
<211> LENGTH: 28
<212> TYPE: PRT
<213> ORGANISM: Artificial
<220> FEATURE:
<223> OTHER INFORMATION: Peptidyl ghrelin analog
```

```
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 289

Gly Ser Glu Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 290
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 290

Gly Xaa Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 291
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 291

Gly Xaa Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 292
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 292

Gly Xaa Ser Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 293
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

```
<400> SEQUENCE: 293

Gly Xaa Glu Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25

<210> SEQ ID NO 294
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 294

Gly Xaa Ser Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 295
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 295

Gly Xaa Glu Phe Leu Ser Pro Glu His Xaa Arg Val Gln Gln Arg Glu
```

Glu Ser Lys Lys Pro Pro Ala Lys Leu Gln Pro Arg
            20                  25

<210> SEQ ID NO 296
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 296

Gly Ser Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 297
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 297

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 298
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl

```
<220> FEATURE:
<221> NAME/KEY: MOD_RES
<222> LOCATION: (28)..(28)
<223> OTHER INFORMATION: AMIDATION

<400> SEQUENCE: 298

Gly Ser Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 299
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 299

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 300
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 300

Gly Xaa Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 301
<211> LENGTH: 28
```

```
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 301

Gly Xaa Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 302
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 302

Gly Xaa Ser Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 303
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
```

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 303

Gly Xaa Glu Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 304
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 304

Gly Xaa Ser Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 305
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
```

```
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 305

Gly Xaa Glu Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 306
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 306

Gly Ser Ser Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 307
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 307

Gly Ser Ser Phe Leu Ser Pro Glu His Gln Arg Val Gln Gln Arg Lys
1               5                   10                  15

Glu Ser Ser Lys Pro Pro Ala Lys Leu Gln Pro Arg
            20                  25
```

<210> SEQ ID NO 308
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 308

Gly Ser Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 309
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 309

Gly Ser Glu Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 310
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)

-continued

```
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 310

Gly Xaa Ser Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 311
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 311

Gly Xaa Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 312
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

```
<400> SEQUENCE: 312

Gly Xaa Ser Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 313
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 313

Gly Xaa Glu Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 314
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 314

Gly Xaa Ser Phe Leu Ser Pro Glu His Xaa Arg Val Gln Gln Arg Lys
```

```
                1               5                  10                  15
Glu Ser Glu Lys Pro Pro Ala Lys Leu Gln Pro Arg
                20                  25

<210> SEQ ID NO 315
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 315

Gly Xaa Glu Phe Leu Ser Pro Glu His Xaa Arg Val Gln Gln Arg Lys
1               5                  10                  15

Glu Ser Glu Lys Pro Pro Ala Lys Leu Gln Pro Arg
                20                  25

<210> SEQ ID NO 316
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 316

Gly Ser Ser Phe Leu Ser Pro Glu His Gln Arg Val Gln Gln Arg Lys
1               5                  10                  15

Glu Ser Lys Glu Pro Pro Ala Lys Leu Gln Pro Arg
                20                  25

<210> SEQ ID NO 317
<211> LENGTH: 28
<212> TYPE: PRT
<213> ORGANISM: Artificial
<220> FEATURE:
<223> OTHER INFORMATION: Peptidyl ghrelin analog
```

```
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 317

Gly Ser Ser Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 318
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 318

Gly Ser Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 319
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 319

Gly Ser Glu Phe Leu Ser Pro Glu His Gln Arg Val Gln Gln Arg Lys
```

Glu Ser Lys Ser Pro Pro Ala Lys Leu Gln Pro Arg
            20                  25

<210> SEQ ID NO 320
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 320

Gly Xaa Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 321
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 321

Gly Xaa Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 322
<211> LENGTH: 28
<212> TYPE: PRT
<213> ORGANISM: Artificial
<220> FEATURE:
<223> OTHER INFORMATION: Peptidyl ghrelin analog

```
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 322

Gly Xaa Ser Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25

<210> SEQ ID NO 323
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 323

Gly Xaa Glu Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25

<210> SEQ ID NO 324
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
```

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 324

Gly Xaa Ser Phe Leu Ser Pro Glu His Xaa Arg Val Gln Gln Arg Lys
 1               5                  10                  15

Glu Ser Lys Glu Pro Pro Ala Lys Leu Gln Pro Arg
            20                  25

<210> SEQ ID NO 325
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 325

Gly Xaa Glu Phe Leu Ser Pro Glu His Xaa Arg Val Gln Gln Arg Lys
 1               5                  10                  15

Glu Ser Lys Glu Pro Pro Ala Lys Leu Gln Pro Arg
            20                  25

<210> SEQ ID NO 326
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (3)..(3)
<223> OTHER INFORMATION: modified with NH-heptyl or o-hexyl
<220> FEATURE:
<221> NAME/KEY: MOD_RES
<222> LOCATION: (28)..(28)
<223> OTHER INFORMATION: AMIDATION
```

<400> SEQUENCE: 326

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 327
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (2)..(2)
<223> OTHER INFORMATION: modified with (des)
<220> FEATURE:
<221> NAME/KEY: MOD_RES
<222> LOCATION: (28)..(28)
<223> OTHER INFORMATION: AMIDATION

<400> SEQUENCE: 327

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 328
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(2)
<223> OTHER INFORMATION: modified with (des)
<220> FEATURE:
<221> NAME/KEY: MOD_RES
<222> LOCATION: (28)..(28)
<223> OTHER INFORMATION: AMIDATION

<400> SEQUENCE: 328

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 329
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 329

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

```
<210> SEQ ID NO 330
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (3)..(3)
<223> OTHER INFORMATION: Xaa = Ser or Thr
<220> FEATURE:
<221> NAME/KEY: MISC_FEATURE
<222> LOCATION: (4)..(4)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(4-pyridiyl)Ala (4-Pal)
<220> FEATURE:
<221> NAME/KEY: MOD_RES
<222> LOCATION: (28)..(28)
<223> OTHER INFORMATION: AMIDATION

<400> SEQUENCE: 330

Gly Xaa Xaa Xaa Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 331
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 331

Xaa Ser Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 332
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with n-octanoyl, isobutyryl, or
      n-butyryl
<220> FEATURE:
<221> NAME/KEY: MOD_RES
<222> LOCATION: (28)..(28)
<223> OTHER INFORMATION: AMIDATION

<400> SEQUENCE: 332
```

-continued

```
Gly Ser Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

<210> SEQ ID NO 333
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with myristyl
<220> FEATURE:
<221> NAME/KEY: MOD_RES
<222> LOCATION: (28)..(28)
<223> OTHER INFORMATION: AMIDATION

<400> SEQUENCE: 333

```
Gly Xaa Ser Phe Leu Ser Pro Glu His Gln Arg Val Gln Gln Arg Lys
1               5                   10                  15

Lys Ser Lys Lys Pro Pro Ala Lys Leu Gln Pro Arg
            20                  25
```

<210> SEQ ID NO 334
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with myristyl
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with myristyl
<220> FEATURE:
<221> NAME/KEY: MOD_RES
<222> LOCATION: (28)..(28)
<223> OTHER INFORMATION: AMIDATION

<400> SEQUENCE: 334

```
Gly Xaa Ser Phe Leu Ser Pro Glu His Gln Arg Val Gln Gln Arg Lys
1               5                   10                  15

Lys Ser Lys Lys Pro Pro Ala Lys Leu Gln Pro Arg
            20                  25
```

<210> SEQ ID NO 335
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MOD_RES
<222> LOCATION: (1)..(1)
<223> OTHER INFORMATION: modified with acyl (Ac) or n-butyryl
<220> FEATURE:
<221> NAME/KEY: MISC_FEATURE
<222> LOCATION: (2)..(2)

```
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 335

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 336
<211> LENGTH: 27
<212> TYPE: DNA
<213> ORGANISM: Artificial sequence
<220> FEATURE:
<223> OTHER INFORMATION: Primer

<400> SEQUENCE: 336
atgtggaacg cgacgcccag cgaagag                                      27

<210> SEQ ID NO 337
<211> LENGTH: 27
<212> TYPE: DNA
<213> ORGANISM: Artificial sequence
<220> FEATURE:
<223> OTHER INFORMATION: Primer

<400> SEQUENCE: 337
tcatgtatta atactagatt ctgtcca                                      27

<210> SEQ ID NO 338
<211> LENGTH: 28
<212> TYPE: PRT
<213> ORGANISM: Homo sapiens

<400> SEQUENCE: 338

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 339
<211> LENGTH: 7
<212> TYPE: PRT
<213> ORGANISM: Artificial sequence
<220> FEATURE:
<223> OTHER INFORMATION: Synthetic growth hormone secretagogue - GHRP-I
<220> FEATURE:
<221> NAME/KEY: MISC_FEATURE
<222> LOCATION: (3)..(3)
<223> OTHER INFORMATION: Xaa = D-beta-(2'-naphthyl)-L-Ala (D-2'-Nal)
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 339

Ala His Xaa Ala Trp Xaa Lys
1               5
```

```
<210> SEQ ID NO 340
<211> LENGTH: 6
<212> TYPE: PRT
<213> ORGANISM: Artificial sequence
<220> FEATURE:
<223> OTHER INFORMATION: Synthetic growth hormone secretagogue - GHRP-2
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MISC_FEATURE
<222> LOCATION: (2)..(2)
<223> OTHER INFORMATION: Xaa = D-beta-(2'-naphthyl)-L-Ala (D-2'-Nal)
<220> FEATURE:
<221> NAME/KEY: MISC_FEATURE
<222> LOCATION: (5)..(5)
<223> OTHER INFORMATION: Xaa = D-naphthyl-L-Ala (D-Nal)
<220> FEATURE:
<221> NAME/KEY: MOD_RES
<222> LOCATION: (6)..(6)
<223> OTHER INFORMATION: AMIDATION

<400> SEQUENCE: 340

Xaa Xaa Ala Trp Xaa Lys
1               5

<210> SEQ ID NO 341
<211> LENGTH: 6
<212> TYPE: PRT
<213> ORGANISM: Artificial sequence
<220> FEATURE:
<223> OTHER INFORMATION: Synthetic growth hormone secretagogue -
      Hexarelin
<220> FEATURE:
<221> NAME/KEY: MISC_FEATURE
<222> LOCATION: (2)..(2)
<223> OTHER INFORMATION: Xaa = D-2-Me-Trp
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 341

His Xaa Ala Trp Xaa Lys
1               5

<210> SEQ ID NO 342
<211> LENGTH: 6
<212> TYPE: PRT
<213> ORGANISM: Artificial sequence
<220> FEATURE:
<223> OTHER INFORMATION: Growth hormone releasing peptide
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION
```

```
<400> SEQUENCE: 342

His Xaa Ala Trp Xaa Lys
1               5
```

COMPOSITIONS AND METHODS FOR STIMULATING GASTROINTESTINAL MOTILITY

This application is a United States national stage filing under 35 U.S.C. §371 of international (PCT) application No. PCT/US2006/038027, filed Sep. 28, 2006 and designating the US, which claims priority to U.S. provisional application 60/721,916, filed Sep. 29, 2005.

BACKGROUND OF THE INVENTION

1. Field of the Invention

The present invention is directed to methods for stimulating the motility of the gastrointestinal system in a patient which comprises administering peptidyl analogs that possess agonistic ghrelin activity, a prodrug thereof, or a pharmaceutically acceptable salt of said analogs or said prodrug.

2. Description of the Related Art

Gastrointestinal (GI) motility is a coordinated neuromuscular process that transports nutrients through the digestive system (Scarpignato, C., Dig. Dis., (1997), 15:112), the impairment of which may result in a variety of ailments including gastroesophageal reflux disease (GERD), gastroparesis (e.g., diabetic and post-surgical), irritable bowel syndrome (IBS), constipation (e.g. that associated with the hypomotility phase of IBS), emesis (e.g., that caused by cancer chemotherapy agents), ileus and colonic pseudo-obstruction (U.S. Pat. No. 6,548,501; U.S. Patent Application No. 20040266989). These various complications of interrupted GI motility contribute significantly to the health care burdens of industrialized nations (U.S. Pat. No. 6,548,501; Feighner, S. D. et al., Science, (1999), 284:2184-8).

"Ileus" refers to the obstruction of the bowel or gut, especially the colon (see, e.g., *Dorland's Illustrated Medical Dictionary*, p. 816, 27th ed. (W.B. Saunders Company, Philadelphia 1988)). Generally, any trauma to the bowel resulting in the release of inflammatory mediators leading to activation of inhibitory neural reflexes will result in the onset of ileus. Ileus may be diagnosed by the disruption of the normal coordinated movements of the gut, resulting in failure of the propulsion of intestinal contents (Resnick, J., Am. J. of Gastroentero., (1997), 92:751; Resnick, J., Am. J. of Gastroentero., (1997), 92:934). Ileus should be distinguished from constipation, which refers to infrequent or difficulty in evacuating the feces (see, e.g., *Dorland's Illustrated Medical Dictionary*, p. 375, 27th ed. (W.B. Saunders Company, Philadelphia 1988)).

Ileus may be brought about by a variety of causes such as parturition; intestinal ischaemia; retroperitoneal haematoma; intraabdominal sepsis; intraperitoneal inflammation, e.g., acute appendicitis, choecystitis, pancreatitis; fractures of the spine; ureteric colic; thoracic lesions; basal pneumonia; rib fractures; myocardial infarction; and metabolic disturbances. Post-partum ileus is a common problem for women in the period following childbirth and is thought to be caused by fluctuations in natural opioid levels as a result of birthing stress. Patients having undergone procedures such as major abdominal surgery including laparotomy for abdominal abscess or small intestinal transplantation (SITx), chest, pelvic or orthopedic surgery, often suffer from a period of transient impairment of bowel function called post-surgical or post-operative ileus (referred to hereinafter as POI).

POI commonly occurs for 24 to 72 hours following surgery. In some instances, the bowel dysfunction may become quite severe, lasting for more than a week and affecting more than one portion of the GI tract (Livingston, E. H. et al., Digest. Dis. and Sci., (1990), 35:121). Gastrointestinal dysmotility associated with POI is generally most severe in the colon. POI is characterized by abdominal nausea, distension, vomiting, obstipation, inability to eat and cramps. POI not only delays the normal resumption of food intake after surgery and prolongs hospitalization, but also fosters postoperative complications, especially aspiration pneumonia.

The administration of opioid analgesics to a patient after surgery may often contribute to and/or exacerbate existing bowel dysfunction, thereby delaying recovery of normal bowel function. Since virtually all patients receive opioid analgesics, such as morphine or other narcotics for pain relief after surgery, particularly major surgery, current post-surgical pain treatment may actually slow recovery of normal bowel function, resulting in a delay in hospital discharge and increasing the cost of medical care.

Agents which act to affect gastrointestinal motility may also confer beneficial effects upon patients suffering from emesis. Emesis, or vomiting, is often preceded by retching and may be accompanied by dry heaves. Emesis may be caused by imbalances in the digestive tract, such as ileus, dyspepsia, or inflammation of the gastric wall, or by imbalances in the sensory system or brain, such as motion sickness, migraine or tumors. Emesis may be self-induced such as in anorexia or bulimia, and it may also occur in response to severe pain, emotional responses (e.g., to disagreeable sights or odors), or pregnancy. Emesis is a common complication following the administration of many medications, particularly anti-cancer treatments such as chemotherapy. Prolonged episodes or repetitive emesis may result in a variety of injuries to the organism, including dehydration and electrolyte imbalances (Quigley, E. M. et al., Gastroentero., (2001), 120:263-86).

Agents which act to affect gastrointestinal motility may also confer beneficial effects upon patients suffering from gastroparesis. Gastroparesis, also called delayed gastric emptying, is a disorder in which the nerves to the stomach are damaged or stop working and the stomach takes too long to empty its contents. For example, following damage to the vagus nerve, the nerve which controls the movement of food through the digestive tract, the muscles of the stomach and intestines do not work normally and the movement of food is slowed or stopped. High blood glucose causes chemical changes in nerves and damages the blood vessels that carry oxygen and nutrients to the nerves. If blood glucose levels remain high over a long period of time, as is often the case in diabetes, the vagus nerve can be damaged; gastroparesis often occurs in people with type 1 diabetes or type 2 diabetes (Murray, C. D. et al., Gut, (2005), 54:1693-8).

The traditional therapies for impaired GI motility, such as that of ileus, gastroparesis and emesis, are considered ineffective. Current therapies for treating ileus include functional stimulation of the intestinal tract, stool softeners, laxatives such as Dulcolax®, lubricants, intravenous hydration, nasogastric suction, prokinetic agents, early enteral feeding, and nasogastric decompression. Nasogastric intubation to decompress the stomach has also traditionally been used to treat ileus.

Traditional pharmaceuticals used to treat impaired GI motility, such as that of ileus, include drugs that act to increase colonic motility, such as Leu13-motilin and prostaglandin F2 alpha, and prokinetic agents, such as Cisapride®. PROPULSID®, which contains Cisapride® monohydrate, is an oral gastrointestinal agent (U.S. Pat. No. 4,962,115) indicated for the symptomatic treatment of adult patients with nocturnal heartburn due to gastroesophageal reflux disease. Other prokinetic agents include, for example, metoclopramide, domperidone, ondansetron, tropisetron, mosap ride and itopride. Other treatments include administering adenosine-antagonizing pyrazolopyridine compounds (U.S. Pat. No. 6,214,843); pituitary adenylate cyclase activating peptide (PACAP) receptor antagonist in combination with a vasoactive intestinal peptide (VIP) receptor antagonist (U.S. Pat. No. 6,911,430); fedotozine (U.S. Pat. No. 5,362,756); neuropeptides (U.S. Pat. No. 5,929,035); and proteinase-activated receptor-2 antagonists (U.S. Pat. No. 5,929,035). In extreme cases, ileus has been treated with surgical intervention to unblock the colon.

These therapeutic regimens, however, suffer from numerous problems. For instance, PROPULSID® was recently removed from the market due to its potential to induce cardiac arrhythmias (U.S. Pat. No. 6,548,501). Adolor Corporation is presently in phase III clinical trials for a therapy to treat postoperative ileus using Alvimopan (Entereg®). Adolor's therapy, however, utilizes opioid receptor antagonists which merely block the side effects of opiate analgesics, rather than actually relieving the ileus condition. The phase III trials demonstrate marginal efficacy and minimal applicability for the treatment of ileus, particularly postoperative ileus.

Furthermore, these prior art methods for treatment of impaired GI motility lack specificity for different types of impairments, e.g., postoperative ileus or post-partum ileus. Also, these prior art methods offer no means for the prevention of impaired GI motility, such as that of ileus, gastroparesis and emesis. If impaired GI motility, such as that of ileus, gastroparesis and emesis, could be prevented or more effectively treated, hospital stays, recovery times, and medical costs would be significantly decreased with the additional benefit of minimizing patient discomfort.

Drugs which selectively target gut motility to correct gastrointestinal dysfunction caused by postoperative ileus would be ideal candidates for preventing and/or treating post-surgical and post-partum ileus. Such drugs would also be excellent candidates for the treatment of gastroparesis and/or emesis, particularly emesis associated with chemotherapies or other drug induced gastrointestinal dysfunction. Of those, drugs that do not interfere with the effects of opioid analgesics would be of special benefit in that they may be administered simultaneously with drugs for pain management with limited side effects.

Peptides affecting the release of growth hormone (GH) are now thought to exhibit gastrokinetic or "prokinetic" effects (U.S. Pat. No. 6,548,501; Peeters, T. L., J. Physiol. Pharmacol., (2003), 54 (supp 4):95-103 and references therein; Trudel, L. et al, J. Physiol. Gastrointest. Liver Physiol., (2002), 282:G948-52). Such growth hormone-releasing peptides, or GHRPs, are also referred to as growth hormone secretagogues (GHS). Exemplary growth hormone-releasing peptides (GHRPs) believed to exhibit prokinetic effects include GHRP-1, GHRP-2 and ghrelin.

Ghrelin, a recently discovered orexigenic hormone, is produced as a preprohormone that is proteolytically processed to yield a peptide of the following sequence: H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (Kojima, M. et al., Nature, (1999), 402(6762):656-60; (SEQ ID NO; 338)). Ghrelin is produced by epithelial cells lining the fundus of the stomach and functions to stimulate appetite; its levels increase prior to a meal and decrease thereafter.

Ghrelin powerfully stimulates GH secretion from the anterior pituitary gland, mainly at the hypothalamic level, through its interaction with growth hormone secretagoue receptor (GHS-R) both in animals and in humans (Ukkola, O. et al., 2002 Ann. Med., (2002), 34:102-8; (Kojima, M. et al., Nature, (1999), 402(6762):656-60).

The native structures of ghrelin from several mammalian and non-mammalian species are known (Kaiya, H. et al., J. of Biol. Chem., (2001), 276:40441-8 and International Patent Application PCT/JP00/04907 [WO 01/07475]). A core region present in ghrelin is responsible for observed activity at the GHS receptor. The core region comprises the four N-terminal amino acids wherein the serine in the third position is normally modified with n-octanoic acid. In addition to acylation by n-octanoic acid, native ghrelin may also be acylated with n-decanoic acid (Kaiya, H. et al., J. of Biol. Chem., (2001), 276:40441-8).

Prior to the discovery that ghrelin is a native ligand for the GHS receptor, it was known that GHRPs controlled the release of growth hormone from the pituitary somatotrops. The hexapeptide His-D-Trp-Ala-Trp-D-Phe-Lys-amide (GHRP-6; (SEQ ID NO:342)), was found to release growth hormone from the somatotrops in a dose-dependent manner in several species including man (Bowers, C. Y. et al., Endocrinology, (1984), 114(5):1537-45). Subsequent chemical studies on GHRP-6 led to the identification of other potent, synthetic GHSs such as GHRP-I, GHRP-2 and hexarelin (Cheng, K. et al., Endocrinology, (1989), 124(6):2791-8; Bowers, C. Y., *Novel GH-Releasing Peptides*, Molecular and Clinical Advances in Pituitary Disorders, Ed: Melmed, S., Endocrine Research and Education, Inc., Los Angeles, Calif., USA, (1993), 153-7; and Deghenghi, R. et al., Life Sci., (1994), 54(18):1321-8). The structures of these compounds are as shown:

```
GHRP-I    Ala-His-D-(2')-Nal-Ala-Trp-D-Phe-Lys-NH2;
          (SEQ ID NO: 339)

GHRP-2    D-Ala-D-(2')-Nal-Ala-Trp-D-Nal-Lys-NH2;
          and (SEQ ID NO: 340)

Hexarelin His-D-2-MeTrp-Ala-Trp-D-Phe-Lys-NH2.
          (SEQ ID NO: 341)
```

GHRP-I, GHRP-2, GHRP-6, and hexarelin are classified as synthetic GHSs.

A number of recent studies have demonstrated the potential use of GHSs such as ghrelin, GHRP-6 and others to stimulate motor activity in the intestinal tract and to treat conditions such as ileus and emesis. For example, ghrelin and GHRP-6 have been shown to accelerate gastric emptying in rats and mice (Peeters, T. L., J. Physiol. Pharmacol., (2003), 54 (supp 4):95-103). In rats, ghrelin has been shown to reverse the delay of gastric emptying in a post-operative ileus model (Peeters, T. L., J. Physiol. Pharmacol., (2003), 54 (supp 4):95-103; Trudel, L. et al., J. Physiol. Gastrointest. Liver Physiol., (2002), 282(6):G948-52) and in laparectomized dogs, ghrelin was shown to improve POI in the treated animals (Trudel, L. et al, Peptides, (2003), 24:531-4). In septic mice, ghrelin and GHRP-6 accelerated gastric emptying although had little effect upon increasing transit in the small intestine (De Winter, B. Y. et al., Neurogastroenterol. Motil., (2004), 16:439-46).

In experiments designed to mimic hospitalization conditions for a human patient experiencing POI, laparectomized rats were exposed to opiates as well as ghrelin analog RC-1139 (Poitras, P. et al., Peptides, (2005), 26:1598-601). In an assay measuring gastric empyting, RC-1139 was shown to reverse POI in the control and laparectomized rats in the presence of morphine. It is thus believed that ghrelin exhibits gastrokinetic effects without interfering with opiate activity.

Ferrets exposed to the cytotoxic anti-cancer agent cisplatin exhibited significantly reduced occurrences of retching and vomiting following intracerebroventricular administration of ghrelin (Rudd, J. A. et al., Neurosci. Lett., (2006), 392:79-83) thus confirming the ability of ghrelin to reduce emesis in a manner consistent with its role in modulating gastro-intestinal functions. It is thought that ghrelin's role in modulating gastric motility is independent of the GH-secretory activation and may be mediated by the vagal-cholinergic muscarinic pathway (U.S. Patent Application No. 20060025566).

Ghrelin has also been shown to increase gastric emptying in patients with diabetic gastroparesis (Murray, C. D. et al., Gut, (2005), 54:1693-8).

It is interesting to note that in the studies referenced above, the ghrelin or ghrelin analog was administered using intraperitoneal (ip), intravenous (iv) or intracerebroventricular (icv) injection. Other disclosures (U.S. Pat. No. 6,548,501; U.S. Patent Application No. 20020042419; U.S. Patent Application No. 20050187237; U.S. Patent Application No. 20060025566) report on the oral administration of GHSs as a means to treat impaired gastrointestinal motility.

Very few compounds are known in the art to be useful for treating impaired GI motility and more compounds affecting gastrointestinal motility, e.g. stimulation of motility, would be highly desirable. Compounds affecting gastrointestinal kinetics are useful in the treatment of interruptions in normal GI functions such as ileus and emesis.

SUMMARY OF THE INVENTION

The present invention relates to a method of stimulating gastrointestinal motility in a patient (e.g., a mammal such as a human). The method includes the step of administering a therapeutically effective amount of a peptidyl analog of ghrelin to said patient experiencing or at risk of experiencing gastrointestinal dysmotility.

In one aspect, the present invention provides a method of treating gastrointestinal dysmotility conditions by administering a therapeutically effective amount of a peptidyl analog of ghrelin or prodrug thereof suitable for attenuating such gastrointestinal conditions where the analog or prodrug comprises a compound according to Formula (I), Formula (II) or Formula (III), or a pharmaceutically acceptable salt thereof. The method of the invention is useful for promoting gastric and gastrointestinal motility in a patient (e.g., a mammal such as a human) and as such, is useful for treating conditions benefiting from improved gastric and gastrointestinal motility such as gastroesophageal reflux disease (GERD), IBS, constipation, ileus, emesis, gastroparesis, colonic pseudoobstruction, and the like.

In another aspect, the invention provides a method of treating ileus, gastroparesis or emesis by administering a therapeutically effective amount of a peptidyl analog of ghrelin suitable for attenuating ileus, emesis, or gastroparesis. In yet another aspect, the condition treated by the method of the invention is ileus, such as post-operative ileus and the operation may be a gastrointestinal surgery. In yet another aspect of the invention, the condition treated by the method of the invention is emesis, such as emesis associated with or provoked by the administration of an anti-cancer chemotherapeutic agent. In yet another aspect, the condition treated by the method of the invention is gastroparesis, such as diabetic gastroparesis. The diabetes may be Type I or Type II diabetes.

In one aspect, the invention provides a method of treating gastrointestinal conditions such as GERD, IBS, constipation, ileus, emesis, gastroparesis, and colonic pseudo-obstruction and the like, by administering a therapeutically effective amount of a peptidyl ghrelin analog according to the following formula (I):

$(R^2R^3)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$R^1$ wherein:

$A^1$ is Gly, Aib, Ala, β-Ala, or Acc;

$A^2$ is Ser, Aib, Act, Ala, Acc, Abu, Ava, Thr, or Val;

$A^3$ is Ser, Ser(C(O)—$R^4$), Asp(O—$R^8$), Asp(NH—$R^9$), Cys(S—$R^{14}$), Dap(S(O)$_2$—$R^{10}$), Dab(S(O)$_2$—$R^{11}$), Glu(O—$R^6$), Glu(NH—$R^7$), Thr, Thr(C(O)—$R^5$), or HN—CH((CH$_2$)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, ($X^1$, $X^2$, $X^3$, $X^4$, $X^5$)Phe, Taz, 2-Thi, 3-Thi, Trp, or Tyr;

$A^5$ is Leu, Abu, Acc, Aib, Ala, Cha, Ile, hLeu, Nle, Nva, Phe, Tle, or Val;

$A^6$ is Ser, Abu, Acc, Act, Aib, Ala, Gly, Thr, or Val;

$A^7$ is Pro, Dhp, Dmt, 3-Hyp, 4-Hyp, Inc, Ktp, Oic, Pip, Thz, Tic, or deleted;

$A^8$ is Glu, Acc, Aib, Arg, Asn, Asp, Dab, Dap, Gln, Lys, Orn, HN—CH((CH$_2$)$_n$—N($R^{12}R^{13}$))—C(O), or deleted;

$A^9$ is H is, Apc, Aib, Acc, 2-Fua, 2-Pal, 3-Pal, 4-Pal, Taz, 2-Thi, 3-Thi, ($X^1$, $X^2$, $X^3$, $X^4$, $X^5$-)Phe or deleted;

$A^{10}$ is Gln, Acc, Aib, Asn, Asp, Glu, or deleted;

$A^{11}$ is Arg, Apc, hArg, Dab, Dap, Lys, Orn, HN—CH((CH$_2$)$_n$—N($R^{12}R^{13}$))—C(O), or deleted;

$A^{12}$ is Val, Abu, Acc, Aib, Ala, Cha, Nva, Gly, Ile, Leu, Nle, Tle, or deleted;

$A^{13}$ is Gln, Acc, Aib, Asn, Asp, Glu, or deleted;

$A^{14}$ is Gln, Acc, Aib, Asn, Asp, Glu, or deleted;

$A^{15}$ is Arg, hArg, Acc, Aib, Apc, Dab, Dap, Lys, Orn, HN—CH((CH)$_n$—N($R^{12}R^{13}$))—C(O), or deleted;

$A^{16}$ is Lys, Acc, Aib, Apc, Arg, hArg, Dab, Dap, Orn, HN—CH((CH$_2$)$_n$—N($R^{12}R^{13}$))—C(O), or deleted;

$A^{17}$ is Glu, Arg, Asn, Asp, Dab, Dap, Gln, Lys, Orn, HN—CH((CH$_2$)—N($R^{12}R^{13}$))—C(O), or deleted;

$A^{18}$ is Ser, Abu, Acc, Act, Aib, Ala, Thr, Val, or deleted;

$A^{19}$ is Lys, Acc, Aib, Apc, Arg, hArg, Dab, Dap, Orn, HN—CH((CH$_2$)$_n$—N($R^{12}R^{13}$))—C(O), or deleted;

$A^{20}$ is Lys, Acc, Aib, Apc, Arg, hArg, Dab, Dap, Orn, HN—CH((CH$_2$)$_n$—N($R^{12}R^{13}$))—C(O), or deleted;

$A^{21}$ is Pro, Dhp, Dmt, 3-Hyp, 4-Hyp, Inc, Ktp, Oic, Pip, Thz, Tic, or deleted;

$A^{22}$ is Pro, Dhp, Dmt, 3-Hyp, 4-Hyp, Inc, Ktp, Oic, Pip, Thz, Tic, or deleted;

$A^{23}$ is Abu, Acc, Act, Aib, Ala, Apc, Gly, Nva, Val, or deleted;

$A^{24}$ is Lys, Acc, Aib, Apc, Arg, hArg, Dab, Dap, Orn, HN—CH((CH$_2$)$_n$—N($R^{12}R^{13}$))—C(O), or deleted;

$A^{25}$ is Leu, Abu, Acc, Aib, Ala, Cha, Ile, hLeu, Nle, Nva, Phe, Tle, Val, or deleted;

$A^{26}$ is Gln, Aib, Asn, Asp, Glu, or deleted;

$A^{27}$ is Pro, Dhp, Dmt, 3-Hyp, 4-Hyp, Inc, Ktp, Oic, Pip, Thz, Tic, or deleted;

$A^{28}$ is Acc, Aib, Apc, Arg, hArg, Dab, Dap, Lys, Orn, HN—CH((CH$_2$)$_n$—N($R^{12}R^{13}$))—C(O), or deleted;

$R^1$ is —OH, —NH$_2$, —(C$_1$-C$_{30}$)alkoxy, or NH—$X^6$—CH$_2$-$Z^0$, wherein $X^6$ is a (C$_1$-C$_{12}$)alkyl, (C$_2$-C$_{12}$)alkenyl, and $Z^0$ is —H, —OH, —CO$_2$H or —C(O)—NH$_2$;

$R^2$ and $R^3$ each is, independently for each occurrence, H, (C$_1$-C$_{20}$)alkyl or (C$_1$-C$_{20}$)acyl;

$R^4$, $R^5$, $R^6$, $R^7$, $R^8$, $R^9$, $R^{10}$, $R^{11}$ and $R^{14}$ each is, independently for each occurrence, (C$_1$-C$_{40}$)alkyl, (C$_2$-C$_{40}$)alkenyl, substituted (C$_1$-C$_{40}$) alkyl, substituted (C$_2$-C$_{40}$) alkenyl, alkylaryl, substituted alklyaryl, aryl or substituted aryl;

$R^{12}$ and $R^{13}$ each is, independently for each occurrence, H, $(C_1-C_{40})$alkyl, $(C_1-C_{40})$acyl, $(C_1-C_{30})$alkylsulfonyl, or —C(NH)—Nh, wherein when $R^{12}$ is $(C_1-C_{40})$acyl, $(C_1-C_{30})$alkylsulfonyl, or —C(NH)—$NH_2$, then $R^{13}$ is H or $(C_1-C_{40})$alkyl;

n is, independently for each occurrence, 1, 2, 3, 4 or 5;

$X^1$, $X^2$, $X^3$, $X^4$, and $X^5$ each is, independently for each occurrence, H, F, Cl, Br, I, $(C_{1-10})$alkyl, substituted $(C_{1-10})$alkyl, aryl, substituted aryl, OH, $NH_2$, $NO_2$, or CN;

provided that the peptide contains at least one amino acid selected from the groups consisting of:

$A^2$ is Aib, Acc, or Act;
$A^3$ is Dap(S(O)$_2$—$R^{10}$), Dab(S(O)$_2$—$R^{11}$), Glu(NH-Hexyl), or Cys(S-Decyl);
$A^5$ is Abu, Acc, Aib, Ala, Cha, Ile, hLeu, Nle, Nva, Phe, Tle, or Val;
$A^6$ is Abu, Acc, Act, Aib, Ala, Gly, Thr or Val;
$A^7$ is Dhp, Dmt, 3-Hyp, 4-Hyp, Inc, Ktp, Oic, Pip, Thz or Tic;
$A^8$ is Acc, Aib, Arg, Asn, Asp, Dab, Dap, Gln, Lys, Orn, or HN—CH((CH$_2$)$_n$—N($R^{12}R^{13}$))—C(O);
$A^9$ is Aib, Acc, Apc, 2-Fua, 2-Pal, 3-Pal, 4-Pal, Taz, 2-Thi, 3-Thi, or ($X^1$, $X^2$, $X^3$, $X^4$, $X^5$-)Phe; and
$A^{10}$ is Acc, Aib, Asn, Asp, or Glu;

and further provided that the peptide is not (Lys$^8$)hGhrelin (1-8)-$NH_2$ or (Arg$^8$)hGhrelin(1-8)-$NH_2$; or a pharmaceutically acceptable salt thereof.

In another aspect, the invention provides a preferred group of compounds according to formula (I), wherein:
$A^1$ is Gly or Aib;
$A^2$ is Ser, Aib, A5c, Act, or Ava;
$A^3$ is Ser(C(O)—$R^4$), Glu(O—$R^6$), Glu(NH—$R^7$), Dap(S(O)$_2$—$R^{10}$), or Dab(S(O)$_2$—$R^{11}$);
$A^4$ is Phe;
$A^5$ is Leu, Acc, Aib, Cha, or hLeu;
$A^6$ is Ser, Abu, Act, Aib, or Thr;
$A^7$ is Pro, Dhp, Dmt, 4-Hyp, Ktp, Pip, Tic, or Thz;
$A^8$ is Glu or Aib;
$A^9$ is H is, Aib, Apc, 2-Fua, 2-Pal, 3-Pal, 4-Pal, Taz, or 2-Thi;
$A^{10}$ is Gln or Aib;
$A^{11}$ is Arg;
$A^{12}$ is Aib, Val or Acc;
$A^{13}$ is Gln;
$A^{14}$ is Gin;
$A^{15}$ is Arg or Orn;
$A^{16}$ is Lys or Apc;
$A^{17}$ is Glu;
$A^{18}$ is Ser;
$A^{19}$ is Lys;
$A^{20}$ is Lys;
$A^{21}$ is Pro;
$A^{22}$ is Pro;
$A^{23}$ is Ala;
$A^{24}$ is Lys;
$A^{25}$ is Leu;
$A^{26}$ is Gln;
$A^{27}$ is Pro; and
$A^{28}$ is Arg, or a pharmaceutically acceptable salt thereof.

In yet another aspect, the invention provides a preferred group of compounds according to formula (I), wherein:
$R^2$ and $R^3$ each is, independently, H, Acyl, n-butyryl, isobutyryl, or n-octanoyl;
$R^4$ is octyl;
$R^6$ is hexyl;
$R^7$ is hexyl;
$R^{10}$ is octyl; and
$R^{11}$ is octyl, or a pharmaceutically acceptable salt thereof, wherein Acc is, independently for each occurrence, A5c or A6c.

In yet another aspect, the invention provides a preferred group of compounds according to formula (I), where the compound is:

```
(Dap³(octanesulfonyl))hGhrelin(1-28)-NH₂;  (SEQ ID NO: 1) Example #75

(Aib²,A6c⁵)hGhrelin(1-28)-NH₂;  (SEQ ID NO: 2) Example #96

(A6c⁵)hGhrelin(1-28)-NH₂;  (SEQ ID NO: 3)

(Aib²,⁶)hGhrelin(1-28)-NH₂;  (SEQ ID NO: 4) Example #108

(Aib²,A5c¹²)hGhrelin(1-28)-NH₂;  (SEQ ID NO: 5)

(Aib²,A5c¹²,Orn¹⁵)hGhrelin(1-28)-NH₂;  (SEQ ID NO: 6)

(Aib²,A5c¹²,Apc¹⁶)hGhrelin(1-28)-NH₂;  (SEQ ID NO: 7)

(Aib²,Act⁶)hGhrelin(1-28)-NH₂;  (SEQ ID NO: 7)

(Aib²,3-Pal⁹)hGhrelin(1-28)-NH₂;  (SEQ ID NO: 8) Example #29

(Aib²,Dmt⁷)hGhrelin(1-28)-NH₂;  (SEQ ID NO: 9)

(Aib²,Thz⁷)hGhrelin(1-28)-NH₂;  (SEQ ID NO: 9)

(A5c²)hGhrelin(1-28)-NH₂;  (SEQ ID NO: 10) Example #52

(Act²)hGhrelin(1-28)-NH₂;  (SEQ ID NO: 10) Example #94

(Aib²,A5c⁵)hGhrelin(1-28)-NH₂;  (SEQ ID NO: 2)

(Aib²,A6c⁵)hGhrelin(1-28)-NH₂;  (SEQ ID NO: 2)

(Aib²,⁵)hGhrelin(1-28)-NH₂;  (SEQ ID NO: 2)

(Aib²,hLeu⁵)hGhrelin(1-28)-NH₂;  (SEQ ID NO: 2)
```

(Aib², Cha⁵)hGhrelin(1-28)-NH₂; (SEQ ID NO: 2)

(Aib²,⁶)hGhrelin(1-28)-NH₂; (SEQ ID NO: 4)

(Aib², Act⁶)hGhrelin(1-28)-NH₂; (SEQ ID NO: 4) Example #114

(Aib², Thr⁶)hGhrelin(1-28)-NH₂; (SEQ ID NO: 4)

(Aib², Abu⁶)hGhrelin(1-28)-NH₂; (SEQ ID NO: 4) Example #88

(Aib², 4-Hyp⁷)hGhrelin(1-28)-NH₂; (SEQ ID NO: 9) Example #36

(Aib², Thz⁷)hGhrelin(1-28)-NH₂; (SEQ ID NO: 9) Example #54

(Aib², Pip⁷)hGhrelin(1-28)-NH₂; (SEQ ID NO: 9) Example #65

(Aib², Dhp⁷)hGhrelin(1-28)-NH₂; (SEQ ID NO: 9) Example #44

(Aib², Ktp⁷)hGhrelin(1-28)-NH₂; (SEQ ID NO: 9)

(Aib²,⁸)hGhrelin(1-28)-NH₂; (SEQ ID NO: 11) Example #49

(Aib², 2-Pal⁹)hGhrelin(1-28)-NH₂; (SEQ ID NO: 8)

(Aib², 3-Pal⁹)hGhrelin(1-28)-NH₂; (SEQ ID NO: 8)

(Aib², 4-Pal⁹)hGhrelin(1-28)-NH₂; (SEQ ID NO: 8) Example #55

(Aib², Taz⁹)hGhrelin(1-28)-NH₂; (SEQ ID NO: 8) Example #27

(Aib², 2-Thi⁹)hGhrelin(1-28)-NH₂; (SEQ ID NO: 8)

(Aib², 2-Fua⁹)hGhrelin(1-28)-NH₂; (SEQ ID NO: 8)

(Aib², Apc⁹)hGhrelin(1-28)-NH₂; (SEQ ID NO: 8)

(Aib²,⁹)hGhrelin(1-28)-NH₂; (SEQ ID NO: 8)

(Aib²,¹⁰)hGhrelin(1-28)-NH₂; (SEQ ID NO: 12) Example #48

(Aib², Tic⁷)hGhrelin(1-28)-NH₂; (SEQ ID NO: 9) Example #53

(Aib⁶)hGhrelin(1-28)-NH₂; (SEQ ID NO: 13)

(A5c⁵)hGhrelin(1-28)-NH₂; (SEQ ID NO: 3)

(A6c⁵)hGhrelin(1-28)-NH₂; (SEQ ID NO: 3) Example #102

(Act⁶)hGhrelin(1-28)-NH₂; (SEQ ID NO: 13)

(3-Pal⁹)hGhrelin(1-28)-NH₂; (SEQ ID NO: 14) Example #32

(Dmt⁷)hGhrelin(1-28)-NH₂; (SEQ ID NO: 15)

(Thz⁷)hGhrelin(1-28)-NH₂; (SEQ ID NO: 15)

(Aib⁵)hGhrelin(1-28)-NH₂; (SEQ ID NO: 3)

(hLeu⁵)hGhrelin(1-28)-NH₂; (SEQ ID NO: 3)

(Cha⁵)hGhrelin(1-28)-NH₂; (SEQ ID NO: 3)

(Thr⁶)hGhrelin(1-28)-NH₂; (SEQ ID NO: 13)

(Abu⁶)hGhrelin(1-28)-NH₂; (SEQ ID NO: 13)

(4-Hyp⁷)hGhrelin(1-28)-NH₂; (SEQ ID NO: 15)

(Pip⁷)hGhrelin(1-28)-NH₂; (SEQ ID NO: 15)

(Dhp⁷)hGhrelin(1-28)-NH₂; (SEQ ID NO: 15)

(Ktp⁷)hGhrelin(1-28)-NH₂; (SEQ ID NO: 15)

(Aib⁸)hGhrelin(1-28)-NH₂; (SEQ ID NO: 16) Example #10

(2-Pal⁹)hGhrelin(1-28)-NH₂; (SEQ ID NO: 14)

(3-Pal⁹)hGhrelin(1-28)-NH₂; (SEQ ID NO: 14)

(4-Pal⁹)hGhrelin(1-28)-NH₂; (SEQ ID NO: 14)

-continued (Taz$^9$)hGhrelin(1-28)-NH$_2$; (SEQ ID NO: 14)

(2-Thi$^9$)hGhrelin(1-28)-NH$_2$; (SEQ ID NO: 14) Example #26

(2-Fua$^9$)hGhrelin(1-28)-NH$_2$; (SEQ ID NO: 14)

(Apc$^9$)hGhrelin(1-28)-NH$_2$; (SEQ ID NO: 14)

(Aib$^9$)hGhrelin(1-28)-NH$_2$; (SEQ ID NO: 14)

(Aib$^{10}$)hGhrelin(1-28)-NH$_2$; (SEQ ID NO: 17)

(Aib$^2$,Dap$^3$(octanesulfonyl),A6c$^5$)hGhrelin(1-28)-NH$_2$; (SEQ ID NO: 18)

(Dap$^3$(octanesulfonyl),A6c$^5$)hGhrelin(1-28)-NH$_2$; (SEQ ID NO: 19)

(Aib$^{2,6}$,Dap$^3$(octanesulfonyl))hGhrelin(1-28)-NH$_2$; (SEQ ID NO: 20)

(Aib$^2$,Dap$^3$(octanesulfonyl),A5c$^{12}$)hGhrelin(1-28)-NH$_2$; (SEQ ID NO: 21)

(Aib$^2$,Dap$^3$(octanesulfonyl),A5c$^{12}$,Orn$^{15}$)hGhrelin(1-28)-NH$_2$; (SEQ ID NO: 22)

(Aib$^2$,Dap$^3$(octanesulfonyl),A5c$^{12}$,Apc$^{16}$)hGhrelin(1-28)-NH$_2$; (SEQ ID NO: 23)

(Aib$^2$,Dap$^3$(octanesulfonyl),Act$^6$)hGhrelin(1-28)-NH$_2$; (SEQ ID NO: 20)

(Aib$^2$,Dap$^3$(octanesulfonyl),3-Pal$^9$)hGhrelin(1-28)-NH$_2$; (SEQ ID NO: 24)

(Aib$^2$,Dap$^3$(octanesulfonyl),Dmt$^7$)hGhrelin(1-28)-NH$_2$; (SEQ ID NO: 25)

(Aib$^2$,Dap$^3$(octanesulfonyl),Thz$^7$)hGhrelin(1-28)-NH$_2$; (SEQ ID NO: 25)

(A5c$^2$,Dap$^3$(octanesulfonyl))hGhrelin(1-28)-NH$_2$; (SEQ ID NO: 26)

(Act$^2$,Dap$^3$(octanesulfonyl))hGhrelin(1-28)-NH$_2$; (SEQ ID NO: 26)

(Aib$^2$,Dap$^3$(octanesulfonyl),A5c$^5$)hGhrelin(1-28)-NH$_2$; (SEQ ID NO: 18)

(Aib$^{2,5}$,Dap$^3$(octanesulfonyl))hGhrelin(1-28)-NH$_2$; (SEQ ID NO: 18)

(Aib$^2$,Dap$^3$(octanesulfonyl),hLeu$^5$)hGhrelin(1-28)-NH$_2$; (SEQ ID NO: 18)

(Aib$^2$,Dap$^3$(octanesulfonyl),Cha$^5$)hGhrelin(1-28)-NH$_2$; (SEQ ID NO: 18)

(Aib$^{2,6}$,Dap$^3$(octanesulfonyl))hGhrelin(1-28)-NH$_2$; (SEQ ID NO: 20)

(Aib$^2$,Dap$^3$(octanesulfonyl),Thr$^6$)hGhrelin(1-28)-NH$_2$; (SEQ ID NO: 20)

(Aib$^2$,Dap$^3$(octanesulfonyl),Abu$^6$)hGhrelin(1-28)-NH$_2$; (SEQ ID NO: 20)

(Aib$^2$,Dap$^3$(octanesulfonyl),4-Hyp$^7$)hGhrelin(1-28)-NH$_2$; (SEQ ID NO: 25)

(Aib$^2$,Dap$^3$(octanesulfonyl),Pip$^7$)hGhrelin(1-28)-NH$_2$; (SEQ ID NO: 25)

(Aib$^2$,Dap$^3$(octanesulfonyl),Dhp$^7$)hGhrelin(1-28)-NH$_2$; (SEQ ID NO: 25)

(Aib$^2$,Dap$^3$(octanesulfonyl),Ktp$^7$)hGhrelin(1-28)-NH$_2$; (SEQ ID NO: 25)

(Aib$^{2,8}$,Dap$^3$(octanesulfonyl))hGhrelin(1-28)-NH$_2$; (SEQ ID NO: 27)

(Aib$^2$,Dap$^3$(octanesulfonyl),2-Pal$^9$)hGhrelin(1-28)-NH$_2$; (SEQ ID NO: 24)

(Aib$^2$,Dap$^3$(octanesulfonyl),3-Pal$^9$)hGhrelin(1-28)-NH$_2$; (SEQ ID NO: 24)

(Aib$^2$,Dap$^3$(octanesulfonyl),4-Pal$^9$)hGhrelin(1-28)-NH$_2$; (SEQ ID NO: 24)

(Aib$^2$,Dap$^3$(octanesulfonyl),Taz$^9$)hGhrelin(1-28)-NH$_2$; (SEQ ID NO: 24)

(Aib$^2$,Dap$^3$(octanesulfonyl),2-Thi$^9$)hGhrelin(1-28)-NH$_2$; (SEQ ID NO: 24)

(Aib$^2$,Dap$^3$(octanesulfonyl),2-Fua$^9$)hGhrelin(1-28)-NH$_2$; (SEQ ID NO: 24)

(Aib$^2$,Dap$^3$(octanesulfonyl),Apc$^9$)hGhrelin(1-28)-NH$_2$; (SEQ ID NO: 24)

(Aib$^{2,9}$,Dap$^3$(octanesulfonyl))hGhrelin(1-28)-NH$_2$; (SEQ ID NO: 24)

(Aib$^{2,10}$,Dap$^3$(octanesulfonyl))hGhrelin(1-28)-NH$_2$; (SEQ ID NO: 28)

(Dap$^3$(octanesulfonyl),A6c$^5$)hGhrelin(1-28)-NH$_2$; (SEQ ID NO: 19)

-continued (Dap³(octanesulfonyl),Aib⁶)hGhrelin(1-28)-NH₂; (SEQ ID NO: 29)

(Dap³(octanesulfonyl),A5c¹²)hGhrelin(1-28)-NH₂; (SEQ ID NO: 30)

(Dap³(octanesulfonyl),A5c¹²,Orn¹⁵)hGhrelin(1-28)-NH₂; (SEQ ID NO: 31)

(Dap³(octanesulfonyl),A5c¹²,Apc¹⁶)hGhrelin(1-28)-NH₂; (SEQ ID NO: 32)

(Dap³(octanesulfonyl),Act⁶)hGhrelin(1-28)-NH₂; (SEQ ID NO: 29)

(Dap³(octanesulfonyl),3-Pal⁹)hGhrelin(1-28)-NH₂; (SEQ ID NO: 33)

(Dap³(octanesulfonyl),Dmt⁷)hGhrelin(1-28)-NH₂; (SEQ ID NO: 34)

(Dap³(octanesulfonyl),Thz⁷)hGhrelin(1-28)-NH₂; (SEQ ID NO: 34)

(Dap³(octanesulfonyl),A5c⁵)hGhrelin(1-28)-NH₂; (SEQ ID NO: 19)

(Dap³(octanesulfonyl),Aib⁵)hGhrelin(1-28)-NH₂; (SEQ ID NO: 19)

(Dap³(octanesulfonyl),hLeu⁵)hGhrelin(1-28)-NH₂; (SEQ ID NO: 19)

(Dap³(octanesulfonyl),Cha⁵)hGhrelin(1-28)-NH₂; (SEQ ID NO: 19)

(Dap³(octanesulfonyl),Thr⁶)hGhrelin(1-28)-NH₂; (SEQ ID NO: 29)

(Dap³(octanesulfonyl),Abu⁶)hGhrelin(1-28)-NH₂; (SEQ ID NO: 29)

(Dap³(octanesulfonyl),4-Hyp⁷)hGhrelin(1-28)-NH₂; (SEQ ID NO: 34)

(Dap³(octanesulfonyl),Pip⁷)hGhrelin(1-28)-NH₂; (SEQ ID NO: 34)

(Dap³(octanesulfonyl),Dhp⁷)hGhrelin(1-28)-NH₂; (SEQ ID NO: 34)

(Dap³(octanesulfonyl),Ktp⁷)hGhrelin(1-28)-NH₂; (SEQ ID NO: 34)

(Dap³(octanesulfonyl),Aib⁸)hGhrelin(1-28)-NH₂; (SEQ ID NO: 35)

(Dap³(octanesulfonyl),2-Pal⁹)hGhrelin(1-28)-NH₂; (SEQ ID NO: 33)

(Dap³(octanesulfonyl),3-Pal⁹)hGhrelin(1-28)-NH₂; (SEQ ID NO: 33)

(Dap³(octanesulfonyl),4-Pal⁹)hGhrelin(1-28)-NH₂; (SEQ ID NO: 33)

(Dap³(octanesulfonyl),Taz⁹)hGhrelin(1-28)-NH₂; (SEQ ID NO: 33)

(Dap³(octanesulfonyl),2-Thi⁹)hGhrelin(1-28)-NH₂; (SEQ ID NO: 33)

(Dap³(octanesulfonyl),2-Fua⁹)hGhrelin(1-28)-NH₂; (SEQ ID NO: 33)

(Dap³(octanesulfonyl),Apc⁹)hGhrelin(1-28)-NH₂; (SEQ ID NO: 33)

(Dap³(octanesulfonyl),Aib⁹)hGhrelin(1-28)-NH₂; (SEQ ID NO: 33)

(Dap³(octanesulfonyl),Aib¹⁰)hGhrelin(1-28)-NH₂; (SEQ ID NO: 36)

(Dap³(octanesulfonyl),A5c¹²,Orn¹⁵)hGhrelin(1-28)-NH₂; (SEQ ID NO: 31)

(Dab³(octanesulfonyl),A5c¹²,Orn¹⁵)hGhrelin(1-28)-NH₂; (SEQ ID NO: 31)

(Aib²,A6c⁵,A5c¹²,Orn¹⁵)hGhrelin(1-28)-NH₂; (SEQ ID NO: 37)

(A6c⁵,A5c¹²,Orn¹⁵)hGhrelin(1-28)-NH₂; (SEQ ID NO: 38)

(Aib²,⁶,A5c¹²,Orn¹⁵)hGhrelin(1-28)-NH₂; (SEQ ID NO: 39)

(Aib²,Act⁶,A5c¹²,Orn¹⁵)hGhrelin(1-28)-NH₂; (SEQ ID NO: 39)

(Aib²,3-Pal⁹,A5c¹²,Orn¹⁵)hGhrelin(1-28)-NH₂; (SEQ ID NO: 40)

(Aib²,Dmt⁷,A5c¹²,Orn¹⁵)hGhrelin(1-28)-NH₂; (SEQ ID NO: 41)

(Aib²,Thz⁷,A5c¹²,Orn¹⁵)hGhrelin(1-28)-NH₂; (SEQ ID NO: 41)

(Aib²,A5c⁵,A5c¹²,Orn¹⁵)hGhrelin(1-28)-NH₂; (SEQ ID NO: 37)

(Aib²,⁵,A5c¹²,Orn¹⁵)hGhrelin(1-28)-NH₂; (SEQ ID NO: 37)

(Aib²,hLeu⁵,A5c¹²,Orn¹⁵)hGhrelin(1-28)-NH₂; (SEQ ID NO: 37)

(Aib²,Cha⁵,A5c¹²,Orn¹⁵)hGhrelin(1-28)-NH₂; (SEQ ID NO: 37)

-continued (Aib$^{2,6}$,A5c$^{12}$,Orn$^{15}$)hGhrelin(1-28)-NH$_2$; (SEQ ID NO: 39)

(Aib$^2$,Thr$^6$,A5c$^{12}$,Orn$^{15}$)hGhrelin(1-28)-NH$_2$; (SEQ ID NO: 39)

(Aib$^2$,Abu$^6$,A5c$^{12}$,Orn$^{15}$)hGhrelin(1-28)-NH$_2$; (SEQ ID NO: 39)

(Aib$^2$,4-Hyp$^7$,A5c$^{12}$,Orn$^{15}$)hGhrelin(1-28)-NH$_2$; (SEQ ID NO: 41)

(Aib$^2$,Pip$^7$,A5c$^{12}$,Orn$^{15}$)hGhrelin(1-28)-NH$_2$; (SEQ ID NO: 41)

(Aib$^2$,Dhp$^7$,A5c$^{12}$,Orn$^{15}$)hGhrelin(1-28)-NH$_2$; (SEQ ID NO: 41)

(Aib$^2$,Ktp$^7$,A5c$^{12}$,Orn$^{15}$)hGhrelin(1-28)-NH$_2$; (SEQ ID NO: 41)

(Aib$^{2,8}$,A5c$^{12}$,Orn$^{15}$)hGhrelin(1-28)-NH$_2$; (SEQ ID NO: 42)

(Aib$^2$,2-Pal$^9$,A5c$^{12}$,Orn$^{15}$)hGhrelin(1-28)-NH$_2$; (SEQ ID NO: 40)

(Aib$^2$,3-Pal$^9$,A5c$^{12}$,Orn$^{15}$)hGhrelin(1-28)-NH$_2$; (SEQ ID NO: 40)

(Aib$^2$,4-Pal$^9$,A5c$^{12}$,Orn$^{15}$)hGhrelin(1-28)-NH$_2$; (SEQ ID NO: 40)

(Aib$^2$,Taz$^9$,A5c$^{12}$,Orn$^{15}$)hGhrelin(1-28)-NH$_2$; (SEQ ID NO: 40)

(Aib$^2$,2-Thi$^9$,A5c$^{12}$,Orn$^{15}$)hGhrelin(1-28)-NH$_2$; (SEQ ID NO: 40)

(Aib$^2$,2-Fua$^9$,A5c$^{12}$,Orn$^{15}$)hGhrelin(1-28)-NH$_2$; (SEQ ID NO: 40)

(Aib$^2$,Apc$^9$,A5c$^{12}$,Orn$^{15}$)hGhrelin(1-28)-NH$_2$; (SEQ ID NO: 40)

(Aib$^{2,9}$,A5c$^{12}$,Orn$^{15}$)hGhrelin(1-28)-NH$_2$; (SEQ ID NO: 40)

(Aib$^{2,10}$,A5c$^{12}$,Orn$^{15}$)hGhrelin(1-28)-NH$_2$; (SEQ ID NO: 43)

(Dap$^3$(octanesulfonyl),A5c$^{12}$,Apc$^{16}$)hGhrelin(1-28)-NH$_2$; (SEQ ID NO: 32)

(Dab$^3$(octanesulfonyl),A5c$^{12}$,Apc$^{16}$)hGhrelin(1-28)-NH$_2$; (SEQ ID NO: 32)

(Aib$^2$,A6c$^5$,A5c$^{12}$,Apc$^{16}$)hGhrelin(1-28)-NH$_2$; (SEQ ID NO: 44)

(A6c$^5$,A5c$^{12}$,Apc$^{16}$)hGhrelin(1-28)-NH$_2$; (SEQ ID NO: 45)

(Aib$^{2,6}$,A5c$^{12}$,Apc$^{16}$)hGhrelin(1-28)-NH$_2$; (SEQ ID NO: 46)

(Aib$^2$,Act$^6$,A5c$^{12}$,Apc$^{16}$)hGhrelin(1-28)-NH$_2$; (SEQ ID NO: 46)

(Aib$^2$,3-Pal$^9$,A5c$^{12}$,Apc$^{16}$)hGhrelin(1-28)-NH$_2$; (SEQ ID NO: 47)

(Aib$^2$,Dmt$^7$,A5c$^{12}$,Apc$^{16}$)hGhrelin(1-28)-NH$_2$; (SEQ ID NO: 48)

(Aib$^2$,Thz$^7$,A5c$^{12}$,Apc$^{16}$)hGhrelin(1-28)-NH$_2$; (SEQ ID NO: 48)

(Aib$^2$,A5c$^{5,12}$,Apc$^{16}$)hGhrelin(1-28)-NH$_2$; (SEQ ID NO: 44)

(Aib$^{2,5}$,A5c$^{12}$,Apc$^{16}$)hGhrelin(1-28)-NH$_2$; (SEQ ID NO: 44)

(Aib$^2$,hLeu$^5$,A5c$^{12}$,Apc$^{16}$)hGhrelin(1-28)-NH$_2$; (SEQ ID NO: 44)

(Aib$^2$,Cha$^5$,A5c$^{12}$,Apc$^{16}$)hGhrelin(1-28)-NH$_2$; (SEQ ID NO: 44)

(Aib$^{2,6}$,A5c$^{12}$,Apc$^{16}$)hGhrelin(1-28)-NH$_2$; (SEQ ID NO: 46)

(Aib$^2$,Thr$^6$,A5c$^{12}$,Apc$^{16}$)hGhrelin(1-28)-NH$_2$; (SEQ ID NO: 46)

(Aib$^2$,Abu$^6$,A5c$^{12}$,Apc$^{16}$)hGhrelin(1-28)-NH$_2$; (SEQ ID NO: 46)

(Aib$^2$,4-Hyp$^7$,A5c$^{12}$,Apc$^{16}$)hGhrelin(1-28)-NH$_2$; (SEQ ID NO: 48)

(Aib$^2$,Pip$^7$,A5c$^{12}$,Apc$^{16}$)hGhrelin(1-28)-NH$_2$; (SEQ ID NO: 48)

(Aib$^2$,Dhp$^7$,A5c$^{12}$,Apc$^{16}$)hGhrelin(1-28)-NH$_2$; (SEQ ID NO: 48)

(Aib$^2$,Ktp$^7$,A5c$^{12}$,Apc$^{16}$)hGhrelin(1-28)-NH$_2$; (SEQ ID NO: 48)

(Aib$^{2,8}$,A5c$^{12}$,Apc$^{16}$)hGhrelin(1-28)-NH$_2$; (SEQ ID NO: 49)

(Aib$^2$,2-Pal$^9$,A5c$^{12}$,Apc$^{16}$)hGhrelin(1-28)-NH$_2$; (SEQ ID NO: 47)

(Aib$^2$,3-Pal$^9$,A5c$^{12}$,Apc$^{16}$)hGhrelin(1-28)-NH$_2$; (SEQ ID NO: 47)

(Aib², 4-Pal⁹, A5c¹², Apc¹⁶)hGhrelin(1-28)-NH₂; (SEQ ID NO: 47)

(Aib², Taz⁹, A5c¹², Apc¹⁶)hGhrelin(1-28)-NH₂; (SEQ ID NO: 47)

(Aib², 2-Thi⁹, A5c¹², Apc¹⁶)hGhrelin(1-28)-NH₂; (SEQ ID NO: 47)

(Aib², 2-Fua⁹, A5c¹², Apc¹⁶)hGhrelin(1-28)-NH₂; (SEQ ID NO: 47)

(Aib², Apc⁹, A5c¹², Apc¹⁶)hGhrelin(1-28)-NH₂; (SEQ ID NO: 47)

(Aib²,⁹, A5c¹², Apc¹⁶)hGhrelin(1-28)-NH₂; (SEQ ID NO: 47)

(Aib²,¹⁰, A5c¹², Apc¹⁶)hGhrelin(1-28)-NH₂; (SEQ ID NO: 50)

(A6c⁵, A5c¹², Orn¹⁵)hGhrelin(1-28)-NH₂; (SEQ ID NO: 38)

(Aib⁶, A5c¹², Orn¹⁵)hGhrelin(1-28)-NH₂; (SEQ ID NO: 51)

(Act⁶, A5c¹², Orn¹⁵)hGhrelin(1-28)-NH₂; (SEQ ID NO: 51)

(3-Pal⁹, A5c¹², Orn¹⁵)hGhrelin(1-28)-NH₂; (SEQ ID NO: 52)

(Dmt⁷, A5c¹², Orn¹⁵)hGhrelin(1-28)-NH₂; (SEQ ID NO: 53)

(Thz⁷, A5c¹², Orn¹⁵)hGhrelin(1-28)-NH₂; (SEQ ID NO: 53)

(A5c⁵, A5c¹², Orn¹⁵)hGhrelin(1-28)-NH₂; (SEQ ID NO: 38)

(Aib⁵, A5c¹², Orn¹⁵)hGhrelin(1-28)-NH₂; (SEQ ID NO: 38)

(hLeu⁵, A5c¹², Orn¹⁵)hGhrelin(1-28)-NH₂; (SEQ ID NO: 38)

(Cha⁵, A5c¹², Orn¹⁵)hGhrelin(1-28)-NH₂; (SEQ ID NO: 38)

(Aib⁶, A5c¹², Orn¹⁵)hGhrelin(1-28)-NH₂; (SEQ ID NO: 51)

(Thr⁶, A5c¹², Orn¹⁵)hGhrelin(1-28)-NH₂; (SEQ ID NO: 51)

(Abu⁶, A5c¹², Orn¹⁵)hGhrelin(1-28)-NH₂; (SEQ ID NO: 51)

(4-Hyp⁷, A5c¹², Orn¹⁵)hGhrelin(1-28)-NH₂; (SEQ ID NO: 53)

(Pip⁷, A5c¹², Orn¹⁵)hGhrelin(1-28)-NH₂; (SEQ ID NO: 53)

(Dhp⁷, A5c¹², Orn¹⁵)hGhrelin(1-28)-NH₂; (SEQ ID NO: 53)

(Ktp⁷, A5c¹², Orn¹⁵)hGhrelin(1-28)-NH₂; (SEQ ID NO: 53)

(Aib⁸, A5c¹², Orn¹⁵)hGhrelin(1-28)-NH₂; (SEQ ID NO: 54)

(2-Pal⁹, A5c¹², Orn¹⁵)hGhrelin(1-28)-NH₂; (SEQ ID NO: 52)

(3-Pal⁹, A5c¹², Orn¹⁵)hGhrelin(1-28)-NH₂; (SEQ ID NO: 52)

(4-Pal⁹, A5c¹², Orn¹⁵)hGhrelin(1-28)-NH₂; (SEQ ID NO: 52)

(Taz⁹, A5c¹², Orn¹⁵)hGhrelin(1-28)-NH₂; (SEQ ID NO: 52)

(2-Thi⁹, A5c¹², Orn¹⁵)hGhrelin(1-28)-NH₂; (SEQ ID NO: 52)

(2-Fua⁹, A5c¹², Orn¹⁵)hGhrelin(1-28)-NH₂; (SEQ ID NO: 52)

(Apc⁹, A5c¹², Orn¹⁵)hGhrelin(1-28)-NH₂; (SEQ ID NO: 52)

(Aib⁹, A5c¹², Orn¹⁵)hGhrelin(1-28)-NH₂; (SEQ ID NO: 52)

(Aib¹⁰, A5c¹², Orn¹⁵)hGhrelin(1-28)-NH₂; (SEQ ID NO: 55)

(Aib⁶, A5c¹², Apc¹⁶)hGhrelin(1-28)-NH₂; (SEQ ID NO: 56)

(A5c⁵, A5c¹², Apc¹⁶)hGhrelin(1-28)-NH₂; (SEQ ID NO: 45)

(Act⁶, A5c¹², Apc¹⁶)hGhrelin(1-28)-NH₂; (SEQ ID NO: 56)

(3-Pal⁹, A5c¹², Apc¹⁶)hGhrelin(1-28)-NH₂; (SEQ ID NO: 57)

(Dmt⁷, A5c¹², Apc¹⁶)hGhrelin(1-28)-NH₂; (SEQ ID NO: 58)

(Thz⁷, A5c¹², Apc¹⁶)hGhrelin(1-28)-NH₂; (SEQ ID NO: 58)

(Aib⁵, A5c¹², Apc¹⁶)hGhrelin(1-28)-NH₂; (SEQ ID NO: 45)

(hLeu⁵,A5c¹²,Apc¹⁶)hGhrelin(1-28)-NH₂; (SEQ ID NO: 45)

(Cha⁵,A5c¹²,Apc¹⁶)hGhrelin(1-28)-NH₂; (SEQ ID NO: 45)

(Thr⁶,A5c¹²,Apc¹⁶)hGhrelin(1-28)-NH₂; (SEQ ID NO: 56)

(Abu⁶,A5c¹²,Apc¹⁶)hGhrelin(1-28)-NH₂; (SEQ ID NO: 56)

(4-Hyp⁷,A5c¹²,Apc¹⁶)hGhrelin(1-28)-NH₂; (SEQ ID NO: 58)

(Pip⁷,A5c¹²,Apc¹⁶)hGhrelin(1-28)-NH₂; (SEQ ID NO: 58)

(Dhp⁷,A5c¹²,Apc¹⁶)hGhrelin(1-28)-NH₂; (SEQ ID NO: 58)

(Ktp⁷,A5c¹²,Apc¹⁶)hGhrelin(1-28)-NH₂; (SEQ ID NO: 58)

(Aib⁸,A5c¹²,Apc¹⁶)hGhrelin(1-28)-NH₂; (SEQ ID NO: 59)

(2-Pal⁹,A5c¹²,Apc¹⁶)hGhrelin(1-28)-NH₂; (SEQ ID NO: 57)

(3-Pal⁹,A5c¹²,Apc¹⁶)hGhrelin(1-28)-NH₂; (SEQ ID NO: 57)

(4-Pal⁹,A5c¹²,Apc¹⁶)hGhrelin(1-28)-NH₂; (SEQ ID NO: 57)

(Taz⁹,A5c¹²,Apc¹⁶)hGhrelin(1-28)-NH₂; (SEQ ID NO: 57)

(2-Thi⁹,A5c¹²,Apc¹⁶)hGhrelin(1-28)-NH₂; (SEQ ID NO: 57)

(2-Fua⁹,A5c¹²,Apc¹⁶)hGhrelin(1-28)-NH₂; (SEQ ID NO: 57)

(Apc⁹,A5c¹²,Apc¹⁶)hGhrelin(1-28)-NH₂; (SEQ ID NO: 57)

(Aib⁹,A5c¹²,Apc¹⁶)hGhrelin(1-28)-NH₂; (SEQ ID NO: 57)

(Aib¹⁰,A5c¹²,Apc¹⁶)hGhrelin(1-28)-NH₂; (SEQ ID NO: 60)

(Aib²,Glu³(NH-hexyl),A6c⁵)hGhrelin(1-28)-NH₂; (SEQ ID NO: 61)

(Glu³(NH-hexyl),A6c⁵)hGhrelin(1-28)-NH₂; (SEQ ID NO: 62)

(Aib²,⁶,Glu³(NH-hexyl))hGhrelin(1-28)-NH₂; (SEQ ID NO: 63)

(Aib²,Glu³(NH-hexyl),Act⁶)hGhrelin(1-28)-NH₂; (SEQ ID NO: 63)

(Aib²,Glu³(NH-hexyl),3-Pal⁹)hGhrelin(1-28)-NH₂; (SEQ ID NO: 64)

(Aib²,Glu³(NH-hexyl),Dmt⁷)hGhrelin(1-28)-NH₂; (SEQ ID NO: 65)

(Aib²,Glu³(NH-hexyl),Thz⁷)hGhrelin(1-28)-NH₂; (SEQ ID NO: 65)

(Aib²,Glu³(NH-hexyl),A5c⁵)hGhrelin(1-28)-NH₂; (SEQ ID NO: 61)

(Aib²,⁵,Glu³(NH-hexyl))hGhrelin(1-28)-NH₂; (SEQ ID NO: 61)

(Aib²,Glu³(NH-hexyl),hLeu⁵)hGhrelin(1-28)-NH₂; (SEQ ID NO: 61)

(Aib²,Cha⁵)hGhrelin(1-28)-NH₂; (SEQ ID NO: 2) Example #81

(Aib²,⁶,Glu³(NH-hexyl))hGhrelin(1-28)-NH₂; (SEQ ID NO: 63)

(Aib²,Glu³(NH-hexyl),Thr⁶)hGhrelin(1-28)-NH₂; (SEQ ID NO: 63)

(Aib²,Glu³(NH-hexyl),Abu⁶)hGhrelin(1-28)-NH₂; (SEQ ID NO: 63)

(Aib²,Glu³(NH-hexyl),4-Hyp⁷)hGhrelin(1-28)-NH₂; (SEQ ID NO: 65) Example #79

(Aib²,Glu³(NH-hexyl),Pip⁷)hGhrelin(1-28)-NH₂; (SEQ ID NO: 65)

(Aib²,Glu³(NH-hexyl),Dhp⁷)hGhrelin(1-28)-NH₂; (SEQ ID NO: 65)

(Aib²,Glu³(NH-hexyl),Ktp⁷)hGhrelin(1-28)-NH₂; (SEQ ID NO: 65)

(Aib²,⁸,Glu³(NH-hexyl))hGhrelin(1-28)-NH₂; (SEQ ID NO: 27) Example #56

(Aib²,Glu³(NH-hexyl),2-Pal⁹)hGhrelin(1-28)-NH₂; (SEQ ID NO: 64)

(Aib²,Glu³(NH-hexyl),3-Pal⁹)hGhrelin(1-28)-NH₂; (SEQ ID NO: 64) Example #80

(Aib²,Glu³(NH-hexyl),4-Pal⁹)hGhrelin(1-28)-NH₂; (SEQ ID NO: 64) Example #85

-continued (Aib², Glu³(NH-hexyl), Taz⁹)hGhrelin(1-28)-NH₂; (SEQ ID NO: 64) Example #43

(Aib², Glu³(NH-hexyl), 2-Thi⁹)hGhrelin(1-28)-NH₂; (SEQ ID NO: 64) Example #51

(Aib², Glu³(NH-hexyl), 2-Fua⁹)hGhrelin(1-28)-NH₂; (SEQ ID NO: 64)

(Aib², Glu³(NH-hexyl), Apc⁹)hGhrelin(1-28)-NH₂; (SEQ ID NO: 64)

(Aib²,⁹, Glu³(NH-hexyl))hGhrelin(1-28)-NH₂; (SEQ ID NO: 64)

(Aib²,¹⁰, Glu³(NH-hexyl))hGhrelin(1-28)-NH₂; (SEQ ID NO: 28) Example #59

(Glu³(NH-hexyl), Aib⁶)hGhrelin(1-28)-NH₂; (SEQ ID NO: 66)

(Glu³(NH-hexyl), A5c⁵)hGhrelin(1-28)-NH₂; (SEQ ID NO: 62)

(Glu³(NH-hexyl), Act⁶)hGhrelin(1-28)-NH₂; (SEQ ID NO: 66)

(Glu³(NH-hexyl), 3-Pal⁹)hGhrelin(1-28)-NH₂; (SEQ ID NO: 67)

(Glu³(NH-hexyl), Dmt⁷)hGhrelin(1-28)-NH₂; (SEQ ID NO: 68)

(Glu³(NH-hexyl), Thz⁷)hGhrelin(1-28)-NH₂; (SEQ ID NO: 68)

(Glu³(NH-hexyl), Aib⁵)hGhrelin(1-28)-NH₂; (SEQ ID NO: 62)

(Glu³(NH-hexyl), hLeu⁵)hGhrelin(1-28)-NH₂; (SEQ ID NO: 62)

(Glu³(NH-hexyl), Cha⁵)hGhrelin(1-28)-NH₂; (SEQ ID NO: 62)

(Glu³(NH-hexyl), Thr⁶)hGhrelin(1-28)-NH₂; (SEQ ID NO: 66)

(Glu³(NH-hexyl), Abu⁶)hGhrelin(1-28)-NH₂; (SEQ ID NO: 66)

(Glu³(NH-hexyl), 4-Hyp⁷)hGhrelin(1-28)-NH₂; (SEQ ID NO: 68) Example #82

(Glu³(NH-hexyl), Pip⁷)hGhrelin(1-28)-NH₂; (SEQ ID NO: 68)

(Glu³(NH-hexyl), Dhp⁷)hGhrelin(1-28)-NH₂; (SEQ ID NO: 68)

(Glu³(NH-hexyl), Ktp⁷)hGhrelin(1-28)-NH₂; (SEQ ID NO: 68)

(Glu³(NH-hexyl), Aib⁸)hGhrelin(1-28)-NH₂; (SEQ ID NO: 35) Example #35

(Glu³(NH-hexyl), 2-Pal⁹)hGhrelin(1-28)-NH₂; (SEQ ID NO: 67)

(Glu³(NH-hexyl), 3-Pal⁹)hGhrelin(1-28)-NH₂; (SEQ ID NO: 67)

(Glu³(NH-hexyl), 4-Pal⁹)hGhrelin(1-28)-NH₂; (SEQ ID NO: 67)

(Glu³(NH-hexyl), Taz⁹)hGhrelin(1-28)-NH₂; (SEQ ID NO: 67)

(Glu³(NH-hexyl), 2-Thi⁹)hGhrelin(1-28)-NH₂; (SEQ ID NO: 67)

(Glu³(NH-hexyl), 2-Fua⁹)hGhrelin(1-28)-NH₂; (SEQ ID NO: 67)

(Glu³(NH-hexyl), Apc⁹)hGhrelin(1-28)-NH₂; (SEQ ID NO: 67)

(Glu³(NH-hexyl), Aib⁹)hGhrelin(1-28)-NH₂; (SEQ ID NO: 67)

(Glu³(NH-hexyl), Aib¹⁰)hGhrelin(1-28)-NH₂; (SEQ ID NO: 36)

(Aib², Glu³(NH-hexyl), A6c⁵, A5c¹², Orn¹⁵)hGhrelin(1-28)-NH₂; (SEQ ID NO: 69)

(A6c⁵, Glu³(NH-hexyl), A5c¹², Orn¹⁵)hGhrelin(1-28)-NH₂; (SEQ ID NO: 70)

(Aib²,⁶, Glu³(NH-hexyl), A5c¹², Orn¹⁵)hGhrelin(1-28)-NH₂; (SEQ ID NO: 71)

(Aib², Glu³(NH-hexyl), Act⁶, A5c¹², Orn¹⁵)hGhrelin(1-28)-NH₂; (SEQ ID NO: 71)

(Aib², Glu³(NH-hexyl), 3-Pal⁹, A5c¹², Orn¹⁵)hGhrelin(1-28)-NH₂; (SEQ ID NO: 72)

(Aib², Glu³(NH-hexyl), Dmt⁷, A5c¹², Orn¹⁵)hGhrelin(1-28)-NH₂; (SEQ ID NO: 73)

(Aib², Glu³(NH-hexyl), Thz⁷, A5c¹², Orn¹⁵)hGhrelin(1-28)-NH₂; (SEQ ID NO: 73)

(Aib², Glu³(NH-hexyl), A5c⁵, A5c¹², Orn¹⁵)hGhrelin(1-28)-NH₂; (SEQ ID NO: 69)

(Aib²,⁵, Glu³(NH-hexyl), A5c¹², Orn¹⁵)hGhrelin(1-28)-NH₂; (SEQ ID NO: 69)

(Aib², hLeu⁵, A5c¹², Orn¹⁵)hGhrelin(1-28)-NH₂; (SEQ ID NO: 37)

-continued (Aib$^2$,Glu$^3$(NH-hexyl),Cha$^5$,A5c$^{12}$,Orn$^{15}$)hGhrelin(1-28)-NH$_2$; (SEQ ID NO: 69)

(Aib$^{2,6}$,Glu$^3$(NH-hexyl),A5c$^{12}$,Orn$^{15}$)hGhrelin(1-28)-NH$_2$; (SEQ ID NO: 71)

(Aib$^2$,Glu$^3$(NH-hexyl),Thr$^6$,A5c$^{12}$,Orn$^{15}$)hGhrelin(1-28)-NH$_2$; (SEQ ID NO: 71)

(Aib$^2$,Glu$^3$(NH-hexyl),Abu$^6$,A5c$^{12}$,Orn$^{15}$)hGhrelin(1-28)-NH$_2$; (SEQ ID NO: 71)

(Aib$^2$,Glu$^3$(NH-hexyl),4-Hyp$^7$,A5c$^{12}$,Orn$^{15}$)hGhrelin(1-28)-NH$_2$; (SEQ ID NO: 73)

(Aib$^2$,Glu$^3$(NH-hexyl),Pip$^7$,A5c$^{12}$,Orn$^{15}$)hGhrelin(1-28)-NH$_2$; (SEQ ID NO: 73)

(Aib$^2$,Glu$^3$(NH-hexyl),Dhp$^7$,A5c$^{12}$,Orn$^{15}$)hGhrelin(1-28)-NH$_2$; (SEQ ID NO: 73)

(Aib$^2$,Glu$^3$(NH-hexyl),Ktp$^7$,A5c$^{12}$,Orn$^{15}$)hGhrelin(1-28)-NH$_2$; (SEQ ID NO: 73)

(Aib$^{2,8}$,Glu$^3$(NH-hexyl),A5c$^{12}$,Orn$^{15}$)hGhrelin(1-28)-NH$_2$; (SEQ ID NO: 74)

(Aib$^2$,Glu$^3$(NH-hexyl),2-Pal$^9$,A5c$^{12}$,Orn$^{15}$)hGhrelin(1-28)-NH$_2$; (SEQ ID NO: 72)

(Aib$^2$,Glu$^3$(NH-hexyl),3-Pal$^9$,A5c$^{12}$,Orn$^{15}$)hGhrelin(1-28)-NH$_2$; (SEQ ID NO: 72)

(Aib$^2$,Glu$^3$(NH-hexyl),4-Pal$^9$,A5c$^{12}$,Orn$^{15}$)hGhrelin(1-28)-NH$_2$; (SEQ ID NO: 72)

(Aib$^2$,Glu$^3$(NH-hexyl),Taz$^9$,A5c$^{12}$,Orn$^{15}$)hGhrelin(1-28)-NH$_2$; (SEQ ID NO: 72)

(Aib$^2$,Glu$^3$(NH-hexyl),2-Thi$^9$,A5c$^{12}$,Orn$^{15}$)hGhrelin(1-28)-NH$_2$; (SEQ ID NO: 72)

(Aib$^2$,Glu$^3$(NH-hexyl),2-Fua$^9$,A5c$^{12}$,Orn$^{15}$)hGhrelin(1-28)-NH$_2$; (SEQ ID NO: 72)

(Aib$^2$,Glu$^3$(NH-hexyl),Apc$^9$,A5c$^{12}$,Orn$^{15}$)hGhrelin(1-28)-NH$_2$; (SEQ ID NO: 72)

(Aib$^{2,9}$,Glu$^3$(NH-hexyl),A5c$^{12}$,Orn$^{15}$)hGhrelin(1-28)-NH$_2$; (SEQ ID NO: 72)

(Aib$^{2,12}$,Glu$^3$(NH-hexyl),4-Pal$^9$,Orn$^{15}$)hGhrelin(1-28)-NH$_2$; (SEQ ID NO: 75) Example #89

(Aib$^{2,10}$,Glu$^3$(NH-hexyl),A5c$^{12}$,Orn$^{15}$)hGhrelin(1-28)-NH$_2$; (SEQ ID NO: 76)

(Aib$^2$,Glu$^3$(NH-hexyl),A6c$^5$,A5c$^{12}$,Apc$^{16}$)hGhrelin(1-28)-NH$_2$; (SEQ ID NO: 77)

(Glu$^3$(NH-hexyl),A6c$^5$,A5c$^{12}$,Apc$^{16}$)hGhrelin(1-28)-NH$_2$; (SEQ ID NO: 78)

(Aib$^{2,6}$,Glu$^3$(NH-hexyl),A5c$^{12}$,Apc$^{16}$)hGhrelin(1-28)-NH$_2$; (SEQ ID NO: 79)

(Aib$^2$,Glu$^3$(NH-hexyl),Act$^6$,A5c$^{12}$,Apc$^{16}$)hGhrelin(1-28)-NH$_2$; (SEQ ID NO: 79)

(Aib$^2$,Glu$^3$(NH-hexyl),3-Pal$^9$,A5c$^{12}$,Apc$^{16}$)hGhrelin(1-28)-NH$_2$; (SEQ ID NO: 80)

(Aib$^2$,Glu$^3$(NH-hexyl),Dmt$^7$,A5c$^{12}$,Apc$^{16}$)hGhrelin(1-28)-NH$_2$; (SEQ ID NO: 81)

(Aib$^2$,Glu$^3$(NH-hexyl),Thz$^7$,A5c$^{12}$,Apc$^{16}$)hGhrelin(1-28)-NH$_2$; (SEQ ID NO: 81)

(Aib$^2$,Glu$^3$(NH-hexyl),A5c$^{5,\,12}$,Apc$^{16}$)hGhrelin(1-28)-NH$_2$; (SEQ ID NO: 77)

(Aib$^{2,5}$,Glu$^3$(NH-hexyl),A5c$^{12}$,Apc$^{16}$)hGhrelin(1-28)-NH$_2$; (SEQ ID NO: 77)

(Aib$^2$,Glu$^3$(NH-hexyl),hLeu$^5$,A5c$^{12}$,Apc$^{16}$)hGhrelin(1-28)-NH$_2$; (SEQ ID NO: 77)

(Aib$^2$,Glu$^3$(NH-hexyl),Cha$^5$,A5c$^{12}$,Apc$^{16}$)hGhrelin(1-28)-NH$_2$; (SEQ ID NO: 77)

(Aib$^{2,6}$,Glu$^3$(NH-hexyl),A5c$^{12}$,Apc$^{16}$)hGhrelin(1-28)-NH$_2$; (SEQ ID NO: 79)

(Aib$^2$,Glu$^3$(NH-hexyl),Thr$^6$,A5c$^{12}$,Apc$^{16}$)hGhrelin(1-28)-NH$_2$; (SEQ ID NO: 79)

(Aib$^2$,Glu$^3$(NH-hexyl),Abu$^6$,A5c$^{12}$,Apc$^{16}$)hGhrelin(1-28)-NH$_2$; (SEQ ID NO: 79)

(Aib$^2$,Glu$^3$(NH-hexyl),4-Hyp$^7$,A5c$^{12}$,Apc$^{16}$)hGhrelin(1-28)-NH$_2$; (SEQ ID NO: 81)

(Aib$^2$,Glu$^3$(NH-hexyl),Pip$^7$,A5c$^{12}$,Apc$^{16}$)hGhrelin(1-28)-NH$_2$; (SEQ ID NO: 81)

(Aib$^2$,Glu$^3$(NH-hexyl),Dhp$^7$,A5c$^{12}$,Apc$^{16}$)hGhrelin(1-28)-NH$_2$; (SEQ ID NO: 81)

(Aib$^2$,Glu$^3$(NH-hexyl),Ktp$^7$,A5c$^{12}$,Apc$^{16}$)hGhrelin(1-28)-NH$_2$; (SEQ ID NO: 81)

(Aib$^{2,8}$,Glu$^3$(NH-hexyl),A5c$^{12}$,Apc$^{16}$)hGhrelin(1-28)-NH$_2$; (SEQ ID NO: 82)

(Aib$^2$,Glu$^3$(NH-hexyl),2-Pal$^9$,A5c$^{12}$,Apc$^{16}$)hGhrelin(1-28)-NH$_2$; (SEQ ID NO: 80)

(Aib$^2$,Glu$^3$(NH-hexyl),3-Pal$^9$,A5c$^{12}$,Apc$^{16}$)hGhrelin(1-28)-NH$_2$; (SEQ ID NO: 80)

(Aib², Glu³(NH-hexyl), 4-Pal⁹, A5c¹², Apc¹⁶)hGhrelin(1-28)-NH₂; (SEQ ID NO: 80)

(Aib², Glu³(NH-hexyl), Taz⁹, A5c¹², Apc¹⁶)hGhrelin(1-28)-NH₂; (SEQ ID NO: 80)

(Aib², Glu³(NH-hexyl), 2-Thi⁹, A5c¹², Apc¹⁶)hGhrelin(1-28)-NH₂; (SEQ ID NO: 80)

(Aib², Glu³(NH-hexyl), 2-Fua⁹, A5c¹², Apc¹⁶)hGhrelin(1-28)-NH₂; (SEQ ID NO: 80)

(Aib², Glu³(NH-hexyl), Apc⁹, A5c¹², Apc¹⁶)hGhrelin(1-28)-NH₂; (SEQ ID NO: 80)

(Aib²,⁹, Glu³(NH-hexyl), A5c¹², Apc¹⁶)hGhrelin(1-28)-NH₂; (SEQ ID NO: 80)

(Aib²,¹⁰, Glu³(NH-hexyl), A5c¹², Apc¹⁶)hGhrelin(1-28)-NH₂; (SEQ ID NO: 83)

(Glu³(O-hexyl))hGhrelin(1-28)-NH₂; (SEQ ID NO: 1) Example #21

(Aib²)hGhrelin(1-28)-NH₂; (SEQ ID NO: 10) Example #25

(Glu³(NH-hexyl))hGhrelin(1-28)-NH₂; (SEQ ID NO: 1) Example #76

(Aib², Glu³(O-hexyl))hGhrelin(1-28)-NH₂; (SEQ ID NO: 84)

(Aib¹, Glu³(O-hexyl))hGhrelin(1-28)-NH₂; (SEQ ID NO: 85)

(Aib², Glu³(NH-hexyl))hGhrelin(1-28)-NH₂; (SEQ ID NO: 84) Example #8

(Dap³(1-octanesulfonyl))hGhrelin(1-28)-NH₂; (SEQ ID NO: 1)

(Aib², Dap³(1-octanesulfonyl))hGhrelin(1-28)-NH₂; (SEQ ID NO: 84)

(Aib¹, Dap³(1-octanesulfonyl))hGhrelin(1-28)-NH₂; (SEQ ID NO: 85)

(Ava², Dap³(1-octanesulfonyl))hGhrelin(2-28)-NH₂; (SEQ ID NO: 86)

(Ac-Gly¹)hGhrelin(1-5)-NH₂; (SEQ ID NO: 87)

(Ac-Gly¹)hGhrelin(1-6)-NH₂; (SEQ ID NO: 88)

(Ac-Gly¹)hGhrelin(1-7)-NH₂; (SEQ ID NO: 89)

(Ac-Gly¹, Aib²)hGhrelin(1-28)-NH₂; (SEQ ID NO: 90) Example #63

(Ac-Gly¹, Aib², Glu³(NH-hexyl))hGhrelin(1-5)-NH₂; (SEQ ID NO: 91)

(Ac-Gly¹, Aib², Glu³(NH-hexyl))hGhrelin(1-6)-NH₂; (SEQ ID NO: 92)

(Ac-Gly¹, Aib², Glu³(NH-hexyl))hGhrelin(1-7)-NH₂; (SEQ ID NO: 93)

(Ac-Gly¹, Aib², Glu³(NH-hexyl), Arg⁸)hGhrelin(1-8)-NH₂; (SEQ ID NO: 94)

(Ac-Gly¹, Aib², Glu³(NH-hexyl), Lys⁸)hGhrelin(1-8)-NH₂; (SEQ ID NO: 94)

(n-butyryl-Gly¹)hGhrelin(1-28)-NH₂; (SEQ ID NO: 95) Example #95

(isobutyryl-Gly¹)hGhrelin(1-28)-NH₂; (SEQ ID NO: 95) Example #99

(n-octanoyl-Gly¹)hGhrelin(1-28)-NH₂; (SEQ ID NO: 95) Example #92

Cys³(S(CH₂)₉CH₃)hGhrelin(1-28)-NH₂; (SEQ ID NO: 1) Example #61

(Lys⁵)hGhrelin(1-28)-NH₂ (SEQ ID NO: 3) Example #42

(Aib², Ser³)hGhrelin(1-28)-NH₂; (SEQ ID NO: 10)

(Aib²,⁶, Ser³)hGhrelin(1-28)-NH₂ (SEQ ID NO: 4)

(Aib², Ser³, 3-Pal⁹)hGhrelin(1-28)-NH₂; (SEQ ID NO: 8)

(Aib², Ser³, Thz⁷)hGhrelin(1-28)-NH₂; (SEQ ID NO: 9)

(Aib², Ser³, Cha⁵)hGhrelin(1-28)-NH₂; (SEQ ID NO: 2)

(Aib², Ser³, Abu⁶)hGhrelin(1-28)-NH₂; (SEQ ID NO: 4)

(Aib², Ser³, 4-Hyp⁷)hGhrelin(1-28)-NH₂; (SEQ ID NO: 9)

(Aib², Ser³, Taz⁹)hGhrelin(1-28)-NH₂; (SEQ ID NO: 8)

(Aib², Ser³, Dhp⁷)hGhrelin(1-28)-NH₂; (SEQ ID NO: 9)

(Aib²,⁸, Ser³)hGhrelin(1-28)-NH₂; (SEQ ID NO: 11)

-continued (Aib², Ser³, Pip⁷)hGhrelin(1-28)-NH₂; (SEQ ID NO: 9)

(Ac-Gly¹, Aib²,¹⁰, Ser³)hGhrelin(1-28)-NH₂; (SEQ ID NO: 96)

(Aib²,¹⁰, Ser³)hGhrelin(1-28)-NH₂; (SEQ ID NO: 12)

(n-butyryl-Gly¹, Aib², Ser³)hGhrelin(1-28)-NH₂; (SEQ ID NO: 97)

(Ac-Gly¹, Aib², Ser³)hGhrelin(1-28)-NH₂; (SEQ ID NO: 97)

(Aib², Ser³, Tic⁷)hGhrelin(1-28)-NH₂; (SEQ ID NO: 9)

(Ac-Gly¹, Aib², Ser³, Arg⁸)hGhrelin(1-28)-NH₂; (SEQ ID NO: 98)

(Ser³, Aib⁸)hGhrelin(1-28)-NH₂; (SEQ ID NO: 16)

(Ser³, Taz⁹)hGhrelin(1-28)-NH₂; (SEQ ID NO: 14)

(Ser³, 3-Pal⁹)hGhrelin(1-28)-NH₂; (SEQ ID NO: 14)

(Ser³, 4-Pal⁹)hGhrelin(1-28)-NH₂; (SEQ ID NO: 14)

(Aib², Ser³, 2-Thi⁹)hGhrelin(1-28)-NH₂; (SEQ ID NO: 8)

(Ser³, 2-Thi⁹)hGhrelin(1-28)-NH₂; (SEQ ID NO: 14)

(Ser³, 4-Hyp⁷)hGhrelin(1-28)-NH₂; (SEQ ID NO: 15)

(Aib², Ser³, Tic⁷)hGhrelin(1-28)-NH₂; (SEQ ID NO: 9)

(Aib², Thr³)hGhrelin(1-28)-NH₂; (SEQ ID NO: 99)

(Aib²,⁶, Thr³)hGhrelin(1-28)-NH₂; (SEQ ID NO: 99)

(A5c⁵, Thr³)hGhrelin(1-28)-NH₂; (SEQ ID NO: 100)

(Aib², Thr³, 3-Pal⁹)hGhrelin(1-28)-NH₂; (SEQ ID NO: 101)

(Aib², Thr³, Thz⁷)hGhrelin(1-28)-NH₂; (SEQ ID NO: 102)

(Aib², Thr³, Cha⁵)hGhrelin(1-28)-NH₂; (SEQ ID NO: 103)

(Aib², Thr³, Abu⁶)hGhrelin(1-28)-NH₂; (SEQ ID NO: 99)

(Aib², Thr³, 4-Hyp⁷)hGhrelin(1-28)-NH₂; (SEQ ID NO: 102)

(Aib², Thr³, Taz⁹)hGhrelin(1-28)-NH₂; (SEQ ID NO: 101)

(Aib², Thr³, Dhp⁷)hGhrelin(1-28)-NH₂; (SEQ ID NO: 102)

(Aib²,⁸, Thr³)hGhrelin(1-28)-NH₂; (SEQ ID NO: 11)

(Aib², Thr³, Pip⁷)hGhrelin(1-28)-NH₂; (SEQ ID NO: 102)

(Ac-Gly¹, Aib²,¹⁰, Thr³)hGhrelin(1-28)-NH₂; (SEQ ID NO: 104)

(Aib²,¹⁰, Thr³)hGhrelin(1-28)-NH₂; (SEQ ID NO: 106)

(n-butyryl-Gly¹, Aib², Thr³)hGhrelin(1-28)-NH₂; (SEQ ID NO: 105)

(Ac-Gly¹, Aib², Thr³)hGhrelin(1-28)-NH₂; (SEQ ID NO: 105)

(Aib², Thr³, Tic⁷)hGhrelin(1-28)-NH₂; (SEQ ID NO: 102)

(Ac-Gly¹, Aib², Thr³, Arg⁸)hGhrelin(1-28)-NH₂; (SEQ ID NO: 90)

(Thr³, Aib⁸)hGhrelin(1-28)-NH₂; (SEQ ID NO: 107)

(Thr³, Taz⁹)hGhrelin(1-28)-NH₂; (SEQ ID NO: 108)

(Thr³, 3-Pal⁹)hGhrelin(1-28)-NH₂; (SEQ ID NO: 108)

(Thr³, 4-Pal⁹)hGhrelin(1-28)-NH₂; (SEQ ID NO: 108)

(Aib², Thr³, 2-Thi⁹)hGhrelin(1-28)-NH₂; (SEQ ID NO: 101)

(Thr³, 2-Thi⁹)hGhrelin(1-28)-NH₂; (SEQ ID NO: 108)

(Thr³, 4-Hyp⁷)hGhrelin(1-28)-NH₂; (SEQ ID NO: 109)

(Aib², Thr³, Tic⁷)hGhrelin(1-28)-NH₂; (SEQ ID NO: 102)

(Ac-Gly¹, Glu³(NH-hexyl))hGhrelin(1-28)-NH₂; or (SEQ ID NO: 110)

or pharmaceutically acceptable salts thereof.

In one aspect, the invention provides a method of treating gastrointestinal conditions such as gastroesophageal reflux disease, IBS, constipation, ileus, emesis, gastroparesis, and colonic pseudo-obstruction and the like, by administering a therapeutically effective amount of a peptidyl ghrelin analog according to the following formula (II):

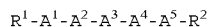

wherein:

A¹ is Aib, Apc or Inp;
A² is D-Bal, D-Bip, D-Bpa, D-Dip, D-1-Nal, D-2-Nal, D-Ser(Bzl), or D-Trp;
A³ is D-Bal, D-Bip, D-Bpa, D-Dip, D-1-Nal, D-2-Nal, D-Ser(Bzl), or D-Trp;
A⁴ is 2-Fua, Orn, 2-Pal, 3-Pal, 4-Pal, Pff, Phe, Pim, Taz, 2-Thi, 3-Thi, Thr(Bzl);
A⁵ is Apc, Dab, Dap, Lys, Orn, or deleted;
R¹ is hydrogen, $(C_{1-6})$alkyl, $(C_{5-14})$aryl, $(C_{1-6})$alkyl$(C_{5-14})$aryl, $(C_{3-8})$cycloakyl, or $(C_{2-10})$acyl; and
R² is OH or NH₂;
provided that when A⁵ is Dab, Dap, Lys, or Orn, then:
A² is D-Bip, D-Bpa, D-Dip or D-Bal; or
A³ is D-Bip, D-Bpa, D-Dip or D-Bal; or
A⁴ is 2-Thi, 3-Thi, Taz, 2-Fua, 2-Pal, 3-Pal, 4-Pal, Orn, Thr(Bzl), or Pff;

when A¹ is deleted, then:
A³ is D-Bip, D-Bpa, or D-Dip; or
A⁴ is 2-Fua, Pff, Taz, or Thr(Bzl); or
A¹ is Apc when
A² is D-Bip, D-Bpa, D-Dip or D-Bal; or
A³ is D-Bip, D-Bpa, D-Dip or D-Bal; or
A⁴ is 2-Thi, 3-Thi, Orn, 2-Pal, 3-Pal or 4-Pal;
or a pharmaceutically acceptable salt thereof.

In yet another aspect, the invention provides a preferred compound of formula (II), wherein:
A¹ is Aib, Apc or H-Inp;
A² is D-Bal, D-Bip, D-Bpa, D-Dip, D-1-Nal, D-2-Nal, D-Ser(Bzl), or D-Trp;
A³ is D-Bal, D-Bpa, D-Dip, D-1-Nal, D-2-Nal, or D-Trp;
A⁴ is Orn, 3-Pal, 4-Pal, Pff, Phe, Pim, Taz, 2-Thi, or Thr(Bzl); and
A⁵ is Apc, Lys, or deleted;
or a pharmaceutically acceptable salt thereof.

In yet another aspect of the immediately foregoing group of compounds, the invention provides a preferred compound of formula (II), wherein:
A¹ is Apc or H-Inp;
A² is D-Bal, D-Bip, D-1-Nal, or D-2-Nal;
A³ is D-Bal, D-1-Nal, D-2-Nal, or D-Trp;
A⁴ is 3-Pal, 4 Pal, Pff, Phe, Pim, Taz, 2-Thi, or Thr(Bzl); and
or a pharmaceutically acceptable salt thereof.

In yet another aspect, the invention provides a preferred group of compounds according to formula (I), where the compound is:

```
Inp-D-2-Nal-D-Trp-Phe-Lys-NH₂        (SEQ ID NO: 111) Example 2

H-Inp-D-1-Nal-D-Trp-3-Pal-Lys-NH₂;   (SEQ ID NO: 112) Example #50

H-Inp-D-2-Nal-D-Trp-4-Pal-Lys-NH₂;   (SEQ ID NO: 113)

H-Inp-D-2-Nal-D-Trp-Orn-Lys-NH₂;     (SEQ ID NO: 113) Example #116

H-Inp-D-Bip-D-Trp-Phe-Lys-NH₂;       (SEQ ID NO: 111) Example #66

H-Inp-D-2-Nal-D-Trp-Thr(Bzl)-Lys-NH₂; (SEQ ID NO: 113)

H-Inp-D-2-Nal-D-Trp-Pff-Lys-NH₂;     (SEQ ID NO: 113) Example #100

H-Inp-D-2-Nal-D-Trp-2-Thi-Lys-NH₂;   (SEQ ID NO: 113) Example #15

H-Inp-D-2-Nal-D-Trp-Taz-Lys-NH₂;     (SEQ ID NO: 113) Example #37

H-Inp-D-Dip-D-Trp-Phe-Lys-NH₂;       (SEQ ID NO: 111) Example #105

H-Inp-D-Bpa-D-Trp-Phe-Lys-NH₂;       (SEQ ID NO: 111) Example #109

H-Inp-D-2-Nal-D-Bpa-Phe-Lys-NH₂;     (SEQ ID NO: 114) Example #118

H-Inp-D-2-Nal-D-Trp-3-Pal-NH₂;       (SEQ ID NO: 115) Example #93

H-Inp-D-2-Nal-D-Trp-4-Pal-NH₂;       (SEQ ID NO: 115) Example #112

H-Inp-D-1-Nal-D-Trp-3-Pal-NH₂;       (SEQ ID NO: 116) Example #97

H-Inp-D-Bip-D-Trp-Phe-NH₂;           (SEQ ID NO: 117) Example #98

H-Inp-D-2-Nal-D-Trp-Thr(Bzl)-NH₂;    (SEQ ID NO: 115) Example #87

H-Inp-D-2-Nal-D-Trp-Pff-NH₂;         (SEQ ID NO: 115) Example #103

H-Inp-D-2-Nal-D-Trp-2-Thi-NH₂;       (SEQ ID NO: 115) Example #84
```

-continued

H-Inp-D-2-Nal-D-Trp-Taz-NH$_2$; (SEQ ID NO: 115) Example #90

H-Inp-D-Dip-D-Trp-Phe-NH$_2$; (SEQ ID NO: 117) Example #111

H-Inp-D-2-Nal-D-Dip-Phe-NH$_2$; (SEQ ID NO: 118) Example #110

H-Inp-D-Bal-D-Trp-Phe-NH$_2$; (SEQ ID NO: 119) Example #78

H-Inp-D-2-Nal-D-Bal-Phe-NH$_2$; (SEQ ID NO: 118) Example #101

H-Inp-D-2-Nal-D-Trp-3-Pal-Lys-NH$_2$; (SEQ ID NO: 113) Example #71

H-Inp-D-Trp-D-2-Nal(Ψ)-Pim; (SEQ ID NO: 120) Example #115

H-Inp-D-Bal-D-Trp-2-Thi-Lys-NH$_2$; (SEQ ID NO: 121) Example #12

H-Inp-D-Bal-D-Trp-Phe-Lys-NH$_2$; (SEQ ID NO: 111) Example #5

H-Inp-D-1-Nal-D-Trp-2-Thi-Lys-NH$_2$; (SEQ ID NO: 112) Example #3

H-Inp-D-2-Nal-D-Trp-Phe-Apc-NH$_2$; (SEQ ID NO: 122) Example #28

H-Inp-D-1-Nal-D-Trp-Phe-Apc-NH$_2$; (SEQ ID NO: 122) Example #6

H-Inp-D-Bal-D-Trp-Phe-Apc-NH$_2$; (SEQ ID NO: 122) Example #19

H-Apc-D-2-Nal-D-Trp-Phe-Lys-NH$_2$; (SEQ ID NO: 123) Example #11

H-Apc-D-1-Nal-D-Trp-2-Thi-Lys-NH$_2$; (SEQ ID NO: 124) Example #1

H-Inp-D-1-Nal-D-Trp-2-Thi-NH$_2$; (SEQ ID NO: 116) Example #39

H-Apc-D-1-Nal-D-Trp-Phe-NH$_2$; (SEQ ID NO: 125) Example #31

H-Inp-D-2-Nal-D-Trp(Ψ)-Pim; (SEQ ID NO: 126) Example #113

H-Inp-D-1-Nal-D-Trp(Ψ)-Pim; (SEQ ID NO: 126) Example #107

H-Inp-D-Bal-D-Trp(Ψ)-Pim; (SEQ ID NO: 126) Example #106

H-Aib-D-Ser(Bzl)-D-Trp(Ψ)-Pim; (SEQ ID NO: 127) Example #119

H-Inp-D-1-Nal-D-Trp-Taz-Lys-NH$_2$; (SEQ ID NO: 112) Example #57

H-Inp-D-Bal-D-Trp-Taz-Lys-NH$_2$; (SEQ ID NO: 121) Example #23

H-Apc-D-1-Nal-D-Trp-Taz-Lys-NH$_2$; (SEQ ID NO: 124) Example #14

H-Apc-D-Bal-D-Trp-Taz-Lys-NH$_2$; (SEQ ID NO: 128) Example #20

H-Apc-D-Bal-D-Trp-2-Thi-Lys-NH$_2$; (SEQ ID NO: 128) Example #7

H-Apc-D-Bal-D-Trp-Phe-Lys-NH$_2$; (SEQ ID NO: 123) Example #4

H-Apc-D-1-Nal-D-Trp-Phe-Apc-NH$_2$; (SEQ ID NO: 129) Example #18

H-Apc-D-Bal-D-Trp-Phe-Apc-NH$_2$; (SEQ ID NO: 130) Example #33

H-Apc-D-1-Nal-D-1-Nal-Phe-Apc-NH$_2$; (SEQ ID NO: 129) Example #74

H-Apc-D-1-Nal-D-2-Nal-Phe-Apc-NH$_2$; (SEQ ID NO: 129) Example #73

H-Apc-D-1-Nal-D-1-Nal-Phe-Lys-NH$_2$; (SEQ ID NO: 131) Example #64

H-Apc-D-Bal-D-1-Nal-Phe-Apc-NH$_2$; (SEQ ID NO: 130) Example #83

H-Apc-D-Bal-D-2-Nal-Phe-Apc-NH$_2$; (SEQ ID NO: 130) Example #69

H-Apc-D-Bal-D-1-Nal-Phe-Lys-NH$_2$; (SEQ ID NO: 132)

H-Apc-D-Bal-D-2-Nal-Phe-Lys-NH$_2$; (SEQ ID NO: 132) Example #30

H-Apc-D-1-Nal-D-Trp-2-Thi-NH$_2$; (SEQ ID NO: 133) Example #34

H-Apc-D-Bal-D-Trp-Phe-NH$_2$; (SEQ ID NO: 125) Example #41

H-Apc-D-1-Nal-D-Trp-Taz-NH$_2$; (SEQ ID NO: 133) Example #67

H-Apc-D-Bal-D-Trp-2-Thi-NH$_2$; (SEQ ID NO: 144) Example #47

H-Apc-D-Bal-D-Trp-Taz-NH$_2$; (SEQ ID NO: 144) Example #72

-continued

H-Apc-D-2-Nal-D-Trp-2-Thi-NH$_2$; (SEQ ID NO: 134) Example #45

H-Apc-D-2-Nal-D-Trp-Taz-NH$_2$; (SEQ ID NO: 134) Example #77

H-Inp-D-1-Nal-D-Trp-Taz-Apc-NH$_2$; (SEQ ID NO: 135) Example #60

H-Inp-D-Bal-D-Trp-Taz-Apc-NH$_2$; (SEQ ID NO: 135) Example #38

H-Apc-D-1-Nal-D-Trp-Taz-Apc-NH$_2$; (SEQ ID NO: 136) Example #46

H-Apc-D-Bal-D-Trp-Taz-Apc-NH$_2$; (SEQ ID NO: 136) Example #58

H-Apc-D-1-Nal-D-Trp-2-Fua-Apc-NH$_2$; (SEQ ID NO: 137)

H-Apc-D-1-Nal-D-Trp-2-Fua-Lys-NH$_2$; (SEQ ID NO: 124)

H-Apc-D-1-Nal-D-Trp-2-Fua-NH$_2$; (SEQ ID NO: 133)

H-Apc-D-1-Nal-D-Trp-2-Pal-NH$_2$; (SEQ ID NO: 133)

H-Apc-D-1-Nal-D-Trp-3-Pal-NH$_2$; (SEQ ID NO: 133)

H-Apc-D-1-Nal-D-Trp-3-Thi-Apc-NH$_2$; (SEQ ID NO: 137)

H-Apc-D-1-Nal-D-Trp-3-Thi-Lys-NH$_2$; (SEQ ID NO: 124)

H-Apc-D-1-Nal-D-Trp-3-Thi-NH$_2$; (SEQ ID NO: 133)

H-Apc-D-1-Nal-D-Trp-4-Pal-NH$_2$; (SEQ ID NO: 133)

H-Apc-D-1-Nal-D-Trp-Pff-Apc-NH$_2$; (SEQ ID NO: 137)

H-Apc-D-1-Nal-D-Trp-Pff-Lys-NH$_2$; (SEQ ID NO: 124)

H-Apc-D-1-Nal-D-Trp-Pff-NH$_2$; (SEQ ID NO: 133)

H-Apc-D-2-Nal-D-Trp-2-Fua-Apc-NH$_2$; (SEQ ID NO: 138)

H-Apc-D-2-Nal-D-Trp-2-Fua-Lys-NH$_2$; (SEQ ID NO: 139)

H-Apc-D-2-Nal-D-Trp-2-Fua-NH$_2$; (SEQ ID NO: 134)

H-Apc-D-2-Nal-D-Trp-2-Pal-NH$_2$; (SEQ ID NO: 134)

H-Apc-D-2-Nal-D-Trp-2-Thi-Apc-NH$_2$; (SEQ ID NO: 138)

H-Apc-D-2-Nal-D-Trp-2-Thi-Lys-NH$_2$; (SEQ ID NO: 139)

H-Apc-D-2-Nal-D-Trp-3-Pal-NH$_2$; (SEQ ID NO: 134)

H-Apc-D-2-Nal-D-Trp-3-Thi-Apc-NH$_2$; (SEQ ID NO: 138)

H-Apc-D-2-Nal-D-Trp-3-Thi-Lys-NH$_2$; (SEQ ID NO: 139)

H-Apc-D-2-Nal-D-Trp-3-Thi-NH$_2$; (SEQ ID NO: 134)

H-Apc-D-2-Nal-D-Trp-4-Pal-NH$_2$; (SEQ ID NO: 134)

H-Apc-D-2-Nal-D-Trp-Pff-Apc-NH$_2$; (SEQ ID NO: 138)

H-Apc-D-2-Nal-D-Trp-Pff-Lys-NH$_2$; (SEQ ID NO: 139)

H-Apc-D-2-Nal-D-Trp-Pff-NH$_2$; (SEQ ID NO: 134)

H-Apc-D-2-Nal-D-Trp-Taz-Apc-NH$_2$; (SEQ ID NO: 136)

H-Apc-D-2-Nal-D-Trp-Taz-Lys-NH$_2$; (SEQ ID NO: 139)

H-Apc-D-Bal-D-Bal-2-Fua-Apc-NH$_2$; (SEQ ID NO: 140)

H-Apc-D-Bal-D-Bal-2-Fua-Lys-NH$_2$; (SEQ ID NO: 141)

H-Apc-D-Bal-D-Bal-2-Fua-NH$_2$; (SEQ ID NO: 142)

H-Apc-D-Bal-D-Bal-2-Pal-NH$_2$; (SEQ ID NO: 142)

H-Apc-D-Bal-D-Bal-2-Thi-Apc-NH$_2$; (SEQ ID NO: 140)

H-Apc-D-Bal-D-Bal-2-Thi-Lys-NH$_2$; (SEQ ID NO: 141)

-continued

H-Apc-D-Bal-D-Bal-2-Thi-NH$_2$; (SEQ ID NO: 142)

H-Apc-D-Bal-D-Bal-3-Pal-NH$_2$; (SEQ ID NO: 142)

H-Apc-D-Bal-D-Bal-3-Thi-Apc-NH$_2$; (SEQ ID NO: 140)

H-Apc-D-Bal-D-Bal-3-Thi-Lys-NH$_2$; (SEQ ID NO: 141)

H-Apc-D-Bal-D-Bal-3-Thi-NH$_2$; (SEQ ID NO: 142)

H-Apc-D-Bal-D-Bal-4-Pal-NH$_2$; (SEQ ID NO: 142)

H-Apc-D-Bal-D-Bal-Pff-Apc-NH$_2$; (SEQ ID NO: 140)

H-Apc-D-Bal-D-Bal-Pff-Lys-NH$_2$; (SEQ ID NO: 141)

H-Apc-D-Bal-D-Bal-Pff-NH$_2$; (SEQ ID NO: 142)

H-Apc-D-Bal-D-Bal-Phe-Apc-NH$_2$; (SEQ ID NO: 130)

H-Apc-D-Bal-D-Bal-Phe-Lys-NH$_2$; (SEQ ID NO: 132)

H-Apc-D-Bal-D-Bal-Phe-NH$_2$; (SEQ ID NO: 142)

H-Apc-D-Bal-D-Bal-Taz-Apc-NH$_2$; (SEQ ID NO: 140)

H-Apc-D-Bal-D-Bal-Taz-Lys-NH$_2$; (SEQ ID NO: 141)

H-Apc-D-Bal-D-Bal-Taz-NH$_2$; (SEQ ID NO: 142)

H-Apc-D-Bal-D-Trp-2-Fua-Apc-NH$_2$; (SEQ ID NO: 143)

H-Apc-D-Bal-D-Trp-2-Fua-Lys-NH$_2$; (SEQ ID NO: 128)

H-Apc-D-Bal-D-Trp-2-Fua-NH$_2$; (SEQ ID NO: 144)

H-Apc-D-Bal-D-Trp-2-Pal-NH$_2$; (SEQ ID NO: 144)

H-Apc-D-Bal-D-Trp-3-Pal-NH$_2$; (SEQ ID NO: 144)

H-Apc-D-Bal-D-Trp-3-Thi-Apc-NH$_2$; (SEQ ID NO: 143)

H-Apc-D-Bal-D-Trp-3-Thi-Lys-NH$_2$; (SEQ ID NO: 128)

H-Apc-D-Bal-D-Trp-3-Thi-NH$_2$; (SEQ ID NO: 144)

H-Apc-D-Bal-D-Trp-4-Pal-NH$_2$; (SEQ ID NO: 144)

H-Apc-D-Bal-D-Trp-Pff-Apc-NH$_2$; (SEQ ID NO: 143)

H-Apc-D-Bal-D-Trp-Pff-Lys-NH$_2$; (SEQ ID NO: 128)

H-Apc-D-Bal-D-Trp-Pff-NH$_2$; (SEQ ID NO: 144)

H-Inp-D-1-Nal-D-Bal-2-Fua-Lys-NH$_2$; (SEQ ID NO: 145)

H-Inp-D-1-Nal-D-Bal-2-Fua-NH$_2$; (SEQ ID NO: 146)

H-Inp-D-1-Nal-D-Bal-2-Thi-Lys-NH$_2$; (SEQ ID NO: 145)

H-Inp-D-1-Nal-D-Bal-3-Thi-Lys-NH$_2$; (SEQ ID NO: 145)

H-Inp-D-1-Nal-D-Bal-Pff-Lys-NH$_2$; (SEQ ID NO: 145)

H-Inp-D-1-Nal-D-Bal-Pff-NH$_2$; (SEQ ID NO: 146)

H-Inp-D-1-Nal-D-Bal-Phe-Lys-NH$_2$; (SEQ ID NO: 145)

H-Inp-D-1-Nal-D-Bal-Taz-Lys-NH$_2$; (SEQ ID NO: 145)

H-Inp-D-1-Nal-D-Bal-Taz-NH$_2$; (SEQ ID NO: 146)

H-Inp-D-1-Nal-D-Trp-2-Fua-Apc-NH$_2$; (SEQ ID NO: 147)

H-Inp-D-1-Nal-D-Trp-2-Fua-Lys-NH$_2$; (SEQ ID NO: 112)

H-Inp-D-1-Nal-D-Trp-2-Fua-NH$_2$; (SEQ ID NO: 116)

H-Inp-D-1-Nal-D-Trp-3-Thi-Apc-NH$_2$; (SEQ ID NO: 147)

H-Inp-D-1-Nal-D-Trp-3-Thi-Lys-NH$_2$; (SEQ ID NO: 112)

H-Inp-D-1-Nal-D-Trp-Pff-Apc-NH$_2$; (SEQ ID NO: 147)

H-Inp-D-1-Nal-D-Trp-Pff-Lys-NH$_2$; (SEQ ID NO: 112)

H-Inp-D-1-Nal-D-Trp-Pff-NH$_2$; (SEQ ID NO: 116)

H-Inp-D-1-Nal-D-Trp-Taz-NH$_2$; (SEQ ID NO: 116)

H-Inp-D-2-Nal-D-Trp-2-Fua-Apc-NH$_2$; (SEQ ID NO: 148)

H-Inp-D-2-Nal-D-Trp-2-Fua-NH$_2$; (SEQ ID NO: 115)

H-Inp-D-2-Nal-D-Trp-2-Thi-Apc-NH$_2$; (SEQ ID NO: 148)

H-Inp-D-2-Nal-D-Trp-3-Thi-Apc-NH$_2$; (SEQ ID NO: 148)

H-Inp-D-2-Nal-D-Trp-3-Thi-Lys-NH$_2$; (SEQ ID NO: 113)

H-Inp-D-2-Nal-D-Trp-3-Thi-NH$_2$; (SEQ ID NO: 115)

H-Inp-D-2-Nal-D-Trp-Pff-Apc-NH$_2$; (SEQ ID NO: 148)

H-Inp-D-2-Nal-D-Trp-Pff-NH$_2$; (SEQ ID NO: 115)

H-Inp-D-2-Nal-D-Trp-Taz-Apc-NH$_2$; (SEQ ID NO: 135)

H-Inp-D-2-Nal-D-Trp-Taz-NH$_2$; (SEQ ID NO: 115)

H-Inp-D-Bal-D-Bal-2-Fua-Lys-NH$_2$; (SEQ ID NO: 149)

H-Inp-D-Bal-D-Bal-2-Fua-NH$_2$; (SEQ ID NO: 150)

H-Inp-D-Bal-D-Bal-2-Thi-Lys-NH$_2$; (SEQ ID NO: 149)

H-Inp-D-Bal-D-Bal-3-Thi-Lys-NH$_2$; (SEQ ID NO: 149)

H-Inp-D-Bal-D-Bal-Pff-Lys-NH$_2$; (SEQ ID NO: 149)

H-Inp-D-Bal-D-Bal-Pff-NH$_2$; (SEQ ID NO: 150)

H-Inp-D-Bal-D-Bal-Phe-Lys-NH$_2$; (SEQ ID NO: 149)

H-Inp-D-Bal-D-Bal-Taz-Lys-NH$_2$; (SEQ ID NO: 149)

H-Inp-D-Bal-D-Bal-Taz-NH$_2$; (SEQ ID NO: 150)

H-Inp-D-Bal-D-Trp-2-Fua-Apc-NH$_2$; (SEQ ID NO: 151)

H-Inp-D-Bal-D-Trp-2-Fua-Lys-NH$_2$; (SEQ ID NO: 121)

H-Inp-D-Bal-D-Trp-2-Fua-NH$_2$; (SEQ ID NO: 152)

H-Inp-D-Bal-D-Trp-3-Thi-Apc-NH$_2$; (SEQ ID NO: 151)

H-Inp-D-Bal-D-Trp-3-Thi-Lys-NH$_2$; (SEQ ID NO: 121)

H-Inp-D-Bal-D-Trp-Pff-Apc-NH$_2$; (SEQ ID NO: 151)

H-Inp-D-Bal-D-Trp-Pff-Lys-NH$_2$; (SEQ ID NO: 121)

H-Inp-D-Bal-D-Trp-Pff-NH$_2$; (SEQ ID NO: 152)

H-Inp-D-Bal-D-Trp-Taz-NH$_2$; (SEQ ID NO: 152)

H-Inp-D-Bip-D-Bal-2-Fua-Lys-NH$_2$; (SEQ ID NO: 153)

H-Inp-D-Bip-D-Bal-2-Fua-NH$_2$; (SEQ ID NO: 154)

H-Inp-D-Bip-D-Bal-2-Thi-Lys-NH$_2$; (SEQ ID NO: 153)

H-Inp-D-Bip-D-Bal-3-Thi-Lys-NH$_2$; (SEQ ID NO: 153)

H-Inp-D-Bip-D-Bal-Pff-Lys-NH$_2$; (SEQ ID NO: 153)

H-Inp-D-Bip-D-Bal-Pff-NH$_2$; or (SEQ ID NO: 154)

H-Inp-D-Bip-D-Bal-Taz-Lys-NH$_2$; (SEQ ID NO: 153)

H-Inp-D-Bip-D-Bal-Taz-NH$_2$; (SEQ ID NO: 154)

-continued

H-Inp-D-Bip-D-Trp-2-Fua-Lys-NH$_2$; (SEQ ID NO: 155)

H-Inp-D-Bip-D-Trp-2-Fua-NH$_2$; (SEQ ID NO: 156)

H-Inp-D-Bip-D-Trp-2-Thi-Lys-NH$_2$; (SEQ ID NO: 155)

H-Inp-D-Bip-D-Trp-3-Thi-Lys-NH$_2$; (SEQ ID NO: 155)

H-Inp-D-Bip-D-Trp-Pff-Lys-NH$_2$; (SEQ ID NO: 155)

H-Inp-D-Bip-D-Trp-Pff-NH$_2$; (SEQ ID NO: 156)

H-Inp-D-Bip-D-Trp-Taz-Lys-NH$_2$; or (SEQ ID NO: 155)

H-Inp-D-Bip-D-Trp-Taz-NH$_2$; (SEQ ID NO: 156)

H-Inp-D-1-Nal-D-Trp-3-Pal-Lys-NH$_2$; (SEQ ID NO: 112)

H-Inp-D-2-Nal-D-Trp-4-Pal-Lys-NH$_2$; (SEQ ID NO: 113) Example #91

H-Inp-D-2-Nal-D-Trp-Orn-Lys-NH$_2$; (SEQ ID NO: 113)

H-Inp-D-Bip-D-Trp-Phe-Lys-NH$_2$; (SEQ ID NO: 111)

H-Inp-D-2-Nal-D-Trp-Thr(Bzl)-Lys-NH$_2$; (SEQ ID NO: 113) Example #70

H-Inp-D-2-Nal-D-Trp-Pff-Lys-NH$_2$; (SEQ ID NO: 113)

H-Inp-D-2-Nal-D-Trp-2-Thi-Lys-NH$_2$; (SEQ ID NO: 113)

H-Inp-D-2-Nal-D-Trp-Taz-Lys-NH$_2$; (SEQ ID NO: 113)

H-Inp-D-Dip-D-Trp-Phe-Lys-NH$_2$; (SEQ ID NO: 111)

H-Inp-D-Bpa-D-Trp-Phe-Lys-NH$_2$; (SEQ ID NO: 111)

H-Inp-D-2-Nal-D-Bpa-Phe-Lys-NH$_2$; (SEQ ID NO: 114)

H-Inp-D-2-Nal-D-Trp-Thr(Bzl)-NH$_2$; (SEQ ID NO: 115)

H-Inp-D-2-Nal-D-Trp-Pff-NH$_2$; (SEQ ID NO: 115)

H-Inp-D-2-Nal-D-Trp-Taz-NH$_2$; (SEQ ID NO: 115)

H-Inp-D-2-Nal-D-Dip-Phe-NH$_2$; (SEQ ID NO: 118)

H-Inp-D-2-Nal-D-Trp-3-Pal-Lys-NH$_2$; (SEQ ID NO: 113)

H-Inp-D-Trp-D-2-Nal(Ψ)-Pim; (SEQ ID NO: 120)

H-Inp-D-Bal-D-Trp-2-Thi-Lys-NH$_2$; (SEQ ID NO: 121)

H-Inp-D-Bal-D-Trp-Phe-Lys-NH$_2$; (SEQ ID NO: 111)

H-Inp-D-1-Nal-D-Trp-2-Thi-Lys-NH$_2$; (SEQ ID NO: 112)

H-Inp-D-2-Nal-D-Trp-Phe-Apc-NH$_2$; (SEQ ID NO: 122)

H-Inp-D-1-Nal-D-Trp-Phe-Apc-NH$_2$; (SEQ ID NO: 122)

H-Inp-D-Bal-D-Trp-Phe-Apc-NH$_2$; (SEQ ID NO: 122)

H-Apc-D-2-Nal-D-Trp-Phe-Lys-NH$_2$; (SEQ ID NO: 123)

H-Apc-D-1-Nal-D-Trp-2-Thi-Lys-NH$_2$; (SEQ ID NO: 124)

H-Inp-D-2-Nal-D-Trp(Ψ)-Pim; (SEQ ID NO: 126)

H-Inp-D-1-Nal-D-Trp(Ψ)-Pim; (SEQ ID NO: 126)

H-Inp-D-Bal-D-Trp(Ψ)-Pim; (SEQ ID NO: 126)

H-Aib-D-Ser(Bzl)-D-Trp(Ψ)-Pim; (SEQ ID NO: 127)

H-Inp-D-1-Nal-D-Trp-Taz-Lys-NH$_2$; (SEQ ID NO: 112)

H-Inp-D-Bal-D-Trp-Taz-Lys-NH$_2$; (SEQ ID NO: 121)

H-Apc-D-1-Nal-D-Trp-Taz-Lys-NH$_2$; (SEQ ID NO: 124)

H-Apc-D-Bal-D-Trp-Taz-Lys-NH$_2$; (SEQ ID NO: 128)

-continued

H-Apc-D-Bal-D-Trp-2-Thi-Lys-NH$_2$; (SEQ ID NO: 128)

H-Apc-D-Bal-D-Trp-Phe-Lys-NH$_2$; (SEQ ID NO: 123)

H-Apc-D-1-Nal-D-Trp-Phe-Apc-NH$_2$; (SEQ ID NO: 129)

H-Apc-D-Bal-D-Trp-Phe-Apc-NH$_2$; (SEQ ID NO: 130)

H-Apc-D-1-Nal-D-1-Nal-Phe-Apc-NH$_2$; (SEQ ID NO: 129)

H-Apc-D-1-Nal-D-2-Nal-Phe-Apc-NH$_2$; (SEQ ID NO: 129)

H-Apc-D-1-Nal-D-1-Nal-Phe-Lys-NH$_2$; (SEQ ID NO: 131)

H-Apc-D-Bal-D-1-Nal-Phe-Apc-NH$_2$; (SEQ ID NO: 130)

H-Apc-D-Bal-D-2-Nal-Phe-Apc-NH$_2$; (SEQ ID NO: 130)

H-Apc-D-Bal-D-1-Nal-Phe-Lys-NH$_2$; (SEQ ID NO: 132)

H-Apc-D-Bal-D-2-Nal-Phe-Lys-NH$_2$; (SEQ ID NO: 132)

H-Apc-D-1-Nal-D-Trp-2-Thi-NH$_2$; (SEQ ID NO: 133)

H-Apc-D-Bal-D-Trp-Phe-NH$_2$; (SEQ ID NO: 157)

H-Apc-D-1-Nal-D-Trp-Taz-NH$_2$; (SEQ ID NO: 133)

H-Apc-D-Bal-D-Trp-2-Thi-NH$_2$; (SEQ ID NO: 157)

H-Apc-D-Bal-D-Trp-Taz-NH$_2$; (SEQ ID NO: 157)

H-Apc-D-2-Nal-D-Trp-2-Thi-NH$_2$; (SEQ ID NO: 134)

H-Apc-D-2-Nal-D-Trp-Taz-NH$_2$; (SEQ ID NO: 134)

H-Inp-D-1-Nal-D-Trp-Taz-Apc-NH$_2$; (SEQ ID NO: 135)

H-Inp-D-Bal-D-Trp-Taz-Apc-NH$_2$; (SEQ ID NO: 135)

H-Apc-D-1-Nal-D-Trp-Taz-Apc-NH$_2$; (SEQ ID NO: 136)

H-Apc-D-Bal-D-Trp-Taz-Apc-NH$_2$; (SEQ ID NO: 136)

H-Inp-D-2-Nal-D-Trp-3-Thi-Lys-NH$_2$; (SEQ ID NO: 113)

H-Inp-D-Bal-D-Trp-3-Thi-Lys-NH$_2$; (SEQ ID NO: 121)

H-Inp-D-Bal-D-Trp-2-Fua-Lys-NH$_2$; (SEQ ID NO: 121)

H-Inp-D-Bal-D-Trp-Pff-Lys-NH$_2$; (SEQ ID NO: 121)

H-Inp-D-Bal-D-Trp-3-Thi-Apc-NH$_2$; (SEQ ID NO: 151)

H-Inp-D-Bal-D-Trp-2-Fua-Apc-NH$_2$; (SEQ ID NO: 151)

H-Inp-D-Bal-D-Trp-Pff-Apc-NH$_2$; (SEQ ID NO: 151)

H-Apc-D-Bal-D-Trp-3-Thi-Lys-NH$_2$; (SEQ ID NO: 128)

H-Apc-D-Bal-D-Trp-2-Fua-Lys-NH$_2$; (SEQ ID NO: 128)

H-Apc-D-Bal-D-Trp-Pff-Lys-NH$_2$; (SEQ ID NO: 128)

H-Inp-D-Bal-D-Bal-Phe-Lys-NH$_2$; (SEQ ID NO: 149)

H-Inp-D-Bal-D-Bal-2-Thi-Lys-NH$_2$; (SEQ ID NO: 149)

H-Inp-D-Bal-D-Bal-3-Thi-Lys-NH$_2$; (SEQ ID NO: 149)

H-Inp-D-Bal-D-Bal-Taz-Lys-NH$_2$; (SEQ ID NO: 149)

H-Inp-D-Bal-D-Bal-2-Fua-Lys-NH$_2$; (SEQ ID NO: 149)

H-Inp-D-Bal-D-Bal-Pff-Lys-NH$_2$; (SEQ ID NO: 149)

H-Apc-D-Bal-D-Bal-Phe-Lys-NH$_2$; (SEQ ID NO: 132)

H-Apc-D-Bal-D-Bal-2-Thi-Lys-NH$_2$; (SEQ ID NO: 141)

-continued

H-Apc-D-Bal-D-Bal-3-Thi-Lys-NH$_2$; (SEQ ID NO: 141)

H-Apc-D-Bal-D-Bal-Taz-Lys-NH$_2$; (SEQ ID NO: 141)

H-Apc-D-Bal-D-Bal-2-Fua-Lys-NH$_2$; (SEQ ID NO: 141)

H-Apc-D-Bal-D-Bal-Pff-Lys-NH$_2$; (SEQ ID NO: 141)

H-Inp-D-1-Nal-D-Trp-3-Thi-Lys-NH$_2$; (SEQ ID NO: 112)

H-Inp-D-1-Nal-D-Trp-2-Fua-Lys-NH$_2$; (SEQ ID NO: 112)

H-Inp-D-1-Nal-D-Trp-Pff-Lys-NH$_2$; (SEQ ID NO: 112)

H-Inp-D-1-Nal-D-Bal-Phe-Lys-NH$_2$; (SEQ ID NO: 158)

H-Inp-D-1-Nal-D-Bal-2-Thi-Lys-NH$_2$; (SEQ ID NO: 158)

H-Inp-D-1-Nal-D-Bal-3-Thi-Lys-NH$_2$; (SEQ ID NO: 158)

H-Inp-D-1-Nal-D-Bal-Taz-Lys-NH$_2$; (SEQ ID NO: 158)

H-Inp-D-1-Nal-D-Bal-2-Fua-Lys-NH$_2$; (SEQ ID NO: 158)

H-Inp-D-1-Nal-D-Bal-Pff-Lys-NH$_2$; (SEQ ID NO: 158)

H-Inp-D-2-Nal-D-Trp-2-Thi-Apc-NH$_2$; (SEQ ID NO: 159)

H-Inp-D-2-Nal-D-Trp-3-Thi-Apc-NH$_2$; (SEQ ID NO: 159)

H-Inp-D-2-Nal-D-Trp-Taz-Apc-NH$_2$; (SEQ ID NO: 135)

H-Inp-D-2-Nal-D-Trp-2-Fua-Apc-NH$_2$; (SEQ ID NO: 159)

H-Inp-D-2-Nal-D-Trp-Pff-Apc-NH$_2$; (SEQ ID NO: 159)

H-Inp-D-1-Nal-D-Trp-3-Thi-Apc-NH$_2$; (SEQ ID NO: 160)

H-Inp-D-1-Nal-D-Trp-2-Fua-Apc-NH$_2$; (SEQ ID NO: 160)

H-Inp-D-1-Nal-D-Trp-Pff-Apc-NH$_2$; (SEQ ID NO: 160)

H-Apc-D-1-Nal-D-Trp-3-Thi-Lys-NH$_2$; (SEQ ID NO: 124)

H-Apc-D-1-Nal-D-Trp-2-Fua-Lys-NH$_2$; (SEQ ID NO: 124)

H-Apc-D-1-Nal-D-Trp-Pff-Lys-NH$_2$; (SEQ ID NO: 124)

H-Apc-D-2-Nal-D-Trp-2-Thi-Lys-NH$_2$; (SEQ ID NO: 139)

H-Apc-D-2-Nal-D-Trp-3-Thi-Lys-NH$_2$; (SEQ ID NO: 139)

H-Apc-D-2-Nal-D-Trp-Taz-Lys-NH$_2$; (SEQ ID NO: 139)

H-Apc-D-2-Nal-D-Trp-2-Fua-Lys-NH$_2$; (SEQ ID NO: 139)

H-Apc-D-2-Nal-D-Trp-Pff-Lys-NH$_2$; (SEQ ID NO: 139)

H-Inp-D-Bip-D-Trp-2-Thi-Lys-NH$_2$; (SEQ ID NO: 155)

H-Inp-D-Bip-D-Trp-3-Thi-Lys-NH$_2$; (SEQ ID NO: 155)

H-Inp-D-Bip-D-Trp-Taz-Lys-NH$_2$; (SEQ ID NO: 155)

H-Inp-D-Bip-D-Trp-2-Fua-Lys-NH$_2$; (SEQ ID NO: 155)

H-Inp-D-Bip-D-Trp-Pff-Lys-NH$_2$; (SEQ ID NO: 155)

H-Inp-D-Bip-D-Bal-2-Thi-Lys-NH$_2$; (SEQ ID NO: 153)

H-Inp-D-Bip-D-Bal-3-Thi-Lys-NH$_2$; (SEQ ID NO: 153)

H-Inp-D-Bip-D-Bal-Taz-Lys-NH$_2$; (SEQ ID NO: 153)

H-Inp-D-Bip-D-Bal-2-Fua-Lys-NH$_2$; (SEQ ID NO: 153)

H-Inp-D-Bip-D-Bal-Pff-Lys-NH$_2$; (SEQ ID NO: 153)

H-Apc-D-Bal-D-Trp-3-Thi-Apc-NH$_2$; (SEQ ID NO: 143)

H-Apc-D-Bal-D-Trp-2-Fua-Apc-NH$_2$; (SEQ ID NO: 143)

-continued

H-Apc-D-Bal-D-Trp-Pff-Apc-NH$_2$; (SEQ ID NO: 143)

H-Apc-D-Bal-D-Bal-Phe-Apc-NH$_2$; (SEQ ID NO: 130)

H-Apc-D-Bal-D-Bal-2-Thi-Apc-NH$_2$; (SEQ ID NO: 140)

H-Apc-D-Bal-D-Bal-3-Thi-Apc-NH$_2$; (SEQ ID NO: 140)

H-Apc-D-Bal-D-Bal-Taz-Apc-NH$_2$; (SEQ ID NO: 140)

H-Apc-D-Bal-D-Bal-2-Fua-Apc-NH$_2$; (SEQ ID NO: 140)

H-Apc-D-Bal-D-Bal-Pff-Apc-NH$_2$; (SEQ ID NO: 140)

H-Apc-D-1-Nal-D-Trp-3-Thi-Apc-NH$_2$; (SEQ ID NO: 137)

H-Apc-D-1-Nal-D-Trp-2-Fua-Apc-NH$_2$; (SEQ ID NO: 137)

H-Apc-D-1-Nal-D-Trp-Pff-Apc-NH$_2$; (SEQ ID NO: 137)

H-Apc-D-2-Nal-D-Trp-2-Thi-Apc-NH$_2$; (SEQ ID NO: 138)

H-Apc-D-2-Nal-D-Trp-3-Thi-Apc-NH$_2$; (SEQ ID NO: 138)

H-Apc-D-2-Nal-D-Trp-Taz-Apc-NH$_2$; (SEQ ID NO: 136)

H-Apc-D-2-Nal-D-Trp-2-Fua-Apc-NH$_2$; (SEQ ID NO: 138)

H-Apc-D-2-Nal-D-Trp-Pff-Apc-NH$_2$; (SEQ ID NO: 138)

H-Inp-D-Bal-D-Trp-Taz-NH$_2$; (SEQ ID NO: 152)

H-Inp-D-Bal-D-Trp-2-Fua-NH$_2$; (SEQ ID NO: 152)

H-Inp-D-Bal-D-Trp-Pff-NH$_2$; (SEQ ID NO: 152)

H-Apc-D-Bal-D-Trp-3-Thi-NH$_2$; (SEQ ID NO: 157)

H-Apc-D-Bal-D-Trp-2-Fua-NH$_2$; (SEQ ID NO: 157)

H-Apc-D-Bal-D-Trp-Pff-NH$_2$ (SEQ ID NO: 157)

H-Apc-D-Bal-D-Trp-4-Pal-NH$_2$; (SEQ ID NO: 157)

H-Apc-D-Bal-D-Trp-3-Pal-NH$_2$; (SEQ ID NO: 157)

H-Apc-D-Bal-D-Trp-2-Pal-NH$_2$; (SEQ ID NO: 157)

H-Inp-D-Bal-D-Bal-Taz-NH$_2$; (SEQ ID NO: 150)

H-Inp-D-Bal-D-Bal-2-Fua-NH$_2$; (SEQ ID NO: 150)

H-Inp-D-Bal-D-Bal-Pff-NH$_2$; (SEQ ID NO: 150)

H-Apc-D-Bal-D-Bal-Phe-NH$_2$; (SEQ ID NO: 142)

H-Apc-D-Bal-D-Bal-2-Thi-NH$_2$; (SEQ ID NO: 142)

H-Apc-D-Bal-D-Bal-3-Thi-NH$_2$; (SEQ ID NO: 142)

H-Apc-D-Bal-D-Bal-Taz-NH$_2$; (SEQ ID NO: 142)

H-Apc-D-Bal-D-Bal-2-Fua-NH$_2$; (SEQ ID NO: 142)

H-Apc-D-Bal-D-Bal-Pff-NH$_2$; (SEQ ID NO: 142)

H-Apc-D-Bal-D-Bal-4-Pal-NH$_2$; (SEQ ID NO: 142)

H-Apc-D-Bal-D-Bal-3-Pal-NH$_2$; (SEQ ID NO: 142)

H-Apc-D-Bal-D-Bal-2-Pal-NH$_2$; (SEQ ID NO: 142)

H-Inp-D-1-Nal-D-Trp-Taz-NH$_2$; (SEQ ID NO: 116)

H-Inp-D-1-Nal-D-Trp-2-Fua-NH$_2$; (SEQ ID NO: 116)

H-Inp-D-1-Nal-D-Trp-Pff-NH$_2$; (SEQ ID NO: 116)

H-Inp-D-1-Nal-D-Bal-Taz-NH$_2$; (SEQ ID NO: 161)

-continued

H-Inp-D-1-Nal-D-Bal-2-Fua-NH$_2$; (SEQ ID NO: 161)

H-Inp-D-1-Nal-D-Bal-Pff-NH$_2$; (SEQ ID NO: 161)

H-Inp-D-2-Nal-D-Trp-Taz-NH$_2$; (SEQ ID NO: 115)

H-Inp-D-2-Nal-D-Trp-2-Fua-NH$_2$; (SEQ ID NO: 115)

H-Inp-D-2-Nal-D-Trp-Pff-NH$_2$; (SEQ ID NO: 115)

H-Apc-D-1-Nal-D-Trp-3-Thi-N$_2$; (SEQ ID NO: 133)

H-Apc-D-1-Nal-D-Trp-2-Fua-NH$_2$; (SEQ ID NO: 133)

H-Apc-D-1-Nal-D-Trp-Pff-NH$_2$; (SEQ ID NO: 133)

H-Apc-D-1-Nal-D-Trp-4-Pal-NH$_2$; (SEQ ID NO: 133)

H-Apc-D-1-Nal-D-Trp-3-Pal-NH$_2$; (SEQ ID NO: 133)

H-Apc-D-1-Nal-D-Trp-2-Pal-NH$_2$; (SEQ ID NO: 133)

H-Apc-D-2-Nal-D-Trp-3-Thi-NH$_2$; (SEQ ID NO: 134)

H-Apc-D-2-Nal-D-Trp-2-Fua-NH$_2$; (SEQ ID NO: 134)

H-Apc-D-2-Nal-D-Trp-Pff-NH$_2$; (SEQ ID NO: 134)

H-Apc-D-2-Nal-D-Trp-4-Pal-NH$_2$; (SEQ ID NO: 134)

H-Apc-D-2-Nal-D-Trp-3-Pal-NH$_2$; (SEQ ID NO: 134)

H-Apc-D-2-Nal-D-Trp-2-Pal-NH$_2$; (SEQ ID NO: 134)

H-Inp-D-Bip-D-Trp-Taz-NH$_2$; (SEQ ID NO: 156)

H-Inp-D-Bip-D-Trp-2-Fua-NH$_2$; (SEQ ID NO: 156)

H-Inp-D-Bip-D-Trp-Pff-NH$_2$; (SEQ ID NO: 156)

H-Inp-D-Bip-D-Bal-Taz-NH$_2$; (SEQ ID NO: 154)

H-Inp-D-Bip-D-Bal-2-Fua-NH$_2$; or (SEQ ID NO: 154)

H-Inp-D-Bip-D-Bal-Pff-NH$_2$; (SEQ ID NO: 154)

H-Inp-D-1-Nal-D-Trp-2-Thi-Apc-NH$_2$; (SEQ ID NO: 147) Example #24

H-Inp-D-Bal-D-Trp-2-Thi-Apc-NH$_2$; (SEQ ID NO: 151) Example #9

H-Apc-D-1-Nal-D-Trp-2-Thi-Apc-NH$_2$; (SEQ ID NO: 137) Example #17

H-Apc-D-Bal-D-Trp-2-Thi-Apc-NH$_2$; or (SEQ ID NO: 143) Example #22

H-Apc-D-1-Nal-D-Trp-Phe-Lys-NH$_2$ (SEQ ID NO: 131) Example #13 or a pharmaceutically acceptable salts thereof.

In yet another aspect, the invention provides a method of treating gastrointestinal conditions such as gastroesophageal reflux disease, IBS, constipation, ileus, emesis, gastroparesis, and colonic pseudo-obstruction and the like, by administering a therapeutically effective amount of a peptidyl ghrelin analog according to the following formula (III):

$(R^2R^3)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$R^1$ wherein:

$A^1$ is Gly, Aib, Ala, β-Ala, Acc or Gly(myristyl);

$A^2$ is Ser, Aib, Ala, Acc, Abu, Act, Ava, Thr or Val;

$A^3$ is Ser, Ser(C(O)—$R^4$), Asp(O—$R^8$), Asp(NH—$R^9$), Cys(S—$R^{14}$), Dap(S(O)$_2$—$R^{10}$), Dab(S(O)$_2$—$R^{11}$), Glu(O—$R^6$), Glu(NH—$R^7$), Thr(C(O)—$R^5$) or HN—CH((CH)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, ($X^1$, $X^2$, $X^3$, $X^4$, $X^5$)Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

$A^6$ is Ser, Abu, Acc, Act, Aib, Ala, Gly, Thr or Val;

$A^7$ is Pro, Dhp, Dmt, 3-Hyp, 4-Hyp, Inc, Ktp, Oic, Pip, Thz or Tic;

$A^8$ is Glu, Acc, Aib, Arg, Asn, Asp, Dab, Dap, Gln, Lys, Orn or HN—CH((CH$_2$)$_n$—N($R^{12}R^{13}$))—C(O);

$A^9$ is H is, Apc, Aib, Acc, 2-Fua, 2-Pal, 3-Pal, 4-Pal, Taz, 2-Thi, 3-Thi or ($X^1$, $X^2$, $X^3$, $X^4$, $X^5$-)Phe;

$A^{10}$ is Gln, Acc, Aib, Asn, Asp or Glu;

$A^{11}$ is Arg, Apc, hArg, Dab, Dap, Lys, Orn or HN—CH((CH$_2$)$_n$—N($R^{12}R^{13}$))—C(O);

$A^{12}$ is Val, Abu, Acc, Aib, Ala, Cha, Nva, Gly, Ile, Leu, Nle, Tle or Cha;

$A^{13}$ is Gln, Acc, Aib, Asn, Asp or Glu;

$A^{14}$ is Gln, Acc, Aib, Asn, Asp or Glu;

$A^{15}$ is Arg, hArg, Acc, Aib, Apc, Dab, Dap, Lys, Orn, Ser(C(O)—$R^4$), Thr(C(O)—$R^5$), Glu(O—$R^6$), Glu(NH—

R⁷), Asp(O—R⁸), Asp(NH—R⁹), Dap(S(O)₂—R¹⁰), Dab(S(O)₂—R¹¹), HN—CH((CH)ₙ—N(R¹²R¹³))—C(O), Cys(S—R¹⁴), Cys(R¹⁵), hCys(S—R¹⁶) or hCys(R¹⁷);

A¹⁶ is Lys, Acc, Aib, Apc, Arg, hArg, Dab, Dap, Orn, Ser(C(O)—R⁴), Thr(C(O)—R⁵), Glu(O—R⁶), Glu(NH—R⁷), Asp(O—R⁸), Asp(NH—R⁹), Dap(S(O)₂—R¹⁰), Dab(S(O)₂—R¹¹), HN—CH((CH₂)ₙ—N(R¹²R¹³))—C(O), Cys(S—R¹⁴), Cys(R¹⁵), hCys(S—R¹⁶), hCys(R¹⁷) or deleted;

A¹⁷ is Glu, Arg, Asn, Asp, Dab, Dap, Gln, Lys, Orn, Ser(C(O)—R⁴), Thr(C(O)—R⁵), Glu(O—R⁶), Glu(NH—R⁷), Asp(O—R⁸), Asp(NH—R⁹), Dap(S(O)₂—R¹⁰), Dab(S(O)₂—R¹¹), HN—CH((CH₂)ₙ—N(R¹²R¹³))—C(O), Cys(SR¹⁴), Cys(R¹⁵), hCys(S—R¹⁶), hCys(R¹⁷), Lys(biotinyl) or deleted;

A¹⁸ is Ser, Abu, Acc, Act, Aib, Ala, Thr, Val, Ser(C(O)—R⁴), Thr(C(O)—R⁵), Glu(O—R⁶), Glu(NH—R⁷), Asp(O—R⁸), Asp(NH—R⁹), Dap(S(O)₂—R¹⁰), Dab(S(O)₂—R¹¹), HN—CH((CH₂)ₙ—N(R¹²R¹³))—C(O), Cys(S—R¹⁴), Cys(R¹⁵), hCys(S—R¹⁶), hCys(R¹⁷) or deleted;

A¹⁹ is Lys, Acc, Aib, Apc, Arg, hArg, Dab, Dap, Orn, Ser(C(O)—R⁴), Thr(C(O)—R⁵), Glu(O—R⁶), Glu(NH—R⁷), Asp(O—R⁸), Asp(NH—R⁹), Dap(S(O)₂—R¹⁰), Dab(S(O)₂—R¹¹), HN—CH((CH₂)ₙ—N(R¹²R¹³))—C(O), Cys(S—R¹⁴), Cys(R¹⁵), hCys(S—R¹¹), hCys(R¹⁷) or deleted;

A²⁰ is Lys, Acc, Aib, Apc, Arg, hArg, Dab, Dap, Orn, Ser(C(O)—R⁴), Thr(C(O)—R⁵), Glu(O—R⁶), Glu(NH—R⁷), Asp(O—R⁸), Asp(NH—R⁹), Dap(S(O)₂—R¹⁰), Dab(S(O)₂—R¹¹), HN—CH((CH₂)ₙ—N(R¹²R¹³))—C(O), Cys(S—R¹⁴), Cys(R¹⁵), hCys(S—R¹⁶), hCys(R¹⁷) or deleted;

A²¹ is Pro, Dhp, Dmt, Inc, 3-Hyp, 4-Hyp, Ktp, Oic, Pip, Thz, Tic or deleted;

A²² is Pro, Dhp, Dmt, 3-Hyp, 4-Hyp, Inc, Ktp, Oic, Pip, Thz, Tic or deleted;

A23 is Abu, Acc, Act, Aib, Ala, Apc, Gly, Nva, Val or deleted;

A²⁴ is Lys, Acc, Aib, Apc, Arg, hArg, Dab, Dap, Orn, HN—CH((CH₂)ₙ—N(R¹²R¹³))—C(O) or deleted;

A²⁵ is Leu, Abu, Acc, Aib, Ala, Cha, Ile, hLeu, Nle, Nva, Phe, Tle, Val or deleted;

A²⁶ is Gln, Aib, Asn, Asp, Glu or deleted;

A²⁷ is Pro, Dhp, Dmt, 3-Hyp, 4-Hyp, Inc, Ktp, Oic, Pip, Thz, Tic or deleted;

A²⁸ is Acc, Aib, Apc, Arg, hArg, Dab, Dap, Lys, Orn, HN—CH((CH₂)ₙ—N(R¹²R¹³))—C(O) or deleted;

R¹ is —OH, —NH₂, —(C₁-C₃₀)alkoxy or NH—X⁶—CH₂-Z⁰, wherein X⁶ is a (C₁-C₁₂)alkyl, (C₂-C₁₂)alkenyl and Z⁰ is —H, —OH, —CO₂H or —C(O)—NH₂;

R² and R³ is, independently for each occurrence thereof, selected from the group consisting of H, (C₁-C₃₀)alkyl, (C₁-C₃₀)heteroalkyl, (C₁-C₃₀)acyl, (C₂-C₃₀)alkenyl, (C₂-C₃₀)alkynyl, aryl(C₁-C₃₀)alkyl, aryl(C₁-C₃₀)acyl, substituted (C₁-C₃₀)alkyl, substituted (C₁-C₃₀)heteroalkyl, substituted (C₂-C₃₀)acyl, substituted (C₂-C₃₀)alkenyl, substituted aryl (C₁-C₃₀)alkyl and substituted aryl(C₁-C₃₀)acyl;

R⁴, R⁵, R¹, R⁷, R⁸, R⁹, R¹⁰, R¹¹, R¹⁴, R¹⁵, R¹⁶ and R¹⁷ is, independently for each occurrence thereof, selected from the group consisting of (C₁-C₄₀)alkyl, (C₂-C₄₀)alkenyl, substituted (C₁-C₄₀) alkyl, substituted (C₂-C₄₀) alkenyl, alkylaryl, substituted alklyaryl, aryl and substituted aryl;

R¹² and R¹³ is, independently for each occurrence thereof, selected from the group consisting of H, (C₁-C₄₀)alkyl, (C₁-C₄₀)acyl, (C₁-C₃₀)alkylsulfonyl, biotinyl and —C(NH)—NH₂, X¹, X², X³, X⁴, and X⁵ is, independently for each occurrence thereof, selected from the group consisting of H, F, Cl, Br, I, (C₁-₁₀)alkyl, substituted (C₁-₁₀)alkyl, aryl, substituted aryl, OH, NH₂, NO₂ and CN; and n is, independently for each occurrence thereof, 1, 2, 3, 4 or 5;

provided that:

(I). when R² is (C₁-C₃₀)acyl, aryl(C₁-C₃₀)acyl, substituted (C₂-C₃₀)acyl, or substituted aryl(C₁-C₃₀)acyl, R³ is H, (C₁-C₃₀)alkyl, (C₁-C₃₀)heteroalkyl, (C₂-C₃₀)alkenyl, aryl(C₁-C₃₀)alkyl, substituted (C₁-C₃₀)alkyl, substituted (C₁-C₃₀) heteroalkyl, substituted (C₂-C₃₀)alkenyl or substituted aryl (C₁-C₃₀)alkyl;

(II). when R¹² is (C₁-C₃₀)acyl, (C₁-C₃₀)alkylsulfonyl, biotinyl or —C(NH)—NFL, then R¹³ is H or (C₁-C₄₀)alkyl;

(III). at least one of A¹⁵, A¹⁶, A¹⁷, A¹⁸, A¹⁹ or A²⁰ must be selected from the group consisting of Ser(C(O)—R⁴), Thr(C(O)—R⁵), Glu(O—R⁶), Glu(NH—R⁷), Asp(O—R⁸), Asp(NH—R⁹), Dap(S(O)₂—R¹⁰), Dab(S(O)₂—R¹¹), HN—CH((CH₂)ₙ—N(R¹²R¹³))—C(O), Cys(S—R¹⁴), Cys(R¹⁵), hCys(S—R¹⁶) and hCys(R¹⁷); and (IV). when any of the group consisting of A¹⁵, A¹⁶, A¹⁷, A¹⁹ and A²⁰ is HN—CH((CH₂)ₙ—N(R¹²R¹³))—C(O), then R¹² must be biotinyl;

or a pharmaceutically acceptable salt thereof.

In yet another aspect, the invention provides a preferred group of compounds according to formula (III), where in:

each of R² and R³ is, independently for each occurrence thereof, selected from the group consisting of H, acyl, n-butyryl, isobutyryl and n-octanoyl;

R⁴ is heptyl;

R⁶ is hexyl;

R⁷ is hexyl;

R¹⁰ is octyl;

R¹¹ is heptyl; and provided that when Acc is substituted for one of the naturally-occurring residues, it is, independently for each occurrence, A3c, A4c, A5c or A6c;

or pharmaceutically acceptable salts thereof.

In yet another aspect, the invention provides a preferred group of compounds according to formula (III), where the compound is:

```
(Ser(n-octanoyl)¹⁵)hGhrelin(1-28)-NH₂;  (SEQ ID NO: 162)

(Glu(NH-hexyl)¹⁵)hGhrelin(1-28)-NH₂;  (SEQ ID NO: 163)

(Glu(NH-hexyl)³,¹⁵)hGhrelin(1-28)-NH₂;  (SEQ ID NO: 164)

(Glu(NH-hexyl)³,Ser(n-octanoyl)¹⁵)hGhrelin(1-28)-NH₂;  (SEQ ID NO: 165)

(Aib²,Glu(NH-hexyl)¹⁵)hGhrelin(1-28)-NH₂;  (SEQ ID NO: 166)

(Aib²,Glu(NH-hexyl)³,¹⁵)hGhrelin(1-28)-NH₂;  (SEQ ID NO: 167)

(Aib²,⁸,Glu(NH-hexyl)¹⁵)hGhrelin(1-28)-NH₂;  (SEQ ID NO: 168)

(Aib²,⁸,Glu(NH-hexyl)³,¹⁵)hGhrelin(1-28)-NH₂;  (SEQ ID NO: 169)
```

-continued (Aib$^{2,10}$,Glu(NH-hexyl)$^{15}$)hGhrelin(1-28)-NH$_2$; (SEQ ID NO: 170)

(Aib$^{2,10}$,Glu(NH-hexyl)$^{3,15}$)hGhrelin(1-28)-NH$_2$; (SEQ ID NO: 171)

(Ser(n-octanoyl)$^{16}$)hGhrelin(1-28)-NH$_2$; (SEQ ID NO: 172)

(Glu(NH-hexyl)$^{16}$)hGhrelin(1-28)-NH$_2$; (SEQ ID NO: 173)

(Glu(NH-hexyl)$^{3,16}$)hGhrelin(1-28)-NH$_2$; (SEQ ID NO: 174)

(Glu(NH-hexyl)$^{3}$,Ser(n-octanoyl)$^{16}$)hGhrelin(1-28)-NH$_2$; (SEQ ID NO: 175)

(Aib$^{2}$,Glu(NH-hexyl)$^{16}$)hGhrelin(1-28)-NH$_2$; (SEQ ID NO: 176)

(Aib$^{2}$,Glu(NH-hexyl)$^{3,16}$)hGhrelin(1-28)-NH$_2$; (SEQ ID NO: 177)

(Aib$^{2,8}$,Glu(NH-hexyl)$^{16}$)hGhrelin(1-28)-NH$_2$; (SEQ ID NO: 178)

(Aib$^{2,8}$,Glu(NH-hexyl)$^{3,16}$)hGhrelin(1-28)-NH$_2$; (SEQ ID NO: 179)

(Aib$^{2,10}$,Glu(NH-hexyl)$^{16}$)hGhrelin(1-28)-NH$_2$; (SEQ ID NO: 180)

(Aib$^{2,10}$,Glu(NH-hexyl)$^{3,16}$)hGhrelin(1-28)-NH$_2$; (SEQ ID NO: 181)

(Ser(n-octanoyl)$^{17}$)hGhrelin(1-28)-NH$_2$; (SEQ ID NO: 182)

(Glu(NH-hexyl)$^{17}$)hGhrelin(1-28)-NH$_2$; (SEQ ID NO: 183)

(Glu(NH-hexyl)$^{3,17}$)hGhrelin(1-28)-NH$_2$; (SEQ ID NO: 184)

(Glu(NH-hexyl)$^{3}$,Ser(n-octanoyl)$^{17}$)hGhrelin(1-28)-NH$_2$; (SEQ ID NO: 185)

(Dap(octanesulfonyl)$^{17}$)hGhrelin(1-28)-NH$_2$; (SEQ ID NO: 186)

(Dap(octanesulfonyl)$^{3,17}$)hGhrelin(1-28)-NH$_2$; (SEQ ID NO: 187)

(Dap(octanesulfonyl)$^{3}$,Glu(NH-hexyl)$^{17}$)hGhrelin(1-28)-NH$_2$; (SEQ ID NO: 188)

(Dap(octanesulfonyl)$^{3}$,Ser(n-octanoyl)$^{17}$)hGhrelin(1-28)-NH$_2$; (SEQ ID NO: 189)

(Glu(NH-hexyl)$^{3}$,Dap(octanesulfonyl)$^{17}$)hGhrelin(1-28)-NH$_2$; (SEQ ID NO: 190)

(Cys(S—(CH$_2$)$_9$CH$_3$)$^{17}$)hGhrelin(1-28)-NH$_2$; (SEQ ID NO: 191)

(Cys(S—(CH$_2$)$_9$CH$_3$)$^{3,17}$)hGhrelin(1-28)-NH$_2$; (SEQ ID NO: 192)

(Glu(NH-hexyl)$^{3}$,Cys(S—(CH$_2$)$_9$CH$_3$)$^{17}$)hGhrelin(1-28)-NH$_2$; (SEQ ID NO: 193)

(Cys(S—(CH$_2$)$_9$CH$_3$)$^{3}$,Glu(NH-hexyl)$^{17}$)hGhrelin(1-28)-NH$_2$; (SEQ ID NO: 194)

(Cys(S—(CH$_2$)$_9$CH$_3$)$^{3}$,Ser(n-octanoyl)$^{17}$)hGhrelin(1-28)-NH$_2$; (SEQ ID NO: 195)

(Aib$^{2}$,Glu(NH-hexyl)$^{17}$)hGhrelin(1-28)-NH$_2$; (SEQ ID NO: 196)

(Aib$^{2}$,Glu(NH-hexyl)$^{3,17}$)hGhrelin(1-28)-NH$_2$; (SEQ ID NO: 197)

(Aib$^{2}$,Thz$^{7}$,Glu(NH-hexyl)$^{17}$)hGhrelin(1-28)-NH$_2$; (SEQ ID NO: 198)

(Aib$^{2}$,4-Hyp$^{7}$,Glu(NH-hexyl)$^{17}$)hGhrelin(1-28)-NH$_2$; (SEQ ID NO: 198)

(Aib$^{2}$,Dhp$^{7}$,Glu(NH-hexyl)$^{17}$)hGhrelin(1-28)-NH$_2$; (SEQ ID NO: 198)

(Aib$^{2}$,Pip$^{7}$,Glu(NH-hexyl)$^{17}$)hGhrelin(1-28)-NH$_2$; (SEQ ID NO: 198)

(Aib$^{2}$,Tic$^{7}$,Glu(NH-hexyl)$^{17}$)hGhrelin(1-28)-NH$_2$; (SEQ ID NO: 198)

(Aib$^{2}$,Glu(NH-hexyl)$^{3,17}$,Thz$^{7}$)hGhrelin(1-28)-NH$_2$; (SEQ ID NO: 199)

(Aib$^{2}$,Glu(NH-hexyl)$^{3,17}$,4-Hyp$^{7}$)hGhrelin(1-28)-NH$_2$; (SEQ ID NO: 200)

(Aib$^{2}$,Glu(NH-hexyl)$^{3,17}$,Dhp$^{7}$)hGhrelin(1-28)-NH$_2$; (SEQ ID NO: 200)

(Aib$^{2}$,Glu(NH-hexyl)$^{3,17}$,Pip$^{7}$)hGhrelin(1-28)-NH$_2$; (SEQ ID NO: 200)

(Aib$^{2}$,Glu(NH-hexyl)$^{3,17}$,Tic$^{7}$)hGhrelin(1-28)-NH$_2$; (SEQ ID NO: 200)

(Aib$^{2,8}$,Glu(NH-hexyl)$^{17}$)hGhrelin(1-28)-NH$_2$; (SEQ ID NO: 201)

(Aib$^{2,8}$,Glu(NH-hexyl)$^{3,17}$)hGhrelin(1-28)-NH$_2$; (SEQ ID NO: 202) Example #16

-continued (Aib², 3-Pal⁹, Glu(NH-hexyl)¹⁷)hGhrelin(1-28)-NH₂; (SEQ ID NO: 203)

(Aib², 4-Pal⁹, Glu(NH-hexyl)¹⁷)hGhrelin(1-28)-NH₂; (SEQ ID NO: 203)

(Aib², Taz⁹, Glu(NH-hexyl)¹⁷)hGhrelin(1-28)-NH₂; (SEQ ID NO: 203)

(Aib², 2-Thi⁹, Glu(NH-hexyl)¹⁷)hGhrelin(1-28)-NH₂; (SEQ ID NO: 203)

(Aib², Glu(NH-hexyl)³,¹⁷, 3-Pal⁹)hGhrelin(1-28)-NH₂; (SEQ ID NO: 204)

(Aib², Glu(NH-hexyl)³,¹⁷, 4-Pal⁹)hGhrelin(1-28)-NH₂; (SEQ ID NO: 204)

(Aib², Glu(NH-hexyl)³,¹⁷, Taz⁹)hGhrelin(1-28)-NH₂; (SEQ ID NO: 204)

(Aib², Glu(NH-hexyl)³,¹⁷, 2-Thi⁹)hGhrelin(1-28)-NH₂; (SEQ ID NO: 204)

(Aib²,¹⁰, Glu(NH-hexyl)¹⁷)hGhrelin(1-28)-NH₂; (SEQ ID NO: 205)

(Aib²,¹⁰, Glu(NH-hexyl)³,¹⁷)hGhrelin(1-28)-NH₂; (SEQ ID NO: 206)

(Aib⁸, Glu(NH-hexyl)¹⁷)hGhrelin(1-28)-NH₂; (SEQ ID NO: 207)

(Taz⁹, Glu(NH-hexyl)¹⁷)hGhrelin(1-28)-NH₂; (SEQ ID NO: 208)

(3-Pal⁹, Glu(NH-hexyl)¹⁷)hGhrelin(1-28)-NH₂; (SEQ ID NO: 208)

(4-Pal⁹, Glu(NH-hexyl)¹⁷)hGhrelin(1-28)-NH₂; (SEQ ID NO: 208)

(2-Thi⁹, Glu(NH-hexyl)¹⁷)hGhrelin(1-28)-NH₂; (SEQ ID NO: 208)

(Glu(NH-hexyl)³,¹⁷, Aib⁸)hGhrelin(1-28)-NH₂; (SEQ ID NO: 209)

(Glu(NH-hexyl)³,¹⁷, Taz⁹)hGhrelin(1-28)-NH₂; (SEQ ID NO: 210)

(Glu(NH-hexyl)³,¹⁷, 3-Pal⁹)hGhrelin(1-28)-NH₂; (SEQ ID NO: 210)

(Glu(NH-hexyl)³,¹⁷, 4-Pal⁹)hGhrelin(1-28)-NH₂; (SEQ ID NO: 210)

(Glu(NH-hexyl)³,¹⁷, 2-Thi⁹)hGhrelin(1-28)-NH₂; (SEQ ID NO: 210)

(Aib¹,²,¹⁰, Glu(NH-hexyl)¹⁷)hGhrelin(1-28)-NH₂; (SEQ ID NO: 211)

(Aib¹,²,¹⁰, Glu(NH-hexyl)³,¹⁷)hGhrelin(1-28)-NH₂; (SEQ ID NO: 212)

(A5c², Glu(NH-hexyl)¹⁷)hGhrelin(1-28)-NH₂; (SEQ ID NO: 196)

(A5c², Glu(NH-hexyl)³,¹⁷)hGhrelin(1-28)-NH₂; (SEQ ID NO: 197)

(Glu(1-heptanol)³,¹⁷)hGhrelin(1-28)-NH₂; (SEQ ID NO: 184)

(Asp(1-heptanol)³,¹⁷)hGhrelin(1-28)-NH₂; (SEQ ID NO: 213)

(Glu(NH-hexyl)³,¹⁷)hGhrelin(1-28)-NH₂; (SEQ ID NO: 184)

(Asp(NH-hexyl)³,¹⁷)hGhrelin(1-28)-NH₂; (SEQ ID NO: 213)

(Aib², Glu(NH-hexyl)³,¹⁷)hGhrelin(1-28)-NH₂; (SEQ ID NO: 197)

(Lys(biotinyl)¹⁷)hGhrelin(1-28)-NH₂; (SEQ ID NO: 214)

(Ser(n-octanoyl)¹⁸)hGhrelin(1-28)-NH₂; (SEQ ID NO: 215)

(Glu(NH-hexyl)¹⁸)hGhrelin(1-28)-NH₂; (SEQ ID NO: 216)

(Glu(NH-hexyl)³,¹⁸)hGhrelin(1-28)-NH₂; (SEQ ID NO: 217)

(Glu(NH-hexyl)³, Ser(n-octanoyl)¹⁸)hGhrelin(1-28)-NH₂; (SEQ ID NO: 218)

(Aib², Glu(NH-hexyl)¹⁸)hGhrelin(1-28)-NH₂; (SEQ ID NO: 219)

(Aib², Glu(NH-hexyl)³,¹⁸)hGhrelin(1-28)-NH₂; (SEQ ID NO: 220)

(Aib²,⁸, Glu(NH-hexyl)¹⁸)hGhrelin(1-28)-NH₂; (SEQ ID NO: 221)

(Aib²,⁸, Glu(NH-hexyl)³,¹⁸)hGhrelin(1-28)-NH₂; (SEQ ID NO: 222)

(Aib²,¹⁰, Glu(NH-hexyl)¹⁸)hGhrelin(1-28)-NH₂; (SEQ ID NO: 223)

(Aib²,¹⁰, Glu(NH-hexyl)³,¹⁸)hGhrelin(1-28)-NH₂; (SEQ ID NO: 224)

(Ser(n-octanoyl)¹⁹)hGhrelin(1-28)-NH₂; (SEQ ID NO: 225)

-continued (Glu(NH-hexyl)$^{19}$)hGhrelin(1-28)-NH$_2$; (SEQ ID NO: 226)

(Glu(NH-hexyl)$^{3,19}$)hGhrelin(1-28)-NH$_2$; (SEQ ID NO: 227)

(Glu(NH-hexyl)$^3$,Ser(n-octanoyl)$^{19}$)hGhrelin(1-28)-NH$_2$; (SEQ ID NO: 228)

(Aib$^2$,Glu(NH-hexyl)$^{19}$)hGhrelin(1-28)-NH$_2$; (SEQ ID NO: 229)

(Aib$^2$,Glu(NH-hexyl)$^{3,19}$)hGhrelin(1-28)-NH$_2$; (SEQ ID NO: 230)

(Aib$^{2,8}$,Glu(NH-hexyl)$^{19}$)hGhrelin(1-28)-NH$_2$; (SEQ ID NO: 231)

(Aib$^{2,8}$,Glu(NH-hexyl)$^{3,19}$)hGhrelin(1-28)-NH$_2$; (SEQ ID NO: 232)

(Aib$^{2,10}$,Glu(NH-hexyl)$^{19}$)hGhrelin(1-28)-NH$_2$; (SEQ ID NO: 233)

(Aib$^{2,10}$,Glu(NH-hexyl)$^{3,19}$)hGhrelin(1-28)-NH$_2$; (SEQ ID NO: 234)

(Ser(n-octanoyl)$^{20}$)hGhrelin(1-28)-NH$_2$; (SEQ ID NO: 235)

(Glu(NH-hexyl)$^{20}$)hGhrelin(1-28)-NH$_2$; (SEQ ID NO: 236)

(Glu(NH-hexyl)$^{3,20}$)hGhrelin(1-28)-NH$_2$; (SEQ ID NO: 237)

(Glu(NH-hexyl)$^3$,Ser(n-octanoyl)$^{20}$)hGhrelin(1-28)-NH$_2$; (SEQ ID NO: 238)

(Aib$^2$,Glu(NH-hexyl)$^{20}$)hGhrelin(1-28)-NH$_2$; (SEQ ID NO: 239)

(Aib$_2$,Glu(NH-hexyl)$^{3,20}$)hGhrelin(1-28)-NH$_2$; (SEQ ID NO: 240)

(Aib$^{2,8}$,Glu(NH-hexyl)$^{20}$)hGhrelin(1-28)-NH$_2$; (SEQ ID NO: 241)

(Aib$^{2,8}$,Glu(NH-hexyl)$^{3,20}$)hGhrelin(1-28)-NH$_2$; (SEQ ID NO: 242)

(Aib$^{2,10}$,Glu(NH-hexyl)$^{20}$)hGhrelin(1-28)-NH$_2$; (SEQ ID NO: 243)

(Aib$^{2,10}$,Glu(NH-hexyl)$^{3,20}$)hGhrelin(1-28)-NH$_2$; (SEQ ID NO: 244)

(Ac-Gly$^1$,Glu(NH-hexyl)$^{17}$)hGhrelin(1-28)-NH$_2$; (SEQ ID NO: 245)

(Ac-Gly$^1$,Ser(n-octanoyl)$^{17}$)hGhrelin(1-28)-NH$_2$; (SEQ ID NO: 246)

(Ac-Gly$^1$,Glu(NH-hexyl)$^{3,17}$)hGhrelin(1-28)-NH$_2$; (SEQ ID NO: 247)

(Ac-Gly$^1$,Glu(NH-hexyl)$^3$,Ser(n-octanoyl)$^{17}$)hGhrelin(1-28)-NH$_2$; (SEQ ID NO: 248)

(Ac-Gly$^1$,Dap(octanesulfonyl)$^{17}$)hGhrelin(1-28)-NH$_2$; (SEQ ID NO: 249)

(Ac-Gly$^1$,Dap(octanesulfonyl)$^{3,17}$)hGhrelin(1-28)-NH$_2$; (SEQ ID NO: 250)

(Ac-Gly$^1$,Dap(octanesulfonyl)$^3$,Glu(NH-Hexyl)$^{17}$)hGhrelin(1-28)-NH$_2$; (SEQ ID NO: 251)

(Ac-Gly$^1$,Dap(octanesulfonyl)$^3$,Ser(n-octanoyl)$^{17}$)hGhrelin(1-28)-NH$_2$; (SEQ ID NO: 252)

(Ac-Gly$^1$,Glu(NH-hexyl)$^3$,Dap(octanesulfonyl)$^{17}$)hGhrelin(1-28)-NH$_2$; (SEQ ID NO: 253)

(Ac-Gly$^1$,Cys(S—(CH$_2$)$_9$CH$_3$)$^{17}$)hGhrelin(1-28)-NH$_2$; (SEQ ID NO: 254)

(Ac-Gly$^1$,Cys(S—(CH$_2$)$_9$CH$_3$)$^{3,17}$)hGhrelin(1-28)-NH$_2$; (SEQ ID NO: 255)

(Ac-Gly$^1$,Glu(NH-hexyl)$^3$,Cys(S—(CH$_2$)$_9$CH$_3$)$^{17}$)hGhrelin(1-28)-NH$_2$; (SEQ ID NO: 256)

(Ac-Gly$^1$,Cys(S—(CH$_2$)$_9$CH$_3$)$^3$,Glu(NH-hexyl)$^{17}$)hGhrelin(1-28)-NH$_2$; (SEQ ID NO: 257)

(Ac-Gly$^1$,Cys(S—(CH$_2$)$_9$CH$_3$)$^3$,Ser(n-octanoyl)$^{17}$)hGhrelin(1-28)-NH$_2$; (SEQ ID NO: 258)

(Ac-Gly$^1$,Aib$^2$,Glu(NH-hexyl)$^{17}$)hGhrelin(1-28)-NH$_2$; (SEQ ID NO: 259)

(Ac-Gly$^1$,Aib$^2$,Thz$^7$,Glu(NH-hexyl)$^{17}$)hGhrelin(1-28)-NH$_2$; (SEQ ID NO: 260)

(Ac-Gly$^1$,Aib$^2$,4-Hyp$^7$,Glu(NH-hexyl)$^{17}$)hGhrelin(1-28)-NH$_2$; (SEQ ID NO: 260)

(Ac-Gly$^1$,Aib$^2$,Dhp$^7$,Glu(NH-hexyl)$^{17}$)hGhrelin(1-28)-NH$_2$; (SEQ ID NO: 260)

(Ac-Gly$^1$,Aib$^2$,Pip$^7$,Glu(NH-hexyl)$^{17}$)hGhrelin(1-28)-NH$_2$; (SEQ ID NO: 260)

(Ac-Gly$^1$,Aib$^2$,Tic$^7$,Glu(NH-hexyl)$^{17}$)hGhrelin(1-28)-NH$_2$; (SEQ ID NO: 260)

(Ac-Gly$^1$,Aib$^2$,Glu(NH-hexyl)$^{3,17}$,Thz$^7$)hGhrelin(1-28)-NH$_2$; (SEQ ID NO: 261)

-continued (Ac-Gly$^1$,Aib$^2$,Glu(NH-hexyl)$^{3,17}$,4-Hyp$^7$)hGhrelin(1-28)-NH$_2$; (SEQ ID NO: 261)

(Ac-Gly$^1$,Aib$^2$,Glu(NH-hexyl)$^{3,17}$,Dhp$^7$)hGhrelin(1-28)-NH$_2$; (SEQ ID NO: 261)

(Ac-Gly$^1$,Aib$^2$,Glu(NH-hexyl)$^{3,17}$,Pip$^7$)hGhrelin(1-28)-NH$_2$; (SEQ ID NO: 261)

(Ac-Gly$^1$,Aib$^2$,Glu(NH-hexyl)$^{3,17}$,Tic$^7$)hGhrelin(1-28)-NH$_2$; (SEQ ID NO: 261)

(Ac-Gly$^1$,Aib$^{2,8}$,Glu(NH-hexyl)$^{17}$)hGhrelin(1-28)-NH$_2$; (SEQ ID NO: 262)

(Ac-Gly$^1$,Aib$^2$,3-Pal$^9$,Glu(NH-hexyl)$^{17}$)hGhrelin(1-28)-NH$_2$; (SEQ ID NO: 263)

(Ac-Gly$^1$,Aib$^2$,4-Pal$^9$,Glu(NH-hexyl)$^{17}$)hGhrelin(1-28)-NH$_2$; (SEQ ID NO: 263)

(Ac-Gly$^1$,Aib$^2$,Taz$^9$,Glu(NH-hexyl)$^{17}$)hGhrelin(1-28)-NH$_2$; (SEQ ID NO: 263)

(Ac-Gly$^1$,Aib$^2$,2-Thi$^9$,Glu(NH-hexyl)$^{17}$)hGhrelin(1-28)-NH$_2$; (SEQ ID NO: 263)

(Ac-Gly$^1$,Aib$^2$,Glu(NH-hexyl)$^{3,17}$,3-Pal$^9$)hGhrelin(1-28)-NH$_2$; (SEQ ID NO: 264)

(Ac-Gly$^1$,Aib$^2$,Glu(NH-hexyl)$^{3,17}$,4-Pal$^9$)hGhrelin(1-28)-NH$_2$; (SEQ ID NO: 264)

(Ac-Gly$^1$,Aib$^2$,Glu(NH-hexyl)$^{3,17}$,Taz$^9$)hGhrelin(1-28)-NH$_2$; (SEQ ID NO: 264)

(Ac-Gly$^1$,Aib$^2$,Glu(NH-hexyl)$^{3,17}$,2-Thi$^9$)hGhrelin(1-28)-NH$_2$; (SEQ ID NO: 264)

(Ac-Gly$^1$,Aib$^{2,10}$,Glu(NH-hexyl)$^{17}$)hGhrelin(1-28)-NH$_2$; (SEQ ID NO: 265)

(Ac-Gly$^1$,Aib$^{2,10}$,Glu(NH-hexyl)$^{3,17}$)hGhrelin(1-28)-NH$_2$; (SEQ ID NO: 266)

(Ac-Gly$^1$,Aib$^8$,Glu(NH-hexyl)$^{17}$)hGhrelin(1-28)-NH$_2$; (SEQ ID NO: 267)

(Ac-Gly$^1$,Taz$^9$,Glu(NH-hexyl)$^{17}$)hGhrelin(1-28)-NH$_2$; (SEQ ID NO: 268)

(Ac-Gly$^1$,3-Pal$^9$,Glu(NH-hexyl)$^{17}$)hGhrelin(1-28)-NH$_2$; (SEQ ID NO: 268)

(Ac-Gly$^1$,4-Pal$^9$,Glu(NH-hexyl)$^{17}$)hGhrelin(1-28)-NH$_2$; (SEQ ID NO: 268)

(Ac-Gly$^1$,2-Thi$^9$,Glu(NH-hexyl)$^{17}$)hGhrelin(1-28)-NH$_2$; (SEQ ID NO: 268)

(Ac-Gly$^1$,Glu(NH-hexyl)$^{3,17}$,Aib$^8$)hGhrelin(1-28)-NH$_2$; (SEQ ID NO: 269)

(Ac-Gly$^1$,Glu(NH-hexyl)$^{3,17}$,Taz$^9$)hGhrelin(1-28)-NH$_2$; (SEQ ID NO: 270)

(Ac-Gly$^1$,Glu(NH-hexyl)$^{3,17}$,3-Pal$^9$)hGhrelin(1-28)-NH$_2$; (SEQ ID NO: 270)

(Ac-Gly$^1$,Glu(NH-hexyl)$^{3,17}$,4-Pal$^9$)hGhrelin(1-28)-NH$_2$; (SEQ ID NO: 270)

(Ac-Gly$^1$,Glu(NH-hexyl)$^{3,17}$,2-Thi$^9$)hGhrelin(1-28)-NH$_2$; (SEQ ID NO: 270)

(Ac-Aib$^1$,Aib$^{2,10}$,Glu(NH-hexyl)$^{17}$)hGhrelin(1-28)-NH$_2$; (SEQ ID NO: 271)

(Ac-Aib$^1$,Aib$^{2,10}$,Glu(NH-hexyl)$^{3,17}$)hGhrelin(1-28)-NH$_2$; (SEQ ID NO: 272)

(Ac-Gly$^1$,A5c$^2$,Glu(NH-hexyl)$^{17}$)hGhrelin(1-28)-NH$_2$; (SEQ ID NO: 259)

(Ac-Gly$^1$,A5c$^2$,Glu(NH-hexyl)$^{3,17}$)hGhrelin(1-28)-NH$_2$; (SEQ ID NO: 273)

(Ac-Gly$^1$,Glu(1-heptanol)$^{3,17}$)hGhrelin(1-28)-NH$_2$; (SEQ ID NO: 247)

(Ac-Gly$^1$,Asp(1-heptanol)$^{3,17}$)hGhrelin(1-28)-NH$_2$; (SEQ ID NO: 274)

(Ac-Gly$^1$,Glu(NH-hexyl)$^{3,17}$)hGhrelin(1-28)-NH$_2$; (SEQ ID NO: 247)

(Ac-Gly$^1$,Asp(NH-hexyl)$^{3,17}$)hGhrelin(1-28)-NH$_2$; (SEQ ID NO: 274)

(Ac-Gly$^1$,Aib$^{2,10}$,Glu(NH-hexyl)$^3$,Lys(biotinyl)$^{17}$)hGhrelin(1-28)-NH$_2$; (SEQ ID NO: 275)

(Ac-Gly$^1$,Glu(NH-hexyl)$^{15}$)hGhrelin(1-28)-NH$_2$; (SEQ ID NO: 276)

(Ac-Gly$^1$,Ser(n-octanoyl)$^{15}$)hGhrelin(1-28)-NH$_2$; (SEQ ID NO: 277)

(Ac-Gly$^1$,Glu(NH-hexyl)$^{3,15}$)hGhrelin(1-28)-NH$_2$; (SEQ ID NO: 278)

(Ac-Gly$^1$,Glu(NH-hexyl)$^3$,Ser(n-octanoyl)$^{15}$)hGhrelin(1-28)-NH$_2$; (SEQ ID NO: 279)

(Ac-Gly$^1$,Aib$^2$,Glu(NH-hexyl)$^{15}$)hGhrelin(1-28)-NH$_2$; (SEQ ID NO: 280)

(Ac-Gly$^1$,Aib$^2$,Glu(NH-hexyl)$^{3,15}$)hGhrelin(1-28)-NH$_2$; (SEQ ID NO: 281)

(Ac-Gly$^1$,Aib$^{2,8}$,Glu(NH-hexyl)$^{15}$)hGhrelin(1-28)-NH$_2$; (SEQ ID NO: 282)

-continued (Ac-Gly$^1$,Aib$^{2,8}$,Glu(NH-hexyl)$^{3,15}$)hGhrelin(1-28)-NH$_2$; (SEQ ID NO: 283)

(Ac-Gly$^1$,Aib$^{2,10}$,Glu(NH-hexyl)$^{15}$)hGhrelin(1-28)-NH$_2$; (SEQ ID NO: 284)

(Ac-Gly$^1$,Aib$^{2,10}$,Glu(NH-hexyl)$^{3,15}$)hGhrelin(1-28)-NH$_2$; (SEQ ID NO: 285)

(Ac-Gly$^1$,Glu(NH-hexyl)$^{16}$)hGhrelin(1-28)-NH$_2$; (SEQ ID NO: 286)

(Ac-Gly$^1$,Ser(n-octanoyl)$^{16}$)hGhrelin(1-28)-NH$_2$; (SEQ ID NO: 287)

(Ac-Gly$^1$,Glu(NH-hexyl)$^{3,16}$)hGhrelin(1-28)-NH$_2$; (SEQ ID NO: 288)

(Ac-Gly$^1$,Glu(NH-hexyl)$^3$,Ser(n-octanoyl)$^{16}$)hGhrelin(1-28)-NH$_2$; (SEQ ID NO: 289)

(Ac-Gly$^1$,Aib$^2$,Glu(NH-hexyl)$^{16}$)hGhrelin(1-28)-NH$_2$; (SEQ ID NO: 290)

(Ac-Gly$^1$,Aib$^2$,Glu(NH-hexyl)$^{3,16}$)hGhrelin(1-28)-NH$_2$; (SEQ ID NO: 291)

(Ac-Gly$^1$,Aib$^{2,8}$,Glu(NH-hexyl)$^{16}$)hGhrelin(1-28)-NH$_2$; (SEQ ID NO: 292)

(Ac-Gly$^1$,Aib$^{2,8}$,Glu(NH-hexyl)$^{3,16}$)hGhrelin(1-28)-NH$_2$; (SEQ ID NO: 293)

(Ac-Gly$^1$,Aib$^{2,10}$,Glu(NH-hexyl)$^{16}$)hGhrelin(1-28)-NH$_2$; (SEQ ID NO: 294)

(Ac-Gly$^1$,Aib$^{2,10}$,Glu(NH-hexyl)$^{3,16}$)hGhrelin(1-28)-NH$_2$; (SEQ ID NO: 295)

(Ac-Gly$^1$,Glu(NH-hexyl)$^{18}$)hGhrelin(1-28)-NH$_2$; (SEQ ID NO: 296)

(Ac-Gly$^1$,Ser(n-octanoyl)$^{18}$)hGhrelin(1-28)-NH$_2$; (SEQ ID NO: 297)

(Ac-Gly$^1$,Glu(NH-hexyl)$^{3,18}$)hGhrelin(1-28)-NH$_2$; (SEQ ID NO: 298)

(Ac-Gly$^1$,Glu(NH-hexyl)$^3$,Ser(n-octanoyl)$^{18}$)hGhrelin(1-28)-NH$_2$; (SEQ ID NO: 299)

(Ac-Gly$^1$,Aib$^2$,Glu(NH-hexyl)$^{18}$)hGhrelin(1-28)-NH$_2$; (SEQ ID NO: 300)

(Ac-Gly$^1$,Aib$^2$,Glu(NH-hexyl)$^{3,18}$)hGhrelin(1-28)-NH$_2$; (SEQ ID NO: 301)

(Ac-Gly$^1$,Aib$^{2,8}$,Glu(NH-hexyl)$^{18}$)hGhrelin(1-28)-NH$_2$; (SEQ ID NO: 302)

(Ac-Gly$^1$,Aib$^{2,8}$,Glu(NH-hexyl)$^{3,18}$)hGhrelin(1-28)-NH$_2$; (SEQ ID NO: 303)

(Ac-Gly$^1$,Aib$^{2,10}$,Glu(NH-hexyl)$^{18}$)hGhrelin(1-28)-NH$_2$; (SEQ ID NO: 304)

(Ac-Gly$^1$,Aib$^{2,10}$,Glu(NH-hexyl)$^{3,18}$)hGhrelin(1-28)-NH$_2$; (SEQ ID NO: 305)

(Ac-Gly$^1$,Glu(NH-hexyl)$^{19}$)hGhrelin(1-28)-NH$_2$; (SEQ ID NO: 306)

(Ac-Gly$^1$,Ser(n-octanoyl)$^{19}$)hGhrelin(1-28)-NH$_2$; (SEQ ID NO: 307)

(Ac-Gly$^1$,Glu(NH-hexyl)$^{3,19}$)hGhrelin(1-28)-NH$_2$; (SEQ ID NO: 308)

(Ac-Gly$^1$,Glu(NH-hexyl)$^3$,Ser(n-octanoyl)$^{19}$)hGhrelin(1-28)-NH$_2$; (SEQ ID NO: 309)

(Ac-Gly$^1$,Aib$^2$,Glu(NH-hexyl)$^{19}$)hGhrelin(1-28)-NH$_2$; (SEQ ID NO: 310)

(Ac-Gly$^1$,Aib$^2$,Glu(NH-hexyl)$^{3,19}$)hGhrelin(1-28)-NH$_2$; (SEQ ID NO: 311)

(Ac-Gly$^1$,Aib$^{2,8}$,Glu(NH-hexyl)$^{19}$)hGhrelin(1-28)-NH$_2$; (SEQ ID NO: 312)

(Ac-Gly$^1$,Aib$^{2,8}$,Glu(NH-hexyl)$^{3,19}$)hGhrelin(1-28)-NH$_2$; (SEQ ID NO: 313)

(Ac-Gly$^1$,Aib$^{2,10}$,Glu(NH-hexyl)$^{19}$)hGhrelin(1-28)-NH$_2$; (SEQ ID NO: 314)

(Ac-Gly$^1$,Aib$^{2,10}$,Glu(NH-hexyl)$^{3,19}$)hGhrelin(1-28)-NH$_2$; (SEQ ID NO: 315)

(Ac-Gly$^1$,Glu(NH-hexyl)$^{20}$)hGhrelin(1-28)-NH$_2$; (SEQ ID NO: 316)

(Ac-Gly$^1$,Ser(n-octanoyl)$^{20}$)hGhrelin(1-28)-NH$_2$; (SEQ ID NO: 317)

(Ac-Gly$^1$,Glu(NH-hexyl)$^{3,20}$)hGhrelin(1-28)-NH$_2$; (SEQ ID NO: 318)

(Ac-Gly$^1$,Glu(NH-hexyl)$^3$,Ser(n-octanoyl)$^{20}$)hGhrelin(1-28)-NH$_2$; (SEQ ID NO: 319)

(Ac-Gly$^1$,Aib$^2$,Glu(NH-hexyl)$^{20}$)hGhrelin(1-28)-NH$_2$; (SEQ ID NO: 320)

(Ac-Gly$^1$,Aib$^2$,Glu(NH-hexyl)$^{3,20}$)hGhrelin(1-28)-NH$_2$; (SEQ ID NO: 321)

(Ac-Gly$^1$,Aib$^{2,8}$,Glu(NH-hexyl)$^{20}$)hGhrelin(1-28)-NH$_2$; (SEQ ID NO: 322)

-continued (Ac-Gly$^1$,Aib$^{2,8}$,Glu(NH-hexyl)$^{3,20}$)hGhrelin(1-28)-NH$_2$;  (SEQ ID NO: 323)

(Ac-Gly$^1$,Aib$^{2,10}$,Glu(NH-hexyl)$^{20}$)hGhrelin(1-28)-NH$_2$;  (SEQ ID NO: 324)

(Ac-Gly$^1$,Aib$^{2,10}$,Glu(NH-hexyl)$^{3,20}$)hGhrelin(1-28)-NH$_2$;  (SEQ ID NO: 325)

or pharmaceutically acceptable salts thereof.

In yet another aspect, the invention provides a method of treating gastrointestinal conditions such as gastroesophageal reflux disease, IBS, constipation, ileus, emesis, gastroparesis, and colonic pseudo-obstruction and the like, by administering a therapeutically effective amount of the following peptidyl ghrelin analogs which do not correspond to any one of formula (I), (II) or (III):

(Asp$^3$(NH-heptyl))hGhrelin(1-28)-NH$_2$  (SEQ ID NO: 326) Example #86

(des-Ser$^2$)hGhrelin(1-28)-NH$_2$;  or (SEQ ID NO: 327) Example #104

(des-Gly$^1$, des-Ser$^2$)hGhrelin(1-28)-NH$_2$;  (SEQ ID NO: 328) Example #117

(Aib$^1$)hGhrelin(1-28)-NH$_2$;  (SEQ ID NO: 329) Example #6

(Asp$^3$(O-hexyl))hGhrelin(1-28)-NH$_2$;  (SEQ ID NO: 326) Example #40

(Aib$^1$,Ser$^3$)hGhrelin(1-28)-NH$_2$;  (SEQ ID NO: 329)

(A5c$^5$,Ser$^3$)hGhrelin(1-28)-NH$_2$;  (SEQ ID NO: 3)

(Aib$^{2,4}$,Ser$^3$,4-Pal$^9$)hGhrelin(1-28)-NH$_2$;  (SEQ ID NO: 330)

(n-octanoyl-Gly$^1$,Ser$^3$)hGhrelin(1-28)-NH$_2$;  (SEQ ID NO: 95)

(isobutyryl-Gly$^1$,Ser$^3$)hGhrelin(1-28)-NH$_2$;  (SEQ ID NO: 95)

(n-butyryl-Gly$^1$,Ser$^3$)hGhrelin(1-28)-NH$_2$;  (SEQ ID NO: 95)

(Aib$^1$,Thr$^3$)hGhrelin(1-28)-NH$_2$;  (SEQ ID NO: 331)

(Aib$^{2,4}$,Thr$^3$,4-Pal$^9$)hGhrelin(1-28)-NH$_2$;  (SEQ ID NO: 330)

(n-octanoyl-Gly$^1$,Thr$^3$)hGhrelin(1-28)-NH$_2$;  (SEQ ID NO: 332)

(isobutyryl-Gly$^1$,Thr$^3$)hGhrelin(1-28)-NH$_2$;  (SEQ ID NO: 332)

(n-butyryl-Gly$^1$,Thr$^3$)hGhrelin(1-28)-NH$_2$;  (SEQ ID NO: 332)

(Ac-Gly$^1$)hGhrelin(1-28)-NH$_2$;  (SEQ ID NO: 95)

(Ac-Gly$^1$,Ser$^3$)hGhrelin(1-28)-NH$_2$,  (SEQ ID NO: 95)

Aib$^2$,Lys(Myristyl)$^{17}$)hGhrelin-(1-28)-NH$_2$;  or (SEQ ID NO: 333)

Gly(myristyl)$^1$-(Aib$^2$,Lys(Myristyl)$^{17}$]hGhrelin-(1-28)-NH$_2$;  (SEQ ID NO: 334)

or pharmaceutically acceptable salts thereof.

The peptidyl analog of ghrelin or prodrug thereof may be administered parenterally, e.g., administered intravenously, subcutaneously, or by implantation of a sustained release formulation. The peptidy analog of ghrelin may also be administered intracerebroventricular (icv) injection. In another embodiment, the peptidyl analog of ghrelin is administered via oral administration. Particularly preferred peptidyl analogs of ghrelin are those compounds of formula (I) or formula (II) or formula (m), as well as the non-conforming compounds indicated above, as well as each of the compounds that are specifically enumerated herein and below in the Examples section of the present disclosure, or a pharmaceutically acceptable salt thereof.

Accordingly, in one aspect, the invention features a method of treating ileus in a patient, which includes identifying a patient suffering from or at risk for ileus and administering to the patient a pharmaceutical composition comprising an effective amount of a peptidyl analog of ghrelin. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In another aspect, the invention features a method of treating post-surgical ileus in a patient. The method includes identifying a patient suffering from post-surgical ileus and administering to the patient a pharmaceutical composition comprising an effective amount of a peptidyl analog of ghrelin effective to treat ileus in the patient. The ileus can be ileus of any part of the gastrointestinal tract, e.g., the stomach, small intestine, and/or large intestine (e.g., the colon). The pharmaceutical composition can be administered to the patient via any route described herein, e.g., via inhalation (of gaseous compositions); orally; and/or by direct administration to the abdominal cavity of the patient. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

The invention also features a method of treating ileus in a patient suffering from or at risk for ileus not caused by abdominal surgery, e.g., ileus caused by any factor described herein other than abdominal surgery. The method includes identifying a patient suffering from or at risk for ileus not caused by abdominal surgery and administering to the patient a pharmaceutical composition comprising an effective amount of a peptidyl analog of ghrelin effective to treat ileus in the patient. Particularly preferred peptidyl analogs of ghrelihn are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In yet another aspect, the invention provides a method of performing surgery on a patient. The method includes identifying a patient in need of surgery, and before, during, and/or after the surgery, administering to the patient an effective amount of a peptidyl analog of ghrelin sufficient to treat ileus in the patient. The surgery can be any surgery that causes and/or puts the patient at risk for ileus. For example, the surgery can involve manipulation (e.g., touching (directly or indirectly)) of the gastrointestinal tract, e.g., the stomach and/or intestines, e.g., small or large intestine (e.g., the colon), and can be a surgery involving laparotomy or not involving laparotomy (e.g., surgeries involving laparoscopy). In certain embodiments, the surgery can be transplant surgery or non-transplant surgery, e.g., surgery involving any organ(s) or tissue(s) in the abdomen, e.g., surgery of the urogenital system (e.g., kidneys, ureter, and/or bladder; and reproductive organs (e.g., uterus, ovaries, and/or fallopian tubes)); the digestive system (e.g., the stomach, small intestine, large intestine (e.g., the colon), appendix, gallbladder, liver, spleen, and/or pancreas); the lymphatic system; the respiratory system (e.g., the lungs); the diaphram; surgery to treat cancer of any organ or tissue within the abdomen; endometrial surgery; and orthopedic surgeries, e.g., hip surgery. Particularly preferred peptidyl analogs of ghrelin are those compounds of formula (I) or formula (II) or formula III as well as each of the compounds that are specifically enumerated herein and below in the Examples section of the present disclosure, or a pharmaceutically acceptable salt thereof.

In still another aspect, the invention provides a method of treating ileus in a patient, which includes identifying a patient suffering from or at risk for ileus and administering to the patient an effective amount of a peptidyl analog of ghrelin for treatment or prevention of ileus. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In another aspect, the invention features a method of treating emesis in a patient, which includes identifying a patient suffering from or at risk for emesis and administering to the patient a pharmaceutical composition comprising an effective amount of a peptidyl analog of ghrelin. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In yet another aspect, the invention features a method of treating emesis provoked by or associated with the administration of anti-cancer chemotherapeutic agents in a patient, which includes identifying a patient suffering from or at risk for emesis provoked by or associated with the administration of anti-cancer chemotherapeutic agents and administering to the patient a pharmaceutical composition comprising a therapeutically effective amount of a peptidyl analog of ghrelin. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In another aspect, the invention features a method of treating gastroparesis in a patient, which includes identifying a patient suffering from or at risk for gastroparesis and administering to the patient a pharmaceutical composition comprising an effective amount of a peptidyl analog of ghrelin. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In yet another aspect, the invention features a method of treating gastroparesis resulting from diabetes in a patient, which includes identifying a patient suffering from or at risk for diabetic gastroparesis and administering to the patient a pharmaceutical composition comprising an effective amount of a peptidyl analog of ghrelin. The diabetes may be Type I or Type II diabetes. Particularly preferred peptidyl analogs of ghrelin are those compounds of formula (I) or formula (II) or formula (III), as well as the non-conforming compounds indicated above and each of the compounds that are specifically enumerated herein and below in the Examples section of the present disclosure, or a pharmaceutically acceptable salt thereof.

In a further aspect, the present invention provides the use of a therapeutically effective amount of a peptidyl ghrelin analog compound according formula (I) or formula (II) or formula (III) as defined hereinabove, as well as the non-conforming compounds indicated above and each of the compounds specifically enumerated herein and below, or pharmaceutically acceptable salts thereof, for the manufacture of a medicament useful to treat gastrointestinal conditions such as gastroesophageal reflux disease, IBS, constipation, ileus, emesis, gastroparesis, and colonic pseudo-obstruction and the like. In yet another embodiment, the gastrointestinal conditions treated are ileus, emesis and gastroparesis. In yet another embodiment, the ilieus is post-operative ileus, the emesis is associated with the administration of anti-cancer chemotherapeutic agents and the gastroparesis is associated with diabetes.

In yet another aspect, the present invention provides a method of eliciting an agonist or an antagonist effect from a ghrelin receptor in a subject in need thereof which comprises administering to said subject an effective amount of a compound of formula (I) or formula (II) or formula (Imi) as defined hereinabove, as well as the non-conforming compounds indicated above and each of the compounds specifically enumerated herein and below or pharmaceutically acceptable salts thereof.

DETAILED DESCRIPTION

Figure 1:
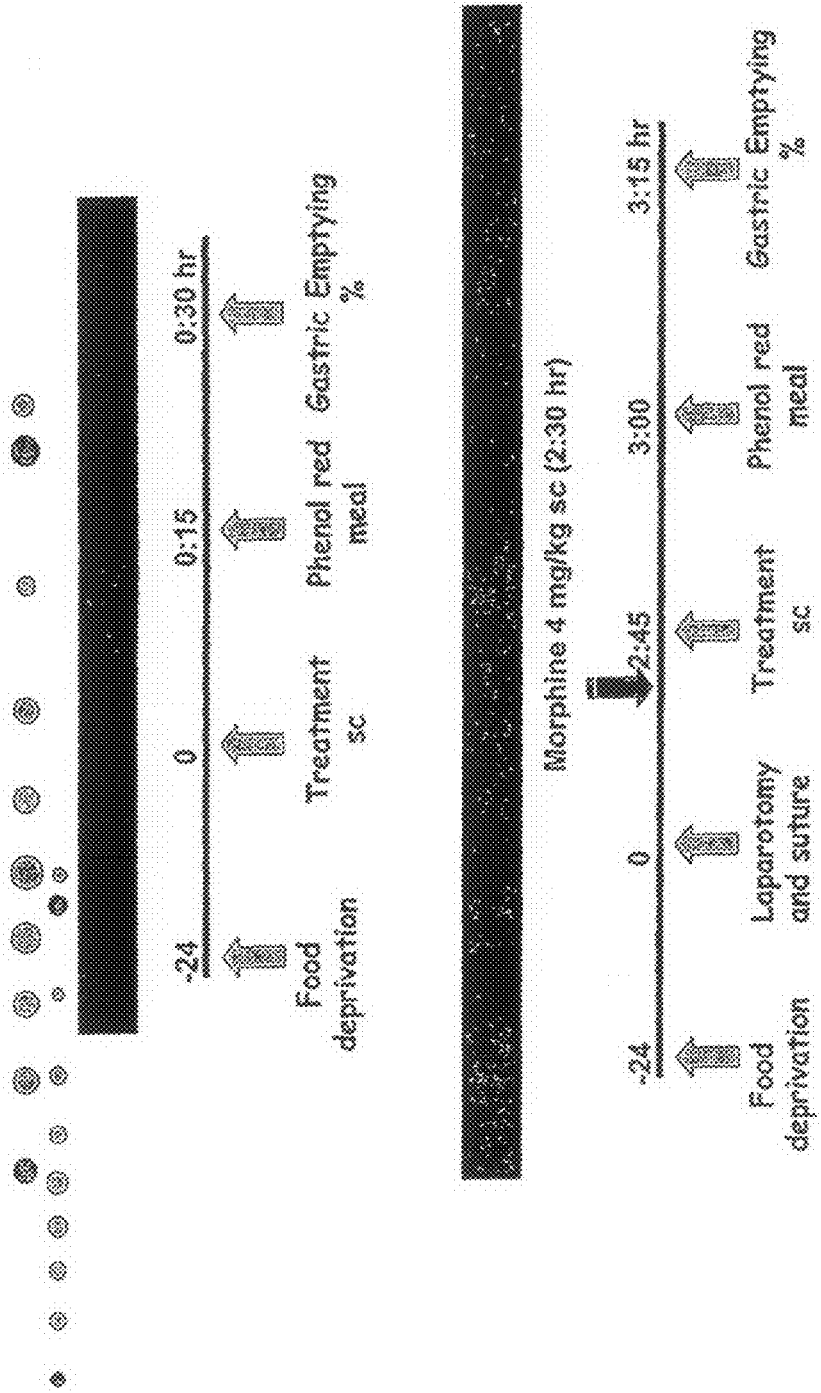
FIG. 1: shows the schematic presentation of the methods used to study gastric emptying in a rat model.
Figure 2:
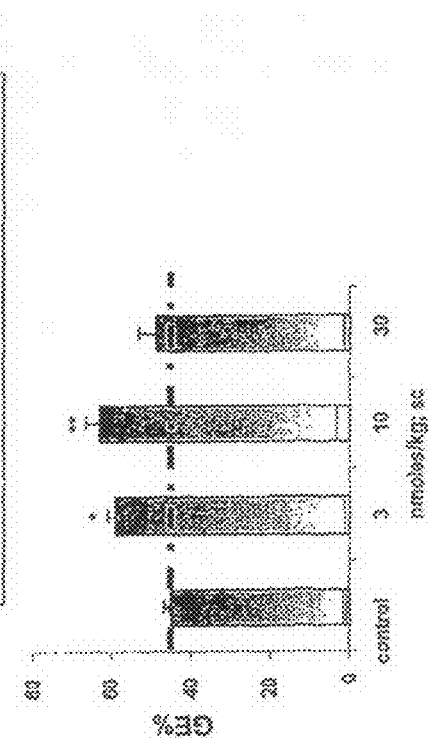
FIG. 2: shows the effect on gastric emptying in normal rats for native ghrelin and Example 19.
Figure 2:
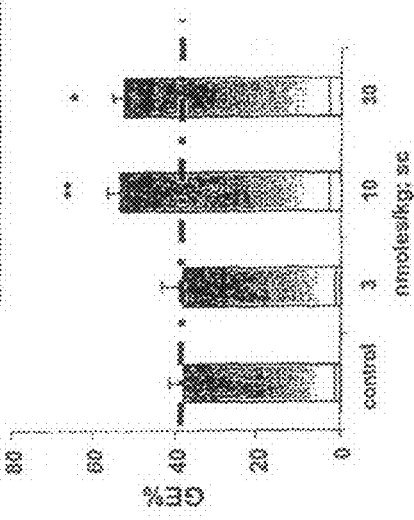
Figure 3:
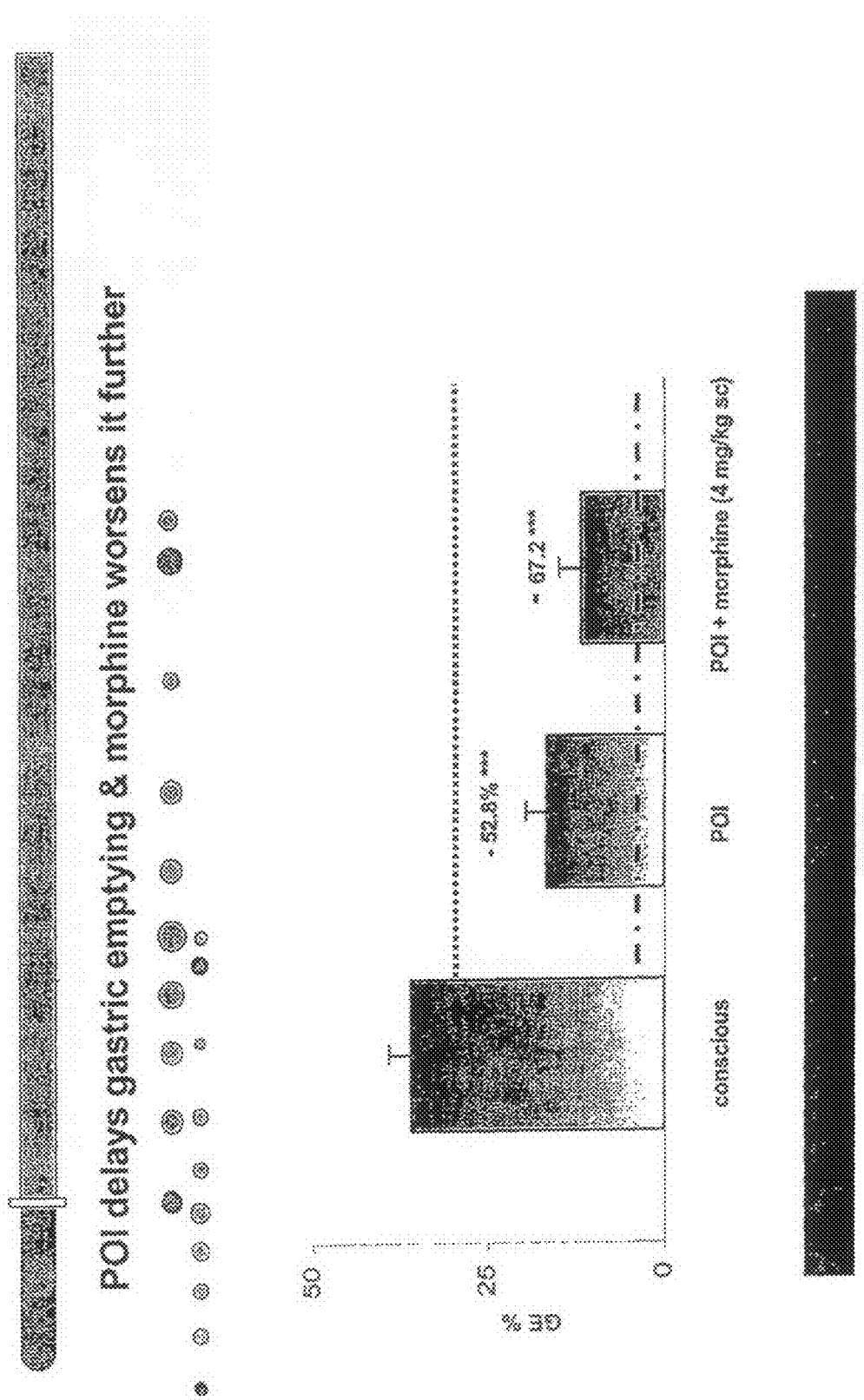
FIG. 3: shows the percent decrease in gastric emptying due to post-operative ileus alone and in combination with morphine.
Figure 4:
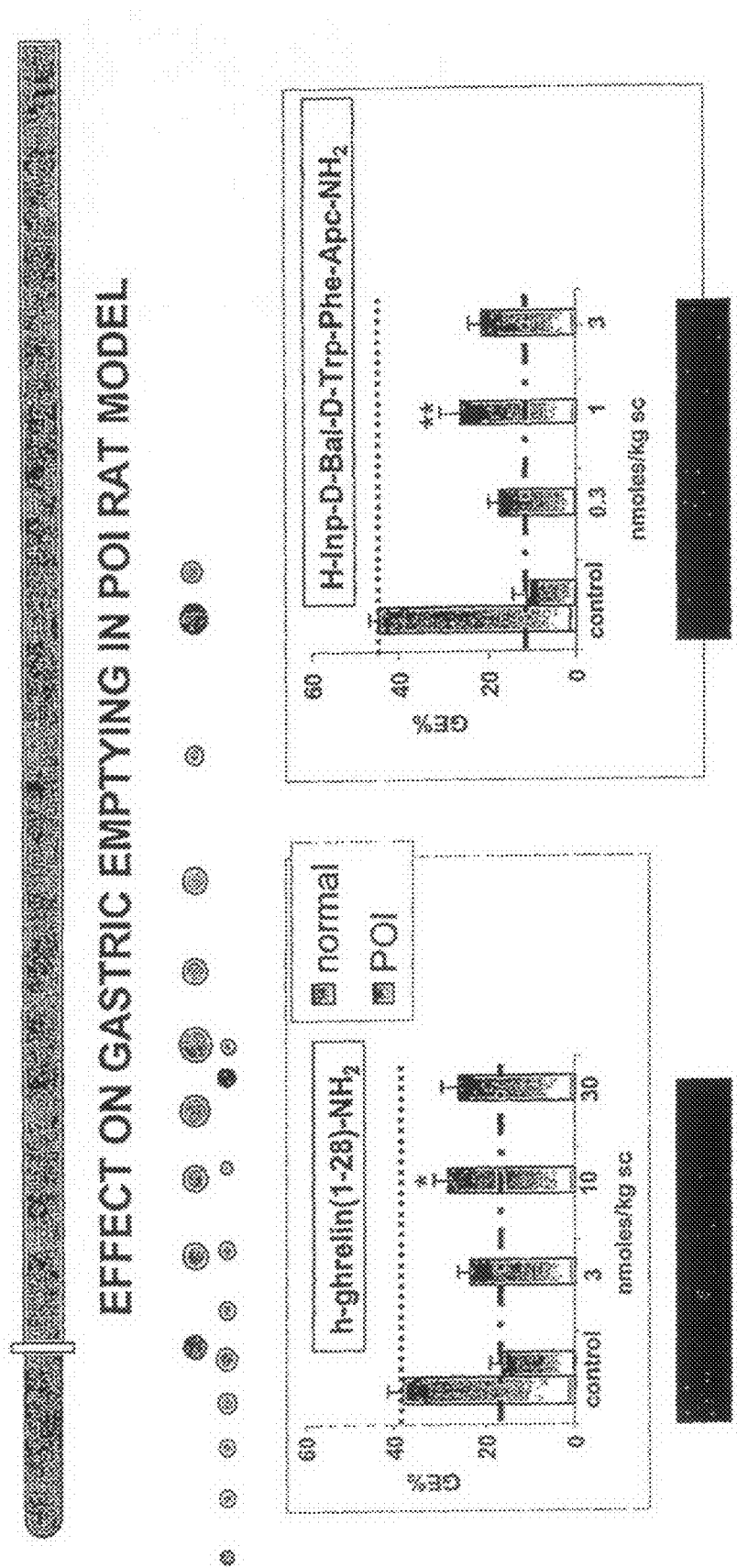
FIG. 4: shows the effect on gastric emptying in post-operative ileus rat model for native ghrelin and Example 19.
Figure 5:
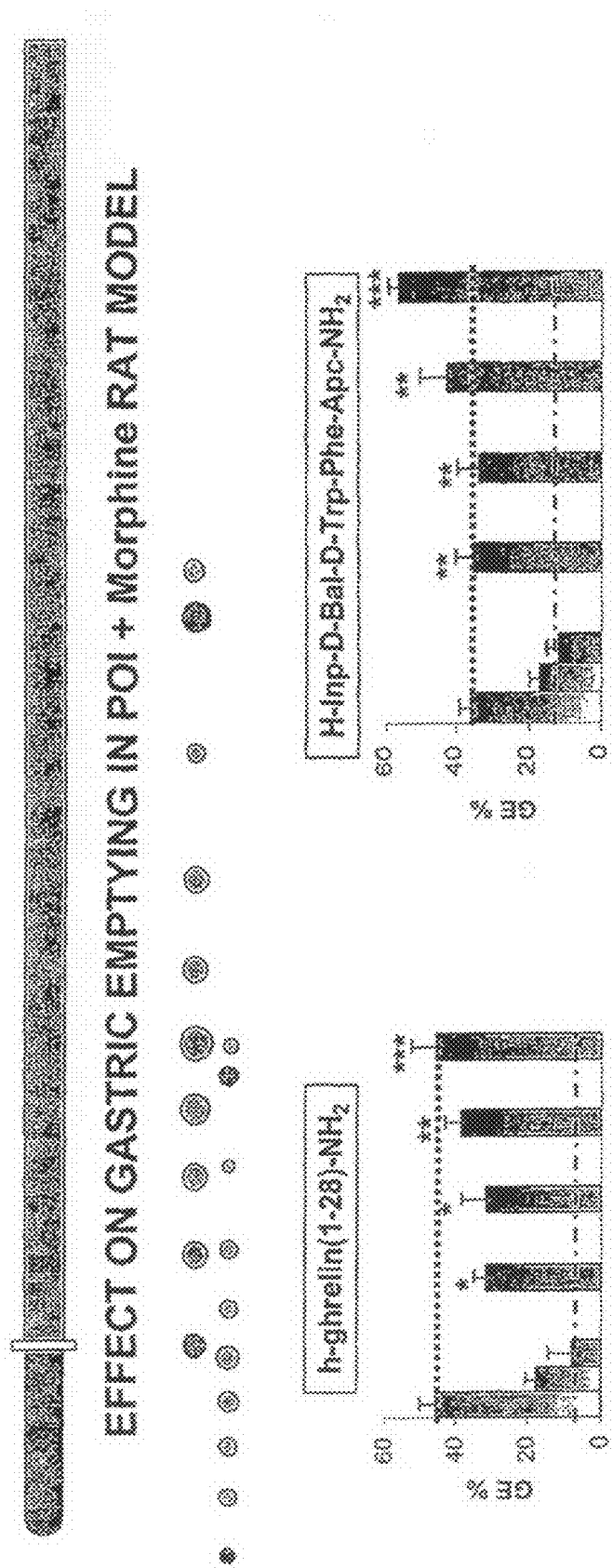
FIG. 5: shows the effect on gastric emptying in post-operative ileus and morphine rat model for native ghrelin and Example 19.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following description of the preferred embodiments and from the claims. Certain amino acids present in compounds of the invention can be and are represented herein as follows:

| Nomenclature and Abbreviations | |
|---|---|
| Symbol | Meaning |
| Abu | α-aminobutyric acid |
| Acc | 1-amino-1-cyclo(C$_3$-C$_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Act | 4-amino-4-carboxytetrahydropyran having the structure: |

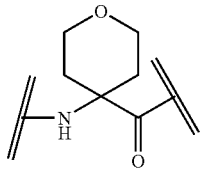

| | |
|---|---|
| Aib | α-aminoisobutyric acid |
| Aic | 2-aminoindan-2-carboxylic acid |
| Ala or A | alanine |
| β-Ala | beta-alanine |
| Apc | denotes the structure: |

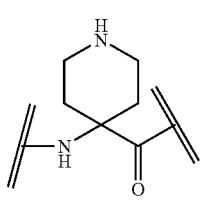

| | |
|---|---|
| Arg or R | arginine |
| hArg | homoarginine |
| Asn or N | asparagine |
| Asp or D | aspartic acid |

-continued

| Nomenclature and Abbreviations | |
|---|---|
| Symbol | Meaning |
| Ava | 5-amino-n-valeric acid |
| D-Bal | D-3-benzothienylalanine having the structure: |

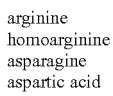

| D-Bip | D-4,4'-biphenylalanine having the structure: |

| D-Bpa | D-4-benzoylphenylalanine having the structure: |

| Cha | β-cyclohexylalanine |
| Cys or C | cysteine |
| hCys | L-homocysteine |
| Dab | 2,4-diaminobutyric acid |
| Dap | 2,3-diaminopropionic acid |
| Dap(octanoyl) | denotes the structure: |

| Dhp | 3,4-dehydroproline |
| Dip | β,β-diphenylalanine having the structure: |

| Dmt | 5,5-dimethylthiazolidine-4-carboxylic acid |
| 2-Fua | β-(2-furyl)-alanine |
| Gln or Q | glutamine |
| Glu or E | glutamic acid |
| Gly or G | glycine |
| His or H | histidine |
| 3-Hyp | trans-3-hydroxy-L-proline, i.e., (2S, 3S)-3-hydroxy- |

Nomenclature and Abbreviations

| Symbol | Meaning |
|---|---|
| 4-Hyp | pyrrolidine-2-carboxylic acid<br>4-hydroxyproline, i.e., (2S, 4R)-4-hydroxypyrrolidine-2-carboxylic acid |
| Ile or I | isoleucine |
| Inc | indoline-2-carboxylic acid |
| Inp | isonipecotic acid |
| Ktp | 4-ketoproline |
| Leu or L | leucine |
| hLeu | homoleucine |
| Lys or K | lysine |
| Lys (biotinyl) | lysine biotinyl having the structure: |

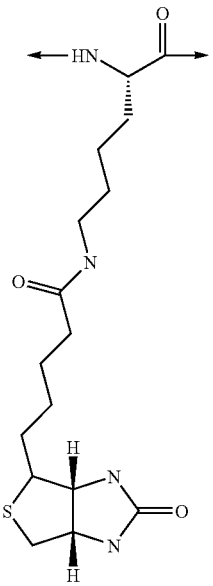

| | |
|---|---|
| Met or M | methionine |
| 1-Nal | β-(1-naphthyl)-L-alanine |
| 2-Nal | β-(2-naphthyl)-L-alanine |
| Nle | norleucine |
| Nva | norvaline |
| Oic | octahydroindole-2-carboxylic acid |
| Orn | ornithine |
| 2-Pal | β-(2-pyridiyl)alanine |
| 3-Pal | β-(3-pyridiyl)alanine |
| 4-Pal | β-(4-pyridiyl)alanine |
| Phe or F | phenylalanine |
| hPhe | homophenylalanine |
| Pff | pentafluorophenylalanine having the structure: |

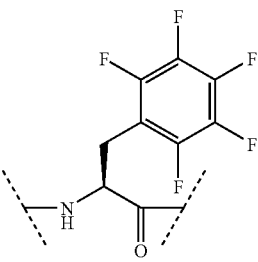

| | |
|---|---|
| Pip | pipecolic acid |
| Pim | 2'-(4-phenyl)imidazolyl having the structure: |

Nomenclature and Abbreviations

| Symbol | Meaning |
|---|---|

[structure shown]

| | |
|---|---|
| Pro or P | proline |
| Ser or S | serine |
| Taz | β-(4-thiazolyl)alanine having the structure: |

[structure shown]

| | |
|---|---|
| 2-Thi | β-(2-thienyl)alanine |
| 3-Thi | β-(3-thienyl)alanine |
| Thr or T | threonine |
| Thz | thiazolidine-4-carboxylic acid |
| Tic | 1,2,3,4-tetrahydroisoquinoline-3-carboxylic acid |
| Tle | tert-leucine |
| Trp or W | tryptophan |
| Tyr or Y | tyrosine |
| Val or V | valine |

When a non-amino acid imidazole moiety (e.g., Pim, defined above) is present at the C-terminus of a compound of the invention, it is understood that the imidazole moiety is attached to the adjacent amino acid via a pseudo-peptide bond (ψ), wherein a bond is form between the position 2 carbon of the imidazole ring and the alpha carbon of the amino acid. For example, in the case where the adjacent amino acid is D-trptophan (D-Trp) and the imidazole moiety is Pim, the C-terminus of the peptide would appear as follows:

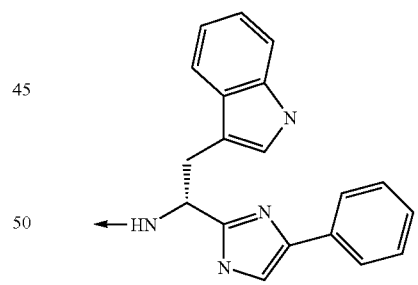

As used herein, Acc encompasses an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c).

As used herein, a "peptidyl analog of ghrelin" encompasses ghrelin analogues and peptidyl analogs thereof which can be used to practice the therapeutic method of the present invention including, but not limited to, the following compounds:

(Dap³(Octanesulfonyl))hGhrelin(1-28)-NH₂; (SEQ ID NO: 1)

(Aib², A6c⁵)hGhrelin(1-28)-NH₂; (SEQ ID NO: 2)

(A6c⁵)hGhrelin(1-28)-NH₂; (SEQ ID NO: 3)

(Aib²,⁶)hGhrelin(1-28)-NH₂; (SEQ ID NO: 4)

(Aib², A5c¹²)hGhrelin(1-28)-NH₂; (SEQ ID NO: 5)

(Aib², A5c¹², Orn¹⁵)hGhrelin(1-28)-NH₂; (SEQ ID NO: 6)

(Aib², A5c¹², Apc¹⁶)hGhrelin(1-28)-NH₂; (SEQ ID NO: 7)

(Aib², Act⁶)hGhrelin(1-28)-NH₂; (SEQ ID NO: 4)

(Aib², 3-Pal⁹)hGhrelin(1-28)-NH₂; (SEQ ID NO: 8)

(Aib², Dmt⁷)hGhrelin(1-28)-NH₂; (SEQ ID NO: 9)

(Aib², Thz⁷)hGhrelin(1-28)-NH₂; (SEQ ID NO: 9)

(A5c²)hGhrelin(1-28)-NH₂; (SEQ ID NO: 10)

(Act²)hGhrelin(1-28)-NH₂; (SEQ ID NO: 10)

(Aib², A5c⁵)hGhrelin(1-28)-NH₂; (SEQ ID NO: 2)

(Aib², A6c⁵)hGhrelin(1-28)-NH₂; (SEQ ID NO: 2)

(Aib²,⁵)hGhrelin(1-28)-NH₂; (SEQ ID NO: 2)

(Aib², hLeu⁵)hGhrelin(1-28)-NH₂; (SEQ ID NO: 2)

(Aib², Cha⁵)hGhrelin(1-28)-NH₂; (SEQ ID NO: 2)

(Aib²,⁶)hGhrelin(1-28)-NH₂; (SEQ ID NO: 4)

(Aib², Act⁶)hGhrelin(1-28)-NH₂; (SEQ ID NO: 4)

(Aib², Thr⁶)hGhrelin(1-28)-NH₂; (SEQ ID NO: 4)

(Aib², Abu⁶)hGhrelin(1-28)-NH₂; (SEQ ID NO: 4)

(Aib², 4-Hyp⁷)hGhrelin(1-28)-NH₂; (SEQ ID NO: 9)

(Aib², Thz⁷)hGhrelin(1-28)-NH₂; (SEQ ID NO: 9)

(Aib², Pip⁷)hGhrelin(1-28)-NH₂; (SEQ ID NO: 9)

(Aib², Dhp⁷)hGhrelin(1-28)-NH₂; (SEQ ID NO: 9)

(Aib², Ktp⁷)hGhrelin(1-28)-NH₂; (SEQ ID NO: 9)

(Aib²,⁸)hGhrelin(1-28)-NH₂; (SEQ ID NO: 11)

(Aib², 2-Pal⁹)hGhrelin(1-28)-NH₂; (SEQ ID NO: 8)

(Aib², 3-Pal⁹)hGhrelin(1-28)-NH₂; (SEQ ID NO: 8)

(Aib², 4-Pal⁹)hGhrelin(1-28)-NH₂; (SEQ ID NO: 8)

(Aib², Taz⁹)hGhrelin(1-28)-NH₂; (SEQ ID NO: 8)

(Aib², 2-Thi⁹)hGhrelin(1-28)-NH₂; (SEQ ID NO: 8)

(Aib², 2-Fua⁹)hGhrelin(1-28)-NH₂; (SEQ ID NO: 8)

(Aib², Apc⁹)hGhrelin(1-28)-NH₂; (SEQ ID NO: 8)

(Aib²,⁹)hGhrelin(1-28)-NH₂; (SEQ ID NO: 8)

(Aib²,¹⁰)hGhrelin(1-28)-NH₂; (SEQ ID NO: 12)

(Aib², Tic⁷)hGhrelin(1-28)-NH₂; (SEQ ID NO: 9)

(Aib⁶)hGhrelin(1-28)-NH₂; (SEQ ID NO: 13)

(A5c⁵)hGhrelin(1-28)-NH₂; (SEQ ID NO: 3)

(A6c⁵)hGhrelin(1-28)-NH₂; (SEQ ID NO: 3)

-continued (Act⁶)hGhrelin(1-28)-NH₂; (SEQ ID NO: 13)

(3-Pal⁹)hGhrelin(1-28)-NH₂; (SEQ ID NO: 14)

(Dmt⁷)hGhrelin(1-28)-NH₂; (SEQ ID NO: 15)

(Thz⁷)hGhrelin(1-28)-NH₂; (SEQ ID NO: 15)

(Aib⁵)hGhrelin(1-28)-NH₂; (SEQ ID NO: 3)

(hLeu⁵)hGhrelin(1-28)-NH₂; (SEQ ID NO: 3)

(Cha⁵)hGhrelin(1-28)-NH₂; (SEQ ID NO: 3)

(Thr⁶)hGhrelin(1-28)-NH₂; (SEQ ID NO: 13)

(Abu⁶)hGhrelin(1-28)-NH₂; (SEQ ID NO: 13)

(4-Hyp⁷)hGhrelin(1-28)-NH₂; (SEQ ID NO: 15)

(Pip⁷)hGhrelin(1-28)-NH₂; (SEQ ID NO: 15)

(Dhp⁷)hGhrelin(1-28)-NH₂; (SEQ ID NO: 15)

(Ktp⁷)hGhrelin(1-28)-NH₂; (SEQ ID NO: 15)

(Aib⁸)hGhrelin(1-28)-NH₂; (SEQ ID NO: 16)

(2-Pal⁹)hGhrelin(1-28)-NH₂; (SEQ ID NO: 14)

(4-Pal⁹)hGhrelin(1-28)-NH₂; (SEQ ID NO: 14)

(Taz⁹)hGhrelin(1-28)-NH₂; (SEQ ID NO: 14)

(2-Thi⁹)hGhrelin(1-28)-NH₂; (SEQ ID NO: 14)

(2-Fua⁹)hGhrelin(1-28)-NH₂; (SEQ ID NO: 14)

(Apc⁹)hGhrelin(1-28)-NH₂; (SEQ ID NO: 14)

(Aib⁹)hGhrelin(1-28)-NH₂; (SEQ ID NO: 14)

(Aib¹⁰)hGhrelin(1-28)-NH₂; (SEQ ID NO: 17)

(Aib², Dap³(Octanesulfonyl), A6c⁵)hGhrelin(1-28)-NH₂; (SEQ ID NO: 18)

(Dap³(Octanesulfonyl), A6c⁵)hGhrelin(1-28)-NH₂; (SEQ ID NO: 19)

(Aib²,⁶, Dap³(Octanesulfonyl))hGhrelin(1-28)-NH₂; (SEQ ID NO: 20)

(Aib², Dap³(Octanesulfonyl), A5c¹²)hGhrelin(1-28)-NH₂; (SEQ ID NO: 21)

(Aib², Dap³(Octanesulfonyl), A5c¹², Orn¹⁵)hGhrelin(1-28)-NH₂; (SEQ ID NO: 22)

(Aib², Dap³(Octanesulfonyl), A5c¹², Apc¹⁶)hGhrelin(1-28)-NH₂; (SEQ ID NO: 23)

(Aib², Dap³(Octanesulfonyl), Act⁶)hGhrelin(1-28)-NH₂; (SEQ ID NO: 20)

(Aib², Dap³(Octanesulfonyl), 3-Pal⁹)hGhrelin(1-28)-NH₂; (SEQ ID NO: 24)

(Aib², Dap³(Octanesulfonyl), Dmt⁷)hGhrelin(1-28)-NH₂; (SEQ ID NO: 25)

(Aib², Dap³(Octanesulfonyl), Thz⁷)hGhrelin(1-28)-NH₂; (SEQ ID NO: 25)

(A5c², Dap³(Octanesulfonyl))hGhrelin(1-28)-NH₂; (SEQ ID NO: 26)

(Act², Dap³(Octanesulfonyl))hGhrelin(1-28)-NH₂; (SEQ ID NO: 26)

(Aib², Dap³(Octanesulfonyl), A5c⁵)hGhrelin(1-28)-NH₂; (SEQ ID NO: 18)

(Aib²,⁵, Dap³(Octanesulfonyl))hGhrelin(1-28)-NH₂; (SEQ ID NO: 18)

(Aib², Dap³(Octanesulfonyl), hLeu⁵)hGhrelin(1-28)-NH₂; (SEQ ID NO: 18)

(Aib², Dap³(Octanesulfonyl), Cha⁵)hGhrelin(1-28)-NH₂; (SEQ ID NO: 18)

(Aib²,⁶, Dap³(Octanesulfonyl))hGhrelin(1-28)-NH₂; (SEQ ID NO: 20)

(Aib², Dap³(Octanesulfonyl), Thr⁶)hGhrelin(1-28)-NH₂; (SEQ ID NO: 20)

-continued (Aib², Dap³(Octanesulfonyl), Abu⁶)hGhrelin(1-28)-NH₂; (SEQ ID NO: 20)

(Aib², Dap³(Octanesulfonyl), 4-Hyp⁷)hGhrelin(1-28)-NH₂; (SEQ ID NO: 25)

(Aib², Dap³(Octanesulfonyl), Pip⁷)hGhrelin(1-28)-NH₂; (SEQ ID NO: 25)

(Aib², Dap³(Octanesulfonyl), Dhp⁷)hGhrelin(1-28)-NH₂; (SEQ ID NO: 25)

(Aib², Dap³(Octanesulfonyl), Ktp⁷)hGhrelin(1-28)-NH₂; (SEQ ID NO: 25)

(Aib²,⁸, Dap³(Octanesulfonyl))hGhrelin(1-28)-NH₂; (SEQ ID NO: 27)

(Aib², Dap³(Octanesulfonyl), 2-Pal⁹)hGhrelin(1-28)-NH₂; (SEQ ID NO: 24)

(Aib², Dap³(Octanesulfonyl), 3-Pal⁹)hGhrelin(1-28)-NH₂; (SEQ ID NO: 24)

(Aib², Dap³(Octanesulfonyl), 4-Pal⁹)hGhrelin(1-28)-NH₂; (SEQ ID NO: 24)

(Aib², Dap³(Octanesulfonyl), Taz⁹)hGhrelin(1-28)-NH₂; (SEQ ID NO: 24)

(Aib², Dap³(Octanesulfonyl), 2-Thi⁹)hGhrelin(1-28)-NH₂; (SEQ ID NO: 24)

(Aib², Dap³(Octanesulfonyl), 2-Fua⁹)hGhrelin(1-28)-NH₂; (SEQ ID NO: 24)

(Aib², Dap³(Octanesulfonyl), Apc⁹)hGhrelin(1-28)-NH₂; (SEQ ID NO: 24)

(Aib²,⁹, Dap³(Octanesulfonyl))hGhrelin(1-28)-NH₂; (SEQ ID NO: 24)

(Aib²,¹⁰, Dap³(Octanesulfonyl))hGhrelin(1-28)-NH₂; (SEQ ID NO: 28)

(Dap³(Octanesulfonyl), A6c⁵)hGhrelin(1-28)-NH₂; (SEQ ID NO: 19)

(Dap³(Octanesulfonyl), Aib⁶)hGhrelin(1-28)-NH₂; (SEQ ID NO: 29)

(Dap³(Octanesulfonyl), A5c¹²)hGhrelin(1-28)-NH₂; (SEQ ID NO: 30)

(Dap³(Octanesulfonyl), A5c¹², Orn¹⁵)hGhrelin(1-28)-NH₂; (SEQ ID NO: 31)

(Dap³(Octanesulfonyl), A5c¹², Apc¹⁶)hGhrelin(1-28)-NH₂; (SEQ ID NO: 32)

(Dap³(Octanesulfonyl), Act⁶)hGhrelin(1-28)-NH₂; (SEQ ID NO: 29)

(Dap³(Octanesulfonyl), 3-Pal⁹)hGhrelin(1-28)-NH₂; (SEQ ID NO: 33)

(Dap³(Octanesulfonyl), Dmt⁷)hGhrelin(1-28)-NH₂; (SEQ ID NO: 34)

(Dap³(Octanesulfonyl), Thz⁷)hGhrelin(1-28)-NH₂; (SEQ ID NO: 34)

(Dap³(Octanesulfonyl), A5c⁵)hGhrelin(1-28)-NH₂; (SEQ ID NO: 19)

(Dap³(Octanesulfonyl), Aib⁵)hGhrelin(1-28)-NH₂; (SEQ ID NO: 19)

(Dap³(Octanesulfonyl), hLeu⁵)hGhrelin(1-28)-NH₂; (SEQ ID NO: 19)

(Dap³(Octanesulfonyl), Cha⁵)hGhrelin(1-28)-NH₂; (SEQ ID NO: 19)

(Dap³(Octanesulfonyl), Thr⁶)hGhrelin(1-28)-NH₂; (SEQ ID NO: 29)

(Dap³(Octanesulfonyl), Abu⁶)hGhrelin(1-28)-NH₂; (SEQ ID NO: 29)

(Dap³(Octanesulfonyl), 4-Hyp⁷)hGhrelin(1-28)-NH₂; (SEQ ID NO: 34)

(Dap³(Octanesulfonyl), Pip⁷)hGhrelin(1-28)-NH₂; (SEQ ID NO: 34)

(Dap³(Octanesulfonyl), Dhp⁷)hGhrelin(1-28)-NH₂; (SEQ ID NO: 34)

(Dap³(Octanesulfonyl), Ktp⁷)hGhrelin(1-28)-NH₂; (SEQ ID NO: 34)

(Dap³(Octanesulfonyl), Aib⁸)hGhrelin(1-28)-NH₂; (SEQ ID NO: 35)

(Dap³(Octanesulfonyl), 2-Pal⁹)hGhrelin(1-28)-NH₂; (SEQ ID NO: 33)

(Dap³(Octanesulfonyl), 3-Pal⁹)hGhrelin(1-28)-NH₂; (SEQ ID NO: 33)

(Dap³(Octanesulfonyl), 4-Pal⁹)hGhrelin(1-28)-NH₂; (SEQ ID NO: 33)

(Dap³(Octanesulfonyl), Taz⁹)hGhrelin(1-28)-NH₂; (SEQ ID NO: 33)

(Dap³(Octanesulfonyl), 2-Thi⁹)hGhrelin(1-28)-NH₂; (SEQ ID NO: 33)

(Dap³(Octanesulfonyl), 2-Fua⁹)hGhrelin(1-28)-NH₂; (SEQ ID NO: 33)

-continued (Dap³(Octanesulfonyl),Apc⁹)hGhrelin(1-28)-NH₂; (SEQ ID NO: 33)

(Dap³(Octanesulfonyl),Aib⁹)hGhrelin(1-28)-NH₂; (SEQ ID NO: 33)

(Dap³(Octanesulfonyl),Aib¹⁰)hGhrelin(1-28)-NH₂; (SEQ ID NO: 36)

(Dap³(Octanesulfonyl),A5c¹²,Orn¹⁵)hGhrelin(1-28)-NH₂; (SEQ ID NO: 31)

(Dab³(Octanesulfonyl),A5c¹²,Orn¹⁵)hGhrelin(1-28)-NH₂; (SEQ ID NO: 31)

(Aib²,A6c⁵,A5c¹²,Orn¹⁵)hGhrelin(1-28)-NH₂; (SEQ ID NO: 37)

(A6c⁵,A5c¹²,Orn¹⁵)hGhrelin(1-28)-NH₂; (SEQ ID NO: 38)

(Aib²,⁶,A5c¹²,Orn¹⁵)hGhrelin(1-28)-NH₂; (SEQ ID NO: 39)

(Aib²,Act⁶,A5c¹²,Orn¹⁵)hGhrelin(1-28)-NH₂; (SEQ ID NO: 39)

(Aib²,3-Pal⁹,A5c¹²,Orn¹⁵)hGhrelin(1-28)-NH₂; (SEQ ID NO: 40)

(Aib²,Dmt⁷,A5c¹²,Orn¹⁵)hGhrelin(1-28)-NH₂; (SEQ ID NO: 41)

(Aib²,Thz⁷,A5c¹²,Orn¹⁵)hGhrelin(1-28)-NH₂; (SEQ ID NO: 41)

(Aib²,A5c⁵,A5c¹²,Orn¹⁵)hGhrelin(1-28)-NH₂; (SEQ ID NO: 37)

(Aib²,⁵,A5c¹²,Orn¹⁵)hGhrelin(1-28)-NH₂; (SEQ ID NO: 37)

(Aib²,hLeu⁵,A5c¹²,Orn¹⁵)hGhrelin(1-28)-NH₂; (SEQ ID NO: 37)

(Aib²,Cha⁵,A5c¹²,Orn¹⁵)hGhrelin(1-28)-NH₂; (SEQ ID NO: 37)

(Aib²,⁶,A5c¹²,Orn¹⁵)hGhrelin(1-28)-NH₂; (SEQ ID NO: 39)

(Aib²,Thr⁶,A5c¹²,Orn¹⁵)hGhrelin(1-28)-NH₂; (SEQ ID NO: 39)

(Aib²,Abu⁶,A5c¹²,Orn¹⁵)hGhrelin(1-28)-NH₂; (SEQ ID NO: 39)

(Aib²,4-Hyp⁷,A5c¹²,Orn¹⁵)hGhrelin(1-28)-NH₂; (SEQ ID NO: 41)

(Aib²,Pip⁷,A5c¹²,Orn¹⁵)hGhrelin(1-28)-NH₂; (SEQ ID NO: 41)

(Aib²,Dhp⁷,A5c¹²,Orn¹⁵)hGhrelin(1-28)-NH₂; (SEQ ID NO: 41)

(Aib²,Ktp⁷,A5c¹²,Orn¹⁵)hGhrelin(1-28)-NH₂; (SEQ ID NO: 41)

(Aib²,⁸,A5c¹²,Orn¹⁵)hGhrelin(1-28)-NH₂; (SEQ ID NO: 42)

(Aib²,2-Pal⁹,A5c¹²,Orn¹⁵)hGhrelin(1-28)-NH₂; (SEQ ID NO: 40)

(Aib²,3-Pal⁹,A5c¹²,Orn¹⁵)hGhrelin(1-28)-NH₂; (SEQ ID NO: 40)

(Aib²,4-Pal⁹,A5c¹²,Orn¹⁵)hGhrelin(1-28)-NH₂; (SEQ ID NO: 40)

(Aib²,Taz⁹,A5c¹²,Orn¹⁵)hGhrelin(1-28)-NH₂; (SEQ ID NO: 40)

(Aib²,2-Thi⁹,A5c¹²,Orn¹⁵)hGhrelin(1-28)-NH₂; (SEQ ID NO: 40)

(Aib²,2-Fua⁹,A5c¹²,Orn¹⁵)hGhrelin(1-28)-NH₂; (SEQ ID NO: 40)

(Aib²,Apc⁹,A5c¹²,Orn¹⁵)hGhrelin(1-28)-NH₂; (SEQ ID NO: 40)

(Aib²,⁹,A5c¹²,Orn¹⁵)hGhrelin(1-28)-NH₂; (SEQ ID NO: 40)

(Aib²,¹⁰,A5c¹²,Orn¹⁵)hGhrelin(1-28)-NH₂; (SEQ ID NO: 43)

(Dap³(Octanesulfonyl),A5c¹²,Apc¹⁶)hGhrelin(1-28)-NH₂; (SEQ ID NO: 32)

(Dab³(Octanesulfonyl),A5c¹²,Apc¹⁶)hGhrelin(1-28)-NH₂; (SEQ ID NO: 32)

(Aib²,A6c⁵,A5c¹²,Apc¹⁶)hGhrelin(1-28)-NH₂; (SEQ ID NO: 44)

(A6c⁵,A5c¹²,Apc¹⁶)hGhrelin(1-28)-NH₂; (SEQ ID NO: 45)

(Aib²,⁶,A5c¹²,Apc¹⁶)hGhrelin(1-28)-NH₂; (SEQ ID NO: 46)

(Aib²,Act⁶,A5c¹²,Apc¹⁶)hGhrelin(1-28)-NH₂; (SEQ ID NO: 46)

(Aib²,3-Pal⁹,A5c¹²,Apc¹⁶)hGhrelin(1-28)-NH₂; (SEQ ID NO: 47)

(Aib², Dmt⁷, A5c¹², Apc¹⁶)hGhrelin(1-28)-NH₂; (SEQ ID NO: 48)

(Aib², Thz⁷, A5c¹², Apc¹⁶)hGhrelin(1-28)-NH₂; (SEQ ID NO: 48)

(Aib², A5c⁵,¹², Apc¹⁶)hGhrelin(1-28)-NH₂; (SEQ ID NO: 44)

(Aib²,⁵, A5c¹², Apc¹⁶)hGhrelin(1-28)-NH₂; (SEQ ID NO: 44)

(Aib², hLeu⁵, A5c¹², Apc¹⁶)hGhrelin(1-28)-NH₂; (SEQ ID NO: 44)

(Aib², Cha⁵, A5c¹², Apc¹⁶)hGhrelin(1-28)-NH₂; (SEQ ID NO: 44)

(Aib²,⁶, A5c¹², Apc¹⁶)hGhrelin(1-28)-NH₂; (SEQ ID NO: 46)

(Aib², Thr⁶, A5c¹², Apc¹⁶)hGhrelin(1-28)-NH₂; (SEQ ID NO: 46)

(Aib², Abu⁶, A5c¹², Apc¹⁶)hGhrelin(1-28)-NH₂; (SEQ ID NO: 46)

(Aib², 4-Hyp⁷, A5c¹², Apc¹⁶)hGhrelin(1-28)-NH₂; (SEQ ID NO: 48)

(Aib², Pip⁷, A5c¹², Apc¹⁶)hGhrelin(1-28)-NH₂; (SEQ ID NO: 48)

(Aib², Dhp⁷, A5c¹², Apc¹⁶)hGhrelin(1-28)-NH₂; (SEQ ID NO: 48)

(Aib², Ktp⁷, A5c¹², Apc¹⁶)hGhrelin(1-28)-NH₂; (SEQ ID NO: 48)

(Aib²,⁸, A5c¹², Apc¹⁶)hGhrelin(1-28)-NH₂; (SEQ ID NO: 49)

(Aib², 2-Pal⁹, A5c¹², Apc¹⁶)hGhrelin(1-28)-NH₂; (SEQ ID NO: 47)

(Aib², 3-Pal⁹, A5c¹², Apc¹⁶)hGhrelin(1-28)-NH₂; (SEQ ID NO: 47)

(Aib², 4-Pal⁹, A5c¹², Apc¹⁶)hGhrelin(1-28)-NH₂; (SEQ ID NO: 47)

(Aib², Taz⁹, A5c¹², Apc¹⁶)hGhrelin(1-28)-NH₂; (SEQ ID NO: 47)

(Aib², 2-Thi⁹, A5c¹², Apc¹⁶)hGhrelin(1-28)-NH₂; (SEQ ID NO: 47)

(Aib², 2-Fua⁹, A5c¹², Apc¹⁶)hGhrelin(1-28)-NH₂; (SEQ ID NO: 47)

(Aib², Apc⁹, A5c¹², Apc¹⁶)hGhrelin(1-28)-NH₂; (SEQ ID NO: 47)

(Aib²,⁹, A5c¹², Apc¹⁶)hGhrelin(1-28)-NH₂; (SEQ ID NO: 47)

(Aib²,¹⁰, A5c¹², Apc¹⁶)hGhrelin(1-28)-NH₂; (SEQ ID NO: 50)

(A6c⁵, A5c¹², Orn¹⁵)hGhrelin(1-28)-NH₂; (SEQ ID NO: 38)

(Aib⁶, A5c¹², Orn¹⁵)hGhrelin(1-28)-NH₂; (SEQ ID NO: 51)

(Act⁶, A5c¹², Orn¹⁵)hGhrelin(1-28)-NH₂; (SEQ ID NO: 51)

(3-Pal⁹, A5c¹², Orn¹⁵)hGhrelin(1-28)-NH₂; (SEQ ID NO: 52)

(Dmt⁷, A5c¹², Orn¹⁵)hGhrelin(1-28)-NH₂; (SEQ ID NO: 53)

(Thz⁷, A5c¹², Orn¹⁵)hGhrelin(1-28)-NH₂; (SEQ ID NO: 53)

(A5c⁵, A5c¹², Orn¹⁵)hGhrelin(1-28)-NH₂; (SEQ ID NO: 38)

(Aib⁵, A5c¹², Orn¹⁵)hGhrelin(1-28)-NH₂; (SEQ ID NO: 38)

(hLeu⁵, A5c¹², Orn¹⁵)hGhrelin(1-28)-NH₂; (SEQ ID NO: 38)

(Cha⁵, A5c¹², Orn¹⁵)hGhrelin(1-28)-NH₂; (SEQ ID NO: 38)

(Aib⁶, A5c¹², Orn¹⁵)hGhrelin(1-28)-NH₂; (SEQ ID NO: 51)

(Thr⁶, A5c¹², Orn¹⁵)hGhrelin(1-28)-NH₂; (SEQ ID NO: 51)

(Abu⁶, A5c¹², Orn¹⁵)hGhrelin(1-28)-NH₂; (SEQ ID NO: 51)

(4-Hyp⁷, A5c¹², Orn¹⁵)hGhrelin(1-28)-NH₂; (SEQ ID NO: 53)

(Pip⁷, A5c¹², Orn¹⁵)hGhrelin(1-28)-NH₂; (SEQ ID NO: 53)

(Dhp⁷, A5c¹², Orn¹⁵)hGhrelin(1-28)-NH₂; (SEQ ID NO: 53)

(Ktp⁷, A5c¹², Orn¹⁵)hGhrelin(1-28)-NH₂; (SEQ ID NO: 53)

(Aib⁸, A5c¹², Orn¹⁵)hGhrelin(1-28)-NH₂; (SEQ ID NO: 54)

-continued (2-Pal⁹,A5c¹²,Orn¹⁵)hGhrelin(1-28)-NH₂; (SEQ ID NO: 52)

(3-Pal⁹,A5c¹²,Orn¹⁵)hGhrelin(1-28)-NH₂; (SEQ ID NO: 52)

(4-Pal⁹,A5c¹²,Orn¹⁵)hGhrelin(1-28)-NH₂; (SEQ ID NO: 52)

(Taz⁹,A5c¹²,Orn¹⁵)hGhrelin(1-28)-NH₂; (SEQ ID NO: 52)

(2-Thi⁹,A5c¹²,Orn¹⁵)hGhrelin(1-28)-NH₂; (SEQ ID NO: 52)

(2-Fua⁹,A5c¹²,Orn¹⁵)hGhrelin(1-28)-NH₂; (SEQ ID NO: 52)

(Apc⁹,A5c¹²,Orn¹⁵)hGhrelin(1-28)-NH₂; (SEQ ID NO: 52)

(Aib⁹,A5c¹²,Orn¹⁵)hGhrelin(1-28)-NH₂; (SEQ ID NO: 52)

(Aib¹⁰,A5c¹²,Orn¹⁵)hGhrelin(1-28)-NH₂; (SEQ ID NO: 55)

(Aib⁶,A5c¹²,Apc¹⁶)hGhrelin(1-28)-NH₂; (SEQ ID NO: 56)

(A5c⁵,A5c¹²,Apc¹⁶)hGhrelin(1-28)-NH₂; (SEQ ID NO: 45)

(Act⁶,A5c¹²,Apc¹⁶)hGhrelin(1-28)-NH₂; (SEQ ID NO: 56)

(3-Pal⁹,A5c¹²,Apc¹⁶)hGhrelin(1-28)-NH₂; (SEQ ID NO: 57)

(Dmt⁷,A5c¹²,Apc¹⁶)hGhrelin(1-28)-NH₂; (SEQ ID NO: 58)

(Thz⁷,A5c¹²,Apc¹⁶)hGhrelin(1-28)-NH₂; (SEQ ID NO: 58)

(Aib⁵,A5c¹²,Apc¹⁶)hGhrelin(1-28)-NH₂; (SEQ ID NO: 45)

(hLeu⁵,A5c¹²,Apc¹⁶)hGhrelin(1-28)-NH₂; (SEQ ID NO: 45)

(Cha⁵,A5c¹²,Apc¹⁶)hGhrelin(1-28)-NH₂; (SEQ ID NO: 45)

(Thr⁶,A5c¹²,Apc¹⁶)hGhrelin(1-28)-NH₂; (SEQ ID NO: 56)

(Abu⁶,A5c¹²,Apc¹⁶)hGhrelin(1-28)-NH₂; (SEQ ID NO: 56)

(4-Hyp⁷,A5c¹²,Apc¹⁶)hGhrelin(1-28)-NH₂; (SEQ ID NO: 58)

(Pip⁷,A5c¹²,Apc¹⁶)hGhrelin(1-28)-NH₂; (SEQ ID NO: 58)

(Dhp⁷,A5c¹²,Apc¹⁶)hGhrelin(1-28)-NH₂; (SEQ ID NO: 58)

(Ktp⁷,A5c¹²,Apc¹⁶)hGhrelin(1-28)-NH₂; (SEQ ID NO: 58)

(Aib⁸,A5c¹²,Apc¹⁶)hGhrelin(1-28)-NH₂; (SEQ ID NO: 59)

(2-Pal⁹,A5c¹²,Apc⁶)hGhrelin(1-28)-NH₂; (SEQ ID NO: 57)

(3-Pal⁹,A5c¹²,Apc¹⁶)hGhrelin(1-28)-NH₂; (SEQ ID NO: 57)

(4-Pal⁹,A5c¹²,Apc¹⁶)hGhrelin(1-28)-NH₂; (SEQ ID NO: 57)

(Taz⁹,A5c¹²,Apc¹⁶)hGhrelin(1-28)-NH₂; (SEQ ID NO: 57)

(2-Thi⁹,A5c¹²,Apc¹⁶)hGhrelin(1-28)-NH₂; (SEQ ID NO: 57)

(2-Fua⁹,A5c¹²,Apc¹⁶)hGhrelin(1-28)-NH₂; (SEQ ID NO: 57)

(Apc⁹,A5c¹²,Apc¹⁶)hGhrelin(1-28)-NH₂; (SEQ ID NO: 57)

(Aib⁹,A5c¹²,Apc¹⁶)hGhrelin(1-28)-NH₂; (SEQ ID NO: 57)

(Aib¹⁰,A5c¹²,Apc¹⁶)hGhrelin(1-28)-NH₂; (SEQ ID NO: 60)

(Aib²,Glu³(NH-Hexyl),A6c⁵)hGhrelin(1-28)-NH₂; (SEQ ID NO: 61)

(Glu³(NH-Hexyl),A6c⁵)hGhrelin(1-28)-NH₂; (SEQ ID NO: 62)

(Aib²,⁶,Glu³(NH-Hexyl))hGhrelin(1-28)-NH₂; (SEQ ID NO: 63)

(Aib²,Glu³(NH-Hexyl),Act⁶)hGhrelin(1-28)-NH₂; (SEQ ID NO: 63)

(Aib²,Glu³(NH-Hexyl),3-Pal⁹)hGhrelin(1-28)-NH₂; (SEQ ID NO: 64)

(Aib²,Glu³(NH-Hexyl),Dmt⁷)hGhrelin(1-28)-NH₂; (SEQ ID NO: 65)

-continued (Aib$^2$,Glu$^3$(NH-Hexyl),Thz$^7$)hGhrelin(1-28)-NH$_2$; (SEQ ID NO: 65)

(Aib$^2$,Glu$^3$(NH-Hexyl),A5c$^5$)hGhrelin(1-28)-NH$_2$; (SEQ ID NO: 61)

(Aib$^{2,5}$,Glu$^3$(NH-Hexyl))hGhrelin(1-28)-NH$_2$; (SEQ ID NO: 61)

(Aib$^2$,Glu$^3$(NH-Hexyl),hLeu$^5$)hGhrelin(1-28)-NH$_2$; (SEQ ID NO: 61)

(Aib$^2$,Cha$^5$)hGhrelin(1-28)-NH$_2$; (SEQ ID NO: 2)

(Aib$^{2,6}$,Glu$^3$(NH-Hexyl))hGhrelin(1-28)-NH$_2$; (SEQ ID NO: 63)

(Aib$^2$,Glu$^3$(NH-Hexyl),Thr$^6$)hGhrelin(1-28)-NH$_2$; (SEQ ID NO: 63)

(Aib$^2$,Glu$^3$(NH-Hexyl),Abu$^6$)hGhrelin(1-28)-NH$_2$; (SEQ ID NO: 63)

(Aib$^2$,Glu$^3$(NH-hexyl),4-Hyp$^7$)hGhrelin(1-28)-NH$_2$; (SEQ ID NO: 65)

(Aib$^2$,Glu$^3$(NH-Hexyl),Pip$^7$)hGhrelin(1-28)-NH$_2$; (SEQ ID NO: 65)

(Aib$^2$,Glu$^3$(NH-Hexyl),Dhp$^7$)hGhrelin(1-28)-NH$_2$; (SEQ ID NO: 65)

(Aib$^2$,Glu$^3$(NH-Hexyl),Ktp$^7$)hGhrelin(1-28)-NH$_2$; (SEQ ID NO: 65)

(Aib$^{2,8}$,Glu$^3$(NH-Hexyl))hGhrelin(1-28)-NH$_2$; (SEQ ID NO: 27)

(Aib$^2$,Glu$^3$(NH-Hexyl),2-Pal$^9$)hGhrelin(1-28)-NH$_2$; (SEQ ID NO: 64)

(Aib$^2$,Glu$^3$(NH-Hexyl),3-Pal$^9$)hGhrelin(1-28)-NH$_2$; (SEQ ID NO: 64)

(Aib$^2$,Glu$^3$(NH-Hexyl),4-Pal$^9$)hGhrelin(1-28)-NH$_2$; (SEQ ID NO: 64)

(Aib$^2$,Glu$^3$(NH-Hexyl),Taz$^9$)hGhrelin(1-28)-NH$_2$; (SEQ ID NO: 64)

(Aib$^2$,Glu$^3$(NH-Hexyl),2-Thi$^9$)hGhrelin(1-28)-NH$_2$; (SEQ ID NO: 64)

(Aib$^2$,Glu$^3$(NH-Hexyl),2-Fua$^9$)hGhrelin(1-28)-NH$_2$; (SEQ ID NO: 64)

(Aib$^2$,Glu$^3$(NH-Hexyl),Apc$^9$)hGhrelin(1-28)-NH$_2$; (SEQ ID NO: 64)

(Aib$^{2,9}$,Glu$^3$(NH-Hexyl))hGhrelin(1-28)-NH$_2$; (SEQ ID NO: 64)

(Aib$^{2,10}$,Glu$^3$(NH-Hexyl))hGhrelin(1-28)-NH$_2$; (SEQ ID NO: 28)

(Glu$^3$(NH-Hexyl),Aib$^6$)hGhrelin(1-28)-NH$_2$; (SEQ ID NO: 66)

(Glu$^3$(NH-Hexyl),A5c$^5$)hGhrelin(1-28)-NH$_2$; (SEQ ID NO: 62)

(Glu$^3$(NH-Hexyl),Act$^6$)hGhrelin(1-28)-NH$_2$; (SEQ ID NO: 66)

(Glu$^3$(NH-Hexyl),3-Pal$^9$)hGhrelin(1-28)-NH$_2$; (SEQ ID NO: 67)

(Glu$^3$(NH-Hexyl),Dmt$^7$)hGhrelin(1-28)-NH$_2$; (SEQ ID NO: 68)

(Glu$^3$(NH-Hexyl),Thz$^7$)hGhrelin(1-28)-NH$_2$; (SEQ ID NO: 68)

(Glu$^3$(NH-Hexyl),Aib$^5$)hGhrelin(1-28)-NH$_2$; (SEQ ID NO: 62)

(Glu$^3$(NH-Hexyl),hLeu$^5$)hGhrelin(1-28)-NH$_2$; (SEQ ID NO: 62)

(Glu$^3$(NH-Hexyl),Cha$^5$)hGhrelin(1-28)-NH$_2$; (SEQ ID NO: 62)

(Glu$^3$(NH-Hexyl),Thr$^6$)hGhrelin(1-28)-NH$_2$; (SEQ ID NO: 66)

(Glu$^3$(NH-Hexyl),Abu$^6$)hGhrelin(1-28)-NH$_2$; (SEQ ID NO: 66)

(Glu$^3$(NH-Hexyl),4-Hyp$^7$)hGhrelin(1-28)-NH$_2$; (SEQ ID NO: 68)

(Glu$^3$(NH-Hexyl),Pip$^7$)hGhrelin(1-28)-NH$_2$; (SEQ ID NO: 68)

(Glu$^3$(NH-Hexyl),Dhp$^7$)hGhrelin(1-28)-NH$_2$; (SEQ ID NO: 68)

(Glu$^3$(NH-Hexyl),Ktp$^7$)hGhrelin(1-28)-NH$_2$; (SEQ ID NO: 68)

(Glu$^3$(NH-hexyl),Aib$^8$)hGhrelin(1-28)-NH$_2$; (SEQ ID NO: 35)

(Glu$^3$(NH-Hexyl),2-Pal$^9$)hGhrelin(1-28)-NH$_2$; (SEQ ID NO: 67)

(Glu$^3$(NH-Hexyl),3-Pal$^9$)hGhrelin(1-28)-NH$_2$; (SEQ ID NO: 67)

(Glu$^3$(NH-Hexyl),4-Pal$^9$)hGhrelin(1-28)-NH$_2$; (SEQ ID NO: 67)

-continued (Glu$^3$(NH-Hexyl),Taz$^9$)hGhrelin(1-28)-NH$_2$; (SEQ ID NO: 67)

(Glu$^3$(NH-Hexyl),2-Thi$^9$)hGhrelin(1-28)-NH$_2$; (SEQ ID NO: 67)

(Glu$^3$(NH-Hexyl),2-Fua$^9$)hGhrelin(1-28)-NH$_2$; (SEQ ID NO: 67)

(Glu$^3$(NH-Hexyl),Apc$^9$)hGhrelin(1-28)-NH$_2$; (SEQ ID NO: 67)

(Glu$^3$(NH-Hexyl),Aib$^9$)hGhrelin(1-28)-NH$_2$; (SEQ ID NO: 67)

(Glu$^3$(NH-Hexyl),Aib$^{10}$)hGhrelin(1-28)-NH$_2$; (SEQ ID NO: 36)

(Aib$^2$,Glu$^3$(NH-Hexyl),A6c$^5$,A5c$^{12}$,Orn$^{15}$)hGhrelin(1-28)-NH$_2$; (SEQ ID NO: 69)

(A6c$^5$,Glu$^3$(NH-Hexyl),A5c$^{12}$,Orn$^{15}$)hGhrelin(1-28)-NH$_2$; (SEQ ID NO: 70)

(Aib$^{2,6}$,Glu$^3$(NH-Hexyl),A5c$^{12}$,Orn$^{15}$)hGhrelin(1-28)-NH$_2$; (SEQ ID NO: 71)

(Aib$^2$,Glu$^3$(NH-Hexyl),Act$^6$,A5c$^{12}$,Orn$^{15}$)hGhrelin(1-28)-NH$_2$; (SEQ ID NO: 71)

(Aib$^2$,Glu$^3$(NH-Hexyl),3-Pal$^9$,A5c$^{12}$,Orn$^{15}$)hGhrelin(1-28)-NH$_2$; (SEQ ID NO: 72)

(Aib$^2$,Glu$^3$(NH-Hexyl),Dmt$^7$,A5c$^{12}$,Orn$^{15}$)hGhrelin(1-28)-NH$_2$; (SEQ ID NO: 73)

(Aib$^2$,Glu$^3$(NH-Hexyl),Thz$^7$,A5c$^{12}$,Orn$^{15}$)hGhrelin(1-28)-NH$_2$; (SEQ ID NO: 73)

(Aib$^2$,Glu$^3$(NH-Hexyl),A5c$^5$,A5c$^{12}$,Orn$^{15}$)hGhrelin(1-28)-NH$_2$; (SEQ ID NO: 69)

(Aib$^{2,5}$,Glu$^3$(NH-Hexyl),A5c$^{12}$,Orn$^{15}$)hGhrelin(1-28)-NH$_2$; (SEQ ID NO: 69)

(Aib$^2$,hLeu$^5$,A5c$^{12}$,Orn$^5$)hGhrelin(1-28)-NH$_2$; (SEQ ID NO: 37)

(Aib$^2$,Glu$^3$(NH-Hexyl),Cha$^5$,A5c$^{12}$,Orn$^5$)hGhrelin(1-28)-NH$_2$; (SEQ ID NO: 69)

(Aib$^{2,6}$,Glu$^3$(NH-Hexyl),A5c$^{12}$,Orn$^{15}$)hGhrelin(1-28)-NH$_2$; (SEQ ID NO: 71)

(Aib$^2$,Glu$^3$(NH-Hexyl),Thr$^6$,A5c$^{12}$,Orn$^{15}$)hGhrelin(1-28)-NH$_2$; (SEQ ID NO: 71)

(Aib$^2$,Glu$^3$(NH-Hexyl),Abu$^6$,A5c$^{12}$,Orn$^{15}$)hGhrelin(1-28)-NH$_2$; (SEQ ID NO: 71)

(Aib$^2$,Glu$^3$(NH-Hexyl),4-Hyp$^7$,A5c$^{12}$,Orn$^{15}$)hGhrelin(1-28)-NH$_2$; (SEQ ID NO: 73)

(Aib$^2$,Glu$^3$(NH-Hexyl),Pip$^7$,A5c$^{12}$,Orn$^{15}$)hGhrelin(1-28)-NH$_2$; (SEQ ID NO: 73)

(Aib$^2$,Glu$^3$(NH-Hexyl),Dhp$^7$,A5c$^{12}$,Orn$^5$)hGhrelin(1-28)-NH$_2$; (SEQ ID NO: 73)

(Aib$^2$,Glu$^3$(NH-Hexyl),Ktp$^7$,A5c$^{12}$,Orn$^{15}$)hGhrelin(1-28)-NH$_2$; (SEQ ID NO: 73)

(Aib$^{2,8}$,Glu$^3$(NH-Hexyl),A5c$^{12}$,Orn$^{15}$)hGhrelin(1-28)-NH$_2$; (SEQ ID NO: 74)

(Aib$^2$,Glu$^3$(NH-Hexyl),2-Pal$^9$,A5c$^{12}$,Orn$^{15}$)hGhrelin(1-28)-NH$_2$; (SEQ ID NO: 72)

(Aib$^2$,Glu$^3$(NH-Hexyl),3-Pal$^9$,A5c$^{12}$,Orn$^{15}$)hGhrelin(1-28)-NH$_2$; (SEQ ID NO: 72)

(Aib$^2$,Glu$^3$(NH-Hexyl),4-Pal$^9$,A5c$^{12}$,Orn$^{15}$)hGhrelin(1-28)-NH$_2$; (SEQ ID NO: 72)

(Aib$^2$,Glu$^3$(NH-Hexyl),Taz$^9$,A5c$^{12}$,Orn$^5$)hGhrelin(1-28)-NH$_2$; (SEQ ID NO: 72)

(Aib$^2$,Glu$^3$(NH-Hexyl),2-Thi$^9$,A5c$^{12}$,Orn$^{15}$)hGhrelin(1-28)-NH$_2$; (SEQ ID NO: 72)

(Aib$^2$,Glu$^3$(NH-Hexyl),2-Fua$^9$,A5c$^{12}$,Orn$^{15}$)hGhrelin(1-28)-NH$_2$; (SEQ ID NO: 72)

(Aib$^2$,Glu$^3$(NH-Hexyl),Apc$^9$,A5c$^{12}$,Orn$^{15}$)hGhrelin(1-28)-NH$_2$; (SEQ ID NO: 72)

(Aib$^{2,9}$,Glu$^3$(NH-Hexyl),A5c$^{12}$,Orn$^{15}$)hGhrelin(1-28)-NH$_2$; (SEQ ID NO: 72)

(Aib$^{2,12}$,Glu$^3$(NH-Hexyl),4-Pal$^9$,Orn$^{15}$)hGhrelin(1-28)-NH$_2$; (SEQ ID NO: 75)

(Aib$^{2,10}$,Glu$^3$(NH-Hexyl),A5c$^{12}$,Orn$^{15}$)hGhrelin(1-28)-NH$_2$; (SEQ ID NO: 76)

(Aib$^2$,Glu$^3$(NH-Hexyl),A6c$^5$,A5c$^{12}$,Apc$^{16}$)hGhrelin(1-28)-NH$_2$; (SEQ ID NO: 77)

(Glu$^3$(NH-Hexyl),A6c$^5$,A5c$^{12}$,Apc$^{16}$)hGhrelin(1-28)-NH$_2$; (SEQ ID NO: 78)

(Aib$^{2,6}$,Glu$^3$(NH-Hexyl),A5c$^{12}$,Apc$^{16}$)hGhrelin(1-28)-NH$_2$; (SEQ ID NO: 79)

(Aib$^2$,Glu$^3$(NH-Hexyl),Act$^6$,A5c$^{12}$,Apc$^{16}$)hGhrelin(1-28)-NH$_2$; (SEQ ID NO: 79)

(Aib$^2$,Glu$^3$(NH-Hexyl),3-Pal$^9$,A5c$^{12}$,Apc$^{16}$)hGhrelin(1-28)-NH$_2$; (SEQ ID NO: 80)

-continued (Aib$^2$,Glu$^3$(NH-Hexyl),Dmt$^7$,A5c$^{12}$,Apc$^{16}$)hGhrelin(1-28)-NH$_2$; (SEQ ID NO: 81)

(Aib$^2$,Glu$^3$(NH-Hexyl),Thz$^7$,A5c$^{12}$,Apc$^{16}$)hGhrelin(1-28)-NH$_2$; (SEQ ID NO: 81)

(Aib$^2$,Glu$^3$(NH-Hexyl),A5c$^{5,12}$,Apc$^{16}$)hGhreLin(1-28)-NH$_2$; (SEQ ID NO: 77)

(Aib$^{2,5}$,Glu$^3$(NH-Hexyl),A5c$^{12}$,Apc$^{16}$)hGhrelin(1-28)-NH$_2$; (SEQ ID NO: 77)

(Aib$^2$,Glu$^3$(NH-Hexyl),hLeu$^5$,A5c$^{12}$,Apc$^{16}$)hGhrelin(1-28)-NH$_2$; (SEQ ID NO: 77)

(Aib$^2$,Glu$^3$(NH-Hexyl),Cha$^5$,A5c$^{12}$,Apc$^{16}$)hGhrelin(1-28)-NH$_2$; (SEQ ID NO: 77)

(Aib$^{2,6}$,Glu$^3$(NH-Hexyl),A5c$^{12}$,Apc$^{16}$)hGhrelin(1-28)-NH$_2$; (SEQ ID NO: 79)

(Aib$^2$,Glu$^3$(NH-Hexyl),Thr$^6$,A5c$^{12}$,Apc$^{16}$)hGhrelin(1-28)-NH$_2$; (SEQ ID NO: 79)

(Aib$^2$,Glu$^3$(NH-Hexyl),Abu$^6$,A5c$^{12}$,Apc$^{16}$)hGhrelin(1-28)-NH$_2$; (SEQ ID NO: 79)

(Aib$^2$,Glu$^3$(NH-Hexyl),4-Hyp$^7$,A5c$^{12}$,Apc$^{16}$)hGhrelin(1-28)-NH$_2$; (SEQ ID NO: 81)

(Aib$^2$,Glu$^3$(NH-Hexyl),Pip$^7$,A5c$^{12}$,Apc$^{16}$)hGhrelin(1-28)-NH$_2$; (SEQ ID NO: 81)

(Aib$^2$,Glu$^3$(NH-Hexyl),Dhp$^7$,A5c$^{12}$,Apc$^{16}$)hGhrelin(1-28)-NH$_2$; (SEQ ID NO: 81)

(Aib$^2$,Glu$^3$(NH-Hexyl),Ktp$^7$,A5c$^{12}$,Apc$^{16}$)hGhrelin(1-28)-NH$_2$; (SEQ ID NO: 81)

(Aib$^{2,8}$,Glu$^3$(NH-Hexyl),A5c$^{12}$,Apc$^{16}$)hGhrelin(1-28)-NH$_2$; (SEQ ID NO: 82)

(Aib$^2$,Glu$^3$(NH-Hexyl),2-Pal$^9$,A5c$^{12}$,Apc$^{16}$)hGhrelin(1-28)-NH$_2$; (SEQ ID NO: 80)

(Aib$^2$,Glu$^3$(NH-Hexyl),3-Pal$^9$,A5c$^{12}$,Apc$^{16}$)hGhrelin(1-28)-NH$_2$; (SEQ ID NO: 80)

(Aib$^2$,Glu$^3$(NH-Hexyl),4-Pal$^9$,A5c$^{12}$,Apc$^{16}$)hGhrelin(1-28)-NH$_2$; (SEQ ID NO: 80)

(Aib$^2$,Glu$^3$(NH-Hexyl),Taz$^9$,A5c$^{12}$,Apc$^{16}$)hGhrelin(1-28)-NH$_2$; (SEQ ID NO: 80)

(Aib$^2$,Glu$^3$(NH-Hexyl),2-Thi$^9$,A5c$^{12}$,Apc$^{16}$)hGhrelin(1-28)-NH$_2$; (SEQ ID NO: 80)

(Aib$^2$,Glu$^3$(NH-Hexyl),2-Fua$^9$,A5c$^{12}$,Apc$^{16}$)hGhrelin(1-28)-NH$_2$; (SEQ ID NO: 80)

(Aib$^2$,Glu$^3$(NH-Hexyl),Apc$^9$,A5c$^{12}$,Apc$^{16}$)hGhrelin(1-28)-NH$_2$; (SEQ ID NO: 80)

(Aib$^{2,9}$,Glu$^3$(NH-Hexyl),A5c$^{12}$,Apc$^{16}$)hGhrelin(1-28)-NH$_2$; (SEQ ID NO: 80)

(Aib$^{2,10}$,Glu$^3$(NH-Hexyl),A5c$^{12}$,Apc$^{16}$)hGhrelin(1-28)-NH$_2$; (SEQ ID NO: 83)

(Glu$^3$(O-hexyl))hGhrelin(1-28)-NH$_2$; (SEQ ID NO: 1)

(Aib$^2$)hGhrelin(1-28)-NH$_2$; (SEQ ID NO: 10)

(Glu$^3$(NH-Hexyl))hGhrelin(1-28)-NH$_2$; (SEQ ID NO: 1)

(Aib$^2$,Glu$^3$(O-Hexyl))hGhrelin(1-28)-NH$_2$; (SEQ ID NO: 84)

(Aib$^1$,Glu$^3$(O-Hexyl))hGhrelin(1-28)-NH$_2$; (SEQ ID NO: 85)

(Aib$^2$,Glu$^3$(NH-Hexyl))hGhrelin(1-28)-NH$_2$; (SEQ ID NO: 84)

(Dap$^3$(1-Octanesulfonyl))hGhrelin(1-28)-NH$_2$; (SEQ ID NO: 1)

(Aib$^2$,Dap$^3$(1-Octanesulfonyl))hGhrelin(1-28)-NH$_2$; (SEQ ID NO: 84)

(Aib$^1$,Dap$^3$(1-Octanesulfonyl))hGhrelin(1-28)-NH$_2$; (SEQ ID NO: 85)

(Ava$^2$,Dap$^3$(1-Octanesulfonyl))hGhrelin(2-28)-NH$_2$; (SEQ ID NO: 86)

(Ac-Gly$^1$)hGhrelin(1-5)-NH$_2$; (SEQ ID NO: 87)

(Ac-Gly$^1$)hGhrelin(1-6)-NH$_2$; (SEQ ID NO: 88)

(Ac-Gly$^1$)hGhrelin(1-7)-NH$_2$; (SEQ ID NO: 89)

(Ac-Gly$^1$,Aib$^2$)hGhrelin(1-28)-NH$_2$; (SEQ ID NO: 90)

(Ac-Gly$^1$,Aib$^2$,Glu$^3$(NH-Hexyl))hGhrelin(1-5)-NH$_2$; (SEQ ID NO: 91)

(Ac-Gly$^1$,Aib$^2$,Glu$^3$(NH-Hexyl))hGhrelin(1-6)-NH$_2$; (SEQ ID NO: 92)

(Ac-Gly$^1$,Aib$^2$,Glu$^3$(NH-Hexyl))hGhrelin(1-7)-NH$_2$; (SEQ ID NO: 93)

(Ac-Gly$^1$,Aib$^2$,Glu$^3$(NH-Hexyl))hGhrelin(1-28)-NH$_2$; (SEQ ID NO: 335)

-continued (Ac-Gly¹,Aib²,Glu³(NH-Hexyl),Arg⁸)hGhrelin(1-8)-NH₂; (SEQ ID NO: 94)

(Ac-Gly¹,Aib²,Glu³(NH-Hexyl),Lys⁸)hGhrelin(1-8)-NH₂; (SEQ ID NO: 94)

(n-Butyryl-Gly¹)hGhrelin(1-28)-NH₂; (SEQ ID NO: 95)

(n-Butyryl-Gly¹,Aib²,Glu³(NH-Hexyl))hGhrelin(1-28)-NH₂; (SEQ ID NO: 335)

(Isobutyryl-Gly¹)hGhrelin(1-28)-NH₂; or (SEQ ID NO: 95)

(n-Octanoyl-Gly¹)hGhrelin(1-28)-NH₂, (SEQ ID NO: 95)
or a pharmaceutically acceptable salt thereof.

Cys³(S(CH₂)₉CH₃)hGhrelin(1-28)-NH₂; (SEQ ID NO: 1)

(Aib²,Ser³)hGhrelin(1-28)-NH₂; (SEQ ID NO: 10)

(Aib²,⁶,Ser³)hGhrelin(1-28)-NH₂ (SEQ ID NO: 4)

(Aib²,Ser³,3-Pal⁹)hGhrelin(1-28)-NH₂; (SEQ ID NO: 8)

(Aib²,Ser³,Thz⁷)hGhrelin(1-28)-NH₂; (SEQ ID NO: 9)

(Aib²,Ser³,Cha⁵)hGhrelin(1-28)-NH₂; (SEQ ID NO: 2)

(Aib²,Ser³,Abu⁶)hGhrelin(1-28)-NH₂; (SEQ ID NO: 4)

(Aib²,Ser³,4-Hyp⁷)hGhrelin(1-28)-NH₂; (SEQ ID NO: 9)

(Aib²,Ser³,Taz⁹)hGhrelin(1-28)-NH₂; (SEQ ID NO: 8)

(Aib²,Ser³,Dhp⁷)hGhrelin(1-28)-NH₂; (SEQ ID NO: 9)

(Aib²,⁸,Ser³)hGhrelin(1-28)-NH₂; (SEQ ID NO: 11)

(Aib²,Ser³,Pip⁷)hGhrelin(1-28)-NH₂; (SEQ ID NO: 9)

(Ac-Gly¹,Aib²,¹⁰,Ser³)hGhrelin(1-28)-NH₂; (SEQ ID NO: 96)

(Aib²,¹⁰,Ser³)hGhrelin(1-28)-NH₂; (SEQ ID NO: 12)

(n-Butyryl-Gly¹,Aib²,Ser³)hGhrelin(1-28)-NH₂; (SEQ ID NO: 97)

(Ac-Gly¹,Aib²,Ser³)hGhrelin(1-28)-NH₂; (SEQ ID NO: 97)

(Aib²,Ser³,Tic⁷)hGhrelin(1-28)-NH₂; (SEQ ID NO: 9)

(Ac-Gly¹,Aib²,Ser³,Arg⁸)hGhrelin(1-28)-NH₂; (SEQ ID NO: 98)

(Ser³,Aib⁸)hGhrelin(1-28)-NH₂; (SEQ ID NO: 16)

(Ser³,Taz⁹)hGhrelin(1-28)-NH₂; (SEQ ID NO: 14)

(Ser³,3-Pal⁹)hGhrelin(1-28)-NH₂; (SEQ ID NO: 14)

(Ser³,4-Pal⁹)hGhrelin(1-28)-NH₂; (SEQ ID NO: 14)

(Aib²,Ser³,2-Thi⁹)hGhrelin(1-28)-NH₂; (SEQ ID NO: 8)

(Ser³,2-Thi⁹)hGhrelin(1-28)-NH₂; (SEQ ID NO: 14)

(Ser³,4-Hyp⁷)hGhrelin(1-28)-NH₂; (SEQ ID NO: 15)

(Aib²,Ser³,Tic⁷)hGhrelin(1-28)-NH₂; (SEQ ID NO: 9)

(Aib²,Thr³)hGhreLin(1-28)-NH₂; (SEQ ID NO: 99)

(Aib²,⁶,Thr³)hGhrelin(1-28)-NH₂; (SEQ ID NO: 99)

(A5c⁵,Thr³)hGhrelin(1-28)-NH₂; (SEQ ID NO: 100)

(Aib²,Thr³,3-Pal⁹)hGhrelin(1-28)-NH₂; (SEQ ID NO: 101)

(Aib²,Thr³,Thz⁷)hGhrelin(1-28)-NH₂; (SEQ ID NO: 102)

(Aib²,Thr³,Cha⁵)hGhrelin(1-28)-NH₂; (SEQ ID NO: 103)

(Aib²,Thr³,Abu⁶)hGhrelin(1-28)-NH₂; (SEQ ID NO: 99)

(Aib²,Thr³,4-Hyp⁷)hGhrelin(1-28)-NH₂; (SEQ ID NO: 102)

-continued (Aib², Thr³, Taz⁹)hGhrelin(1-28)-NH₂; (SEQ ID NO: 101)

(Aib², Thr³, Dhp⁷)hGhreLin(1-28)-NH₂; (SEQ ID NO: 102)

(Aib²,⁸, Thr³)hGhrelin(1-28)-NH₂; (SEQ ID NO: 11)

(Aib², Thr³, Pip⁷)hGhrelin(1-28)-NH₂; (SEQ ID NO: 102)

(Ac-Gly¹, Aib²,¹⁰, Thr³)hGhrelin(1-28)-NH₂; (SEQ ID NO: 104)

(Aib²,¹⁰, Thr³)hGhrelin(1-28)-NH₂; (SEQ ID NO: 106)

(n-Butyryl-Gly¹, Aib², Thr³)hGhrelin(1-28)-NH₂; (SEQ ID NO: 105)

(Ac-Gly¹, Aib², Thr³)hGhrelin(1-28)-NH₂; (SEQ ID NO: 105)

(Aib², Thr³, Tic⁷)hGhrelin(1-28)-NH₂; (SEQ ID NO: 102)

(Ac-Gly¹, Aib², Thr³, Arg⁸)hGhrelin(1-28)-NH₂; (SEQ ID NO: 90)

(Thr³, Aib⁸)hGhrelin(1-28)-NH₂; (SEQ ID NO: 107)

(Thr³, Taz⁹)hGhrelin(1-28)-NH₂; (SEQ ID NO: 108)

(Thr³, 3-Pal⁹)hGhrelin(1-28)-NH₂; (SEQ ID NO: 108)

(Thr³, 4-Pal⁹)hGhrelin(1-28)-NH₂; (SEQ ID NO: 108)

(Aib², Thr³, 2-Thi⁹)hGhrelin(1-28)-NH₂; (SEQ ID NO: 101)

(Thr³, 2-Thi⁹)hGhrelin(1-28)-NH₂; (SEQ ID NO: 108)

(Thr³, 4-Hyp⁷)hGhrelin(1-28)-NH₂; (SEQ ID NO: 109)

(Aib², Thr³, Tic⁷)hGhrelin(1-28)-NH₂; (SEQ ID NO: 102)

(Ac-Gly¹, Glu³(NH-Hexyl))hGhrelin(1-28)-NH₂; or (SEQ ID NO: 110)

H-Inp-D-1-Nal-D-Trp-3-Pal-Lys-NH₂; (SEQ ID NO: 112)

H-Inp-D-2-Nal-D-Trp-4-Pal-Lys-NH₂; (SEQ ID NO: 113)

H-Inp-D-2-Nal-D-Trp-Orn-Lys-NH₂; (SEQ ID NO: 113)

H-Inp-D-Bip-D-Trp-Phe-Lys-NH₂; (SEQ ID NO: 111)

H-Inp-D-2-Nal-D-Trp-Thr(Bzl)-Lys-NH₂; (SEQ ID NO: 113)

H-Inp-D-2-Nal-D-Trp-Pff-Lys-NH₂; (SEQ ID NO: 113)

H-Inp-D-2-Nal-D-Trp-2-Thi-Lys-NH₂; (SEQ ID NO: 113)

H-Inp-D-2-Nal-D-Trp-Taz-Lys-NH₂; (SEQ ID NO: 113)

H-Inp-D-Dip-D-Trp-Phe-Lys-NH₂; (SEQ ID NO: 111)

H-Inp-D-Bpa-D-Trp-Phe-Lys-NH₂; (SEQ ID NO: 111)

H-Inp-D-2-Nal-D-Bpa-Phe-Lys-NH₂; (SEQ ID NO: 114)

H-Inp-D-2-Nal-D-Trp-3-Pal-NH₂; (SEQ ID NO: 115)

H-Inp-D-2-Nal-D-Trp-4-Pal-NH₂; (SEQ ID NO: 115)

H-Inp-D-1-Nal-D-Trp-3-Pal-NH₂; (SEQ ID NO: 116)

H-Inp-D-Bip-D-Trp-Phe-NH₂; (SEQ ID NO: 117)

H-Inp-D-2-Nal-D-Trp-Thr(Bzl)-NH₂; (SEQ ID NO: 115)

H-Inp-D-2-Nal-D-Trp-Pff-NH₂; (SEQ ID NO: 115)

H-Inp-D-2-Nal-D-Trp-2-Thi-NH₂; (SEQ ID NO: 115)

H-Inp-D-2-Nal-D-Trp-Taz-NH₂; (SEQ ID NO: 115)

H-Inp-D-Dip-D-Trp-Phe-NH₂; (SEQ ID NO: 117)

H-Inp-D-2-Nal-D-Dip-Phe-NH₂; (SEQ ID NO: 118)

-continued

H-Inp-D-Bal-D-Trp-Phe-NH$_2$; (SEQ ID NO: 119)

H-Inp-D-2-Nal-D-Bal-Phe-NH$_2$; (SEQ ID NO: 118)

H-Inp-D-2-Nal-D-Trp-3-Pal-Lys-NH$_2$; (SEQ ID NO: 113)

H-Inp-D-Trp-D-2-Nal(Ψ)-Pim; (SEQ ID NO: 120)

H-Inp-D-Bal-D-Trp-2-Thi-Lys-NH$_2$; (SEQ ID NO: 121)

H-Inp-D-Bal-D-Trp-Phe-Lys-NH$_2$; (SEQ ID NO: 111)

H-Inp-D-1-Nal-D-Trp-2-Thi-Lys-NH$_2$; (SEQ ID NO: 112)

H-Inp-D-2-Nal-D-Trp-Phe-Apc-NH$_2$; (SEQ ID NO: 122)

H-Inp-D-1-Nal-D-Trp-Phe-Apc-NH$_2$; (SEQ ID NO: 122)

H-Inp-D-Bal-D-Trp-Phe-Apc-NH$_2$; (SEQ ID NO: 122)

H-Apc-D-2-Nal-D-Trp-Phe-Lys-NH$_2$; (SEQ ID NO: 123)

H-Apc-D-1-Nal-D-Trp-2-Thi-Lys-NH$_2$; (SEQ ID NO: 124)

H-Inp-D-1-Nal-D-Trp-2-Thi-NH$_2$; (SEQ ID NO: 116)

H-Apc-D-1-Nal-D-Trp-Phe-NH$_2$; (SEQ ID NO: 125)

H-Inp-D-2-Nal-D-Trp(Ψ)-Pim; (SEQ ID NO: 126)

H-Inp-D-1-Nal-D-Trp(Ψ)-Pim; (SEQ ID NO: 126)

H-Inp-D-Bal-D-Trp(Ψ)-Pim; (SEQ ID NO: 126)

H-Aib-D-Ser(Bzl)-D-Trp(Ψ)-Pim; (SEQ ID NO: 127)

H-Inp-D-1-Nal-D-Trp-Taz-Lys-NH$_2$; (SEQ ID NO: 112)

H-Inp-D-Bal-D-Trp-Taz-Lys-NH$_2$; (SEQ ID NO: 121)

H-Apc-D-1-Nal-D-Trp-Taz-Lys-NH$_2$; (SEQ ID NO: 124)

H-Apc-D-Bal-D-Trp-Taz-Lys-NH$_2$; (SEQ ID NO: 128)

H-Apc-D-Bal-D-Trp-2-Thi-Lys-NH$_2$; (SEQ ID NO: 128)

H-Apc-D-Bal-D-Trp-Phe-Lys-NH$_2$; (SEQ ID NO: 123)

H-Apc-D-1-Nal-D-Trp-Phe-Apc-NH$_2$; (SEQ ID NO: 129)

H-Apc-D-Bal-D-Trp-Phe-Apc-NH$_2$; (SEQ ID NO: 130)

H-Apc-D-1-Nal-D-1-Nal-Phe-Apc-NH$_2$; (SEQ ID NO: 129)

H-Apc-D-1-Nal-D-2-Nal-Phe-Apc-NH$_2$; (SEQ ID NO: 129)

H-Apc-D-1-Nal-D-1-Nal-Phe-Lys-NH$_2$; (SEQ ID NO: 131)

H-Apc-D-Bal-D-1-Nal-Phe-Apc-NH$_2$; (SEQ ID NO: 130)

H-Apc-D-Bal-D-2-Nal-Phe-Apc-NH$_2$; (SEQ ID NO: 130)

H-Apc-D-Bal-D-1-Nal-Phe-Lys-NH$_2$; (SEQ ID NO: 132)

H-Apc-D-Bal-D-2-Nal-Phe-Lys-NH$_2$; (SEQ ID NO: 132)

H-Apc-D-1-Nal-D-Trp-2-Thi-NH$_2$; (SEQ ID NO: 133)

H-Apc-D-Bal-D-Trp-Phe-NH$_2$; (SEQ ID NO: 125)

H-Apc-D-1-Nal-D-Trp-Taz-NH$_2$; (SEQ ID NO: 133)

H-Apc-D-Bal-D-Trp-2-Thi-NH$_2$; (SEQ ID NO: 144)

H-Apc-D-Bal-D-Trp-Taz-NH$_2$; (SEQ ID NO: 144)

H-Apc-D-2-Nal-D-Trp-2-Thi-NH$_2$; (SEQ ID NO: 134)

H-Apc-D-2-Nal-D-Trp-Taz-NH$_2$; (SEQ ID NO: 134)

H-Inp-D-1-Nal-D-Trp-Taz-Apc-NH$_2$; (SEQ ID NO: 135)

H-Inp-D-Bal-D-Trp-Taz-Apc-NH$_2$; (SEQ ID NO: 135)

H-Apc-D-1-Nal-D-Trp-Taz-Apc-NH$_2$; (SEQ ID NO: 136)

H-Apc-D-Bal-D-Trp-Taz-Apc-NH$_2$; (SEQ ID NO: 136)

H-Apc-D-1-Nal-D-Trp-2-Fua-Apc-NH$_2$; (SEQ ID NO: 137)

H-Apc-D-1-Nal-D-Trp-2-Fua-Lys-NH$_2$; (SEQ ID NO: 124)

H-Apc-D-1-Nal-D-Trp-2-Fua-NH$_2$; (SEQ ID NO: 133)

H-Apc-D-1-Nal-D-Trp-2-Pal-NH$_2$; (SEQ ID NO: 133)

H-Apc-D-1-Nal-D-Trp-3-Pal-NH$_2$; (SEQ ID NO: 133)

H-Apc-D-1-Nal-D-Trp-3-Thi-Apc-NH$_2$; (SEQ ID NO: 137)

H-Apc-D-1-Nal-D-Trp-3-Thi-Lys-NH$_2$; (SEQ ID NO: 124)

H-Apc-D-1-Nal-D-Trp-3-Thi-NH$_2$; (SEQ ID NO: 133)

H-Apc-D-1-Nal-D-Trp-4-Pal-NH$_2$; (SEQ ID NO: 133)

H-Apc-D-1-Nal-D-Trp-Pff-Apc-NH$_2$; (SEQ ID NO: 137)

H-Apc-D-1-Nal-D-Trp-Pff-Lys-NH$_2$; (SEQ ID NO: 124)

H-Apc-D-1-Nal-D-Trp-Pff-NH$_2$; (SEQ ID NO: 133)

H-Apc-D-2-Nal-D-Trp-2-Fua-Apc-NH$_2$; (SEQ ID NO: 138)

H-Apc-D-2-Nal-D-Trp-2-Fua-Lys-NH$_2$; (SEQ ID NO: 139)

H-Apc-D-2-Nal-D-Trp-2-Fua-NH$_2$; (SEQ ID NO: 134)

H-Apc-D-2-Nal-D-Trp-2-Pal-NH$_2$; (SEQ ID NO: 134)

H-Apc-D-2-Nal-D-Trp-2-Thi-Apc-NH$_2$; (SEQ ID NO: 138)

H-Apc-D-2-Nal-D-Trp-2-Thi-Lys-NH$_2$; (SEQ ID NO: 139)

H-Apc-D-2-Nal-D-Trp-3-Pal-NH$_2$; (SEQ ID NO: 134)

H-Apc-D-2-Nal-D-Trp-3-Thi-Apc-NH$_2$; (SEQ ID NO: 138)

H-Apc-D-2-Nal-D-Trp-3-Thi-Lys-NH$_2$; (SEQ ID NO: 139)

H-Apc-D-2-Nal-D-Trp-3-Thi-NH$_2$; (SEQ ID NO: 134)

H-Apc-D-2-Nal-D-Trp-4-Pal-NH$_2$; (SEQ ID NO: 134)

H-Apc-D-2-Nal-D-Trp-Pff-Apc-NH$_2$; (SEQ ID NO: 138)

H-Apc-D-2-Nal-D-Trp-Pff-Lys-NH$_2$; (SEQ ID NO: 139)

H-Apc-D-2-Nal-D-Trp-Pff-NH$_2$; (SEQ ID NO: 134)

H-Apc-D-2-Nal-D-Trp-Taz-Apc-NH$_2$; (SEQ ID NO: 136)

H-Apc-D-2-Nal-D-Trp-Taz-Lys-NH$_2$; (SEQ ID NO: 139)

H-Apc-D-Bal-D-Bal-2-Fua-Apc-NH$_2$; (SEQ ID NO: 140)

H-Apc-D-Bal-D-Bal-2-Fua-Lys-NH$_2$; (SEQ ID NO: 141)

H-Apc-D-Bal-D-Bal-2-Fua-NH$_2$; (SEQ ID NO: 142)

H-Apc-D-Bal-D-Bal-2-Pal-NH$_2$; (SEQ ID NO: 142)

H-Apc-D-Bal-D-Bal-2-Thi-Apc-NH$_2$; (SEQ ID NO: 140)

H-Apc-D-Bal-D-Bal-2-Thi-Lys-NH$_2$; (SEQ ID NO: 141)

H-Apc-D-Bal-D-Bal-2-Thi-NH$_2$; (SEQ ID NO: 142)

H-Apc-D-Bal-D-Bal-3-Pal-NH$_2$; (SEQ ID NO: 142)

H-Apc-D-Bal-D-Bal-3-Thi-Apc-NH$_2$; (SEQ ID NO: 140)

-continued

H-Apc-D-Bal-D-Bal-3-Thi-Lys-NH$_2$; (SEQ ID NO: 141)

H-Apc-D-Bal-D-Bal-3-Thi-NH$_2$; (SEQ ID NO: 142)

H-Apc-D-Bal-D-Bal-4-Pal-NH$_2$; (SEQ ID NO: 142)

H-Apc-D-Bal-D-Bal-Pff-Apc-NH$_2$; (SEQ ID NO: 140)

H-Apc-D-Bal-D-Bal-Pff-Lys-NH$_2$; (SEQ ID NO: 141)

H-Apc-D-Bal-D-Bal-Pff-NH$_2$; (SEQ ID NO: 142)

H-Apc-D-Bal-D-Bal-Phe-Apc-NH$_2$; (SEQ ID NO: 130)

H-Apc-D-Bal-D-Bal-Phe-Lys-NH$_2$; (SEQ ID NO: 132)

H-Apc-D-Bal-D-Bal-Phe-NH$_2$; (SEQ ID NO: 142)

H-Apc-D-Bal-D-Bal-Taz-Apc-NH$_2$; (SEQ ID NO: 140)

H-Apc-D-Bal-D-Bal-Taz-Lys-NH$_2$; (SEQ ID NO: 141)

H-Apc-D-Bal-D-Bal-Taz-NH$_2$; (SEQ ID NO: 142)

H-Apc-D-Bal-D-Trp-2-Fua-Apc-NH$_2$; (SEQ ID NO: 143)

H-Apc-D-Bal-D-Trp-2-Fua-Lys-NH$_2$; (SEQ ID NO: 128)

H-Apc-D-Bal-D-Trp-2-Fua-NH$_2$; (SEQ ID NO: 144)

H-Apc-D-Bal-D-Trp-2-Pal-NH$_2$; (SEQ ID NO: 144)

H-Apc-D-Bal-D-Trp-3-Pal-NH$_2$; (SEQ ID NO: 144)

H-Apc-D-Bal-D-Trp-3-Thi-Apc-NH$_2$; (SEQ ID NO: 143)

H-Apc-D-Bal-D-Trp-3-Thi-Lys-NH$_2$; (SEQ ID NO: 128)

H-Apc-D-Bal-D-Trp-3-Thi-NH$_2$; (SEQ ID NO: 144)

H-Apc-D-Bal-D-Trp-4-Pal-NH$_2$; (SEQ ID NO: 144)

H-Apc-D-Bal-D-Trp-Pff-Apc-NH$_2$; (SEQ ID NO: 143)

H-Apc-D-Bal-D-Trp-Pff-Lys-NH$_2$; (SEQ ID NO: 128)

H-Apc-D-Bal-D-Trp-Pff-NH$_2$; (SEQ ID NO: 144)

H-Inp-D-1-Nal-D-Bal-2-Fua-Lys-NH$_2$; (SEQ ID NO: 145)

H-Inp-D-1-Nal-D-Bal-2-Fua-NH$_2$; (SEQ ID NO: 146)

H-Inp-D-1-Nal-D-Bal-2-Thi-Lys-NH$_2$; (SEQ ID NO: 145)

H-Inp-D-1-Nal-D-Bal-3-Thi-Lys-NH$_{2L}$; (SEQ ID NO: 145)

H-Inp-D-1-Nal-D-Bal-Pff-Lys-NH$_2$; (SEQ ID NO: 145)

H-Inp-D-1-Nal-D-Bal-Pff-NH$_2$; (SEQ ID NO: 146)

H-Inp-D-1-Nal-D-Bal-Phe-Lys-NH$_2$; (SEQ ID NO: 145)

H-Inp-D-1-Nal-D-Bal-Taz-Lys-NH$_2$; (SEQ ID NO: 145)

H-Inp-D-1-Nal-D-Bal-Taz-NH$_2$; (SEQ ID NO: 146)

H-Inp-D-1-Nal-D-Trp-2-Fua-Apc-NH$_2$; (SEQ ID NO: 147)

H-Inp-D-1-Nal-D-Trp-2-Fua-Lys-NH$_2$; (SEQ ID NO: 112)

H-Inp-D-1-Nal-D-Trp-2-Fua-NH$_2$; (SEQ ID NO: 116)

H-Inp-D-1-Nal-D-Trp-3-Thi-Apc-NH$_2$; (SEQ ID NO: 147)

H-Inp-D-1-Nal-D-Trp-3-Thi-Lys-NH$_2$; (SEQ ID NO: 112)

H-Inp-D-1-Nal-D-Trp-Pff-Apc-NH$_2$; (SEQ ID NO: 147)

H-Inp-D-1-Nal-D-Trp-Pff-Lys-NH$_2$; (SEQ ID NO: 112)

H-Inp-D-1-Nal-D-Trp-Pff-NH$_2$; (SEQ ID NO: 116)

-continued

H-Inp-D-1-Nal-D-Trp-Taz-NH$_2$; (SEQ ID NO: 116)

H-Inp-D-2-Nal-D-Trp-2-Fua-Apc-NH$_2$ (SEQ ID NO: 148)

H-Inp-D-2-Nal-D-Trp-2-Fua-NH$_2$; (SEQ ID NO: 115)

H-Inp-D-2-Nal-D-Trp-2-Thi-Apc-NH$_2$ (SEQ ID NO: 148)

H-Inp-D-2-Nal-D-Trp-3-Thi-Apc-NH$_2$ (SEQ ID NO: 148)

H-Inp-D-2-Nal-D-Trp-3-Thi-Lys-NH$_2$; (SEQ ID NO: 113)

H-Inp-D-2-Nal-D-Trp-3-Thi-NH$_2$; (SEQ ID NO: 115)

H-Inp-D-2-Nal-D-Trp-Pff-Apc-NH$_2$; (SEQ ID NO: 148)

H-Inp-D-2-Nal-D-Trp-Pff-NH$_2$; (SEQ ID NO: 115)

H-Inp-D-2-Nal-D-Trp-Taz-Apc-NH$_2$; (SEQ ID NO: 135)

H-Inp-D-2-Nal-D-Trp-Taz-NH$_2$; (SEQ ID NO: 115)

H-Inp-D-Bal-D-Bal-2-Fua-Lys-NH$_2$; (SEQ ID NO: 149)

H-Inp-D-Bal-D-Bal-2-Fua-NH$_2$; (SEQ ID NO: 150)

H-Inp-D-Bal-D-Bal-2-Thi-Lys-NH$_2$; (SEQ ID NO: 149)

H-Irip-D-Bal-D-Bal-3-Thi-Lys-NH$_2$; (SEQ ID NO: 149)

H-Inp-D-Bal-D-Bal-Pff-Lys-NH$_2$; (SEQ ID NO: 149)

H-Inp-D-Bal-D-Bal-Pff-NH$_2$; (SEQ ID NO: 150)

H-Inp-D-Bal-D-Bal-Phe-Lys-NH$_2$; (SEQ ID NO: 149)

H-Inp-D-Bal-D-Bal-Taz-Lys-NH$_2$; (SEQ ID NO: 149)

H-Inp-D-Bal-D-Bal-Taz-NH$_2$; (SEQ ID NO: 150)

H-Inp-D-Bal-D-Trp-2-Fua-Apc-NH$_2$; (SEQ ID NO: 151)

H-Inp-D-Bal-D-Trp-2-Fua-Lys-NH$_2$; (SEQ ID NO: 121)

H-Inp-D-Bal-D-Trp-2-Fua-NH$_2$; (SEQ ID NO: 152)

H-Inp-D-Bal-D-Trp-3-Thi-Apc-NH$_2$; (SEQ ID NO: 151)

H-Inp-D-Bal-D-Trp-3-Thi-Lys-NH$_2$; (SEQ ID NO: 121)

H-Inp-D-Bal-D-Trp-Pff-Apc-NH$_2$; (SEQ ID NO: 151)

H-Inp-D-Bal-D-Trp-Pff-Lys-NH$_2$; (SEQ ID NO: 121)

H-Inp-D-Bal-D-Trp-Pff-NH$_2$; (SEQ ID NO: 152)

H-Inp-D-Bal-D-Trp-Taz-NH$_2$; (SEQ ID NO: 152)

H-Inp-D-Bip-D-Bal-2-Fua-Lys-NH$_2$; (SEQ ID NO: 153)

H-Inp-D-Bip-D-Bal-2-Fua-NH$_2$; (SEQ ID NO: 154)

H-Inp-D-Bip-D-Bal-2-Thi-Lys-NH$_2$; (SEQ ID NO: 153)

H-Inp-D-Bip-D-Bal-3-Thi-Lys-NH$_2$; (SEQ ID NO: 153)

H-Inp-D-Bip-D-Bal-Pff-Lys-NH$_2$; (SEQ ID NO: 153)

H-Inp-D-Bip-D-Bal-Pff-NH$_2$; or (SEQ ID NO: 154)

H-Inp-D-Bip-D-Bal-Taz-Lys-NH$_2$; (SEQ ID NO: 153)

H-Inp-D-Bip-D-Bal-Taz-NH$_2$; (SEQ ID NO: 154)

H-Inp-D-Bip-D-Trp-2-Fua-Lys-NH$_2$; (SEQ ID NO: 155)

H-Inp-D-Bip-D-Trp-2-Fua-NH$_2$; (SEQ ID NO: 156)

H-Inp-D-Bip-D-Trp-2-Thi-Lys-NH$_2$; (SEQ ID NO: 155)

-continued

H-Inp-D-Bip-D-Trp-3-Thi-Lys-NH$_2$; (SEQ ID NO: 155)

H-Lnp-D-Bip-D-Trp-Pff-Lys-NH$_2$; (SEQ ID NO: 155)

H-Inp-D-Bip-D-Trp-Pff-NH$_2$; (SEQ ID NO: 156)

H-Inp-D-Bip-D-Trp-Taz-Lys-NH$_2$; or (SEQ ID NO: 155)

H-Inp-D-Bip-D-Trp-Taz-NH$_2$; (SEQ ID NO: 156)

H-Inp-D-1-Nal-D-Trp-3-Pal-Lys-NH$_2$; (SEQ ID NO: 112)

H-Inp-D-2-Nal-D-Trp-4-Pal-Lys-NH$_2$; (SEQ ID NO: 113)

H-Inp-D-2-Nal-D-Trp-Orn-Lys-NH$_2$; (SEQ ID NO: 113)

H-Inp-D-Bip-D-Trp-Phe-Lys-NH$_2$; (SEQ ID NO: 111)

H-Inp-D-2-Nal-D-Trp-Thr(Bzl)-Lys-NH$_2$; (SEQ ID NO: 113)

H-Inp-D-2-Nal-D-Trp-Pff-Lys-NH$_2$; (SEQ ID NO: 113)

H-Inp-D-2-Nal-D-Trp-2-Thi-Lys-NH$_2$; (SEQ ID NO: 113)

H-Inp-D-2-Nal-D-Trp-Taz-Lys-NH$_2$; (SEQ ID NO: 113)

H-Inp-D-Dip-D-Trp-Phe-Lys-NH$_2$; (SEQ ID NO: 111)

H-Inp-D-Bpa-D-Trp-Phe-Lys-NH$_2$; (SEQ ID NO: 111)

H-Inp-D-2-Nal-D-Bpa-Phe-Lys-NH$_2$; (SEQ ID NO: 114)

H-Inp-D-2-Nal-D-Trp-Thr(Bzl)-NH$_2$; (SEQ ID NO: 115)

H-Inp-D-2-Nal-D-Trp-Pff-NH$_2$; (SEQ ID NO: 115)

H-Inp-D-2-Nal-D-Trp-Taz-NH$_2$; (SEQ ID NO: 115)

H-Inp-D-2-Nal-D-Dip-Phe-NH$_2$; (SEQ ID NO: 118)

H-Inp-D-2-Nal-D-Trp-3-Pal-Lys-NH$_2$; (SEQ ID NO: 113)

H-Inp-D-Trp-D-2-Nal(Ψ)-Pim; (SEQ ID NO: 120)

H-Inp-D-Bal-D-Trp-2-Thi-Lys-NH$_2$; (SEQ ID NO: 121)

H-Inp-D-Bal-D-Trp-Phe-Lys-NH$_2$; (SEQ ID NO: 111)

H-Inp-D-1-Nal-D-Trp-2-Thi-Lys-NH$_2$; (SEQ ID NO: 112)

H-Inp-D-2-Nal-D-Trp-Phe-Apc-NH$_2$; (SEQ ID NO: 122)

H-Inp-D-1-Nal-D-Trp-Phe-Apc-NH$_2$; (SEQ ID NO: 122)

H-Inp-D-Bal-D-Trp-Phe-Apc-NH$_2$; (SEQ ID NO: 122)

H-Apc-D-2-Nal-D-Trp-Phe-Lys-NH$_2$; (SEQ ID NO: 123)

H-Apc-D-1-Nal-D-Trp-2-Thi-Lys-NH$_2$; (SEQ ID NO: 124)

H-Inp-D-2-Nal-D-Trp(Ψ)-Pim; (SEQ ID NO: 126)

H-Inp-D-1-Nal-D-Trp(Ψ)-Pim; (SEQ ID NO: 126)

H-Inp-D-Bal-D-Trp(Ψ)-Pim; (SEQ ID NO: 126)

H-Aib-D-Ser(Bzl)-D-Trp(Ψ)-Pim; (SEQ ID NO: 127)

H-Inp-D-1-Nal-D-Trp-Taz-Lys-NH$_2$; (SEQ ID NO: 112)

H-Inp-D-Bal-D-Trp-Taz-Lys-NH$_2$; (SEQ ID NO: 121)

H-Apc-D-1-Nal-D-Trp-Taz-Lys-NH$_2$; (SEQ ID NO: 124)

H-Apc-D-Bal-D-Trp-Taz-Lys-NH$_2$; (SEQ ID NO: 128)

H-Apc-D-Bal-D-Trp-2-Thi-Lys-NH$_2$; (SEQ ID NO: 128)

H-Apc-D-Bal-D-Trp-Phe-Lys-NH$_2$; (SEQ ID NO: 123)

H-Apc-D-1-Nal-D-Trp-Phe-Apc-NH$_2$; (SEQ ID NO: 129)

-continued

H-Apc-D-Bal-D-Trp-Phe-Apc-NH$_2$; (SEQ ID NO: 130)

H-Apc-D-1-Nal-D-1-Nal-Phe-Apc-NH$_2$; (SEQ ID NO: 129)

H-Apc-D-1-Nal-D-2-Nal-Phe-Apc-NH$_2$; (SEQ ID NO: 129)

H-Apc-D-1-Nal-D-1-Nal-Phe-Lys-NH$_2$; (SEQ ID NO: 131)

H-Apc-D-Bal-D-1-Nal-Phe-Apc-NH$_2$; (SEQ ID NO: 130)

H-Apc-D-Bal-D-2-Nal-Phe-Apc-NH$_2$; (SEQ ID NO: 130)

H-Apc-D-Bal-D-1-Nal-Phe-Lys-NH$_2$; (SEQ ID NO: 132)

H-Apc-D-Bal-D-2-Nal-Phe-Lys-NH$_2$; (SEQ ID NO: 132)

H-Apc-D-1-Nal-D-Trp-2-Thi-NH$_2$; (SEQ ID NO: 133)

H-Apc-D-Bal-D-Trp-Phe-NH$_2$; (SEQ ID NO: 157)

H-Apc-D-1-Nal-D-Trp-Taz-NH$_2$; (SEQ ID NO: 133)

H-Apc-D-Bal-D-Trp-2-Thi-NH$_2$; (SEQ ID NO: 157)

H-Apc-D-Bal-D-Trp-Taz-NH$_2$; (SEQ ID NO: 157)

H-Apc-D-2-Nal-D-Trp-2-Thi-NH$_2$; (SEQ ID NO: 134)

H-Apc-D-2-Nal-D-Trp-Taz-NH$_2$; (SEQ ID NO: 134)

H-Inp-D-1-Nal-D-Trp-Taz-Apc-NH$_2$; (SEQ ID NO: 135)

H-Inp-D-Bal-D-Trp-Taz-Apc-NH$_2$; (SEQ ID NO: 135)

H-Apc-D-1-Nal-D-Trp-Taz-Apc-NH$_2$; (SEQ ID NO: 136)

H-Apc-D-Bal-D-Trp-Taz-Apc-NH$_2$; (SEQ ID NO: 136)

H-Inp-D-2-Nal-D-Trp-3-Thi-Lys-NH$_2$; (SEQ ID NO: 113)

H-Inp-D-Bal-D-Trp-3-Thi-Lys-NH$_2$; (SEQ ID NO: 121)

H-Inp-D-Bal-D-Trp-2-Fua-Lys-NH$_2$; (SEQ ID NO: 121)

H-Inp-D-Bal-D-Trp-Pff-Lys-NH$_2$; (SEQ ID NO: 121)

H-Inp-D-Bal-D-Trp-3-Thi-Apc-NH$_2$; (SEQ ID NO: 151)

H-Inp-D-Bal-D-Trp-2-Fua-Apc-NH$_2$; (SEQ ID NO: 151)

H-Inp-D-Bal-D-Trp-Pff-Apc-NH$_2$; (SEQ ID NO: 151)

H-Apc-D-Bal-D-Trp-3-Thi-Lys-NH$_2$; (SEQ ID NO: 128)

H-Apc-D-Bal-D-Trp-2-Fua-Lys-NH$_2$; (SEQ ID NO: 128)

H-Apc-D-Bal-D-Trp-Pff-Lys-NH$_2$; (SEQ ID NO: 128)

H-Inp-D-Bal-D-Bal-Phe-Lys-NH$_2$; (SEQ ID NO: 149)

H-Inp-D-Bal-D-Bal-2-Thi-Lys-NH$_2$; (SEQ ID NO: 149)

H-Inp-D-Bal-D-Bal-3-Thi-Lys-NH$_2$; (SEQ ID NO: 149)

H-Inp-D-Bal-D-Bal-Taz-Lys-NH$_2$; (SEQ ID NO: 149)

H-Inp-D-Bal-D-Bal-2-Fua-Lys-NH$_2$; (SEQ ID NO: 149)

H-Inp-D-Bal-D-Bal-Pff-Lys-NH$_2$; (SEQ ID NO: 149)

H-Apc-D-Bal-D-BaL-Phe-Lys-NH$_2$; (SEQ ID NO: 132)

H-Apc-D-Bal-D-Bal-2-Thi-Lys-NH$_2$; (SEQ ID NO: 141)

H-Apc-D-Bal-D-Bal-3-Thi-Lys-NH$_2$; (SEQ ID NO: 141)

H-Apc-D-Bal-D-Bal-Taz-Lys-NH$_2$; (SEQ ID NO: 141)

H-Apc-D-Bal-D-Bal-2-Fua-Lys-NH$_2$; (SEQ ID NO: 141)

-continued

H-Apc-D-Bal-D-Bal-Pff-Lys-NH$_2$; (SEQ ID NO: 141)

H-Inp-D-1-Nal-D-Trp-3-Thi-Lys-NH$_2$; (SEQ ID NO: 112)

H-Inp-D-1-Nal-D-Trp-2-Fua-Lys-NH$_2$; (SEQ ID NO: 112)

H-Inp-D-1-Nal-D-Trp-Pff-Lys-NH$_2$; (SEQ ID NO: 112)

H-Inp-D-1-Nal-D-Bal-Phe-Lys-NH$_2$; (SEQ ID NO: 158)

H-Inp-D-1-Nal-D-Bal-2-Thi-Lys-NH$_2$; (SEQ ID NO: 158)

H-Inp-D-1-Nal-D-Bal-3-Thi-Lys-NH$_2$; (SEQ ID NO: 158)

H-Inp-D-1-Nal-D-Bal-Taz-Lys-NH$_2$; (SEQ ID NO: 158)

H-Inp-D-1-Nal-D-Bal-2-Fua-Lys-NH$_2$; (SEQ ID NO: 158)

H-Inp-D-1-Nal-D-Bal-Pff-Lys-NH$_2$; (SEQ ID NO: 158)

H-Inp-D-2-Nal-D-Trp-2-Thi-Apc-NH$_2$; (SEQ ID NO: 159)

H-Inp-D-2-Nal-D-Trp-3-Thi-Apc-NH$_2$; (SEQ ID NO: 159)

H-Inp-D-2-Nal-D-Trp-Taz-Apc-NH$_2$; (SEQ ID NO: 135)

H-Inp-D-2-Nal-D-Trp-2-Fua-Apc-NH$_2$; (SEQ ID NO: 159)

H-Inp-D-2-Nal-D-Trp-Pff-Apc-NH$_2$; (SEQ ID NO: 159)

H-Inp-D-1-Nal-D-Trp-3-Thi-Apc-NH$_2$; (SEQ ID NO: 160)

H-Inp-D-1-Nal-D-Trp-2-Fua-Apc-NH$_2$; (SEQ ID NO: 160)

H-Inp-D-1-Nal-D-Trp-Pff-Apc-NH$_2$; (SEQ ID NO: 160)

H-Apc-D-1-Nal-D-Trp-3-Thi-Lys-NH$_2$; (SEQ ID NO: 124)

H-Apc-D-1-Nal-D-Trp-2-Fua-Lys-NH$_2$; (SEQ ID NO: 124)

H-Apc-D-1-Nal-D-Trp-Pff-Lys-NH$_2$; (SEQ ID NO: 124)

H-Apc-D-2-Nal-D-Trp-2-Thi-Lys-NH$_2$; (SEQ ID NO: 139)

H-Apc-D-2-Nal-D-Trp-3-Thi-Lys-NH$_2$; (SEQ ID NO: 139)

H-Apc-D-2-Nal-D-Trp-Taz-Lys-NH$_2$; (SEQ ID NO: 139)

H-Apc-D-2-Nal-D-Trp-2-Fua-Lys-NH$_2$; (SEQ ID NO: 139)

H-Apc-D-2-Nal-D-Trp-Pff-Lys-NH$_2$; (SEQ ID NO: 139)

H-Inp-D-Bip-D-Trp-2-Thi-Lys-NH$_2$; (SEQ ID NO: 155)

H-Inp-D-Bip-D-Trp-3-Thi-Lys-NH$_2$; (SEQ ID NO: 155)

H-Inp-D-Bip-D-Trp-Taz-Lys-NH$_2$; (SEQ ID NO: 155)

H-Inp-D-Bip-D-Trp-2-Fua-Lys-NH$_2$; (SEQ ID NO: 155)

H-Inp-D-Bip-D-Trp-Pff-Lys-NH$_2$; (SEQ ID NO: 155)

H-Inp-D-Bip-D-Bal-2-Thi-Lys-NH$_2$; (SEQ ID NO: 153)

H-Inp-D-Bip-D-Bal-3-Thi-Lys-NH$_2$; (SEQ ID NO: 153)

H-Inp-D-Bip-D-Bal-Taz-Lys-NH$_2$; (SEQ ID NO: 153)

H-Inp-D-Bip-D-Bal-2-Fua-Lys-NH$_2$; (SEQ ID NO: 153)

H-Inp-D-Bip-D-Bal-Pff-Lys-NH$_2$; (SEQ ID NO: 153)

H-Apc-D-Bal-D-Trp-3-Thi-Apc-NH$_2$; (SEQ ID NO: 143)

H-Apc-D-Bal-D-Trp-2-Fua-Apc-NH$_2$; (SEQ ID NO: 143)

H-Apc-D-Bal-D-Trp-Pff-Apc-NH$_2$; (SEQ ID NO: 143)

H-Apc-D-Bal-D-Bal-Phe-Apc-NH$_2$; (SEQ ID NO: 130)

H-Apc-D-Bal-D-Bal-2-Thi-Apc-NH$_2$; (SEQ ID NO: 140)

-continued

H-Apc-D-Bal-D-Bal-3-Thi-Apc-NH$_2$; (SEQ ID NO: 140)

H-Apc-D-Bal-D-Bal-Taz-Apc-NH$_2$; (SEQ ID NO: 140)

H-Apc-D-Bal-D-Bal-2-Fua-Apc-NH$_2$; (SEQ ID NO: 140)

H-Apc-D-Bal-D-Bal-Pff-Apc-NH$_2$; (SEQ ID NO: 140)

H-Apc-D-1-Nal-D-Trp-3-Thi-Apc-NH$_2$; (SEQ ID NO: 137)

H-Apc-D-1-Nal-D-Trp-2-Fua-Apc-NH$_2$; (SEQ ID NO: 137)

H-Apc-D-1-Nal-D-Trp-Pff-Apc-NH$_2$; (SEQ ID NO: 137)

H-Apc-D-2-Nal-D-Trp-2-Thi-Apc-NH$_2$; (SEQ ID NO: 138)

H-Apc-D-2-Nal-D-Trp-3-Thi-Apc-NH$_2$; (SEQ ID NO: 138)

H-Apc-D-2-Nal-D-Trp-Taz-Apc-NH$_2$; (SEQ ID NO: 136)

H-Apc-D-2-Nal-D-Trp-2-Fua-Apc-NH$_2$; (SEQ ID NO: 138)

H-Apc-D-2-Nal-D-Trp-Pff-Apc-NH$_2$; (SEQ ID NO: 138)

H-Inp-D-Bal-D-Trp-Taz-NH$_2$; (SEQ ID NO: 152)

H-Inp-D-Bal-D-Trp-2-Fua-NH$_2$; (SEQ ID NO: 152)

H-Inp-D-Bal-D-Trp-Pff-NH$_2$; (SEQ ID NO: 152)

H-Apc-D-Bal-D-Trp-3-Thi-NH$_2$; (SEQ ID NO: 157)

H-Apc-D-Bal-D-Trp-2-Fua-NH$_2$; (SEQ ID NO: 157)

H-Apc-D-Bal-D-Trp-Pff-NH$_2$; (SEQ ID NO: 157)

H-Apc-D-Bal-D-Trp-4-Pal-NH$_2$; (SEQ ID NO: 157)

H-Apc-D-Bal-D-Trp-3-Pal-NH$_2$; (SEQ ID NO: 157)

H-Apc-D-Bal-D-Trp-2-Pal-NH$_2$; (SEQ ID NO: 157)

H-Inp-D-Bal-D-Bal-Taz-NH$_2$; (SEQ ID NO: 150)

H-Inp-D-Bal-D-Bal-2-Fua-NH$_2$; (SEQ ID NO: 150)

H-Inp-D-Bal-D-Bal-Pff-NH$_2$; (SEQ ID NO: 150)

H-Apc-D-Bal-D-Bal-Phe-NH$_2$; (SEQ ID NO: 142)

H-Apc-D-Bal-D-Bal-2-Thi-NH$_2$; (SEQ ID NO: 142)

H-Apc-D-Bal-D-Bal-3-Thi-NH$_2$; (SEQ ID NO: 142)

H-Apc-D-Bal-D-Bal-Taz-NH$_2$; (SEQ ID NO: 142)

H-Apc-D-Bal-D-Bal-2-Fua-NH$_2$; (SEQ ID NO: 142)

H-Apc-D-Bal-D-Bal-Pff-NH$_2$; (SEQ ID NO: 142)

H-Apc-D-Bal-D-Bal-4-Pal-NH$_2$; (SEQ ID NO: 142)

H-Apc-D-Bal-D-Bal-3-Pal-NH$_2$; (SEQ ID NO: 142)

H-Apc-D-Bal-D-Bal-2-Pal-NH$_2$; (SEQ ID NO: 142)

H-Inp-D-1-Nal-D-Trp-Taz-NH$_2$; (SEQ ID NO: 116)

H-Inp-D-1-Nal-D-Trp-2-Fua-NH$_2$; (SEQ ID NO: 116)

H-Inp-D-1-Nal-D-Trp-Pff-NH$_2$; (SEQ ID NO: 116)

H-Inp-D-1-Nal-D-Bal-Taz-NH$_2$; (SEQ ID NO: 161)

H-Inp-D-1-Nal-D-Bal-2-Fua-NH$_2$; (SEQ ID NO: 161)

H-Inp-D-1-Nal-D-Bal-Pff-NH$_2$; (SEQ ID NO: 161)

H-Inp-D-2-Nal-D-Trp-Taz-NH$_2$; (SEQ ID NO: 115)

-continued

H-Inp-D-2-Nal-D-Trp-2-Fua-NH$_2$; (SEQ ID NO: 115)

H-Inp-D-2-Nal-D-Trp-Pff-NH$_2$; (SEQ ID NO: 115)

H-Apc-D-1-Nal-D-Trp-3-Thi-NH$_2$; (SEQ ID NO: 133)

H-Apc-D-1-Nal-D-Trp-2-Fua-NH$_2$; (SEQ ID NO: 133)

H-Apc-D-1-Nal-D-Trp-Pff-NH$_2$; (SEQ ID NO: 133)

H-Apc-D-1-Nal-D-Trp-4-Pal-NH$_2$; (SEQ ID NO: 133)

H-Apc-D-1-Nal-D-Trp-3-Pal-NH$_2$; (SEQ ID NO: 133)

H-Apc-D-1-Nal-D-Trp-2-Pal-NH$_2$; (SEQ ID NO: 133)

H-Apc-D-2-Nal-D-Trp-3-Thi-NH$_2$; (SEQ ID NO: 134)

H-Apc-D-2-Nal-D-Trp-2-Fua-NH$_2$; (SEQ ID NO: 134)

H-Apc-D-2-Nal-D-Trp-Pff-NH$_2$; (SEQ ID NO: 134)

H-Apc-D-2-Nal-D-Trp-4-Pal-NH$_2$; (SEQ ID NO: 134)

H-Apc-D-2-Nal-D-Trp-3-Pal-NH$_2$; (SEQ ID NO: 134)

H-Apc-D-2-Nal-D-Trp-2-Pal-NH$_2$; (SEQ ID NO: 134)

H-Inp-D-Bip-D-Trp-Taz-NH$_2$; (SEQ ID NO: 156)

H-Inp-D-Bip-D-Trp-2-Fua-NH$_2$; (SEQ ID NO: 156)

H-Inp-D-Bip-D-Trp-Pff-NH$_2$; (SEQ ID NO: 156)

H-Inp-D-Bip-D-Bal-Taz-NH$_2$; (SEQ ID NO: 154)

H-Inp-D-Bip-D-Bal-2-Fua-NH$_2$; or (SEQ ID NO: 154)

H-Inp-D-Bip-D-Bal-Pff-NH$_2$; (SEQ ID NO: 154)

H-Inp-D-1-Nal-D-Trp-2-Thi-Apc-NH$_2$; (SEQ ID NO: 147)

H-Inp-D-Bal-D-Trp-2-Thi-Apc-NH$_2$; (SEQ ID NO: 151)

H-Apc-D-1-Nal-D-Trp-2-Thi-Apc-NH$_2$; (SEQ ID NO: 137)

H-Apc-D-Bal-D-Trp-2-Thi-Apc-NH$_2$; or (SEQ ID NO: 143)

H-Apc-D-1-Nal-D-Trp-Phe-Lys-NH$_2$; (SEQ ID NO: 131)

(Ser(n-octanoyl)$^{15}$)hGhrelin(1-28)-NH$_2$; (SEQ ID NO: 162)

(Glu(NH-hexyl)$^{15}$)hGhrelin(1-28)-NH$_2$; (SEQ ID NO: 163)

(Glu(NH-hexyl)$^{3,15}$)hGhrelin(1-28)-NH$_2$; (SEQ ID NO: 164)

(Glu(NH-hexyl)$^{3}$,Ser(n-octanoyl)$^{15}$)hGhrelin(1-28)-NH$_2$; (SEQ ID NO: 165)

(Aib$^2$,Glu(NH-hexyl)$^{15}$)hGhrelin(1-28)-NH$_2$; (SEQ ID NO: 166)

(Aib$^2$,Glu(NH-hexyl)$^{3,15}$)hGhrelin(1-28)-NH$_2$; (SEQ ID NO: 167)

(Aib$^{2,8}$,Glu(NH-hexyl)$^{15}$)hGhrelin(1-28)-NH$_2$; (SEQ ID NO: 168)

(Aib$^{2,8}$,Glu(NH-hexyl)$^{3,15}$)hGhrelin(1-28)-NH$_2$; (SEQ ID NO: 169)

(Aib$^{2,10}$,Glu(NH-hexyl)$^{15}$)hGhrelin(1-28)-NH$_2$; (SEQ ID NO: 170)

(Aib$^{2,10}$,Glu(NH-hexyl)$^{3,15}$)hGhrelin(1-28)-NH$_2$; (SEQ ID NO: 171)

(Ser(n-octanoyl)$^{16}$)hGhrelin(1-28)-NH$_2$; (SEQ ID NO: 172)

(Glu(NH-hexyl)$^{16}$)hGhrelin(1-28)-NH$_2$; (SEQ ID NO: 173)

(Glu(NH-hexyl)$^{3,16}$)hGhrelin(1-28)-NH$_2$; (SEQ ID NO: 174)

(Glu(NH-hexyl)$^{3}$,Ser(n-octanoyl)$^{16}$)hGhrelin(1-28)-NH$_2$; (SEQ ID NO: 175)

(Aib$^2$,Glu(NH-hexyl)$^{16}$)hGhrelin(1-28)-NH$_2$; (SEQ ID NO: 176)

(Aib$^2$,Glu(NH-hexyl)$^{3,16}$)hGhrelin(1-28)-NH$_2$; (SEQ ID NO: 177)

-continued (Aib$^{2,8}$,Glu(NH-hexyl)$^{16}$)hGhrelin(1-28)-NH$_2$; (SEQ ID NO: 178)

(Aib$^{2,8}$,Glu(NH-hexyl)$^{3,16}$)hGhrelin(1-28)-NH$_2$; (SEQ ID NO: 179)

(Aib$^{2,10}$,Glu(NH-hexyl)$^{16}$)hGhrelin(1-28)-NH$_2$; (SEQ ID NO: 180)

(Aib$^{2,10}$,Glu(NH-hexyl)$^{3,16}$)hGhrelin(1-28)-NH$_2$; (SEQ ID NO: 181)

(Ser(n-octanoyl)$^{17}$)hGhrelin(1-28)-NH$_2$; (SEQ ID NO: 182)

(Glu(NH-hexyl)$^{17}$)hGhrelin(1-28)-NH$_2$; (SEQ ID NO: 183)

(Glu(NH-hexyl)$^{3,17}$)hGhrelin(1-28)-NH$_2$; (SEQ ID NO: 184)

(Glu(NH-hexyl)$^{3}$,Ser(n-octanoyl)$^{17}$)hGhrelin(1-28)-NH$_2$; (SEQ ID NO: 185)

(Dap(octanesulfonyl)$^{17}$)hGhrelin(1-28)-NH$_2$; (SEQ ID NO: 186)

(Dap(octanesulfonyl)$^{3,17}$)hGhrelin(1-28)-NH$_2$; (SEQ ID NO: 187)

(Dap(octanesulfonyl)$^{3}$,Glu(NH-hexyl)$^{17}$)hGhrelin(1-28)-NH$_2$; (SEQ ID NO: 188)

(Dap(octanesulfonyl)$^{3}$,Ser(n-octanoyl)$^{17}$)hGhrelin(1-28)-NH$_2$; (SEQ ID NO: 189)

(Glu(NH-hexyl)$^{3}$,Dap(octanesulfonyl)$^{17}$)hGhrelin(1-28)-NH$_2$; (SEQ ID NO: 190)

(Cys(S—(CH$_2$)$_9$CH$_3$)$^{17}$)hGhrelin(1-28)-NH$_2$; (SEQ ID NO: 191)

(Cys(S—(CH$_2$)$_9$CH$_3$)$^{3,17}$)hGhrelin(1-28)-NH$_2$; (SEQ ID NO: 192)

(Glu(NH-hexyl)$^{3}$,Cys(S—(CH$_2$)$_9$CH$_3$)$^{17}$)hGhrelin(1-28)-NH$_2$; (SEQ ID NO: 193)

(Cys(S—(CH$_2$)$_9$CH$_3$)$^{3}$,Glu(NH-hexyl)$^{17}$)hGhrelin(1-28)-NH$_2$; (SEQ ID NO: 194)

(Cys(S—(CH$_2$)$_9$CH$_3$)$^{3}$,Ser(n-octanoyl)$^{17}$)hGhrelin(1-28)-NH$_2$; (SEQ ID NO: 195)

(Aib$^{2}$,Glu(NH-hexyl)$^{17}$)hGhrelin(1-28)-NH$_2$; (SEQ ID NO: 196)

(Aib$^{2}$,Glu(NH-hexyl)$^{3,17}$)hGhrelin(1-28)-NH$_2$; (SEQ ID NO: 197)

(Aib$^{2}$,Thz$^{7}$,Glu(NH-hexyl)$^{17}$)hGhrelin(1-28)-NH$_2$; (SEQ ID NO: 198)

(Aib$^{2}$,4-Hyp$^{7}$,Glu(NH-hexyl)$^{17}$)hGhrelin(1-28)-NH$_2$; (SEQ ID NO: 198)

(Aib$^{2}$,Dhp$^{7}$,Glu(NH-hexyl)$^{17}$)hGhrelin(1-28)-NH$_2$; (SEQ ID NO: 198)

(Aib$^{2}$,Pip$^{7}$,Glu(NH-hexyl)$^{17}$)hGhrelin(1-28)-NH$_2$; (SEQ ID NO: 198)

(Aib$^{2}$,Tic$^{7}$,Glu(NH-hexyl)$^{17}$)hGhrelin(1-28)-NH$_2$; (SEQ ID NO: 198)

(Aib$^{2}$,Glu(NH-hexyl)$^{3,17}$,Thz$^{7}$)hGhrelin(1-28)-NH$_2$; (SEQ ID NO: 199)

(Aib$^{2}$,Glu(NH-hexyl)$^{3,17}$,4-Hyp$^{7}$)hGhrelin(1-28)-NH$_2$; (SEQ ID NO: 200)

(Aib$^{2}$,Glu(NH-hexyl)$^{3,17}$,Dhp$^{7}$)hGhrelin(1-28)-NH$_2$; (SEQ ID NO: 200)

(Aib$^{2}$,Glu(NH-hexyl)$^{3,17}$,Pip$^{7}$)hGhrelin(1-28)-NH$_2$; (SEQ ID NO: 200)

(Aib$^{2}$,Glu(NH-hexyl)$^{3,17}$,Tic$^{7}$)hGhrelin(1-28)-NH$_2$; (SEQ ID NO: 200)

(Aib$^{2,8}$,Glu(NH-hexyl)$^{17}$)hGhrelin(1-28)-NH$_2$; (SEQ ID NO: 201)

(Aib$^{2,8}$,Glu(NH-hexyl)$^{3,17}$)hGhrelin(1-28)-NH$_2$; (SEQ ID NO: 202)

(Aib$^{2}$,3-Pal$^{9}$,Glu(NH-hexyl)$^{17}$)hGhrelin(1-28)-NH$_2$; (SEQ ID NO: 203)

(Aib$^{2}$,4-Pal$^{9}$,Glu(NH-hexyl)$^{17}$)hGhrelin(1-28)-NH$_2$; (SEQ ID NO: 203)

(Aib$^{2}$,Taz$^{9}$,Glu(NH-hexyl)$^{17}$)hGhrelin(1-28)-NH$_2$; (SEQ ID NO: 203)

(Aib$^{2}$,2-Thi$^{9}$,Glu(NH-hexyl)$^{17}$)hGhrelin(1-28)-NH$_2$; (SEQ ID NO: 203)

(Aib$^{2}$,Glu(NH-hexyl)$^{3,17}$,3-Pal$^{9}$)hGhrelin(1-28)-NH$_2$; (SEQ ID NO: 204)

(Aib$^{2}$,Glu(NH-hexyl)$^{3,17}$,4-Pal$^{9}$)hGhrelin(1-28)-NH$_2$; (SEQ ID NO: 204)

(Aib$^{2}$,Glu(NH-hexyl)$^{3,17}$,Taz$^{9}$)hGhrelin(1-28)-NH$_2$; (SEQ ID NO: 204)

(Aib$^{2}$,Glu(NH-hexyl)$^{3,17}$,2-Thi$^{9}$)hGhrelin(1-28)-NH$_2$; (SEQ ID NO: 204)

-continued (Aib$^{2,10}$,Glu(NH-hexyl)$^{17}$)hGhrelin(1-28)-NH$_2$; (SEQ ID NO: 205)

(Aib$^{2,10}$,Glu(NH-hexyl)$^{3,17}$)hGhrelin(1-28)-NH$_2$; (SEQ ID NO: 206)

(Aib$^8$,Glu(NH-hexyl)$^{17}$)hGhrelin(1-28)-NH$_2$; (SEQ ID NO: 207)

(Taz$^9$,Glu(NH-hexyl)$^{17}$)hGhrelin(1-28)-NH$_2$; (SEQ ID NO: 208)

(3-Pal$^9$,Glu(NH-hexyl)$^{17}$)hGhrelin(1-28)-NH$_2$; (SEQ ID NO: 208)

(4-Pal$^9$,Glu(NH-hexyl)$^{17}$)hGhrelin(1-28)-NH$_2$; (SEQ ID NO: 208)

(2-Thi$^9$,Glu(NH-hexyl)$^{17}$)hGhrelin(1-28)-NH$_2$; (SEQ ID NO: 208)

(Glu(NH-hexyl)$^{3,17}$,Aib$^8$)hGhrelin(1-28)-NH$_2$; (SEQ ID NO: 209)

(Glu(NH-hexyl)$^{3,17}$,Taz$^9$)hGhrelin(1-28)-NH$_2$; (SEQ ID NO: 210)

(Glu(NH-hexyl)$^{3,17}$,3-Pal$^9$)hGhrelin(1-28)-NH$_2$; (SEQ ID NO: 210)

(Glu(NH-hexyl)$^{3,17}$,4-Pal$^9$)hGhrelin(1-28)-NH$_2$; (SEQ ID NO: 210)

(Glu(NH-hexyl)$^{3,17}$,2-Thi$^9$)hGhrelin(1-28)-NH$_2$; (SEQ ID NO: 210)

(Aib$^{1,2,10}$,Glu(NH-hexyl)$^{17}$)hGhrelin(1-28)-NH$_2$; (SEQ ID NO: 211)

(Aib$^{1,2,10}$,Glu(NH-hexyl)$^{3,17}$)hGhrelin(1-28)-NH$_2$; (SEQ ID NO: 212)

(A5c$^2$,Glu(NH-hexyl)$^{17}$)hGhrelin(1-28)-NH$_2$; (SEQ ID NO: 196)

(A5c$^2$,Glu(NH-hexyl)$^{3,17}$)hGhrelin(1-28)-NH$_2$; (SEQ ID NO: 197)

(Glu(1-heptanol)$^{3,17}$)hGhrelin(1-28)-NH$_2$; (SEQ ID NO: 184)

(Asp(1-heptanol)$^{3,17}$)hGhrelin(1-28)-NH$_2$; (SEQ ID NO: 213)

(Glu(NH-hexyl)$^{3,17}$)hGhrelin(1-28)-NH$_2$; (SEQ ID NO: 184)

(Asp(NH-hexyl)$^{3,17}$)hGhrelin(1-28)-NH$_2$; (SEQ ID NO: 213)

(Aib$^2$,Glu(NH-hexyl)$^{3,17}$)hGhrelin(1-28)-NH$_2$; (SEQ ID NO: 197)

(Lys(biotinyl)$^{17}$)hGhrelin(1-28)-NH$_2$; (SEQ ID NO: 214)

(Ser(n-octanoyl)$^{18}$)hGhrelin(1-28)-NH$_2$; (SEQ ID NO: 215)

(Glu(NH-hexyl)$^{18}$)hGhrelin(1-28)-NH$_2$; (SEQ ID NO: 216)

(Glu(NH-hexyl)$^{3,18}$)hGhrelin(1-28)-NH$_2$; (SEQ ID NO: 217)

(Glu(NH-hexyl)$^3$,Ser(n-octanoyl)$^{18}$)hGhrelin(1-28)-NH$_2$; (SEQ ID NO: 218)

(Aib$^2$,Glu(NH-hexyl)$^{18}$)hGhrelin(1-28)-NH$_2$; (SEQ ID NO: 219)

(Aib$^2$,Glu(NH-hexyl)$^{3,18}$)hGhrelin(1-28)-NH$_2$; (SEQ ID NO: 220)

(Aib$^{2,8}$,Glu(NH-hexyl)$^{18}$)hGhrelin(1-28)-NH$_2$; (SEQ ID NO: 221)

(Aib$^{2,8}$,Glu(NH-hexyl)$^{3,18}$)hGhrelin(1-28)-NH$_2$; (SEQ ID NO: 222)

(Aib$^{2,10}$,Glu(NH-hexyl)$^{18}$)hGhrelin(1-28)-NH$_2$; (SEQ ID NO: 223)

(Aib$^{2,10}$,Glu(NH-hexyl)$^{3,18}$)hGhrelin(1-28)-NH$_2$; (SEQ ID NO: 224)

(Ser(n-octanoyl)$^{19}$)hGhrelin(1-28)-NH$_2$; (SEQ ID NO: 225)

(Glu(NH-hexyl)$^{19}$)hGhrelin(1-28)-NH$_2$; (SEQ ID NO: 226)

(Glu(NH-hexyl)$^{3,19}$)hGhrelin(1-28)-NH$_2$; (SEQ ID NO: 227)

(Glu(NH-hexyl)$^3$,Ser(n-octanoyl)$^{19}$)hGhrelin(1-28)-NH$_2$; (SEQ ID NO: 228)

(Aib$^2$,Glu(NH-hexyl)$^{19}$)hGhrelin(1-28)-NH$_2$; (SEQ ID NO: 229)

(Aib$^2$,Glu(NH-hexyl)$^{3,19}$)hGhrelin(1-28)-NH$_2$; (SEQ ID NO: 230)

(Aib$^{2,8}$,Glu(NH-hexyl)$^{19}$)hGhrelin(1-28)-NH$_2$; (SEQ ID NO: 231)

(Aib$^{2,8}$,Glu(NH-hexyl)$^{3,19}$)hGhrelin(1-28)-NH$_2$; (SEQ ID NO: 232)

(Aib$^{2,10}$,Glu(NH-hexyl)$^{19}$)hGhrelin(1-28)-NH$_2$; (SEQ ID NO: 233)

-continued (Aib$^{2,10}$,Glu(NH-hexyl)$^{3,19}$)hGhrelin(1-28)-NH$_2$; (SEQ ID NO: 234)

(Ser(n-octanoyl)$^{20}$)hGhrelin(1-28)-NH$_2$; (SEQ ID NO: 235)

(Glu(NH-hexyl)$^{20}$)hGhrelin(1-28)-NH$_2$; (SEQ ID NO: 236)

(Glu(NH-hexyl)$^{3,20}$)hGhrelin(1-28)-NH$_2$; (SEQ ID NO: 237)

(Glu(NH-hexyl)$^{3}$,Ser(n-octanoyl)$^{20}$)hGhrelin(1-28)-NH$_2$; (SEQ ID NO: 238)

(Aib$^{2}$,Glu(NH-hexyl)$^{20}$)hGhrelin(1-28)-NH$_2$; (SEQ ID NO: 239)

(Aib$^{2}$,Glu(NH-hexyl)$^{3,20}$)hGhrelin(1-28)-NH$_2$; (SEQ ID NO: 240)

(Aib$^{2,8}$,Glu(NH-hexyl)$^{20}$)hGhrelin(1-28)-NH$_2$; (SEQ ID NO: 241)

(Aib$^{2,8}$,Glu(NH-hexyl)$^{3,20}$)hGhrelin(1-28)-NH$_2$; (SEQ ID NO: 242)

(Aib$^{2,10}$,Glu(NH-hexyl)$^{20}$)hGhrelin(1-28)-NH$_2$; (SEQ ID NO: 243)

(Aib$^{2,10}$,Glu(NH-hexyl)$^{3,20}$)hGhrelin(1-28)-NH$_2$; (SEQ ID NO: 244)

(Ac-Gly$^{1}$,Glu(NH-hexyl)$^{17}$)hGhrelin(1-28)-NH$_2$; (SEQ ID NO: 245)

(Ac-Gly$^{1}$,Ser(n-octanoyl)$^{17}$)hGhrelin(1-28)-NH$_2$; (SEQ ID NO: 246)

(Ac-Gly$^{1}$,Glu(NH-hexyl)$^{3,17}$)hGhrelin(1-28)-NH$_2$; (SEQ ID NO: 247)

(Ac-Gly$^{1}$,Glu(NH-hexyl)$^{3}$,Ser(n-octanoyl)$^{17}$)hGhrelin(1-28)-NH$_2$; (SEQ ID NO: 248)

(Ac-Gly$^{1}$,Dap(octanesulfonyl)$^{17}$)hGhrelin(1-28)-NH$_2$; (SEQ ID NO: 249)

(Ac-Gly$^{1}$,Dap(octanesulfonyl)$^{3,17}$)hGhrelin(1-28)-NH$_2$; (SEQ ID NO: 250)

(Ac-Gly$^{1}$,Dap(octanesulfonyl)$^{3}$,Glu(NH-Hexyl)$^{17}$)hGhrelin(1-28)-NH$_2$; (SEQ ID NO: 251)

(Ac-Gly$^{1}$,Dap(octanesulfonyl)$^{3}$,Ser(n-Octanoyl)$^{17}$)hGhrelin(1-28)-NH$_2$; (SEQ ID NO: 252)

(Ac-Gly$^{1}$,Glu(NH-hexyl)$^{3}$,Dap(octanesulfonyl)$^{17}$)hGhrelin(1-28)-NH$_2$; (SEQ ID NO: 253)

(Ac-Gly$^{1}$,Cys(S—(CH$_2$)$_9$CH$_3$)$^{17}$)hGhrelin(1-28)-NH$_2$; (SEQ ID NO: 254)

(Ac-Gly$^{1}$,Cys(S—(CH$_2$)$_9$CH$_3$)$^{3,17}$)hGhrelin(1-28)-NH$_2$; (SEQ ID NO: 255)

(Ac-Gly$^{1}$,Glu(NH-hexyl)$^{3}$,Cys(S—(CH$_2$)$_9$CH$_3$)$^{17}$)hGhrelin(1-28)-NH$_2$; (SEQ ID NO: 256)

(Ac-Gly$^{1}$,Cys(S—(CH$_2$)$_9$CH$_3$)$^{3}$,Glu(NH-hexyl)$^{17}$)hGhrelin(1-28)-NH$_2$; (SEQ ID NO: 257)

(Ac-Gly$^{1}$,Cys(S—(CH$_2$)$_9$CH$_3$)$^{3}$,Ser(n-octanoyl)$^{17}$)hGhrelin(1-28)-NH$_2$; (SEQ ID NO: 258)

(Ac-Gly$^{1}$,Aib$^{2}$,Glu(NH-hexyl)$^{17}$)hGhrelin(1-28)-NH$_2$; (SEQ ID NO: 259)

(Ac-Gly$^{1}$,Aib$^{2}$,Thz$^{7}$,Glu(NH-hexyl)$^{17}$)hGhrelin(1-28)-NH$_2$; (SEQ ID NO: 260)

(Ac-Gly$^{1}$,Aib$^{2}$,4-Hyp$^{7}$,Glu(NH-hexyl)$^{17}$)hGhrelin(1-28)-NH$_2$; (SEQ ID NO: 260)

(Ac-Gly$^{1}$,Aib$^{2}$,Dhp$^{7}$,Glu(NH-hexyl)$^{17}$)hGhrelin(1-28)-NH$_2$; (SEQ ID NO: 260)

(Ac-Gly$^{1}$,Aib$^{2}$,Pip$^{7}$,Glu(NH-hexyl)$^{17}$)hGhrelin(1-28)-NH$_2$; (SEQ ID NO: 260)

(Ac-Gly$^{1}$,Aib$^{2}$,Tic$^{7}$,Glu(NH-hexyl)$^{17}$)hGhrelin(1-28)-NH$_2$; (SEQ ID NO: 260)

(Ac-Gly$^{1}$,Aib$^{2}$,Glu(NH-hexyl)$^{3,17}$,Thz$^{7}$)hGhrelin(1-28)-NH$_2$; (SEQ ID NO: 261)

(Ac-Gly$^{1}$,Aib$^{2}$,Glu(NH-hexyl)$^{3,17}$,4-Hyp$^{7}$)hGhrelin(1-28)-NH$_2$; (SEQ ID NO: 261)

(Ac-Gly$^{1}$,Aib$^{2}$,Glu(NH-hexyl)$^{3,17}$,Dhp$^{7}$)hGhrelin(1-28)-NH$_2$; (SEQ ID NO: 261)

(Ac-Gly$^{1}$,Aib$^{2}$,Glu(NH-hexyl)$^{3,17}$,Pip$^{7}$)hGhrelin(1-28)-NH$_2$; (SEQ ID NO: 261)

(Ac-Gly$^{1}$,Aib$^{2}$,Glu(NH-hexyl)$^{3,17}$,Tic$^{7}$)hGhrelin(1-28)-NH$_2$; (SEQ ID NO: 261)

(Ac-Gly$^{1}$,Aib$^{2,8}$,Glu(NH-hexyl)$^{17}$)hGhrelin(1-28)-NH$_2$; (SEQ ID NO: 262)

(Ac-Gly$^{1}$,Aib$^{2}$,3-Pal$^{9}$,Glu(NH-hexyl)$^{17}$)hGhrelin(1-28)-NH$_2$; (SEQ ID NO: 263)

(Ac-Gly$^{1}$,Aib$^{2}$,4-Pal$^{9}$,Glu(NH-hexyl)$^{17}$)hGhrelin(1-28)-NH$_2$; (SEQ ID NO: 263)

(Ac-Gly$^{1}$,Aib$^{2}$,Taz$^{9}$,Glu(NH-hexyl)$^{17}$)hGhrelin(1-28)-NH$_2$; (SEQ ID NO: 263)

(Ac-Gly$^1$,Aib$^2$,2-Thi$^9$,Glu(NH-hexyl)$^{17}$)hGhrelin(1-28)-NH$_2$; (SEQ ID NO: 263)

(Ac-Gly$^1$,Aib$^2$,Glu(NH-hexyl)$^{3,17}$,3-Pal$^9$)hGhrelin(1-28)-NH$_2$; (SEQ ID NO: 264)

(Ac-Gly$^1$,Aib$^2$,Glu(NH-hexyl)$^{3,17}$,4-Pal$^9$)hGhrelin(1-28)-NH$_2$; (SEQ ID NO: 264)

(Ac-Gly$^1$,Aib$^2$,Glu(NH-hexyl)$^{3,17}$,Taz$^9$)hGhrelin(1-28)-NH$_2$; (SEQ ID NO: 264)

(Ac-Gly$^1$,Aib$^2$,Glu(NH-hexyl)$^{3,17}$,2-Thi$^9$)hGhrelin(1-28)-NH$_2$; (SEQ ID NO: 264)

(Ac-Gly$^1$,Aib$^{2,10}$,Glu(NH-hexyl)$^{17}$)hGhrelin(1-28)-NH$_2$; (SEQ ID NO: 265)

(Ac-Gly$^1$,Aib$^{2,10}$,Glu(NH-hexyl)$^{3,17}$)hGhrelin(1-28)-NH$_2$; (SEQ ID NO: 266)

(Ac-Gly$^1$,Aib$^8$,Glu(NH-hexyl)$^{17}$)hGhrelin(1-28)-NH$_2$; (SEQ ID NO: 267)

(Ac-Gly$^1$,Taz$^9$,Glu(NH-hexyl)$^{17}$)hGhrelin(1-28)-NH$_2$; (SEQ ID NO: 268)

(Ac-Gly$^1$,3-Pal$^9$,Glu(NH-hexyl)$^{17}$)hGhrelin(1-28)-NH$_2$; (SEQ ID NO: 268)

(Ac-Gly$^1$,4-Pal$^9$,Glu(NH-hexyl)$^{17}$)hGhrelin(1-28)-NH$_2$; (SEQ ID NO: 268)

(Ac-Gly$^1$,2-Thi$^9$,Glu(NH-hexyl)$^{17}$)hGhrelin(1-28)-NH$_2$; (SEQ ID NO: 268)

(Ac-Gly$^1$,Glu(NH-hexyl)$^{3,17}$,Aib$^8$)hGhrelin(1-28)-NH$_2$; (SEQ ID NO: 269)

(Ac-Gly$^1$,Glu(NH-hexyl)$^{3,17}$,Taz$^9$)hGhrelin(1-28)-NH$_2$; (SEQ ID NO: 270)

(Ac-Gly$^1$,Glu(NH-hexyl)$^{3,17}$,3-Pal$^9$)hGhrelin(1-28)-NH$_2$; (SEQ ID NO: 270)

(Ac-Gly$^1$,Glu(NH-hexyl)$^{3,17}$,4-Pal$^9$)hGhrelin(1-28)-NH$_2$; (SEQ ID NO: 270)

(Ac-Gly$^1$,Glu(NH-hexyl)$^{3,17}$,2-Thi$^9$)hGhrelin(1-28)-NH$_2$; (SEQ ID NO: 270)

(Ac-Aib$^1$,Aib$^{2,10}$,Glu(NH-hexyl)$^{17}$)hGhrelin(1-28)-NH$_2$; (SEQ ID NO: 271)

(Ac-Aib$^1$,Aib$^{2,10}$,Glu(NH-hexyl)$^{3,17}$)hGhrelin(1-28)-NH$_2$; (SEQ ID NO: 272)

(Ac-Gly$^1$,A5c$^2$,Glu(NH-hexyl)$^{17}$)hGhrelin(1-28)-NH$_2$; (SEQ ID NO: 259)

(Ac-Gly$^1$,A5c$^2$,Glu(NH-hexyl)$^{3,17}$)hGhrelin(1-28)-NH$_2$; (SEQ ID NO: 273)

(Ac-Gly$^1$,Glu(1-heptanol)$^{3,17}$)hGhrelin(1-28)-NH$_2$; (SEQ ID NO: 247)

(Ac-Gly$^1$,Asp(1-heptanol)$^{3,17}$)hGhrelin(1-28)-NH$_2$; (SEQ ID NO: 274)

(Ac-Gly$^1$,Glu(NH-hexyl)$^{3,17}$)hGhrelin(1-28)-NH$_2$; (SEQ ID NO: 247)

(Ac-Gly$^1$,Asp(NH-hexyl)$^{3,17}$)hGhrelin(1-28)-NH$_2$; (SEQ ID NO: 274)

(Ac-Gly$^1$,Aib$^{2,10}$,Glu(NH-hexyl)$^3$,Lys(biotinyl)$^{17}$)hGhrelin(1-28)-NH$_2$; (SEQ ID NO: 275)

(Ac-Gly$^1$,Glu(NH-hexyl)$^{15}$)hGhrelin(1-28)-NH$_2$; (SEQ ID NO: 276)

(Ac-Gly$^1$,Ser(n-octanoyl)$^{15}$)hGhrelin(1-28)-NH$_2$; (SEQ ID NO: 277)

(Ac-Gly$^1$,Glu(NH-hexyl)$^{3,15}$)hGhrelin(1-28)-NH$_2$; (SEQ ID NO: 278)

(Ac-Gly$^1$,Glu(NH-hexyl)$^3$,Ser(n-octanoyl)$^{15}$)hGhrelin(1-28)-NH$_2$; (SEQ ID NO: 279)

(Ac-Gly$^1$,Aib$^2$,Glu(NH-hexyl)$^{15}$)hGhrelin(1-28)-NH$_2$; (SEQ ID NO: 280)

(Ac-Gly$^1$,Aib$^2$,Glu(NH-hexyl)$^{3,15}$)hGhrelin(1-28)-NH$_2$; (SEQ ID NO: 281)

(Ac-Gly$^1$,Aib$^{2,8}$,Glu(NH-hexyl)$^{15}$)hGhrelin(1-28)-NH$_2$; (SEQ ID NO: 282)

(Ac-Gly$^1$,Aib$^{2,8}$,Glu(NH-hexyl)$^{3,15}$)hGhrelin(1-28)-NH$_2$; (SEQ ID NO: 283)

(Ac-Gly$^1$,Aib$^{2,10}$,Glu(NH-hexyl)$^{15}$)hGhrelin(1-28)-NH$_2$; (SEQ ID NO: 284)

(Ac-Gly$^1$,Aib$^{2,10}$,Glu(NH-hexyl)$^{3,15}$)hGhrelin(1-28)-NH$_2$; (SEQ ID NO: 285)

(Ac-Gly$^1$,Glu(NH-hexyl)$^{16}$)hGhrelin(1-28)-NH$_2$; (SEQ ID NO: 286)

(Ac-Gly$^1$,Ser(n-octanoyl)$^{16}$)hGhrelin(1-28)-NH$_2$; (SEQ ID NO: 287)

(Ac-Gly$^1$,Glu(NH-hexyl)$^{3,16}$)hGhrelin(1-28)-NH$_2$; (SEQ ID NO: 288)

(Ac-Gly$^1$,Glu(NH-hexyl)$^3$,Ser(n-octanoyl)$^{16}$)hGhrelin(1-28)-NH$_2$; (SEQ ID NO: 289)

(Ac-Gly$^1$,Aib$^2$,Glu(NH-hexyl)$^{16}$)hGhrelin(1-28)-NH$_2$; (SEQ ID NO: 290)

-continued (Ac-Gly¹,Aib²,Glu(NH-hexyl)³,¹⁶)hGhrelin(1-28)-NH₂; (SEQ ID NO: 291)

(Ac-Gly¹,Aib²,⁸,Glu(NH-hexyl)¹⁶)hGhrelin(1-28)-NH₂; (SEQ ID NO: 292)

(Ac-Gly¹,Aib²,⁸,Glu(NH-hexyl)³,¹⁶)hGhrelin(1-28)-NH₂; (SEQ ID NO: 293)

(Ac-Gly¹,Aib²,¹⁰,Glu(NH-hexyl)¹⁶)hGhrelin(1-28)-NH₂; (SEQ ID NO: 294)

(Ac-Gly¹,Aib²,¹⁰,Glu(NH-hexyl)³,¹⁶)hGhrelin(1-28)-NH₂; (SEQ ID NO: 295)

(Ac-Gly¹,Glu(NH-hexyl)¹⁸)hGhrelin(1-28)-NH₂; (SEQ ID NO: 296)

(Ac-Gly¹,Ser(n-octanoyl)¹⁸)hGhrelin(1-28)-NH₂; (SEQ ID NO: 297)

(Ac-Gly¹,Glu(NH-hexyl)³,¹⁸)hGhrelin(1-28)-NH₂; (SEQ ID NO: 298)

(Ac-Gly¹,Glu(NH-hexyl)³,Ser(n-octanoyl)¹⁸)hGhrelin(1-28)-NH₂; (SEQ ID NO: 299)

(Ac-Gly¹,Aib²,Glu(NH-hexyl)¹⁸)hGhrelin(1-28)-NH₂; (SEQ ID NO: 300)

(Ac-Gly¹,Aib²,Glu(NH-hexyl)³,¹⁸)hGhrelin(1-28)-NH₂; (SEQ ID NO: 301)

(Ac-Gly¹,Aib²,⁸,Glu(NH-hexyl)¹⁸)hGhrelin(1-28)-NH₂; (SEQ ID NO: 302)

(Ac-Gly¹,Aib²,⁸,Glu(NH-hexyl)³,¹⁸)hGhrelin(1-28)-NH₂; (SEQ ID NO: 303)

(Ac-Gly¹,Aib²,¹⁰,Glu(NH-hexyl)¹⁸)hGhrelin(1-28)-NH₂; (SEQ ID NO: 304)

(Ac-Gly¹,Aib²,¹⁰,Glu(NH-hexyl)³,¹⁸)hGhrelin(1-28)-NH₂; (SEQ ID NO: 305)

(Ac-Gly¹,Glu(NH-hexyl)¹⁹)hGhrelin(1-28)-NH₂; (SEQ ID NO: 306)

(Ac-Gly¹,Ser(n-octanoyl)¹⁹)hGhrelin(1-28)-NH₂; (SEQ ID NO: 307)

(Ac-Gly¹,Glu(NH-hexyl)³,¹⁹)hGhrelin(1-28)-NH₂; (SEQ ID NO: 308)

(Ac-Gly¹,Glu(NH-hexyl)³,Ser(n-octanoyl)¹⁹)hGhrelin(1-28)-NH₂; (SEQ ID NO: 309)

(Ac-Gly¹,Aib²,Glu(NH-hexyl)¹⁹)hGhrelin(1-28)-NH₂; (SEQ ID NO: 310)

(Ac-Gly¹,Aib²,Glu(NH-hexyl)³,¹⁹)hGhrelin(1-28)-NH₂; (SEQ ID NO: 311)

(Ac-Gly¹,Aib²,⁸,Glu(NH-hexyl)¹⁹)hGhrelin(1-28)-NH₂; (SEQ ID NO: 312)

(Ac-Gly¹,Aib²,⁸,Glu(NH-hexyl)³,¹⁹)hGhrelin(1-28)-NH₂; (SEQ ID NO: 313)

(Ac-Gly¹,Aib²,¹⁰,Glu(NH-hexyl)¹⁹)hGhrelin(1-28)-NH₂; (SEQ ID NO: 314)

(Ac-Gly¹,Aib²,¹⁰,Glu(NH-hexyl)³,¹⁹)hGhrelin(1-28)-NH₂; (SEQ ID NO: 315)

(Ac-Gly¹,Glu(NH-hexyl)²⁰)hGhrelin(1-28)-NH₂; (SEQ ID NO: 316)

(Ac-Gly¹,Ser(n-octanoyl)²⁰)hGhrelin(1-28)-NH₂; (SEQ ID NO: 317)

(Ac-Gly¹,Glu(NH-hexyl)³,²⁰)hGhrelin(1-28)-NH₂; (SEQ ID NO: 318)

(Ac-Gly¹,Glu(NH-hexyl)³,Ser(n-octanoyl)²⁰)hGhrelin(1-28)-NH₂; (SEQ ID NO: 319)

(Ac-Gly¹,Aib²,Glu(NH-hexyl)²⁰)hGhrelin(1-28)-NH₂; (SEQ ID NO: 320)

(Ac-Gly¹,Aib²,Glu(NH-hexyl)³,²⁰)hGhrelin(1-28)-NH₂; (SEQ ID NO: 321)

(Ac-Gly¹,Aib²,⁸,Glu(NH-hexyl)²⁰)hGhrelin(1-28)-NH₂; (SEQ ID NO: 322)

(Ac-Gly¹,Aib²,⁸,Glu(NH-hexyl)³,²⁰)hGhrelin(1-28)-NH₂; (SEQ ID NO: 323)

(Ac-Gly¹,Aib²,¹⁰,Glu(NH-hexyl)²⁰)hGhrelin(1-28)-NH₂; (SEQ ID NO: 324)

(Ac-Gly¹,Aib²,¹⁰,Glu(NH-hexyl)³,²⁰)hGhrelin(1-28)-NH₂; (SEQ ID NO: 325)

(Asp³(NH-heptyl))hGhrelin(1-28)-NH₂ (SEQ ID NO: 326) Example #86

(des-Ser²)hGhrelin(1-28)-NH₂; or (SEQ ID NO: 327) Example #104

(des-Gly¹,des-Ser²)hGhrelin(1-28)-NH₂; (SEQ ID NO: 328) Example #117

(Aib¹)hGhrelin(1-28)-NH₂; (SEQ ID NO: 329) Example #6

(Asp³(O-hexyl))hGhrelin(1-28)-NH₂; (SEQ ID NO: 326) Example #40

-continued (Aib¹,Ser³)hGhrelin(1-28)-NH₂; (SEQ ID NO: 329)

(A5c⁵,Ser³)hGhrelin(1-28)-NH₂; (SEQ ID NO: 3)

(Aib²,⁴,Ser³,4-Pal⁹)hGhrelin(1-28)-NH₂; (SEQ ID NO: 330)

(n-octanoyl-Gly¹,Ser³)hGhrelin(1-28)-NH₂; (SEQ ID NO: 95)

(isobutyryl-Gly¹,Ser³)hGhrelin(1-28)-NH₂; (SEQ ID NO: 95)

(n-butyryl-Gly¹,Ser³)hGhrelin(1-28)-NH₂; (SEQ ID NO: 95)

(Aib¹,Thr³)hGhrelin(1-28)-NH₂; (SEQ ID NO: 331)

(Aib²,⁴,Thr³,4-Pal⁹)hGhrelin(1-28)-NH₂; (SEQ ID NO: 330)

(n-octanoyl-Gly¹,Thr³)hGhrelin(1-28)-NH₂; (SEQ ID NO: 332)

(isobutyryl-Gly¹,Thr³)hGhrelin(1-28)-NH₂; (SEQ ID NO: 332)

(n-butyryl-Gly¹,Thr³)hGhrelin(1-28)-NH₂; (SEQ ID NO: 332)

(Ac-Gly¹)hGhrelin(1-28)-NH₂; (SEQ ID NO: 95)

(Ac-Gly¹,Ser³)hGhrelin(1-28)-NH₂, (SEQ ID NO: 95)

Aib²,Lys(Myristyl)¹⁷hGhrelin-(1-28)-NH₂; or (SEQ ID NO: 333)

Gly(myristyl)¹-(Aib²,Lys(Myristyl)¹⁷]hGhrelin-(1-28)-NH₂; (SEQ ID NO: 334)

The present invention includes diastereomers as well as their racemic and resolved enantiomerically pure forms. Ghrelin analogs can contain D-amino acids, L-amino acids or a combination thereof. Preferably, amino acids present in a ghrelin analog are the L-enantiomers.

Preferred derivatives of analogs of the invention comprise D-amino acids, N-alkyl-amino acids, β-amino acids and/or one or more labeled amino acids (including a labeled version of a D-amino acid, N-alkyl-amino acids, or a β-amino acid). A labeled derivative indicates the alteration of an amino acid or amino acid derivative with a detectable label. Examples of detectable labels include luminescent, enzymatic and radioactive labels. Both the type of label and the position of the label can affect analog activity. Labels should be selected and positioned so as not to substantially alter the activity of the ghrelin analog at the GHS receptor. The effect of a particular label and position on ghrelin activity can be determined using assays measuring ghrelin activity and/or binding.

A therapeutically effective amount depends upon the condition being treated, the route of administration chosen, and the specific activity of the compound used and ultimately will be decided by the attending physician or veterinarian (e.g., between 5 g/day to 5 mg/day). In one embodiment, the peptidyl analog of ghrelin is administered to the patient until the symptoms associated with gastrointestinal dysmotility, for example the abdominal nausea, distension, vomiting, obstipation, inability to eat and cramps often associated with postoperative ileus, observed in patient have been alleviated or ceased.

The ileus treatable by the method of the invention can be ileus of any portion of the gastrointestinal tract, e.g., the stomach, small intestine and/or the colon. The ileus can result from any factor that causes ileus, e.g., surgery, e.g., abdominal surgery such as transplantation surgery (e.g., small intestinal transplantation (SITx)) or abdominal surgery other than transplantation surgery (e.g., abdominal surgery involving laparotomy or not involving laparotomy, e.g., laparoscopic procedures); orthopedic surgeries (e.g., hip surgery); parturition; intestinal ischaemia; retroperitoneal haematoma; intraabdominal sepsis; intraperitoneal inflammation, e.g., acute appendicitis, choecystitis, pancreatitis; fractures of the spine; ureteric colic; thoracic lesions; basal pneumonia; rib fractures; myocardial infarction; metabolic disturbances; or any combination thereof.

The peptidyl analog of ghrelin may be injected parenterally, e.g., intravenously, into the bloodstream of the subject being treated, however, it will be readily appreciated by those skilled in the art that the route, such as intravenous, subcutaneous, intramuscular, intraperitoneal, enterally, transdermally, transmucously, sustained released polymer compositions (e.g., a lactic acid polymer or copolymer microparticle or implant), profusion, nasal, oral, etc., will vary with the condition being treated and the activity and bioavailability of the peptidyl analog of ghrelin being used.

While it is possible for the peptidyl analog of ghrelin to be administered as the pure or substantially pure compound, it may also be presented as a pharmaceutical formulation or preparation. The formulations to be used in the present invention, for both humans and animals, comprise any of the peptidyl analog of ghrelin to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. Highly oxidative conditions can lead to the formation of cysteine sulfoxide and to the oxidation of tryptophan. Consequently, it is important to carefully select the excipient.

The pharmaceutical formulation can be administered to the patient by any method known in the art for administering gases, liquids, and/or solids to patients, e.g., via inhalation, insufflation, infusion, injection, and/or ingestion. For example, in one embodiment of the present invention, the pharmaceutical composition is administered to the patient by inhalation. In another embodiment, the pharmaceutical composition is administered to the patient orally. In yet another embodiment, the pharmaceutical composition is administered directly to the abdominal cavity of the patient.

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations such as polyesters containing lactic or glycolic acid residues) are also well known in the art (see, e.g., U.S. Pat. Nos. 3,773,919 and 4,767,628 and PCT Publication WO 94/15587).

In addition to treating postoperative ileus, patients suffering from ileus undergoing the method of the instant application also benefit from other known therapeutic effects of ghrelin such as orexigenic effects, inhibition of inflammatory cytokines, promotion of slow wave sleep and immune enhancing properties.

EXAMPLES

A. Synthesis of Ghrelin Analogs

The ghrelin analogues and compounds of the invention can be produced using the techniques disclosed in the examples herein as well as techniques that are well known in the art. For example, a polypeptide region of a ghrelin analog can be chemically or biochemically synthesized and modified. Examples of techniques for biochemical synthesis involving the introduction of a nucleic acid into a cell and expression of nucleic acids are provided in Ausubel, Current Protocols in Molecular Biology, John Wiley, 1987-1998 and Sambrook et al., in Molecular Cloning, A Laboratory Manual, $2^{nd}$ Edition, Cold Spring Harbor Laboratory Press, 1989. Techniques for chemical synthesis of polypeptides are also well known in the art (See e.g., Vincent in Peptide and Protein Drug Delivery, New York, N.Y., Dekker, 1990). For example, the peptides of this invention can be prepared by standard solid phase peptide synthesis (See, e.g., Stewart, J. M., et al., Solid Phase Synthesis, Pierce Chemical Co., 2d ed. 1984).

The substituents $R^2$ and $R^3$ of the above generic formula may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for 1 hour. If the free acid contains a free hydroxy group, e.g., p-hydroxyphenylpropionic acid, then the coupling should be performed with an additional 3 molar equivalents of HOBT.

When $R^1$ is $NH-X^2-CH_2-CONH_2$, (i.e., $Z^0=CONH_2$), the synthesis of the peptide starts with Fmoc-HN—$X^2$—$CH_2$—COOH coupled to a Rink Amide-MBHA resin (Amide-4-methylbenzylhydryl amine obtained from Novabiochem®, San Diego, Calif.). If $R^1$ is NH—$X^2$—$CH_2$—COOH (i.e., $Z^0$-COOH) the synthesis of the peptide starts with Fmoc-HN—$X^2$—$CH_2$—COOH which is coupled to Wang resin.

In the synthesis of a ghrelin analogue of this invention containing A5c, A6c and/or Aib, the coupling time is 2 hours for these residues and the residue immediately following them.

A protecting group covalently joined to the C-terminal carboxy group reduces the reactivity of the carboxy terminus under in vivo conditions. The carboxy terminus protecting group is preferably attached to the α-carbonyl group of the last amino acid. Preferred carboxy terminus protecting groups include amide, methylamide, and ethylamide.

Examples are provided below to further illustrate different features of the present invention. The examples also illustrate useful methodology for practicing the invention. These examples do not limit the claimed invention.

Synthesis of short amino acid sequences is well established in the peptide art. For example, synthesis of compounds according to formula I such as (Glu$^3$(O-hexyl))hGhrelin(1-28)-NH$_2$ (SEQ ID NO:1), (Aib$^2$)hGhrelin(1-28)-NH$_2$ (SEQ ID NO:10), (Glu$^3$(NH-hexyl))hGhrelin(1-28)-NH$_2$ (SEQ ID NO:1) and (Cys$^3$(S-decyl))hGhrelin(1-28)-NH$_2$ (SEQ ID NO:1) described above, can be achieved by following the protocol set forth in International Patent Publication WO04/009616 at pages 46 to 56 at follows:

Example 1

(Glu$^3$(O-Hexyl))hGhrelin(1-28)-NH$_2$ (SEQ ID NO:1)

The titled peptide was synthesized on an Applied Biosystems (Foster City, Calif.) model 433A peptide synthesizer. 4-(2',4'-Dimethoxyphenyl-Fmoc-aminomethyl)-phenoxyacetamido-norleucyl-MBHA resin (Rink Amide MBHA resin, Novabiochem, San Diego, Calif.) was used with a substitution of 0.72 mmol/g. The Fmoc amino acids (AnaSpec, San Jose, Calif.) were used with the following side chain protection: Fmoc-Arg(Pbf)-OH, Fmoc-Pro-OH, Fmoc-Gln-OH, Fmoc-Leu-OH, Fmoc-Lys(Boc)-OH, Fmoc-Ala-OH, Fmoc-Ser(tBu)-OH, Fmoc-Glu(OtBu)-OH, Fmoc-Val-OH, Fmoc-His(Trt)-OH, Fmoc-Phe-OH, and Fmoc-Asp(OtBu)-OH. Boc-Gly-OH (Midwest Bio-Tech, Fishers, Ind.) was used in position 1. N-α-Fmoc-L-glutamic acid γ-4-{N-(1-(4,4-dimethyl-2,6-dioxocyclohexylidene)-3-methylbutyl)-amino}benzyl ester (Fmoc-Glu(ODmab)-OH) (Chem-Inpex International, Wood Dale, Ill.) was used in position 3. The synthesis was carried out on a 0.25 mmol scale. The Fmoc groups were removed by treatment with 20% piperidine in N-methylpyrrolidone (NMP) for 30 min. In each coupling step, the Fmoc amino acid (1 mmol) was first pre-activated with HBTU (0.9 mmol) and HOBt (0.9 mmol) in DMF and then added to the resin. The ABI 433A peptide synthesizer was programmed to perform the following reaction cycle: (1) washing with NMP, (2) removing Fmoc protecting group with 20% piperidine in NMP for 30 min, (3) washing with NMP, (4) coupling with pre-activated Fmoc amino acid for 1 h.

At the end of assembly of the peptide chain on the Applied Biosystems (ABI) 433A peptide synthesizer, the resin was transferred into a reaction vessel on a shaker for manual synthesis. The Dmab protecting group in the side chain of the Glu residue was removed with a solution of 2% hydrazine in DMF for 2 h. After washing with DMF, the resin was treated with 2.5 mmol of tetramethylfluoroforamidinium hexafluorophosphate (TFFH) (Perseptive Biosystems, Warrington, UK) in dichloromethane (DCM) for 25 min to convert the free carboxylic acid functional group in the side chain of the Glu residue to its acid fluoride. To the mixture were added 5.0 mmol of hexanol, 2.5 mmol of O-(7-azabenzotriazol-1-yl)-1, 1,3,3-tetramethyluronium hexafluorophosphate (HOAT)(Anaspec, San Jose, Calif.), 5.0 mmol of diisopropylethyl amine (DIEA)(Aldrich, Milwaukee, Wis.) and catalytic amount of 4-(dimethylamino)pyridine (DMAP)(Aldrich, Milwaukee, Wis.). The mixture was shaken at room temperature for 2 h. The resin was washed with DMF and DCM and treated overnight with 2.5 mmol of N,N-diisopropylcarbodiimide (DIC) (Chem-Impex International, Wood Dale, Ill.), 2.5 mmol of 1-hexanol, 2.5 mmol of HOBt, and 0.025 mmol of DMAP. After washing and drying, the peptide was cleaved off from the resin by using a mixture of TFA (9.5 mL), HO (0.85 mL) and triisopropylsilane (TIS) (0.85 mL) for 2 h. The resin was filtered off and the filtrate was poured into 70 mL of ether. The precipitate formed was filtered off and washed thoroughly with ether. This crude product was dissolved into 5% acetic acid and purified on a reverse-phase preparative HPLC using a column (4×43 cm) of $C_{18}$ DYNAMAX-100A° (Varian, Walnut Creek, Calif.). The column was eluted with a linear gradient from 75% A and 25% B to 55% A and 45% B in an hour where A was 0.1% TFA in water and B was 0.1% TFA in acetonitrile. The fractions were checked by an analytical HPLC. Those containing pure product were combined and lyophilized to dryness. The purity of the compound was 92.8%. Yield was 8.6%. Electro-spray ionization mass spectrometry (ESI MS) analysis gave a molecular weight for the product of 3369.4 (in agreement with the calculated molecular weight of 3369.9).

Example 2

(Aib$^2$)hGhrelin(1-28)-NH$_2$ (SEQ ID NO:10)

The titled peptide was synthesized according to the procedure described in Example 1 for the synthesis of (Glu$^3$(O-Hexyl))hGhrelin(1-28)-NH$_2$ (SEQ ID NO:1), except as follows: Fmoc-Ser-OH was used at position 3, Fmoc-Aib-OH was used at position 2 and Boc-Gly-OH was used at position 1. After the peptide chain was assembled, the peptide-resin was treated with 25% piperidine in DMF for 3×2 h. The resin was washed with DMF and treated with octanoic acid (2.5 mmol, 10 fold excess), HBTU (2.2 mmol), HOBt (2.2 mmol) and DIEA (7.5 mmol) in DMF for 2 h. The resin was washed with DMF and then treated with octanoic acid (2.5 mmol), DIC (2.5 mmol), HOBt (2.5 mmol) and DMAP (0.025 mmol) in DMF for 2 h. The final cleavage and purification procedures were the same as those in Example 1. The product was found to be homogenous by analytical HPLC, with a purity of 99% in 18.5% yield. Electro-spray ionization mass spectrometry (ESI MS) analysis gave a molecular weight for the product of 3367.6 (in agreement with the calculated molecular weight of 3367.0).

Example 3

(Glu$^3$(NH-Hexyl))hGhrelin(1-28)-NH$_2$ (SEQ ID NO:1)

The titled peptide was synthesized on an Applied Biosystems (Foster City, Calif.) model 430A peptide synthesizer which was modified to do accelerated Boc-chemistry solid phase peptide synthesis. See Schnolzer, et al., Int. J. Peptide Protein Res., 40:180 (1992). 4-Methylbenzhydrylamine (MBHA) resin (Peninsula, Belmont, Calif.), with a substitution of 0.91 mmol/g was used. Boc amino acids (Midwest Bio-Tech, Fishers, Ind.; Novabiochem., San Diego, Calif.) were used with the following side chain protection: Boc-Ala-OH, Boc-Arg(Tos)-OH, Boc-His(DNP)-OH, Boc-Val-OH, Boc-Leu-OH, Boc-Gly-OH, Boc-Gln-OH, Boc-Lys(2ClZ)-OH, Boc-Ser(Bzl)-OH, Boc-Phe-OH, Boc-Glu(OcHex)-OH and Boc-Pro-OH. Fmoc-Glu(OtBu)-OH (Novabiochem., San Diego, Calif.) was used for the residue at position 3 in the sequence. The synthesis was carried out on a 0.25 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min.

At the end of the assembly of the first 25 residues on the ABI 430A peptide synthesizer and before the coupling of Fmoc-Glu(OtBu)-OH, the protected peptide-resin was transferred into a reaction vessel on a shaker for manual synthesis. After removing the Boc protecting group by using 100% TFA for 2×1 min and washing with DMF, the resin was mixed with Fmoc-Glu(OtBu)-OH (2.5 mmol) which was pre-activated with HBTU (2.0 mmol), HOBt (2.0 mmol) and DIEA (1.0 mL) in 4 mL of DMF. The mixture was shaken for 2 h. This coupling step was repeated. After washing with DMF, the resin was treated with a TFA solution containing 5% water and 5% TIS for 2 h to remove the tBu protecting group in the side chain of the Glu residue. The resin was neutralized with 10% DIEA in DMF and washed with DMF and DCM. The resin was then treated with hexylamine (2.0 mmol), DIC (2.0 mmol), HOBt (2.0 mmol) in 5 ml of DCM for 2×2 h. The resin was washed with DMF and treated with 25% piperidine in DMF for 30 min to remove the Fmoc protecting group. After washing with DMF and DCM, the resin was transferred into the reaction vessel on the ABI 430A peptide synthesizer for the assembly of the rest two residues.

At the end of the assembly of the whole peptide chain, the resin was treated with a solution of 20% mercaptoethanol/10% DIEA in DMF for 2×30 min to remove the DNP group on the H is side chain. The N-terminal Boc group was then removed by treatment with 100% TFA for 2×2 min. The peptide-resin was washed with DMF and DCM and dried under reduced pressure. The final cleavage was done by stirring the peptide-resin in 10 mL of HF containing 1 mL of anisole and dithiothreitol (50 mg) at 0° C. for 75 min. HF was removed by a flow of nitrogen. The residue was washed with ether (6×10 mL) and extracted with 4N HOAc (6×10 mL). This crude product was purified on a reverse-phase preparative HPLC using a column (4×43 cm) of $C_{18}$ DYNAMAX-100A° (Varian, Walnut Creek, Calif.). The column was eluted with a linear gradient from 75% A and 25% B to 55% A and 45% B at flow rate of 10 mL/min in an hour where A was 0.1% TFA in water and B was 0.1% TFA in acetonitrile. Fractions were collected and checked on an analytical HPLC. Those containing pure product were combined and lyophilized to dryness. 31.8 mg of a white solid were obtained. Purity was 89% based on analytical HPLC analysis. Electro-spray ionization mass spectrometry (ESI MS) analysis gave the molecular weight at 3368.4 (in agreement with the calculated molecular weight of 3368.9).

Example 4

(Cys$^3$(S-Decyl))hGhrelin(1-28)-NH$_2$ (SEQ ID NO:1)

(i) The titled peptide was synthesized according to the procedure described in Example 3 for the synthesis of (Glu$^3$ (NH-Hexyl))hGhrelin(1-28)-NH (SEQ ID NO:1) with the following modifications: After the assembly of the first 25 residues using Boc chemistry, the last 3 residues were assembled by employing Fmoc chemistry. The following 3 Fmoc amino acids were used: N-α-Fmoc-S-(p-methoxytrityl)-L-cysteine (Fmoc-Cys(Mmt)-OH), Fmoc-Ser(Bzl)-OH and Fmoc-Gly-OH, which were purchased from Novabiochem (San Diego, Calif.). The Fmoc amino acid (1 mmol) was first pre-activated with HBTU (0.9 mmol) and HOBt (0.9 mmol) in DMF before it was coupled to the peptide-resin. The synthesis cycle for the Fmoc amino acids included: (1) washing with NMP, (2) removing Fmoc protecting group with 20% piperidine in NMP for 30 min, (3) washing with NMP, and (4) coupling with pre-activated Fmoc amino acid for 1 h.

(ii) At the end of the assembly of the entire peptide chain, the protected peptide-resin was treated with a solution of 20% mercaptoethanol and 10% DIEA in DMF for 2×30 min to remove the DNP group on the side-chain of the H is residue. The Mmt protecting group in the side-chain of the Cys residue was then removed by using a solution of 1% TFA and 5% TIS in DCM for 30 minutes and the peptide-resin was washed with DMF.

(iii) 1-(2-pyridyldithio)decane was prepared by stirring 2,2'-dipyridyl disulfide (1.06 g, 4.8 mmol), 1-decanethiol (0.83 mL, 4 mmol) and triethylamine (2 mL) in propanol and acetonitrile (1/9, v/v) at room temperature for about 3 hours (See Carlsson et al., *Biochem. J.*, 1978, 173, 723-737). Purification of the crude 1-(2-pyridyldithio)decane was performed using flash chromatography, eluting with a mixed solvent system of DCM/MeOH (10:0.4).

(iv) The peptide-resin from step (ii) was treated with the 1-(2-pyridyldithio)decane from step (iii) and DIEA (3 eq., 0.75 mmol) overnight in a mixed solvent system of DMF/1-propanol (7:3). The resin was then washed with DMF and the N-terminal Fmoc protecting group was removed by treatment with 25% piperidine in DMF for 30 min. The peptide-resin was then washed with DMF and DCM and dried under reduced pressure.

(v) Final cleavage was performed by stirring the peptide-resin in 10 mL of HF containing 1 mL anisole at about 0° C. for about 70 min. The purification procedure was the same as that described in Example 3. The target product (yield 10.2%) was found by analytical HPLC to have a purity of 99.9%. Electro-spray ionization mass spectrometry (ESI-MS) analysis gave the molecular weight at 3432.1 (in agreement with the calculated molecular weight of 3432.1).

Other peptides of the invention can be prepared by a person of ordinary skill in the art using synthetic procedures analogous to those disclosed generally hereinabove in using the protocols set forth in International Patent Publication WO04/009616. Other peptides of the invention can be prepared by a person of ordinary skill in the art using synthetic procedures analogous to those disclosed generally hereinabove.

The synthesis of peptidyl analogs according to formula II, such as H-Inp-D-Bal-D-Trp-Phe-Apc-NH$_2$t SEQ ID NO:122), H-Inp-D-2-Nal-D-Trp(Ψ)-Pim (SEQ ID NO:126) and H-Inp-D-Trp-D-2-Nal(Ψ)-Pim (SEQ ID NO:120) can be achieved by following the protocol set forth in International Patent Publication WO04/014415 at pages 33-44 as follows:

Example 1

H-Apc-D-1-Nal-D-1-Nal-Phe-Apc-NH$_2$ (SEQ ID NO:129)

Each of the reaction wells contained 0.0675 mmol of Rink Amide MBHA resin (substitution=0.72 mmol/g, Novabiochem, San Diego, Calif.). The following Fmoc amino acids (Novabiochem, San Diego, Calif.; Chem-Impex International, Wood Dale, Ill.; SyntheTech, Albany, Oreg.; Pharma Core, High Point, N.C.) were used: Fmoc-Lys(Boc)-OH, Fmoc-Phe-OH, Fmoc-H-Inp-OH, Fmoc-D-1-Nal-OH, Fmoc-D-2-Nal-OH, Fmoc-D-Trp(Boc)-OH, Fmoc-3-Pal-OH, Fmoc-4-Pal-OH, Fmoc-Orn(Boc)-OH, Fmoc-D-Bip-OH, Fmoc-Thr(Bzl)-OH, Fmoc-Pff-OH, Fmoc-2-Thi-OH, Fmoc-Taz-OH, Fmoc-D-Dip-OH, Fmoc-D-Bpa-OH, Fmoc-D-Bal-OH, and Fmoc-Apc(Boc)-OH.

Each of the Fmoc amino acids was dissolved in a 0.3 N solution of HOBt in DMF wherein the concentration of the resulting Fmoc amino acid was 0.3 N. A four fold excess (0.27 mmol, 0.9 mL of the 0.3 N solution) of Fmoc amino acid was used for each coupling. DIC (0.27 mmol, 0.6 mL of 0.45N DIC solution in DMF) was used as the coupling reagent for each coupling. Deprotection was performed by using 20% piperidine in DMF (2×1.5 mL per residue).

The peptides were cleaved from the resin by treating the peptide-resins with 8% triisopropylsilane (TIP) in trifluoroacetic acid (TFA) (1.5 mL per reaction well) at room temperature for 2 h. The resin was removed by filtration. Each filtrate was diluted to 25 mL with ether in a centrifuge tube. The resulting precipitate in each tube was centrifuged and the solvents were decanted from the precipitate. The precipitate in each tube was then dissolved in methanol (3 mL) and diluted with water (1 mL). The purification of the crude products was done on a reverse-phase preparative HPLC using a column (100×21.20 mm, 5μ) of LUNA 5μ C8(2) (Phenomenex, Torrance, Calif.). For each peptide, the column was eluted with a linear gradient from 85% A and 15% B to 25% A and 75% B in 15 min with a flow rate of 25 mL/min. A was 0.1% TFA in water and B was 0.1% TFA in acetonitrile/water (80/20, v/v). The fractions were checked by analytical HPLC and those containing the pure product were combined and lyophilized to dryness.

Yields ranged from 13% to 71% and purity of each of Examples 1-65 exceeded 94% based upon analytical HPLC analysis. Electro-spray ionization mass spectrometry (ES-MS) analysis was performed and observed molecular weights were in agreement with calculated molecular weights. The results are detailed in Table I, below.

Example 2

H-Inp-D-2-Nal-D-Trp(Ψ)-Pim (SEQ ID NO:126)

1.a. BOC-(D)-Trp-OH (4.0 g, 13.1 mmole) (Novabiochem San Diego, Calif.) in methanol (36 ml) and Cs$_2$CO$_3$ (2.14 g, 6.57 mmole) in water (10 ml) were combined and the mixture was swirled until a homogeneous mixture was obtained. Solvents were removed in vacuo and the residue was dissolved in DMF (45 ml). 2-bromoacetophenone (2.61 g, 13.1 mmole) in DMF (9 ml) was added to the solution and the solution was stirred for 30 min. at room temperature. Cesium bromide was removed by filtration and the filtrate was concentrated in vacuo. The resulting concentrate was dissolved in xylenes (45 ml), NH$_4$OAc (17.1 g) was added, and the solution was heated at reflux for 1 hr. The cooled solution was washed two times with saturated NaHCO$_3$ solution (45 ml) and then with saturated NaCl. The resulting organic layer was purified by flash chromatography to yield 4.1 g (77%) of intermediate 1A depicted in Scheme 1A, ("Compound 1A").

Scheme 1A

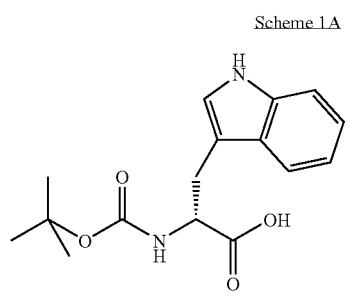

+

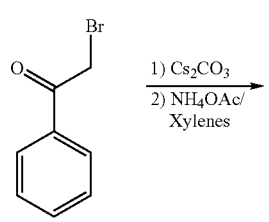

1) Cs$_2$CO$_3$
2) NH$_4$OAc/Xylenes

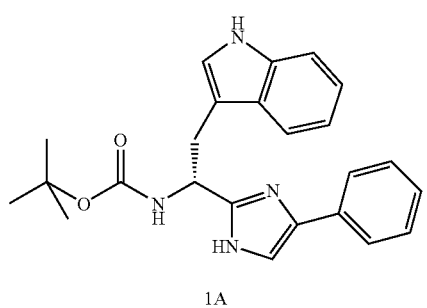

1A

1b. Compound 1A (403 mg) was deblocked using a mixture of trifluoroacetic acid (TFA) (8 ml) dichloromethane (DCM) (8 ml) and triisopropylsilane (TIPS) (1.4 ml). After mixing for one hour the solution was concentrated under a stream of nitrogen. The residue was dissolved in DCM (40 ml), washed two times with a saturated solution of NaHCO$_3$ (40 ml), and then dried over Na$_2$SO$_4$ to yield a solution of the intermediate product 1B, depicted in Scheme 1B, below.

Scheme 1B

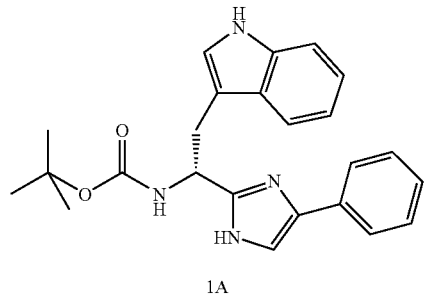

1A

1) TFA/TIPS/DCM

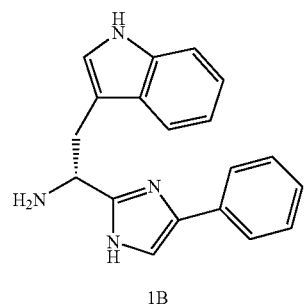

1B

1c.-f. The forgoing solution of the intermediate product 1B was divided into four equal portions and coupled with the pre-activated HOBT esters of FMOC protected amino acids, as summarized in reaction schemes 1C, 1D, 1E, and 1F, below. The amino acid used: FMOC-D-2-Nal-OH (130 mg, 0.30 mmole) (Synthetech Albany, Oreg.)

Each of the immediately foregoing amino acids was pre-activated with HOBT (46 mg, 0.30 mmole) and DIC (38 mg, 0.30 mmole) in DCM (5 ml) for ten minutes before addition to one of the four portions of the forgoing solution of the intermediate product 1B. The coupling reaction was then allowed to proceed for 30 minutes at room temperature.

Scheme 1C

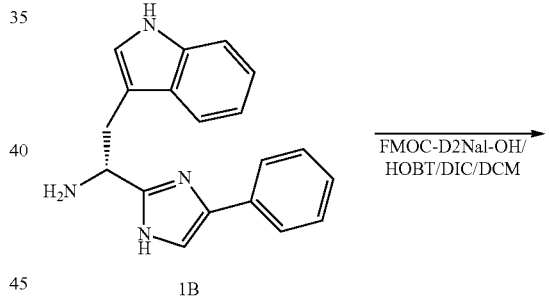

1B

FMOC-D2Nal-OH/HOBT/DIC/DCM

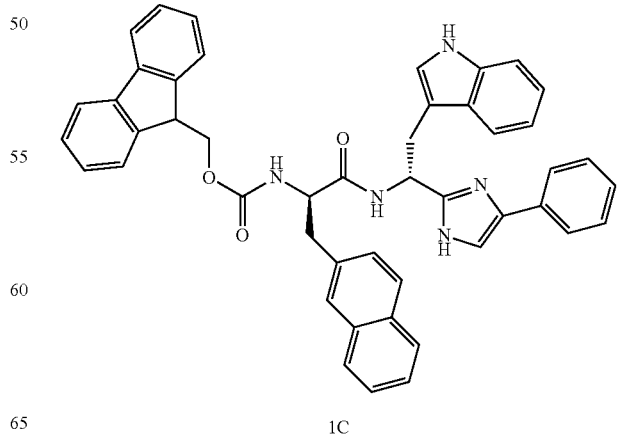

1C

Scheme 1D

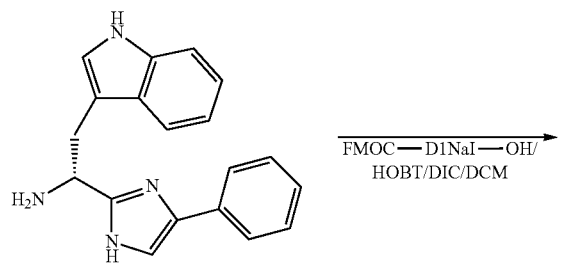

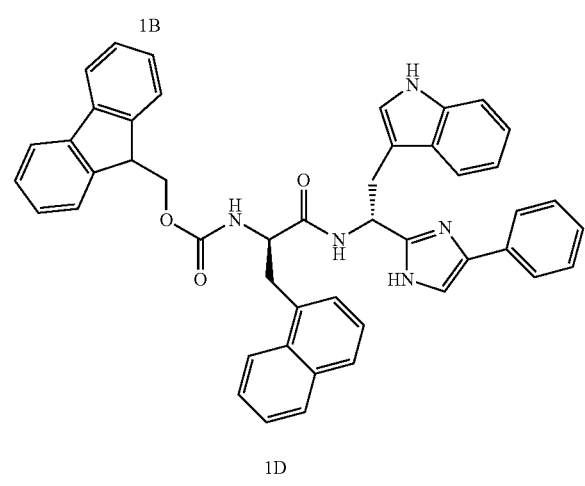

Scheme 1E

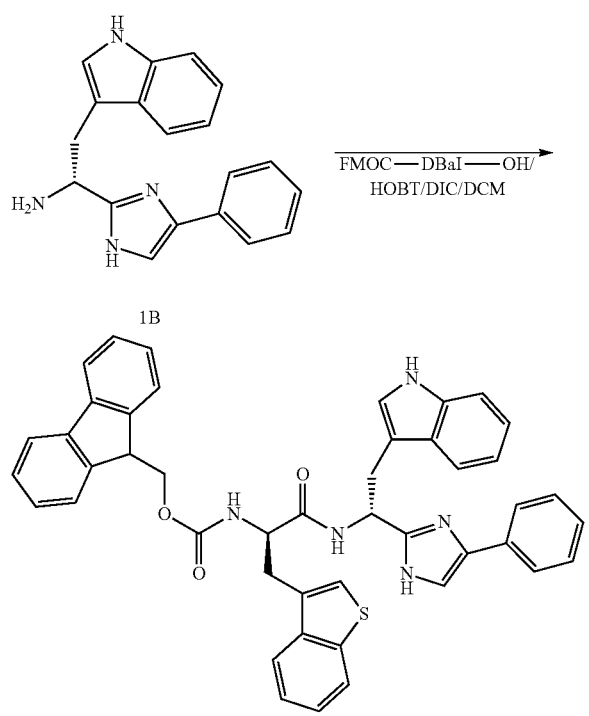

Scheme 1F

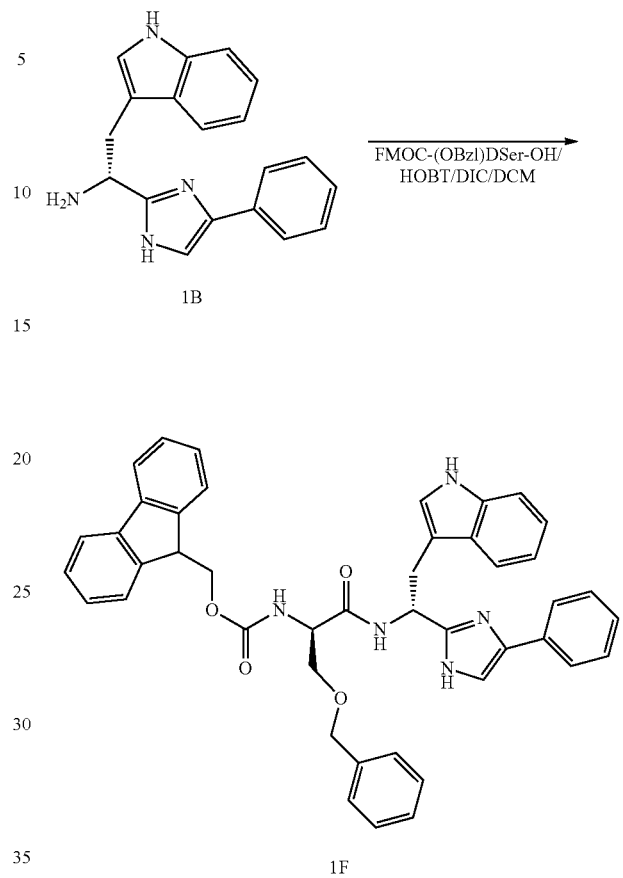

1.g-j. The FMOC group is removed from each of the resulting compounds 1C, 1D, 1E and 1F by addition of tris(2-aminoethyl)amine (0.9 ml) to the respective reaction mixtures from the previous step and mixing for 30 minutes at room temperature. The reaction mixtures containing the deblocked compounds were then washed three times with 10% pH 5.5 phosphate buffer (10 ml).

The resulting free amine solutions were coupled with pre-activated HOBT esters of FMOC-Inp-OH (105 mg, 0.30 mmole) (Chem Impex Wood Dale, Ill.) and was pre-activated with HOBT (46 mg, 0.30 mmole) and DIC (38 mg, 0.30 mmole) in DCM (5 ml) for ten minutes before addition to the appropriate deprotected amine. The coupling reaction was then allowed to proceed for one hour at room temperature.

The FMOC group was removed from the resulting FMOC-protected compounds by addition of tris(2-aminoethyl)amine (0.9 ml) and mixing for 30 minutes. The deblocked compounds were washed three times with 10% pH 5.5 phosphate buffer (10 ml) and the crude products were collected as a precipitate.

The BOC-protected compounds were purified by flash chromatography and then deblocked for one hour with TIPS (0.50 ml), TFA (0.50 ml), in DCM (2.75 ml). The crude products were then concentrated and dried under vacuum.

The foregoing deprotection, coupling, and deprotection steps are summarized in reaction schemes 1G, 1H, 1I and 1J, below Scheme 1G
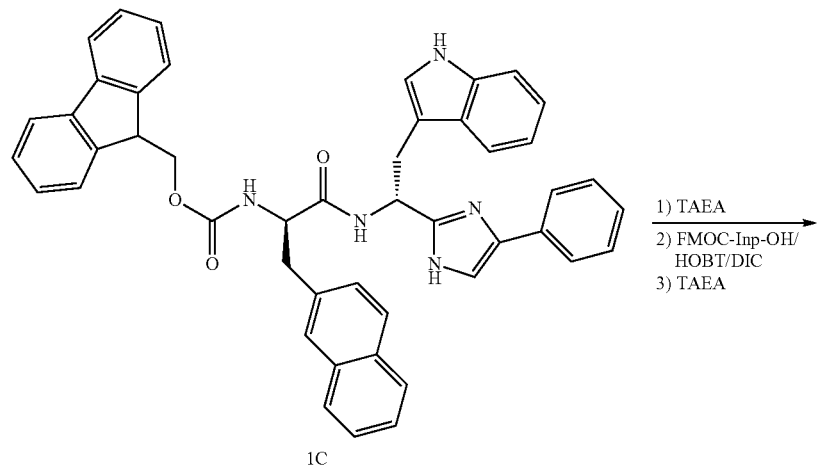
1C
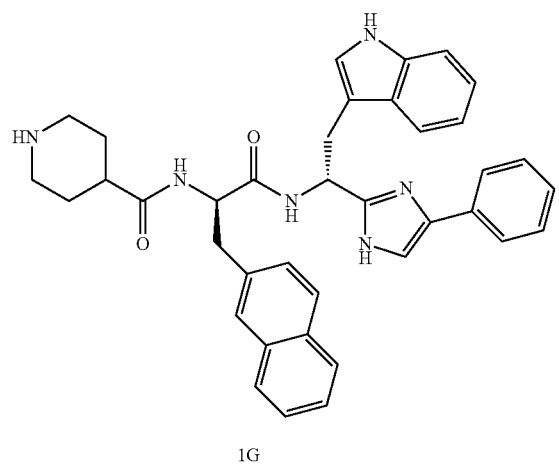
1G
Scheme 1H
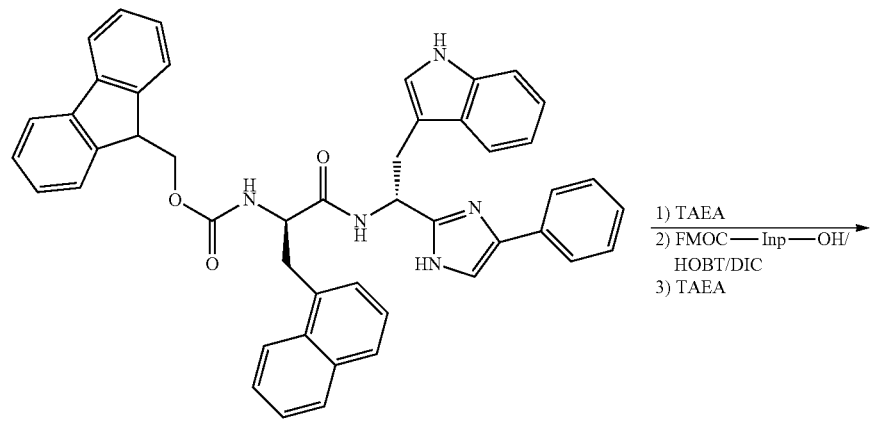
1D

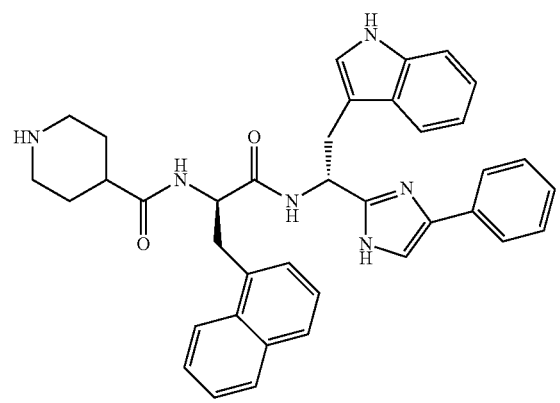
1H
Scheme 1I
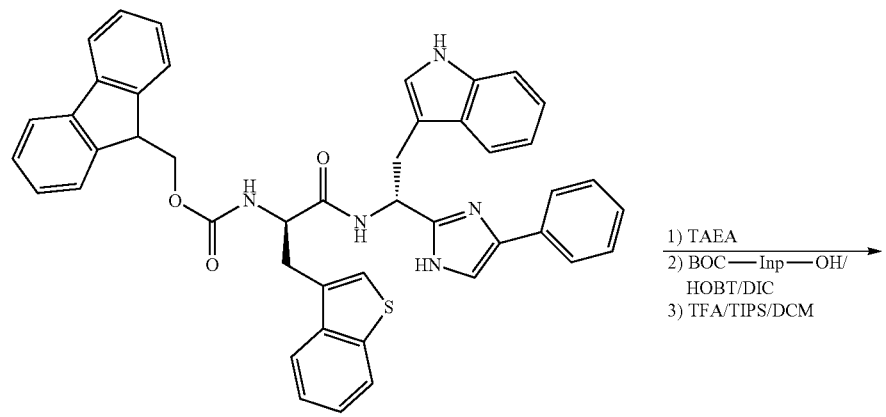
1E
1) TAEA
2) BOC—Inp—OH/ HOBT/DIC
3) TFA/TIPS/DCM
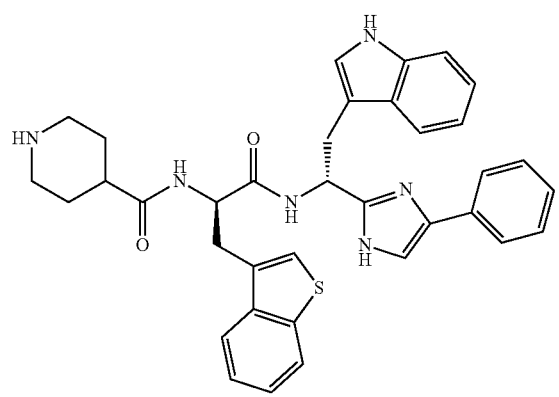
1I

Scheme 1J

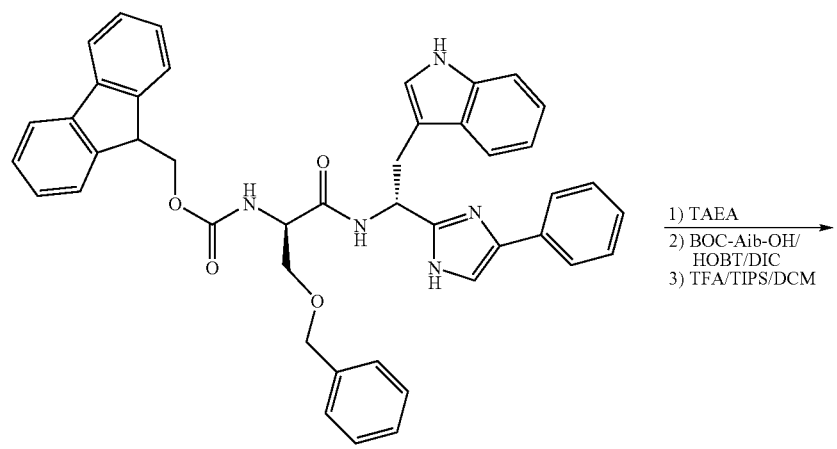

Example 3

H-Inp-D-Trp-D-2-Nal(ψ)-Pim (SEQ ID NO:120)

2.a.1 and 2.a.2.: Compound 2A was made in an analogous manner as was Compound 1A, using BOC-D-2-Nal-OH and 2-bromoacetophenone as starting materials.

Steps 2.a.1. and 2.a.2. are summarized in Scheme 2A, below.

Scheme 2A

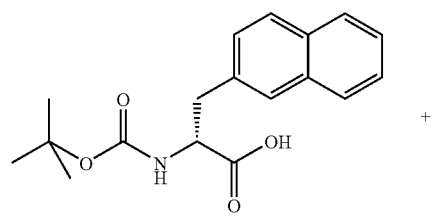

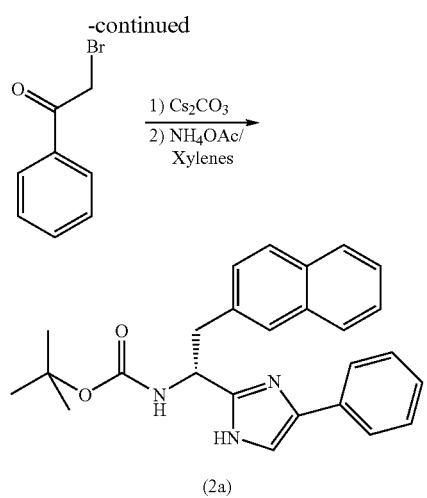

2.b.1. Compound 2A (100 mg, 0.242 mmole) was deblocked in TFA (2 ml) and DCM (2 ml) for one hour. Volatiles were then removed under a stream of nitrogen and the residue was dissolved in DCM (10 ml). The resulting solution washed three times with saturated NaHCO$_3$ (10 ml) to yield a solution of Compound 2A in free amine form.

2.b.2. The active ester of FMOC-D-Trp-(BOC)-OH (153 mg, 0.290 mmole) was preformed with N-hydroxysuccinimide (HOSu; 33 mg, 0.290 mmole) and DIC (37 mg, 0.290 mmole) in DCM (1.5 ml). After one hour diisopropylurea was removed by filtration and the filtrate was added to the Compound 2A (free amine) solution. The resulting solution was diluted with DCM to 4 ml and the coupling reaction allowed to proceed for 30 minutes.

Steps 2.b.1. and 2.b.2. are summarized in Scheme 2B, below.

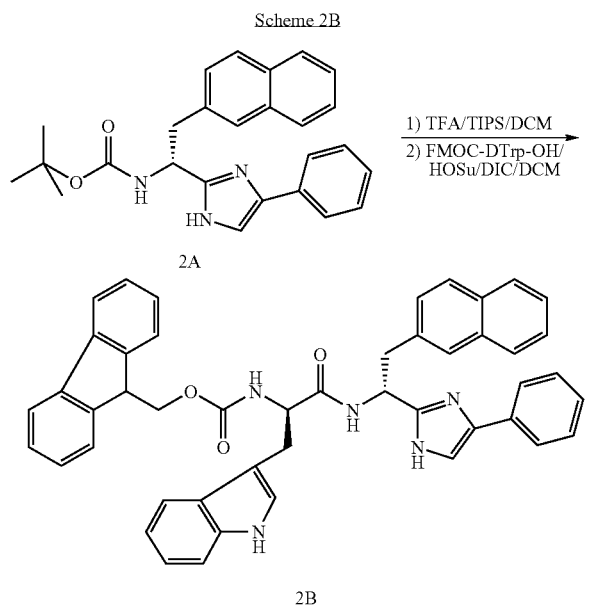

2.c.1 Compound 2B was deblocked by addition of tris(2-aminoethyl)amine (TAEA) (0.9 ml) to the immediately foregoing coupling reaction solution and mixing for 30 minutes at room temperature. The reaction solution was then washed three times with saturated NaCl solution (10 ml) followed by three times with 10% pH 5.5 phosphate buffer (10 ml) to yield a solution of Compound 2B in free amine form.

2.c.2. The active ester of BOC-Inp-OH (66.5 mg, 0.290 mmole) was preformed with HOSu (33 mg, 0.290 mmole) and DIC (37 mg 0.290 mmole) in DCM (1.5 ml). After one hour diisopropylurea was removed by filtration and the filtrate was added to the Compound 2B (free amine) solution. The resulting solution was diluted with DCM to 4 ml and the coupling reaction was allowed to proceed for 12 hours.

The reaction mixture was then washed three times with 10% pH 5.5 phosphate buffer (10 ml) and dried over $Na_2SO_4$. Solvent was removed under vacuum and the concentrate was purified by flash chromatography.

2.c.3. The intermediate was deblocked using TFA (2.75 ml) and TIPS (0.5 ml) in DCM (2.75 ml) for 30 minutes. Volatiles were removed from the reaction mixture under a stream of nitrogen and the residue Was triturated with ether (15 ml). After centrifugation the ether was decanted and the resulting solid was subjected to HPLC to yield purified Compound 70 in 39% yield.

Steps 2.c.1. and 2.c.2. and 2.c.3. are summarized in Scheme 2C, below.

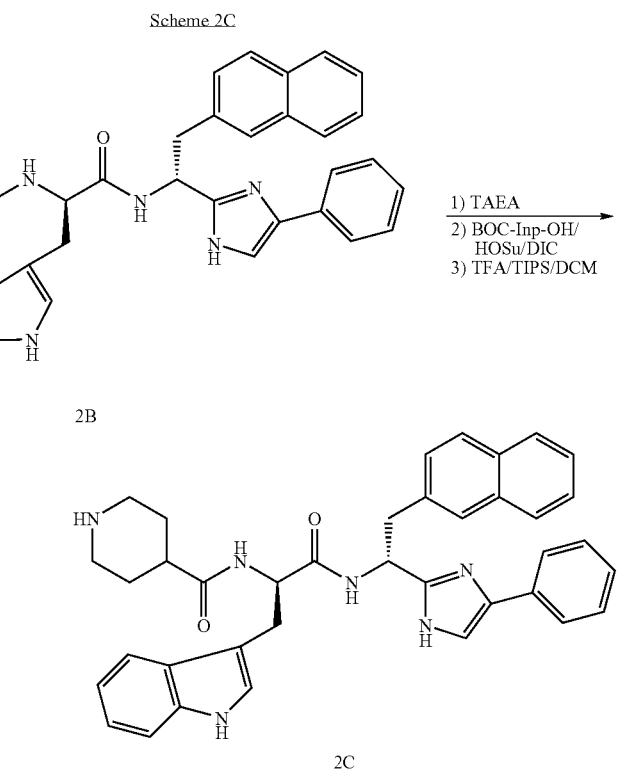

Additional examples for synthesizing compounds according to formula III are provided below to further illustrate different features of the present invention. The examples also illustrate useful methodology for practicing the invention. These examples do not limit the claimed invention.

(Ac-Aib$^1$, Aib$^{2,10}$, Glu(NH-hexyl)$^{3,17}$)hGhrelin(1-28)-NH$_2$ (SEQ ID NO:272)

The title peptide was synthesized on an Applied Biosystems® model 433A peptide synthesizer (obtained from Applied Biosystems®, Foster City, Calif., U.S.A.) using a Fluorenylmethyloxycarbonyl (Fmoc) chemistry. A Rink Amide-4-methylbenzylhydrylamine (MBHA) resin (obtained from Novabiochem®, San Diego, Calif.) with substitution of 0.64 mmol/g was employed. The Fmoc amino acids (obtained from AnaSpec®, San Jose, Calif., U.S.A.) used were Fmoc-Ala-OH, Fmoc-Arg(Pbf)-OH, Fmoc-Aib-OH, Fmoc-Gln(Trt)-OH, Fmoc-Glu(tBu)-OH, Fmoc-His(Trt)-OH, Fmoc-Leu-OH, Fmoc-Lys(Boc)-OH, Fmoc-Phe-OH, Fmoc-Pro-OH, Fmoc-Ser(tBu)-OH and Fmoc-Val-OH. In addition, Fmoc-Glu(O-2-PhiPr)-OH (obtained from Novabiochem®, San Diego, Calif.) was used for the amino acids in 3$^{rd}$ and 17$^{th}$ positions. The synthesis was carried out on a 0.1 mmol scale. The Fmoc groups were removed by treating the resin with a solution of 20% piperidine in N-methylpyrrolidone (NMP) for a period of approximately 30 minutes. In each coupling step, the Fmoc amino acid (3 eq, 0.3 mmol) was first pre-activated in 2 mL solution of 0.45M 2-(1-H-benzotriazole-1-yl)-1,1,2,3-tetramethyluronium-hexafluorophosphate/1-hydroxy-benzotriazole (HBTU/HOBT) in NMP. A solution containing the activated amino acid ester together with 1 mL of diisopropylethylamine (DIEA) and 1 mL of NMP was introduced to the resin. The ABI 433A® peptide synthesizer was programmed to perform the following reaction cycle:

(1) washing with NMP;
(2) removing Fmoc protecting group with 20% piperidine in NMP for 30 minutes;
(3) washing with NMP; and
(4) coupling with pre-activated Fmoc amino acid for approximately 1 or 3 hours.

The resin was coupled successively according to the sequence of the title peptide. After the peptide chain was assembled, the resin was washed completely with N,N-dimethylformamide (DMF) and dichloromethane (DCM).

At the end of the assembly of the peptide chain on the ABI 433A® peptide synthesizer (without the Fmoc-Aib residue in A$^1$), the peptide-resin was transferred to a reaction vessel on a shaker and the Fmoc was removed using 25% piperidine in DMF for 30 minutes. The resin was then washed with DMF. The Fmoc-Aib-OH (0.4 mmole) was coupled using TFFH (Tetramethylfluoroformamidinium Hexafluorophosphate) (obtained from Perceptive Biosystems®, Warrington, U.K.) (0.4 mmole), HOAt (0.4 mmol), DMAP (Dimethylaminopyridine) (0.1 g) and DIEA (1.2 mmole) once for 4 hours and once overnight.

The Fmoc group was removed as above and the peptide was capped using Ac2O (acetic anhydride) (5 mmole) and DIEA (5 mmole) in DMF for approximately 30 minutes. The PhiPr (γ-2-phenylisopropyl ester) groups were removed from the Glutamine residues at A$^3$ and A$^{17}$ by washing with a solution of 3% TFA in DCM twice for a period of 10 minutes for each washing. The Boc that was partially removed from the side chain of Lysine was replaced by using Boc$_2$O (0.8 mmole) and DIEA (0.8 mmole) in DCM overnight. The resin was treated with PyAOP (7-Azabenzotriazol-1-yloxytris(pyrrolidino)phosphonium-hexafluorophosphate) (obtained from Applied Biosystems®, Foster City, Calif., U.S.A.) (0.6 mmole), HOAt (0.6 mmole), DMAP (0.1 g) and DIEA (1.8 mmole) for 10 minutes. Hexyl-NH$_2$(Hexylamine) (obtained from Sigma-Aldrich Chemicals®, St. Louis, Mo., U.S.A.) (2.0 mmole) was then added to the resin solution which was then shaken and allowed to stand overnight.

To cleave the title peptide from the resin, the peptide-resin was treated with a mixture of TFA, H$_2$O and triisopropylsilane (TIS) (9.5 mL/0.85 mL/0.8 mL, respectively) for approximately 4 hours. The cleaved resin was filtered off and the remaining filtrate was poured into 200 mL of ether. A precipitate formed which was then collected by centrifugation. The crude product was dissolved in a mixture of acetonitrile and water which was purified on a reverse-phase preparative HPLC system with a column (4×43 cm) of C18 DYNAMAX-100 A$^0$® (obtained from Varian®, Walnut Creek, Calif., U.S.A.). The column was eluted over approximately 1 hour using a linear gradient of 85% A:15% B to 60% A:40% B, where A was 0.1% TFA in water and B was 0.1% TFA in acetonitrile. The fractions were analyzed by HPLC and those fractions found to contain pure product were pooled and lyophilized to dryness. Approximately 27.1 mg (6.3%) of a white solid was recovered which was assayed using HPLC and found to be approximately 97.5% pure. Electro-spray ionization mass spectrometry (ESI-MS) analysis determined the molecular weight to be 3477.4 which was in agreement with the calculated molecular weight of 3477.19.

(Aib$^{1,2,10}$, Glu(NH-hexyl)$^{3,17}$)hGhrelin(1-28)-NH$_2$ (SEQ ID NO:212)

The titled peptide was synthesized according to the procedure described for Example 158, i.e., (Ac-Aib$^1$, Aib$^{2,10}$, Glu(NH-Hexyl)$^{3,17}$)hGhrelin(1-28)-NH$_2$) with the following exception: After coupling the last Fmoc-Aib-OH in the 1$^{st}$ position on a shaker, the PhiPr protecting groups were removed from the Glutamine residues at A$^3$ and A$^{17}$ by washing with a 3% TFA in DCM twice for intervals lasting approximately 10 minutes. The Boc that was partially removed from the side chain of Lysine was replaced using a solution of Boc$_2$O (0.8 mmole) and DIEA (0.8 mmole) in DCM. After being shaken and standing overnight, the resin was treated with a solution of PyAOP (7-Azabenzotriazol-1-yloxytris(pyrrolidino)phosphonium-hexafluorophosphate) (obtained from Applied Biosystems®, Foster City, Calif., U.S.A.) (0.6 mmole), HOAt (0.6 mmole), DMAP (0.1 g) and DIEA (1.8 mmole) for 10 minutes after which Hexyl-NH$_2$ (Hexylamine) (obtained from Sigma-Aldrich, St. Louis, Mo., U.S.A.) (2.0 mmole) was then added to the solution which was then shaken and allowed to stand overnight. The Fmoc protecting group was then removed using 25% piperidine in DMF. The peptide was cleaved off from the resin and purified on a HPLC system, as detailed in the discussion of the synthesis of Example 158 above.

Using an HPLC assay, the purity of the resulting produce was found to be approximately 96.5%. Electro-spray ionization mass spectrometry (ESI-MS) analysis determined the molecular weight to 3435.00 which was in agreement with the calculated molecular weight of 3435.16.

B. Biological Assays

The activities of the compounds of the invention at the GHS receptor can be and were determined using techniques such as those described in the examples provided below. In different embodiments a ghrelin analog has at least about 50%, at least about 60%, at least about 70%, at least about 80%, or at least about 90%, at least about 95%, at least about 98% or more, functional activity relative to ghrelin as determined using one or more of the functional activity assays described below; and/or has an IC$_{50}$ greater than about 1,000 nM, greater than about 100 nM, or greater than about 50 nM, using the receptor binding assay described below. With respect to $IC_{50}$, greater refers to potency and thus indicates a lesser amount is needed to achieve binding inhibition.

Assays measuring the ability of a compound to bind a GHS receptor employ a GHS receptor, a fragment of the receptor comprising a ghrelin binding site, a polypeptide comprising such a fragment, or a derivative of the polypeptide. Preferably, the assay uses the GHS receptor or a fragment thereof.

A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in ghrelin binding can be readily identified using labeled ghrelin or ghrelin analogs and different receptor fragments. Different strategies can be employed to select fragments to be tested to narrow down the binding region. Examples of such strategies include testing consecutive fragments of about 15 amino acids in length starting at the N-terminus, and testing longer length fragments. If longer length fragments are tested, a fragment binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least 10 compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

B.1 Screening for GHS Receptor Active Compounds

Screening for GHS receptor active compounds is facilitated using a recombinantly expressed receptor. Using a recombinantly expressed GHS receptor offers several advantages such as the ability to express the receptor in a defined cell system so that a response to a compound at the GHS receptor can be more readily differentiated from responses at other receptors. For example, the GHS receptor can be expressed in a cell line such as HEK 293, COS 7, or CHO not normally expressing the receptor by an expression vector, wherein the same cell line without the expression vector can act as a control.

Screening for compounds reducing GHS receptor activity is facilitated through the use of a ghrelin analog in the assay. The use of a ghrelin analog in a screening assay provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G protein coupled activities, and/or in the intracellular messengers. Preferably, GHS receptor activity is measured using techniques such as those measuring intracellular $Ca^{2+}$ Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17 (Button, D. et al., *Cell Calcium*, (1993), 14(9):663-71; and Feighner, S. D. et al., *Science*, (1999), 284(5423):2184-8).

Chimeric receptors containing a ghrelin binding region functionally coupled to a different G-protein can also be used to measure GHS receptor activity. A chimeric GHS receptor contains an N-terminal extracellular domain; a transmembrane domain made up of transmembrane regions, extracellular loop regions, and intracellular loop regions; and an intracellular carboxy terminus. Techniques for producing chimeric receptors and measuring G-protein coupled responses are provided in, for example, International Application Number WO 97/05252, and U.S. Pat. No. 5,264,565, both of which are hereby incorporated by reference herein.

Ghrelin analogs can be used to stimulate GHS receptor activity. Such stimulation can be used, for example, to study the effect of GHS receptor modulation, to study the effect of growth hormone secretion, to look for or study ghrelin antagonists, or to achieve a beneficial effect in a subject. It is contemplated that the ghrelin analogs of the instant invention are useful for stimulating gastrointestinal motility.

B.1.a. Preparation of CHO-KL Cells Expressing the Human Recombinant GHS Receptor The cDNA for human growth hormone secretagogue receptor (hGHS-R, or ghrelin receptor) was cloned by Polymerase Chain Reaction (PCR) using human brain RNA as a template (Clontech, -Palo Alto, Calif.), gene specific primers flanking the full-length coding sequence of hGHS-R, (S: 5'-ATGTGGAACGCGACGCCCCAGCGAAGAG-3' and AS: 5'-TCATGTATTAATACTAGATTCTGTCCA-3'), and Advantage 2 PCR Kit (Clontech, -Palo Alto, Calif.). The PCR product was cloned into the pCR2.1® vector using Original TA® Cloning Kit (Invitrogen, Carlsbad, Calif.). The full length human GHS-R was subcloned into the mammalian expression vector pcDNA 3.1® (Invitrogen, Carlsbad, Calif.). The plasmid was transfected into the Chinese hamster ovary cell line, CHO-K1 (American Type Culture Collection, Rockville, Md.) by calcium phosphate method (Wigler, M. et al., *Cell*, (1977), 11(1):223-32). Single cell clones stably expressing the hGHS-R were obtained by selecting transfected cells grown in cloning rings in RPMI 1640 media supplemented with 10% fetal bovine serum and 1 mM sodium pyruvate containing 0.8 mg/ml G418 (Gibco®, Grand Island, N.Y., U.S.A.).

B.1.b GHS-Receptor Binding Assay:

Membranes for radioligand binding studies can be and were prepared by homogenization of the foregoing CHO-KL cells expressing the human recombinant GHS receptor. The cells were homogenized in 20 ml of ice-cold 50 mM Tris-HCl using a Brinkman Polytron® (Westbury, N.Y.; setting 6, 15 sec). The homogenates were washed twice by centrifugation (39,000 g/10 min) and the final pellets were resuspended in 50 mM Tris-HCl containing 2.5 mM MgCh and 0.1% bovine serum albumin (BSA). For the assay, 0.4 ml aliquots were incubated with 0.05 nM ($^{125}$I)ghrelin (~2000 Ci/mmol, Perkin Elmer Life Sciences, Boston, Mass.) with and without 0.05 ml of unlabeled competing test peptide. After a 60 min incubation at 4° C., the bound ($^{125}$I)ghrelin was separated from free ($^{125}$I)ghrelin by rapid filtration through GF/C filters (Brandel, Gaithersburg, Md.) which had been previously soaked in 0.5% polyethyleneimine/0.1% BSA. The filters were then washed three times with 5-ml aliquots of ice-cold 50 mM Tris-HCl and 0.1% BSA, and the bound radioactivity trapped on the filters was counted by gamma spectrometry (Wallac LKB, Gaithersburg, Md.). Specific binding was defined as the total ($^{125}$I)ghrelin bound minus that bound in the presence of 1000 nM ghrelin (Bachem, Torrence, Calif.).

A selection of the preferred embodiments was tested using the receptor binding assay discussed above and the results are reported in Table 1 presented below.

TABLE 1

Receptor Binding Ki Values for Selected Compounds

| Example # | COMPOUND | Ki (nM) |
|---|---|---|
| #1 | H-Apc-D-1-Nal-D-Trp-2-Thi-Lys-NH$_2$; (SEQ ID NO: 124) | 0.29 |
| #2 | Inp-D-2-Nal-D-Trp-Phe-Lys-NH$_2$ (SEQ ID NO: 111) | 0.30 |
| #3 | H-Inp-D-1-Nal-D-Trp-2-Thi-Lys-NH$_2$ (SEQ ID NO: 112) | 0.31 |
| #4 | H-Apc-D-Bal-D-Trp-Phe-Lys-NH$_2$ (SEQ ID NO: 123) | 0.32 |
| #5 | H-Inp-D-Bal-D-Trp-Phe-Lys-NH$_2$ (SEQ ID NO: 111) | 0.33 |
| #6 | H-Inp-D-1-Nal-D-Trp-Phe-Apc-NH$_2$ (SEQ ID NO: 122) | 0.36 |
| #7 | H-Apc-D-Bal-D-Trp-2-Thi-Lys-NH$_2$ (SEQ ID NO: 128) | 0.36 |
| #8 | (Aib$^2$,Glu$^3$(NH-hexyl))hGhrelin(1-28)-NH$_2$ (SEQ ID NO: 84) | 0.38 |
| #9 | H-Inp-D-Bal-D-Trp-2-Thi-Apc-NH$_2$ (SEQ ID NO: 151) | 0.40 |
| #10 | (Aib$^8$)hGhrelin(1-28)-NH$_2$ (SEQ ID NO: 16) | 0.41 |
| #11 | H-Apc-D-2-Nal-D-Trp-Phe-Lys-NH$_2$ (SEQ ID NO: 123) | 0.42 |
| #12 | H-Inp-D-Bal-D-Trp-2-Thi-Lys-NH$_2$ (SEQ ID NO: 121) | 0.42 |
| #13 | H-Apc-D-1-Nal-D-Trp-Phe-Lys-NH$_2$ (SEQ ID NO: 131) | 0.42 |
| #14 | H-Apc-D-1-Nal-D-Trp-Taz-Lys-NH$_2$ (SEQ ID NO: 124) | 0.45 |
| #15 | H-Inp-D-2-Nal-D-Trp-2-Thi-Lys-NH$_2$ (SEQ ID NO: 113) | 0.45 |
| #16 | (Aib$^{2,8}$,Glu(NH-hexyl)$^{3,17}$)hGhrelin(1-28)-NH$_2$ (SEQ ID NO: 202) | 0.45 |
| #17 | H-Apc-D-1-Nal-D-Trp-2-Thi-Apc-NH$_2$ (SEQ ID NO: 137) | 0.46 |
| #18 | H-Apc-D-1-Nal-D-Trp-Phe-Apc-NH$_2$ (SEQ ID NO: 129) | 0.46 |
| #19 | H-Inp-D-Bal-D-Trp-Phe-Apc-NH$_2$ (SEQ ID NO: 122) | 0.47 |
| #20 | H-Apc-D-Bal-D-Trp-Taz-Lys-NH$_2$ (SEQ ID NO: 128) | 0.50 |
| #21 | (Glu$^3$(O-hexyl))hGhrelin(1-28)-NH$_2$ (SEQ ID NO: 1) | 0.50 |
| #22 | H-Apc-D-Bal-D-Trp-2-Thi-Apc-NH$_2$ (SEQ ID NO: 143) | 0.51 |
| #23 | H-Inp-D-Bal-D-Trp-Taz-Lys-NH$_2$ ; (SEQ ID NO: 121) | 0.52 |
| #24 | H-Inp-D-1-Nal-D-Trp-2-Thi-Apc-NH$_2$ (SEQ ID NO: 147) | 0.53 |
| #25 | (Aib$^2$)hGhrelin(1-28)-NH$_2$ (SEQ ID NO: 10) | 0.57 |
|  | rGhrelin | 0.59 |
| #26 | (2-Thi$^9$)hGhrelin(1-28)-NH$_2$ (SEQ ID NO: 14) | 0.63 |
| #27 | (Aib$^2$,Taz$^9$)hGhrelin(1-28)-NH$_2$ (SEQ ID NO: 8) | 0.63 |
| #28 | H-Inp-D-2-Nal-D-Trp-Phe-Apc-NH$_2$ (SEQ ID NO: 122) | 0.64 |
| #29 | (Aib$^2$,3-Pal$^9$)hGhrelin(1-28)-NH$_2$ (SEQ ID NO: 8) | 0.65 |
| #30 | H-Apc-D-Bal-D-2-Nal-Phe-Lys-NH$_2$ (SEQ ID NO: 132) | 0.68 |
| #31 | H-Apc-D-1-Nal-D-Trp-Phe-NH$_2$ (SEQ ID NO: 125) | 0.70 |
| #32 | (3-Pal$^9$)hGhrelin(1-28)-NH$_2$ (SEQ ID NO: 14) | 0.70 |
| #33 | H-Apc-D-Bal-D-Trp-Phe-Apc-NH$_2$ (SEQ ID NO: 130) | 0.71 |
| #34 | H-Apc-D-1-Nal-D-Trp-2-Thi-NH$_2$ (SEQ ID NO: 133) | 0.73 |

TABLE 1-continued

Receptor Binding Ki Values for Selected Compounds

| Example # | COMPOUND | Ki(nM) |
|---|---|---|
| #35 | (Glu$^3$(NH-Hexyl),Aib$^8$)hGhrelin(1-28)-NH$_2$ (SEQ ID NO: 35) | 0.74 |
| #36 | (Aib$^2$,4-Hyp$^7$)hGhrelin(1-28)-NH$_2$ (SEQ ID NO: 9) | 0.75 |
| #37 | H-Inp-D-2-Nal-D-Trp-Taz-Lys-NH$_2$ (SEQ ID NO: 113) | 0.80 |
| #38 | H-Inp-D-Bal-D-Trp-Taz-Apc-NH$_2$ (SEQ ID NO: 135) | 0.83 |
| #39 | H-Inp-D-1-Nal-D-Trp-2-Thi-NH$_2$ (SEQ ID NO: 116) | 0.87 |
| #40 | (Asp$^3$(O-hexyl))hGhrelin(1-28)-NH$_2$ (SEQ ID NO: 326) | 0.88 |
| #41 | H-Apc-D-Bal-D-Trp-Phe-NH$_2$ (SEQ ID NO: 125) | 0.89 |
| #42 | (Lys$^5$)hGhrelin(1-28)-NH$_2$ (SEQ ID NO: 3) | 0.89 |
| #43 | (Aib$^2$,Glu$^3$(NH-hexyl),Taz$^9$)hGhrelin(1-28)-NH$_2$ (SEQ ID NO: 64) | 0.90 |
| #44 | (Aib$^2$,Dhp$^7$)hGhrelin(1-28)-NH$_2$ (SEQ ID NO: 9) | 0.91 |
| #45 | H-Apc-D-2-Nal-D-Trp-2-Thi-NH$_2$ (SEQ ID NO: 134) | 0.95 |
| #46 | H-Apc-D-1-Nal-D-Trp-Taz-Apc-NH$_2$ (SEQ ID NO: 136) | 0.98 |
| #47 | H-Apc-D-Bal-D-Trp-2-Thi-NH$_2$ (SEQ ID NO: 144) | 0.98 |
| #48 | (Aib$^{2,10}$)hGhrelin(1-28)-NH$_2$ (SEQ ID NO: 12) | 1.02 |
| #49 | (Aib$^{2,8}$)hGhrelin(1-28)-NH$_2$ (SEQ ID NO: 11) | 1.02 |
| #50 | H-Inp-D-1-Nal-D-Trp-3-Pal-Lys-NH$_2$ (SEQ ID NO: 112) | 1.05 |
| #51 | (Aib$^2$,Glu$^3$(NH-hexyl),2-Thi$^9$)hGhrelin(1-28)-NH$_2$ (SEQ ID NO: 64) | 1.06 |
| #52 | (A5c$^2$)hGhrelin(1-28)-NH$_2$ (SEQ ID NO: 10) | 1.07 |
| #53 | (Aib$^2$,Tic$^7$)hGhrelin(1-28)-NH$_2$ (SEQ ID NO: 9) | 1.08 |
| #54 | (Aib$^2$,Thz$^7$)hGhrelin(1-28)-NH$_2$ (SEQ ID NO: 9) | 1.08 |
| #55 | (Aib$^2$,4-Pal$^9$)hGhrelin(1-28)-NH$_2$ (SEQ ID NO: 8) | 1.09 |
| #56 | (Aib$^{2,8}$,Glu$^3$(NH-hexyl))hGhrelin(1-28)-NH$_2$ (SEQ ID NO: 27) | 1.09 |
| #57 | H-Inp-D-1-Nal-D-Trp-Taz-Lys-NH$_2$ (SEQ ID NO: 112) | 1.11 |
| #58 | H-Apc-D-Bal-D-Trp-Taz-Apc-NH$_2$ (SEQ ID NO: 136) | 1.13 |
| #59 | (Aib$^{2,10}$,Glu$^3$(NH-hexyl))hGhrelin(1-28)-NH$_2$ (SEQ ID NO: 28) | 1.14 |
| #60 | H-Inp-D-1-Nal-D-Trp-Taz-Apc-NH$_2$ (SEQ ID NO: 135) | 1.19 |
| #61 | Cys$^3$(S(CH$_2$)$_9$CH$_3$)hGhrelin(1-28)-NH$_2$ (SEQ ID NO: 1) | 1.24 |
| #62 | (Aib$^1$)hGhrelin(1-28)-NH$_2$ (SEQ ID NO: 329) | 1.28 |
| #63 | (Ac-Gly$^1$,Aib$^2$)hGhrelin(1-28)-NH$_2$ (SEQ ID NO: 90) | 1.29 |
| #64 | H-Apc-D-1-Nal-D-1-Nal-Phe-Lys-NH$_2$ (SEQ ID NO: 131) | 1.32 |
| #65 | (Aib$^2$,Pip$^7$)hGhrelin(1-28)-NH$_2$ (SEQ ID NO: 9) | 1.34 |
| #66 | H-Inp-D-Bip-D-Trp-Phe-Lys-NH$_2$ (SEQ ID NO: 111) | 1.35 |
| #67 | H-Apc-D-1-Nal-D-Trp-Taz-NH$_2$ (SEQ ID NO: 133) | 1.41 |
| #68 | H-Apc-D-Bal-D-1-Nal-Phe-Lys-NH$_2$ (SEQ ID NO: 132) | 1.46 |
| #69 | H-Apc-D-Bal-D-2-Nal-Phe-Apc-NH$_2$ (SEQ ID NO: 130) | 1.49 |
| #70 | H-Inp-D-2-Nal-D-Trp-Thr(Bzl)-Lys-NH$_2$ (SEQ ID NO: 113) | 1.55 |
| #71 | H-Inp-D-2-Nal-D-Trp-3-Pal-Lys-NH$_2$ (SEQ ID NO: 113) | 1.58 |

TABLE 1-continued

Receptor Binding Ki Values for Selected Compounds

| Example # | COMPOUND | Ki(nM) |
|---|---|---|
| #72 | H-Apc-D-Bal-D-Trp-Taz-NH$_2$ (SEQ ID NO: 144) | 1.62 |
| #73 | H-Apc-D-1-Nal-D-2-Nal-Phe-Apc-NH$_2$ (SEQ ID NO: 129) | 1.71 |
| #74 | H-Apc-D-1-Nal-D-1-Nal-Phe-Apc-NH$_2$ (SEQ ID NO: 129) | 1.99 |
| #75 | (Dap$^3$(octanesulfonyl))hGhrelin(1-28)-NH$_2$ (SEQ ID NO: 1) | 2.00 |
| #76 | (Glu$^3$(NH-hexyl))hGhrelin(1-28)-NH$_2$ (SEQ ID NO: 1) | 2.03 |
| #77 | H-Apc-D-2-Nal-D-Trp-Taz-NH$_2$ (SEQ ID NO: 134) | 2.11 |
| #78 | H-Inp-D-Bal-D-Trp-Phe-NH$_2$ (SEQ ID NO: 119) | 2.30 |
| #79 | (Aib$^2$,Glu$^3$(NH-hexyl),4-Hyp$^7$)hGhrelin(1-28)-NH$_2$ (SEQ ID NO: 65) | 2.34 |
| #80 | (Aib$^2$,Glu$^3$(NH-hexyl),3-Pal$^9$)hGhrelin(1-28)-NH$_2$ (SEQ ID NO: 64) | 2.35 |
| #81 | (Aib$^2$,Cha$^5$)hGhrelin(1-28)-NH$_2$ (SEQ ID NO: 2) | 2.98 |
| #82 | (Glu$^3$(NH-hexyl),4-Hyp$^7$)hGhrelin(1-28)-NH$_2$ (SEQ ID NO: 68) | 3.36 |
| #83 | H-Apc-D-Bal-D-1-Nal-Phe-Apc-NH$_2$ (SEQ ID NO: 130) | 3.48 |
| #84 | H-Inp-D-2-Nal-D-Trp-2-Thi-NH$_2$ (SEQ ID NO: 115) | 4.11 |
| #85 | (Aib$^2$,Glu$^3$(NH-hexyl),4-Pal$^9$)hGhrelin(1-28)-NH$_2$ (SEQ ID NO: 64) | 4.15 |
| #86 | (Asp$^3$(NH-heptyl))hGhrelin(1-28)-NH$_2$ (SEQ ID NO: 326) | 4.27 |
| #87 | H-Inp-D-2-Nal-D-Trp-Thr(Bzl)-NH$_2$ (SEQ ID NO: 115) | 4.46 |
| #88 | (Aib$^2$,Abu$^6$)hGhrelin(1-28)-NH$_2$ (SEQ ID NO: 4) | 4.60 |
| #89 | (Aib$^{2,12}$,Glu$^3$(NH-hexyl),4-Pal$^9$,Orn$^{15}$)hGhrelin(1-28)-NH$_2$ (SEQ ID NO: 75) | 4.83 |
| #90 | H-Inp-D-2-Nal-D-Trp-Taz-NH$_2$ (SEQ ID NO: 115) | 6.17 |
| #91 | H-Inp-D-2-Nal-D-Trp-4-Pal-Lys-NH$_2$ (SEQ ID NO: 113) | 7.35 |
| #92 | (n-octanoyl-Gly$^1$)hGhrelin(1-28)-NH$_2$ (SEQ ID NO: 95) | 10.19 |
| #93 | H-Inp-D-2-Nal-D-Trp-3-Pal-NH$_2$ (SEQ ID NO: 115) | 11.35 |
| #94 | (Act$^2$)hGhrelin(1-28)-NH$_2$ (SEQ ID NO: 10) | 12.72 |
| #95 | (n-butyryl-Gly$^1$)hGhrelin(1-28)-NH$_2$ (SEQ ID NO: 95) | 12.78 |
| #96 | (Aib$^2$,A6c$^5$)hGhrelin(1-28)-NH$_2$ (SEQ ID NO: 2) | 14.77 |
| #97 | H-Inp-D-1-Nal-D-Trp-3-Pal-NH$_2$ (SEQ ID NO: 116) | 16.10 |
| #98 | H-Inp-D-Bip-D-Trp-Phe-NH$_2$ (SEQ ID NO: 117) | 20.00 |
| #99 | (isobutyryl-Gly$^1$)hGhrelin(1-28)-NH$_2$ (SEQ ID NO: 95) | 21.85 |
| | hGhrelin(1-28)-NH$_2$ | 24.16 |
| #100 | H-Inp-D-2-Nal-D-Trp-Pff-Lys-NH$_2$ (SEQ ID NO: 113) | 25.43 |
| #101 | H-Inp-D-2-Nal-D-Bal-Phe-NH$_2$ (SEQ ID NO: 118) | 27.40 |
| #102 | (A6c$^5$)hGhrelin(1-28)-NH$_2$ (SEQ ID NO: 3) | 35.82 |
| #103 | H-Inp-D-2-Nal-D-Trp-Pff-NH$_2$ (SEQ ID NO: 115) | 36.31 |
| #104 | (des-Ser$^2$)hGhrelin(1-28)-NH$_2$ (SEQ ID NO: 327) | 39.10 |
| #105 | H-Inp-D-Dip-D-Trp-Phe-Lys-NH$_2$ (SEQ ID NO: 111) | 46.78 |
| #106 | H-Inp-D-Bal-D-Trp(Ψ)-Pim (SEQ ID NO: 126) | 48.73 |

TABLE 1-continued

Receptor Binding Ki Values for Selected Compounds

| Example # | COMPOUND | Ki(nM) |
|---|---|---|
| #107 | H-Inp-D-1-Nal-D-Trp(Ψ)-Pim (SEQ ID NO: 126) | 50.55 |
| #108 | (Aib$^{2,6}$)hGhrelin(1-28)-NH$_2$ (SEQ ID NO: 4) | 71.55 |
| #109 | H-Inp-D-Bpa-D-Trp-Phe-Lys-NH$_2$ (SEQ ID NO: 111) | 93.75 |
| #110 | H-Inp-D-2-Nal-D-Dip-Phe-NH$_2$ (SEQ ID NO: 118) | 104.80 |
| #111 | H-Inp-D-Dip-D-Trp-Phe-NH$_2$ (SEQ ID NO: 117) | 104.83 |
| #112 | H-Inp-D-2-Nal-D-Trp-4-Pal-NH$_2$ (SEQ ID NO: 115) | 113.50 |
| #113 | H-Inp-D-2-Nal-D-Trp(Ψ)-Pim (SEQ ID NO: 126) | 116.68 |
| #114 | Aib$^2$,Act$^6$)hGhrelin(1-28)-NH$_2$ (SEQ ID NO: 4) | 155.43 |
| #115 | H-Inp-D-Trp-D-2-Nal(Ψ)-Pim (SEQ ID NO: 120) | 182.00 |
| #116 | H-Inp-D-2-Nal-D-Trp-Orn-Lys-NH$_2$ (SEQ ID NO: 113) | 243.00 |
| #117 | (des-Gly$^1$,des-Ser$^2$)hGhrelin(1-28)-NH$_2$ (SEQ ID NO: 328) | 283.33 |
| #118 | H-Inp-D-2-Nal-D-Bpa-Phe-Lys-NH$_2$ (SEQ ID NO: 114) | 419.00 |
| #119 | H-Aib-D-Ser(Bzl)-D-Trp(Ψ)-Pim (SEQ ID NO: 127) | 753.33 |

B.2. GHS-R Functional Activity Assays

B.2.a. In Vitro GSH Receptor Mediated Intracellular iCa$^{2+}$ Mobilization

The foregoing CHO-KL cells expressing the human GSH receptor were harvested by incubation in a 0.3% EDTA/phosphate buffered saline solution (25° C.) and washed twice by centrifugation. The washed cells were resuspended in Hank's—buffered saline solution (HBSS) for loading of the fluorescent Ca$^{2+}$ indicator Fura-2AM. Cell suspensions of approximately 10$^6$ cells/ml were incubated with 2 µM Fura-2AM for 30 min at about 25° C. Unloaded Fura-2AM was removed by centrifugation twice in HBBS, and the final suspensions were transferred to a spectrofluorometer (Hitachi F-2000) equipped with a magnetic stirring mechanism and a temperature-regulated cuvette holder. After equilibration to 37° C., the ghrelin analogs were added for measurement of intracellular Ca$^{2+}$ mobilization. The excitation and emission wavelengths were 340 and 510 nm, respectively.

B.2.b. In Vivo GH Release/Suppression

As is well known in the art, compounds may be tested for their ability to stimulate or suppress release of growth hormone (GH) in vivo (Deghenghi, R. et al., *Life Sciences*, (1994), 54(18):1321-8; and International Patent Application No. PCT/EP01/07929 [WO 02/08250]). Thus for example in order to ascertain a compound's ability to stimulate GH release in vivo the compound may be injected subcutaneously in 10-day old rats at a dose of, e.g., 300 mg/kg. The circulating GH may be determined at, e.g., 15 minutes after injection and compared to GH levels in rats injected with a solvent control.

B.3. Effect upon Gastrointestinal Motility

Ghrelin has been shown to increase gastric motility and improve gastric emptying in subjects suffering from gastroparesis. Selected compounds of the invention can be and were tested to determine the effect of the compounds upon gastric emptying and intestinal transit.

B.3.a. In Vivo Study of Ghrelin on Intestinal Transit

The effect of native ghrelin and a peptidyl analog of ghrelin, H-Inp-D-Bal-D-Trp-Phe-Apc-NH$_2$ (SEQ ID NO:122) (Example 19) on intestinal transit was conducted. In the study, groups of eight rats were fasted for approximately 24 hours with free access to water. Anesthetized test subjects were administered native ghrelin, the selected analog and atropine as a control. The test subjects were administered a 2 ml charcoal meal by esophageal gavage approximately five minutes after the initial administration of ghrelin, the selected analog or atropine. After approximately an additional 25 minutes, the test subjects were sacrificed by cervical rupture and the small intestines were removed. The distance the charcoal traveled was measured from the pylorus. Both ghrelin and the tested peptidyl analog of ghrelin (H-Inp-D-Bal-D-Trp-Phe-Apc-NH$_2$) (SEQ ID NO:122) accelerated gastric intestinal transit.

B.3.b. In Vivo Study of Ghrelin on Gastric Emptying

Selected compounds of the invention can be and were tested to determine the effect of the compounds upon gastric emptying. The effect of native ghrelin and a peptidyl analog of ghrelin, H-Inp-D-Bal-D-Trp-Phe-Apc-NH$_2$ (SEQ ID NO:122), on gastric emptying was conducted. In the study, groups of eight male Sprague Dawley rats (weighing 200-250 gms) were fasted for approximately 24 hours with free access to water. Native ghrelin, the selected ghrelin analog and a metoclopramide control compound were administered intravenously to anesthetized test subjects. Approximately five minutes after the initial administration of native ghrelin, the selected ghrelin analog or the control compound, a 1.5 ml meal marked with phenol red (0.5 mg/ml phenol red and 1.5% methyl cellulose in whole milk) was administered to each test subject by esophageal gavage. After approximately an additional 20 minutes, the test subjects were sacrificed by cervical rupture and the stomachs removed and individually pulverized. The residual phenol red in the stomach of the test subjects was extracted and was measured spectrophometrically at a wavelength of 560 nm. Both ghrelin and the tested peptidyl analog of ghrelin (H-Inp-D-Bal-D-Trp-Phe-Apc-NH$_2$ (SEQ ID NO:122)) accelerated gastric emptying.

In other experiments, groups of eight male Sprague Dawley rats (weighing 200-250 gms) were fasted for approximately 24 hours with free access to water. The animals were injected subcutaneously with either vehicle or varying doses of native ghrelin or selected ghrelin analogs. After approximately 15 minutes, 1.5 ml of a phenol red marked nutrient meal (0.5 mg/ml phenol red & 1.5% methyl cellulose in whole milk) was administered orally to the rats. After an additional approximately 15 minutes, the subjects were sacrificed by cervical rupture and, after clamping the pylorus & cardia, the stomach was removed. The residual phenol red in the stomach was extracted and measured by spectrophotometric methods at a wavelength of 560 nm. Both ghrelin and the tested peptidyl analog of ghrelin (H-Inp-D-Bal-D-Trp-Phe-Apc-NH$_2$ (SEQ ID NO:122)) accelerated gastric emptying. (see Figures)

B.3.c. Effect on POI in Rat

A 3 centimeter laparotomy was used to induce gastric ileus in male Sprague Dawley rats (weighing 200-250 gms) under isoflurane anesthesia. The abdominal muscles and skin were closed with suture and the animals were allowed to recover for approximately two hours and forty five minutes. At this time, vehicle or selected ghrelin analogs were administered subcutaneously to the laparectomized animals. Approximately 15 minutes after administration of the compounds or vehicle, the phenol red marked meal (see above) was introduced into the animals. After an additional approximately 15 minutes, the subjects were sacrificed by cervical rupture and gastric emptying was measured as described above. Both ghrelin and the tested peptidyl analog of ghrelin (H-Inp-D-Bal-D-Trp-Phe-Apc-NH$_2$ (SEQ ID NO:122)) significantly accelerated gastric emptying under post-operative ileus conditions.

B.3.d. Effect on POI in Rat in the Presence of Morphine

A 3 centimeter laparotomy was used to induce gastric ileus in male Sprague Dawley rats (weighing 200-250 gms) under isoflurane anesthesia. The abdominal muscles and skin were closed with suture and the animals were allowed to recover for approximately 2.5 hours at which time the laparecotomized animals received a subcutaneous administration of 4 mg/kg morphine. Approximately 15 minutes after receiving the morphine, vehicle or selected ghrelin analogs were administered subcutaneously to the laparectomized animals. Approximately 15 minutes after administration of the compounds or vehicle, the phenol red marked meal (see above) was introduced into the animals. After an additional approximately 15 minutes, the subjects were sacrificed by cervical rupture and gastric emptying was measured as described above. As can be seen in the Figures, ghrelin and its analog significantly accelerate gastric emptying in the presence of morphine and post-operative ileus conditions.

One skilled in the art would know that assays similar to those described herein may be used to determine the effect of a ghrelin analog upon gastric emptying and intestinal transit.

Administration

Ghrelin analogs can be formulated and administered to a subject using the guidance provided herein along with techniques well known in the art. The preferred route of administration ensures that an effective amount of compound reaches the target. Guidelines for pharmaceutical administration in general are provided in, for example, Remington's Pharmaceutical Sciences 18$^{th}$ Edition, Ed. Gennaro, Mack Publishing, 1990, and Modem Pharmaceutics 2$^{nd}$ Edition, Eds. Banker and Rhodes, Marcel Dekker, Inc., 1990, both of which are hereby incorporated by reference herein.

Ghrelin analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Ghrelin analogs can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

Ghrelin analogs may also be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Ghrelin analogs can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The patent and scientific literature referred to herein represents knowledge that is available to those with skill in the art. All patents, patent publications and other publications cited herein are hereby incorporated by reference in their entirety.

OTHER EMBODIMENTS

The foregoing description has been limited to specific embodiments of this invention. It will be apparent however, that variations and modifications may be made to the invention, with the attainment of some or all of the advantages of the invention. Such embodiments are also within the scope of the following claims.

---

What is claimed is:

1. A method of stimulating the motility of the gastrointestinal system in a patient, said method comprising administering a peptidyl analog of ghrelin to a patient in need thereof wherein said peptidyl analog of ghrelin comprises the following formula (II):

$$R^1-A^1-A^2-A^3-A^4-A^5-R^2 \quad\quad (II)$$

wherein:
$A^1$ is Aib, Apc or Inp;
$A^2$ is D-Bal, D-Bip, D-Bpa, D-Dip, D-1-Nal, D-2-Nal, D-Ser(Bzl), or D-Trp;
$A^3$ is D-Bal, D-Bip, D-Bpa, D-Dip, D-1-Nal, D-2-Nal, D-Ser(Bzl), or D-Trp;
$A^4$ is 2-Fua, Orn, 2-Pal, 3-Pal, 4-Pal, Pff, Phe, Pim, Taz, 2-Thi, 3-Thi, Thr(Bzl);
$A^5$ is Apc, Dab, Dap, Lys, Orn, or deleted;
$R^1$ is hydrogen, $(C_{1-6})$alkyl, $(C_{5-14})$aryl, $(C_{1-6})$alkyl$(C_{5-14})$aryl, $(C_{3-8})$cycloakyl, or $(C_{2-10})$acyl; and
$R^2$ is OH or $NH_2$;
provided that when $A^5$ is Dab, Dap, Lys, or Orn, then:
$A^2$ is D-Bip, D-Bpa, D-Dip or D-Bal; or
$A^3$ is D-Bip, D-Bpa, D-Dip or D-Bal; or
$A^4$ is 2-Thi, 3-Thi, Taz, 2-Fua, 2-Pal, 3-Pal, 4-Pal, Orn, Thr(Bzl), or Pff;
when $A^5$ is deleted, then:
$A^3$ is D-Bip, D-Bpa, or D-Dip; or
$A^4$ is 2-Fua, Pff, Taz, or Thr(Bzl); or
$A^1$ is Apc when
$A^2$ is D-Bip, D-Bpa, D-Dip or D-Bal; or
$A^3$ is D-Bip, D-Bpa, D-Dip or D-Bal; or
$A^4$ is 2-Thi, 3-Thi, Orn, 2-Pal, 3-Pal or 4-Pal;
or a pharmaceutically acceptable salt thereof.

2. The method of claim 1, wherein said patient is experiencing postoperative ileus following gastrointestinal surgery.

3. The method of either claim 1 or claim 2, wherein said patient is either concurrently being administered or has previously been administered opioid analgesics.

4. The method of claim 3, wherein said peptidyl analog is H-Inp-D-Bal-D-Trp-Phe-Apc-$NH_2$.

5. The method according to claim 1, wherein said patient is a human.

6. The A method according to claim 1, wherein said patient in need of gastrointestinal stimulation is experiencing gastroesophageal reflux disease, ileus, emesis, gastroparesis, IBS, constipation, or colonic pseudo-obstruction.

7. The method according to claim 6, wherein said patient is experiencing ileus, emesis or gastroparesis.

8. The method according to claim 7, wherein said patient is experiencing ileus.

9. The method according to claim 8, wherein said ileus is postoperative ileus.

10. The method according to claim 9, wherein said post-operative ileus follows abdominal surgery.

11. The method according to claim 10, wherein said ileus is of the stomach, small intestine, or large intestine.

12. The method according to claim 8, wherein said ileus is caused by a factor other than abdominal surgery.

13. The method according to claim 12, wherein said ileus is of the stomach, small intestine or large intestine.

14. The method according to claim 1, wherein said therapeutically effective amount of said pharmaceutical composition comprising a peptidyl analog of ghrelin or pharmaceutically acceptable salt thereof and a pharmaceutically acceptable carrier or diluent, is administered intravenously, subcutaneously, orally, or by implantation of a sustained release formulation.

15. A method of stimulating the motility of the gastrointestinal system in a patient wherein said method comprises identifying a patient suffering from or at risk for gastroesophageal reflux disease, ileus, emesis, gastroparesis, IBS, constipation, or colonic pseudo-obstruction, and administering to said patient a therapeutically effective amount a pharmaceutical composition comprising a peptidyl analog of ghrelin or pharmaceutically acceptable salt thereof, and a pharmaceutically acceptable carrier or diluent, according to claim 1.

16. A method of preventing post-operative ileus in a patient in need thereof, wherein said method comprises administering to said patient a therapeutically effective amount a pharmaceutical composition comprising a peptidyl analog of ghrelin or pharmaceutically acceptable salt thereof, and a pharmaceutically acceptable carrier or diluent, according to claim 1, before, during or after a surgery, or a combination thereof.

17. The method of according to claim 16, wherein said administration is before said surgery.

18. The method of according to claim 16, wherein said administration is during said surgery.

19. The method of according to claim 16, wherein said administration is after said surgery.

20. A method of preventing post-operative ileus, gastroesophageal reflux disease, emesis, gastroparesis, IBS, constipation, or colonic pseudo-obstruction in a patient in need thereof by administering to said patient a therapeutically effective amount a pharmaceutical composition comprising a peptidyl analog of ghrelin or pharmaceutically acceptable salt thereof, and a pharmaceutically acceptable carrier or diluent, according to claim 1, wherein said administration is intravenous, subcutaneous, oral, or by implantation of a sustained release formulation.

21. The method according to claim 20, wherein said administration is intravenous.

22. The method according to claim 20, wherein said administration is subcutaneous.

23. The method according to claim 20, wherein said administration is oral.

24. The method according to claim 20, wherein said administration is by implantation of a sustained release formulation.

25. A method of eliciting a response from a ghrelin receptor in a patient in need thereof which comprises administering to said patient a therapeutically effective amount of a pharmaceutical composition comprising a peptidyl analog of ghrelin or pharmaceutically acceptable salt thereof, and a pharmaceutically acceptable carrier or diluent, according to claim 1.

* * * * *